United States Patent
Kawamura et al.

(10) Patent No.: US 8,568,903 B2
(45) Date of Patent: *Oct. 29, 2013

(54) PHENANTHRENE DERIVATIVE, AND MATERIAL FOR ORGANIC EL ELEMENT

(75) Inventors: Masahiro Kawamura, Sodegaura (JP); Kazuki Nishimura, Sodegaura (JP); Yoriyuki Takashima, Sodegaura (JP); Mitsunori Ito, Sodegaura (JP); Toshihiro Iwakuma, Sodegaura (JP); Toshinari Ogiwara, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 389 days.

This patent is subject to a terminal disclaimer.

(21) Appl. No.: 12/667,777

(22) PCT Filed: Jul. 4, 2008

(86) PCT No.: PCT/JP2008/062143
§ 371 (c)(1),
(2), (4) Date: Jan. 5, 2010

(87) PCT Pub. No.: WO2009/008355
PCT Pub. Date: Jan. 15, 2009

(65) Prior Publication Data
US 2010/0327230 A1  Dec. 30, 2010

(30) Foreign Application Priority Data

Jul. 7, 2007 (JP) ................. 2007-179120
Jul. 7, 2007 (JP) ................. 2007-179121

(51) Int. Cl.
*H01L 51/54* (2006.01)
*C09K 11/06* (2006.01)
*C07C 15/30* (2006.01)

(52) U.S. Cl.
USPC ........... 428/690; 428/917; 313/504; 313/506; 585/26; 252/301.16

(58) Field of Classification Search
None
See application file for complete search history.

(56) References Cited

U.S. PATENT DOCUMENTS

| | | | |
|---|---|---|---|
| 7,429,425 B2 * | 9/2008 | Ikeda et al. | 428/690 |
| 2002/0182441 A1 | 12/2002 | Lamansky et al. | |
| 2006/0134456 A1 * | 6/2006 | Ikeda et al. | 428/690 |
| 2006/0228580 A1 | 10/2006 | Jeong et al. | |
| 2007/0152209 A1 | 7/2007 | Uckert | |
| 2008/0074038 A1 * | 3/2008 | Kim et al. | 313/504 |
| 2009/0009066 A1 * | 1/2009 | Nishimura et al. | 313/504 |
| 2009/0230852 A1 * | 9/2009 | Lee et al. | 313/504 |
| 2009/0273278 A1 * | 11/2009 | Lee et al. | 313/504 |
| 2010/0096982 A1 * | 4/2010 | Eum et al. | 313/504 |
| 2010/0331585 A1 * | 12/2010 | Kawamura et al. | 585/26 |
| 2011/0068683 A1 * | 3/2011 | Kawamura et al. | 313/504 |
| 2012/0007059 A1 * | 1/2012 | Iwakuma et al. | 257/40 |

FOREIGN PATENT DOCUMENTS

| | | |
|---|---|---|
| JP | 2001 118683 | 4/2001 |
| JP | 2001 332384 | 11/2001 |
| JP | 2003 142267 | 5/2003 |
| JP | 2004 18510 | 1/2004 |
| JP | 2004 75567 | 3/2004 |
| JP | 2005 8588 | 1/2005 |
| JP | 2005 19219 | 1/2005 |
| JP | 2005 197262 | 7/2005 |
| JP | 2006 151966 | 6/2006 |
| JP | 2007 84485 | 4/2007 |
| WO | 2004 016575 | 2/2004 |
| WO | 2005 112519 | 11/2005 |
| WO | 2006 039982 | 4/2006 |
| WO | 2006 114966 | 11/2006 |
| WO | 2007 046658 | 4/2007 |

OTHER PUBLICATIONS

U.S. Appl. No. 12/933,434, filed Sep. 20, 2010, Kawamura, et al.

(Continued)

*Primary Examiner* — Dawn Garrett
(74) *Attorney, Agent, or Firm* — Oblon, Spivak, McClelland, Maier & Neustadt, L.L.P.

(57) ABSTRACT

A phenanthrene derivative is represented by a formula (1) below. In the formula (1), $Ar^1$ to $Ar^4$ each represent an aromatic hydrocarbon ring group having 6 to 18 carbon atoms for forming the ring. The aromatic hydrocarbon ring group contains none of anthracene skeleton, pyrene skeleton, aceanthrylene skeleton and naphthacene skeleton. L represents a single bond, a substituted or unsubstituted benzene skeleton, naphthalene skeleton, biphenylene skeleton, fluorene skeleton, phenanthrene skeleton, fluoranthene skeleton, triphenylene skeleton, chrysene skeleton, phenyl-naphthalene skeleton or binaphthalene skeleton. $R^1$ and $R^2$ each represent a substituent, the number of which may be 0, 1 or more. $R^1$ and $R^2$ may be bonded in any positions of the phenanthrene skeleton. m, n, l and p each represent 0 or 1 while satisfying m+n+l+p≥1 (m,n≥l,p). a and b each represent an integer of 0 to 8.

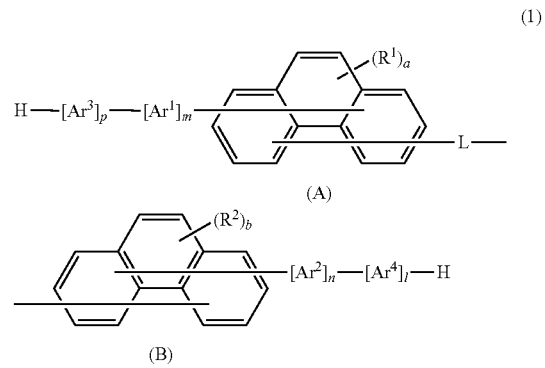

17 Claims, No Drawings

(56) References Cited

OTHER PUBLICATIONS

Shima, K. et al., "Development of Organic EL Device and Composition Materials", CMC Publishing Co. Ltd., pp. 2-5 (Jul. 31, 2006) (with partial English translation).
Laarhoven, W. H. et al., "Chirality and Conformational Changes in 4-Phenylphenanthrenes and 1-Phenylbenzo[c]Phenanthrene Derivatives", Tetrahedron, vol. 34, No. 6, pp. 769-777 (1978).
Liu, Z. et al., "Palladium-Catalyzed, Sequential, Three-Component Cross-Coupling of Aryl Halides, Alkynes, and Arynes", Angewandte Chem, International Edition, vol. 46, No. 14, pp. 2535-2538 (2007).
Dyker, G. et al., "A Survey of Reaction Conditions for Palladium-Catalyzed Processes", Journal of Organometallic Chemistry, vol. 555, No. 1, pp. 141-144 (1998).
U.S. Appl. No. 12/668,105, filed Jan. 7, 2010, Kawamura, et al.
U.S. Appl. No. 13/386,766, filed Jan. 24, 2012, Ogiwara, et al.

* cited by examiner

PHENANTHRENE DERIVATIVE, AND MATERIAL FOR ORGANIC EL ELEMENT

TECHNICAL FIELD

The present invention relates to a phenanthrene derivative and a material for organic EL devices.

BACKGROUND ART

Organic electroluminescence devices (organic EL devices), which include organic emitting layers between anodes and cathodes, are known to emit light using exciton energy generated by recombination of holes and electrons injected into the organic emitting layers.

Such an organic EL device is advantageous as a self-emitting device, and expected to serve as an emitting device excellent in luminous efficiency, image quality, power saving and thin design.

For use of an emitting material in an organic EL device, a doping method, according to which a dopant material is doped to a host material, has been known as a usable method.

In order to efficiently generate exciton from injected energy and to efficiently use exciton energy for light emission, the exciton energy generated by the host is transferred to the dopant, so that light is emitted from the dopant.

For instance, fused aromatic compounds and the like having phenanthrene skeletons shown in Patent Documents 1 to 12 have been used as the host or dopant.

However, while there has recently been an increasing demand for organic EL devices excellent in luminous efficiency, heat resistance and lifetime and free from pixel defects, no organic-EL-device material or no host material has been found capable of providing such excellent organic EL devices.

In this respect, in order to enhance internal quantum efficiency and achieve high luminous efficiency, developments have been made on an emitting material (phosphorescent material) that emits light using triplet exciton. In recent years, there has been a report on a phosphorescent organic device.

Since the internal quantum efficiency can be enhanced up to 75% or more (up to approximately 100% in theory) by using such a phosphorescent material, an organic EL device having high efficiency and consuming less power can be obtained.

However, although exhibiting much higher luminous efficiency, traditional phosphorescent organic EL devices have such a short lifetime as to be practically inapplicable.

Patent Document 1: JP-A-2007-84485
Patent Document 2: JP-A-2006-151966
Patent Document 3: JP-A-2005-19219
Patent Document 4: JP-A-2005-8588
Patent Document 5: JP-A-2004-18510
Patent Document 6: WO2007/46658
Patent Document 7: JP-A-2003-142267
Patent Document 8: JP-A-2004-75567
Patent Document 9: WO2006/114966
Patent Document 10: JP-A-2005-197262
Patent Document 11: WO2004/016575
Patent Document 12: WO2006/039982

DISCLOSURE OF THE INVENTION

Problems to be Solved by the Invention

In order to solve the above-described problems, an aspect of the invention provides a phenanthrene derivative and organic-EL-device material capable of providing an organic EL device excellent in luminous efficiency, heat resistance and lifetime and free from pixel defects.

Means for Solving the Problems

After conducting concentrated studies in order to achieve such an object, the inventors have found that an organic EL device having high efficiency, high heat resistance and long lifetime without pixel defects can be provided by using a phenanthrene derivative represented by the following formula (1) as an organic-EL-device material, and reached the present invention.

A phenanthrene derivative according to an aspect of the invention is represented by a formula (1) below.

[Chemical Formula 1]

$$H-[Ar^3]_p-[Ar^1]_m-(A)(R^1)_a-L-(B)(R^2)_b-[Ar^2]_n-[Ar^4]_l-H \quad (1)$$

In the formula (1), $Ar^1$ to $Ar^4$ each represent an aromatic hydrocarbon ring group having 6 to 18 carbon atoms for forming the ring, the aromatic hydrocarbon ring group containing none of anthracene skeleton, pyrene skeleton, aceanthrylene skeleton and naphthacene skeleton. $Ar^1$ to $Ar^4$ may be bonded in any positions of a phenanthrene skeleton.

$R^1$ and $R^2$ each represent an alkyl group having 1 to 30 carbon atoms, cycloalkyl group having 3 to 30 carbon atoms, alkoxy group having 1 to 20 carbon atoms, cyano group, silyl group having 3 to 30 carbon atoms, halogen atom or aryl group having 6 to 30 carbon atoms. $R^1$ and $R^2$ may be bonded in any positions of the phenanthrene skeleton.

L represents a single bond, a substituted or unsubstituted benzene skeleton, naphthalene skeleton, biphenyl skeleton, fluorene skeleton, fluoranthene skeleton, triphenylene skeleton, chrysene skeleton, phenyl-naphthalene skeleton, binaphthalene skeleton, benzophenanthrene skeleton, dibenzophenanthrene skeleton, benzotriphenylene skeleton, picene skeleton or benzo[b]fluoranthene skeleton.

a represents the number of the substituents $R^1$ directly bonded to a phenanthrene main chain.

b represents the number of the substituents $R^2$ directly bonded to a phenanthrene main chain.

a and b each represent an integer of 0 to 8.

m, n, l and p each represent 0 or 1 while satisfying m+n+l+p≥1 (m,n≥l,p).

Where L is a single bond and either one of $Ar^1$ and $Ar^2$ is a phenanthrene skeleton: when $Ar^1$ is a phenethrene skeleton and the phenanthrene skeleton (A) to which $Ar^1$ is bonded is substituted in 2nd and 7th positions, $Ar^2$ is not equal to $Ar^3$; or when $Ar^2$ is a phenanthrene skeleton and the phenanthrene skeleton (B) to which $Ar^2$ is bonded is substituted in 2nd and 7th positions, $Ar^1$ is not equal to $Ar^4$.

A structure represented by a formula (1-X) below is excluded.

[Chemical Formula 2]

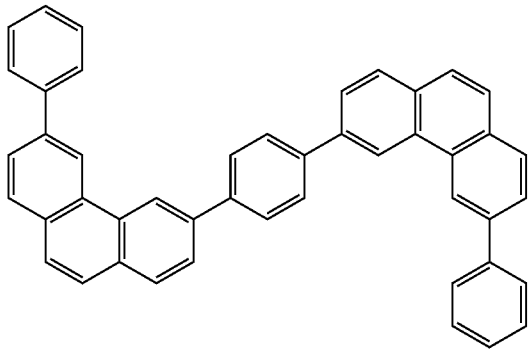

(1-X)

A material for organic EL devices according another aspect of the invention contains the phenanthrene derivative represented by the formula (1).

An organic EL device according to a still further aspect of the invention includes a single-layered or multilayered organic thin-film layer between a cathode and an anode, the organic thin-film layer including an emitting layer, at least one layer of the organic thin-film layer containing the phenanthrene derivative represented by the formula (1).

The aspects of the invention can provide a phenanthrene derivative and organic-EL-device material capable of providing an organic EL device excellent in luminous efficiency, heat resistance and lifetime and free from pixel defects.

BEST MODE FOR CARRYING OUT THE INVENTION

Exemplary preferable embodiment(s) of the invention will be described below.

[Phenanthrene Derivative]

A phenanthrene derivative according to an aspect of the invention is represented by a formula (1) below.

In the formula (1), $Ar^1$ to $Ar^4$ each represent an aromatic hydrocarbon ring group having 6 to 18 carbon atoms for forming the ring, the aromatic hydrocarbon ring group containing none of anthracene skeleton, pyrene skeleton, aceanthrylene skeleton and naphthacene skeleton. $Ar^1$ to $Ar^4$ may be bonded in any positions of a phenanthrene skeleton.

$R^1$ and $R^2$ each represent an alkyl group having 1 to 30 carbon atoms, cycloalkyl group having 3 to 30 carbon atoms, alkoxy group having 1 to 20 carbon atoms, cyano group, silyl group having 3 to 30 carbon atoms, halogen atom or aryl group having 6 to 30 carbon atoms. $R^1$ and $R^2$ may be bonded in any positions of the phenanthrene skeleton.

L represents a single bond, a substituted or unsubstituted benzene skeleton, naphthalene skeleton, biphenyl skeleton, fluorene skeleton, fluoranthene skeleton, triphenylene skeleton, chrysene skeleton, phenyl-naphthalene skeleton, binaphthalene skeleton, benzophenanthrene skeleton, dibenzophenanthrene skeleton, benzotriphenylene skeleton, picene skeleton or benzo[b]fluoranthene skeleton.

a represents the number of the substituents $R^1$ directly bonded to a phenanthrene main chain.

b represents the number of the substituents $R^2$ directly bonded to a phenanthrene main chain.

a and b each represent an integer of 0 to 8.

m, n, l and p each represent 0 or 1 while satisfying $m+n+l+p \geq 1$ $(m,n \geq l,p)$.

Where L is a single bond and either one of $Ar^1$ and $Ar^2$ is a phenanthrene skeleton: when $Ar^1$ is a phenethrene skeleton and the phenanthrene skeleton (A) to which $Ar^1$ is bonded is substituted in 2nd and 7th positions, $Ar^2$ is not equal to $Ar^3$; or when $Ar^2$ is a phenanthrene skeleton and the phenanthrene skeleton (B) to which $Ar^2$ is bonded is substituted in 2nd and 7th positions, $Ar^1$ is not equal to $Ar^4$.

A structure represented by a formula (1-X) below is excluded.

[Chemical Formula 4]

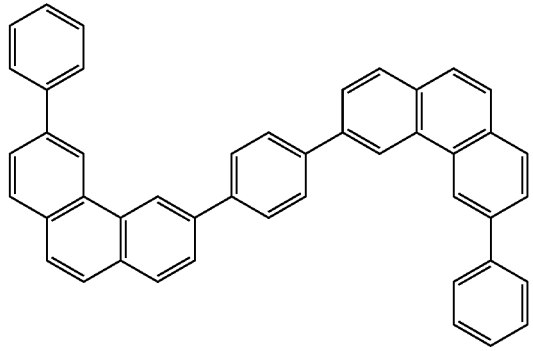

(1-X)

[Chemical Formula 3]

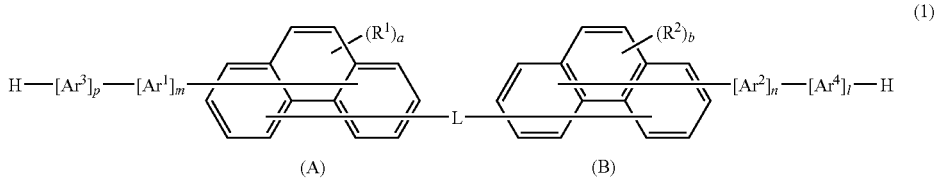

(1)

Herein, the "ring carbon atoms" means carbon atoms that form a saturated ring, unsaturated ring or aromatic ring, and the "ring atoms" means carbon atoms and hetero atoms that form a hetero ring (encompassing a saturated ring, unsaturated ring and aromatic ring).

The phenanthrene derivative according to the aspect of the invention is favorably usable as an organic-EL-device material capable of providing an organic EL device excellent in luminous efficiency, heat resistance and lifetime and free from pixel defects.

Organic compounds having an anthracene skeleton, pyrene skeleton, aceanthrylene skeleton or naphthacene skeleton exhibit such small triplet energy that a phosphorescent organic EL device can hardly provide efficient emission. Thus, it is unfavorable that $Ar^1$ to $Ar^4$ and L have these structures.

In addition, when $Ar^1$ to $Ar^4$ and L have more than 18 ring carbon atoms, the triplet energy is reduced. Hence, unfavorably, the obtained phosphorescent organic EL device would hardly provide efficient emission.

Among compounds represented by the following formulae (1-f), the phenanthrene derivative represented by the following formula (1-f-1) corresponds to a derivative in which L is a single bond and $Ar^1$ is a 2,7-substituted phenanthrene. When $Ar^2=Ar^3$ in the formula (1-f-1), the molecule is highly symmetric with no twist structure. Thus, the derivative would be highly apt to be crystallized, and would hardly maintain their amorphousness while being formed into films. On the other hand, the phenanthrene derivative represented by the following formula (1-f-2) corresponds to a derivative in which L is a single bond and $Ar^2$ is a 2,7-substituted phenanthrene. When $Ar^1=Ar^4$ in the formula (1-f-2), the molecule is highly symmetric with no twist structure. Thus, the derivative would be highly apt to be crystallized, and would hardly maintain their amorphousness while being formed into films. Accordingly, these structures are excluded according to the aspect of the invention.

when $Ar^1$ or $Ar^2$ substitutes a phenanthrene skeleton in 1st, 4th, 5th, 8th, 9th or 10th position);
(2) introducing a sterically-hindered substituent; or
(3) asymmetrically forming the molecule,
it is possible to prevent the crystallization of the compound and to obtain a highly amorphous film.

On the other hand, it has been found possible to further reduce the driving voltage by introducing a phenanthrene derivative having no steric hindrance due to peri hydrogen (e.g., 2,7-substituted phenanthrene skeleton).

Further, the heat resistance and the lifetime have been enhanced by introducing two or more phenanthrene skeletons.

Only the phenanthrene derivative that satisfies all of the above requirements is favorably usable as an organic-EL-device material capable of providing an organic EL device excellent in luminous efficiency, heat resistance and lifetime and free from pixel defects.

In the formula (1), $R^1$ and $R^2$ are each preferably selected from an aryl group having 6 to 30 carbon atoms, alkyl group having 1 to 30 carbon atoms, cycloalkyl group having 3 to 30 carbon atoms, alkoxy group having 1 to 20 carbon atoms, cyano group, silyl group having 3 to 30 carbon atoms and halogen atom.

Examples of the aryl group having 6 to 30 carbon atoms include a phenyl group, a 1-naphthyl group, a 2-naphthyl group, a 1-phenanthryl group, a 2-phenanthryl group, a 3-phenanthryl group, a 4-phenanthryl group, a 9-phenanthryl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-phenylnaphthalene-1-yl group, a 5-phenylnaphthalene-1-yl group, a 6-phenylnaphthalene-2-yl group, a 7-phenylnaph-

[Chemical Formula 5]

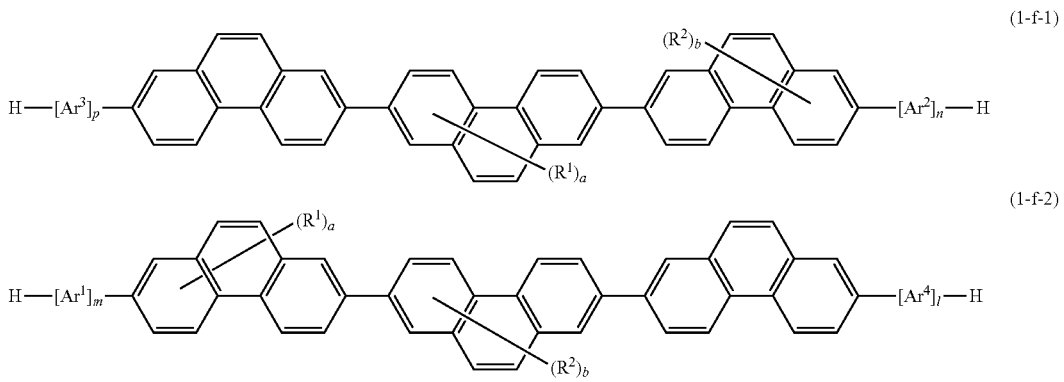

In other words, Groups of compounds having highly symmetric molecular structures are highly apt to be crystallized, so that such groups of compounds would hardly maintain their amorphousness while being formed into films.

In contrast, for instance, by:

(1) introducing a twist in the molecule with use of a steric hindrance caused by a hydrogen atom in the peri position of a molecule to which $Ar^1$ or $Ar^2$ is bonded (e.g., when $Ar^1$ or $Ar^2$ is bonded in α-position of a naphthalene skeleton or thalene-2-yl group, a 2-(naphthalene-2-yl)phenyl group, a 3-(naphthalene-2-yl)phenyl group, a 4-(naphthalene-2-yl) phenyl group, a 2-(naphthalene-1-yl)phenyl group, a 3-(naphthalene-1-yl)phenyl group, a 4-(naphthalene-1-yl) phenyl group, a 2,2'-binaphthyl-6-yl group, a 1,2'-binaphthyl-6-yl group, a 1,1'-binaphthyl-4-yl group, a 1,2'-binaphthyl-4-yl group, a 2-(phenanthrene-9-yl)phenyl group, a 3-(phenanthrene-9-yl)phenyl group, a 4-(phenanthrene-9-yl) phenyl group, a 2-(phenanthrene-2-yl)phenyl group, a 3-(phenanthrene-2-yl)phenyl group, a 4-(phenanthrene-2-yl)

phenyl group, a 6-(phenanthrene-9-yl)naphthalene-2-yl group, a 7-(phenanthrene-9-yl)naphthalene-2-yl group, a 5-(phenanthrene-9-yl)naphthalene-1-yl group, a 4-(phenanthrene-9-yl)naphthalene-1-yl group, a 6-(phenanthrene-2-yl)naphthalene-2-yl group, a 7-(phenanthrene-2-yl)naphthalene-2-yl group, a 5-(phenanthrene-2-yl)naphthalene-1-yl group, a 4-(phenanthrene-2-yl)naphthalene-1-yl group, a 4'-methylbiphenylyl group, and a 4'-t-butyl-p-terphenyl-4-yl group.

Examples of the alkyl group having 1 to 30 carbon atoms include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and a 1,2,3-trinitropropyl group.

Examples of the cycloalkyl group having 3 to 30 carbon atoms include a cyclopentyl group, a cyclohexyl group, a cyclooctyl group, and a 3,5-tetramethylcyclohexyl group, and a cyclohexyl group, a cyclooctyl group, and a 3,5-tetramethylcyclohexyl group are preferred.

The alkoxy group having 1 to 20 carbon atoms is a group represented by —OY. Examples of Y include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and a 1,2,3-trinitropropyl group.

The silyl group having 3 to 30 carbon atoms is preferably, for instance, an alkylsilyl group or an aralkylsilyl group having 3 to 20 carbon atoms. Examples thereof include a trimethylsilyl group, a triethylsilyl group, a tributylsilyl group, a trioctylsilyl group, a triisobutylsilyl group, a dimethylethylsilyl group, a dimethylisopropylsilyl group, a dimethylpropylsilyl group, a dimethylbutylsilyl group, a dimethyltertiarybutylsilyl group, a diethylisopropylsilyl group, a phenyldimethylsilyl group, a diphenylmethylsilyl group, a diphenyltertiarybutyl group, and a triphenylsilyl group.

Examples of the halogen atom represented by $R^1$ and $R^2$ are fluorine, chlorine, bromine, iodine and the like.

In the formula (1), the substituting position of (—$[Ar^1]_m$—$[Ar^3]_l$—H) and (—$[Ar^2]_n$—$[Ar^4]_p$—H) in the phenanthrene skeleton may be 1,2-position, 1,3-position, 1,4-position, 1,5-position, 1,6-position, 1,7-position, 1,8-position, 1,9-position, 1,10-position, 2,3-position, 2,4-position, 2,5-position, 2,6-position, 2,7-position, 2,8-position, 2,9-position, 2,10-position, 3,4-position, 3,5-position, 3,6-position, 3,7-position, 3,8-position, 3,9-position, 3,10-position, 4,5-position, 4,6-position, 4,7-position, 4,8-position, 4,9-position, 4,10-position or 9,10-position. The substituting position is preferably 2,7-position, 2,9 position, 2,10-position, 3,6-position, 4,9-position, 4,10-position and 9,10-position. More preferably, the phenanthrene derivative is a phenanthrene derivative represented by the following general formula (1-a) to (1-f).

[Chemical Formula 6]

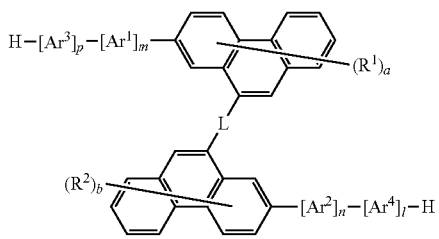

(1-a)

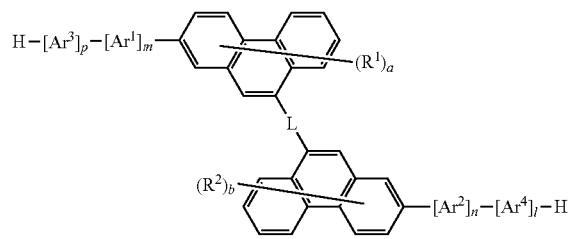

(1-b)

(1-c)

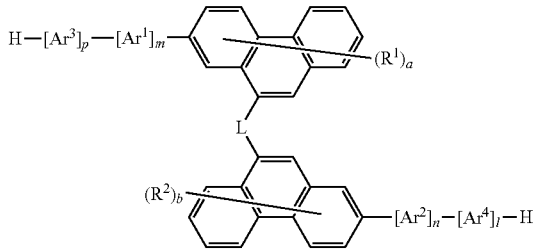

(1-d)

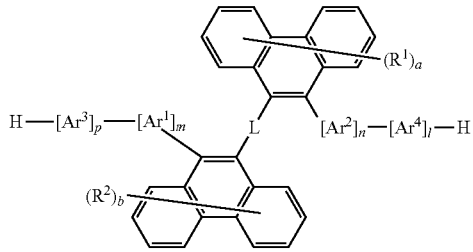

(1-e)

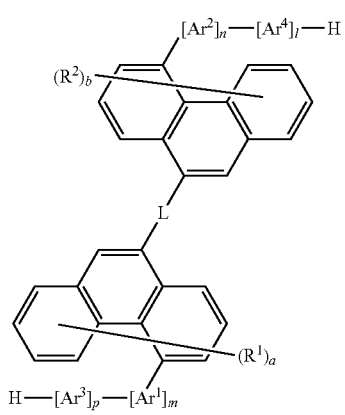

(1-f)

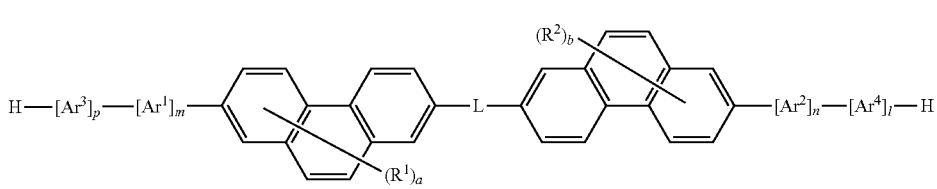

In the phenanthrene derivatives represented by these general formulae (1-a) to (1-f), (—[Ar$^1$]$_m$—[Ar$^3$]$_l$—H) and (—[Ar$^2$]$_n$—[Ar$^4$]$_p$—H) may be equal to or different from each other.

In the formula (1), Ar$^1$ to Ar$^4$ each preferably represent a group selected from a substituted or unsubstituted benzene skeleton, naphthalene skeleton, fluorene skeleton, phenanthrene skeleton, fluoranthene skeleton, triphenylene skeleton and chrysene skeleton.

In the formula (1), L represents a single bond, a substituted or unsubstituted benzene skeleton, naphthalene skeleton, biphenyl skeleton, fluorene skeleton, fluoranthene skeleton, triphenylene skeleton, chrysene skeleton, phenyl-naphthalene skeleton or binaphthalene skeleton.

By employing these structures for Ar$^1$ to Ar$^4$ and L, the triplet energy gap can be made sufficiently large. Thus, the phenanthrene derivative is favorably usable as a phosphorescent host capable of transferring energy to the phosphorescent emitting material.

It should be noted that a "fluorescent host" and a "phosphorescent host" herein respectively mean a host combined with a fluorescent dopant and a host combined with a phosphorescent dopant, and that a distinction between the fluorescent host and phosphorescent host is not unambiguously derived only from a molecular structure of the host in a limited manner.

In other words, the fluorescent host herein means a material for forming a fluorescent-emitting layer containing a fluorescent dopant, and does not mean a host that is only usable as a host of a fluorescent material.

Likewise, the phosphorescent host herein means a material for forming a phosphorescent-emitting layer containing a phosphorescent dopant, and does not mean a host that is only usable as a host of a phosphorescent material.

In the formula (1), a or b is preferably 0, 1 or 2.

When Ar$^1$ to Ar$^4$ and L in the formula (1) have substituent(s), the substituent(s) is preferably a group selected from an alkyl group having 1 to 30 carbon atoms, cycloalkyl group having 3 to 30 carbon atoms, alkoxy group having 1 to 20 carbon atoms, cyano group, silyl group having 3 to 30 carbon atoms and halogen atom.

Examples of the alkyl group, cycloalkyl group, alkoxy group, silyl group and aryl group as the substituent(s) for Ar$^1$ to Ar$^4$ and L are the same as enumerated with respect to R$^1$ and R$^2$.

Examples of the phenanthrene derivative according to the aspect of the invention are as follows.

[Chemical Formula 7]
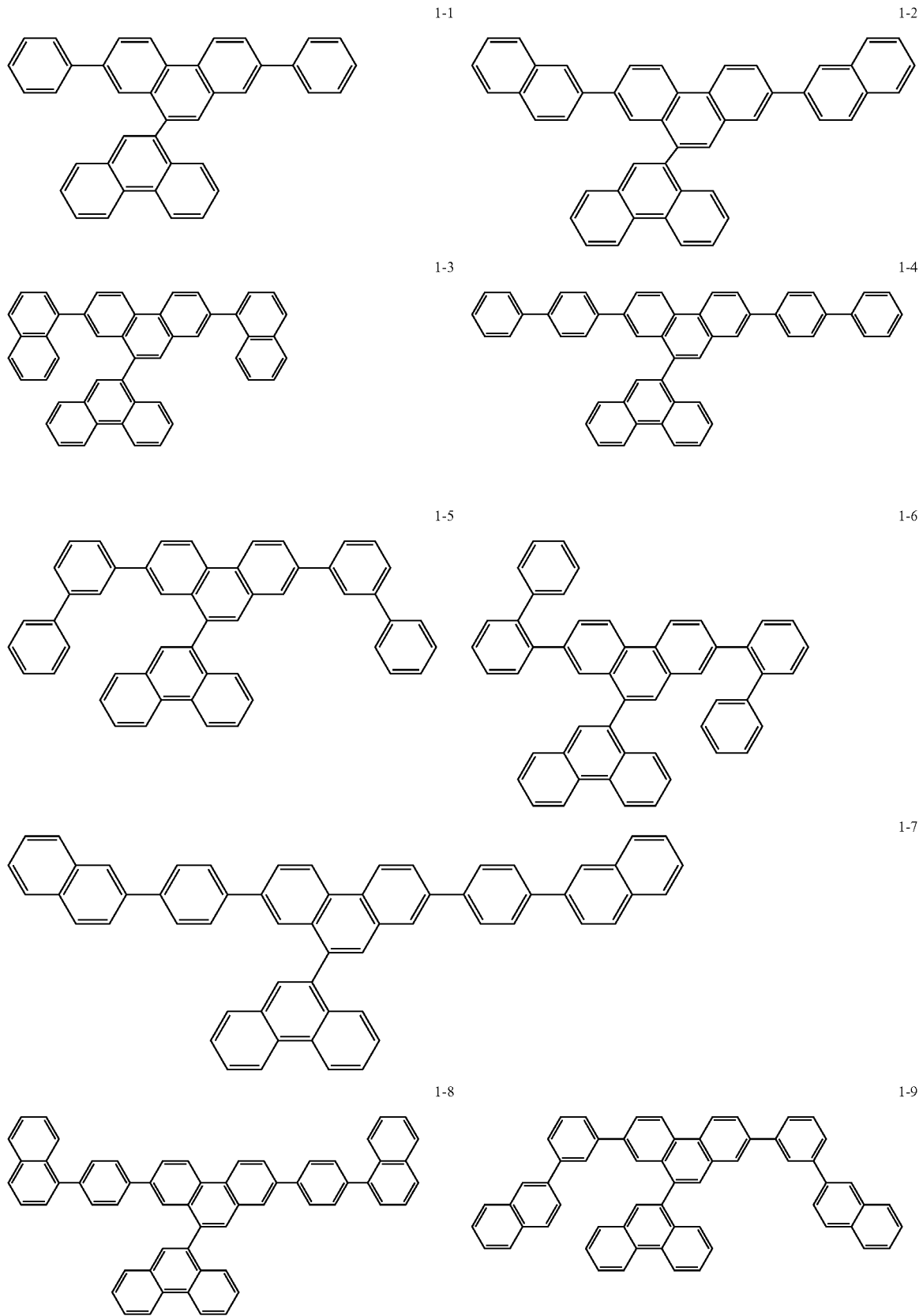

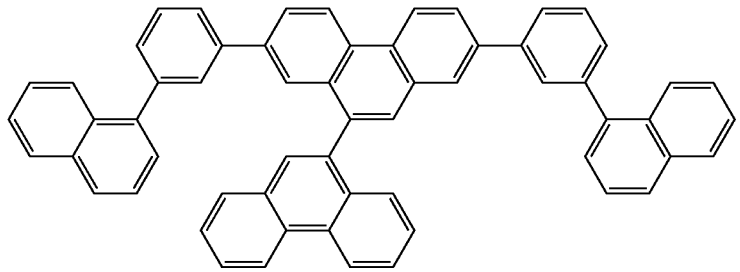
1-10
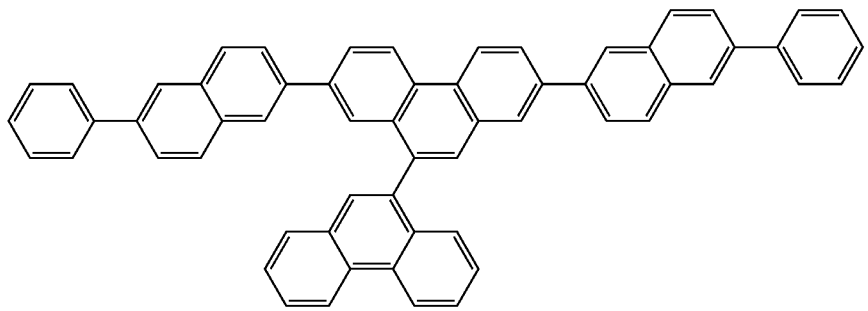
1-11
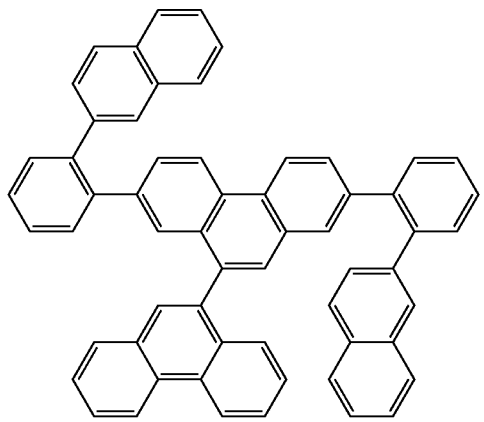
1-12
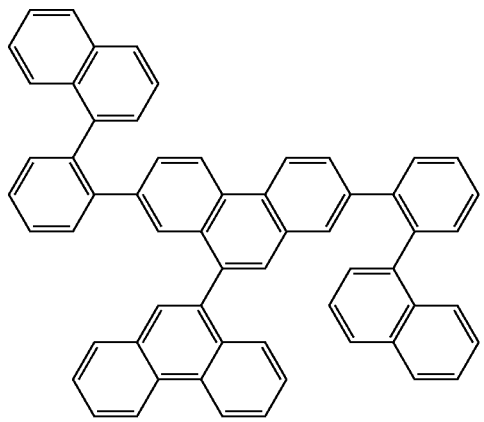
1-13
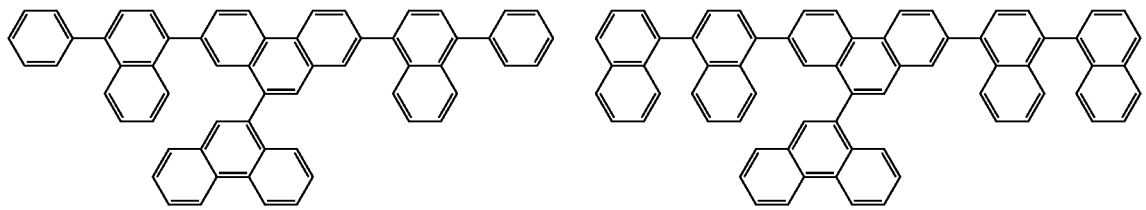
1-14 1-15
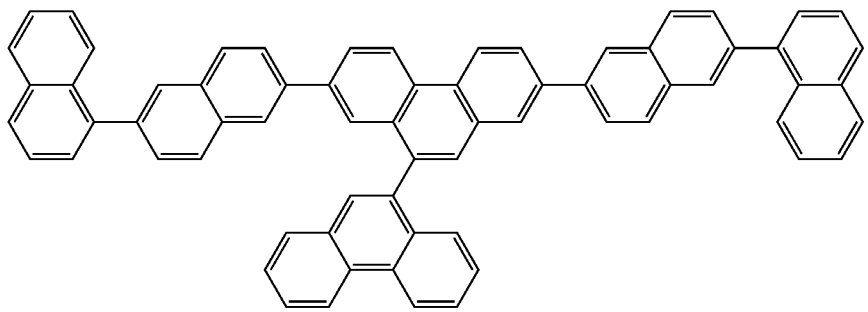
1-16

1-17
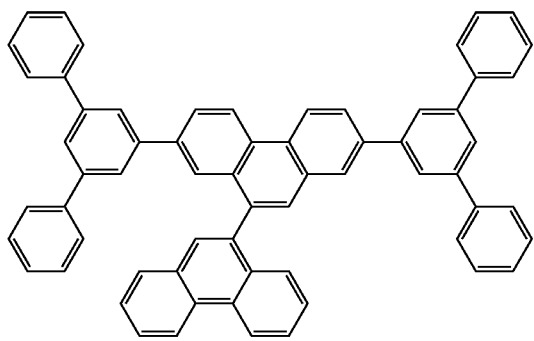
1-18
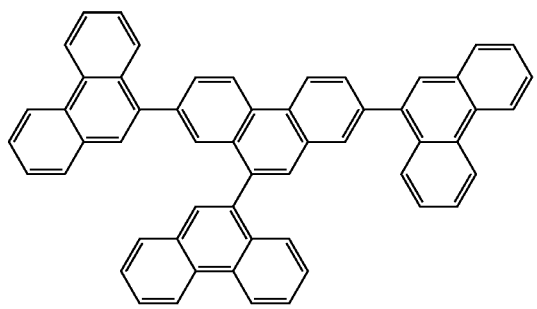
1-19
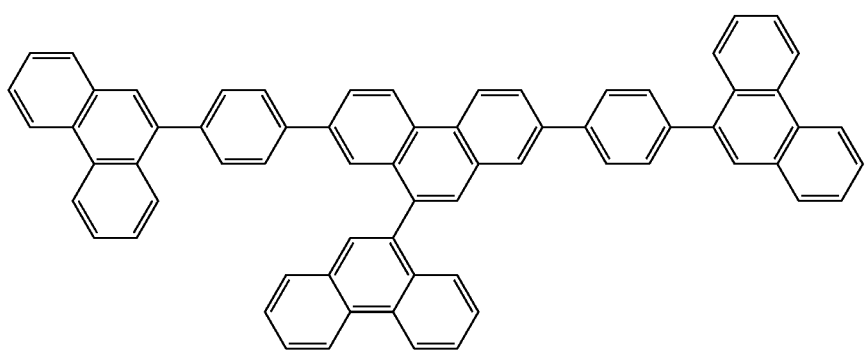
1-20
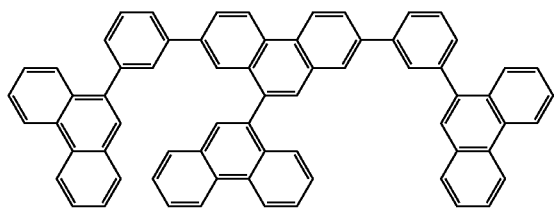
1-21
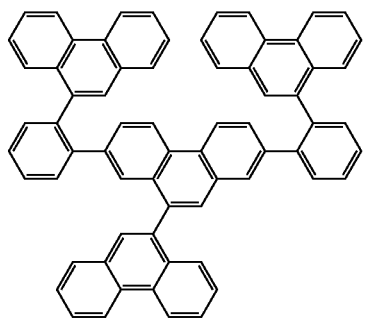
[Chemical Formula 8]
1-22
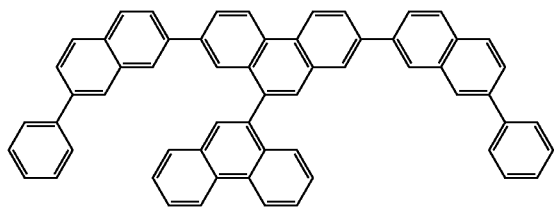
1-23
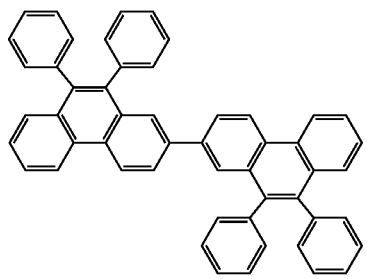

1-24
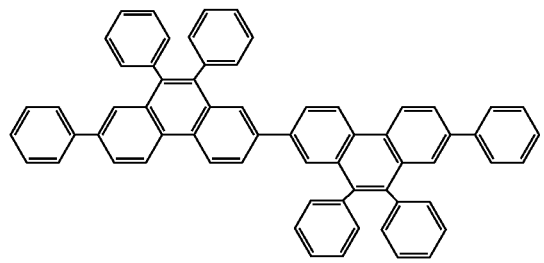
1-25
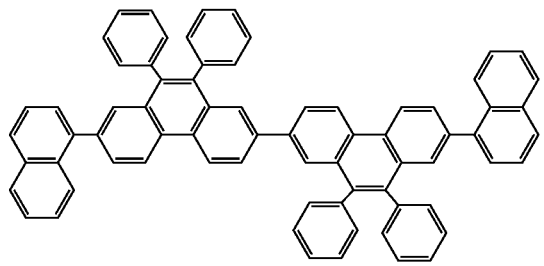
1-26
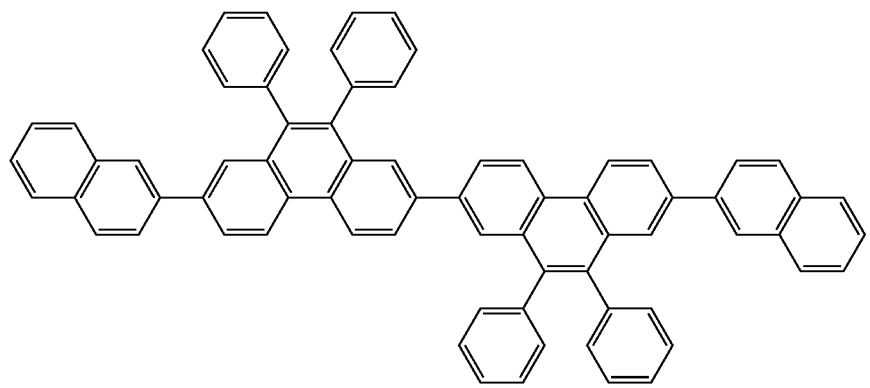
1-27
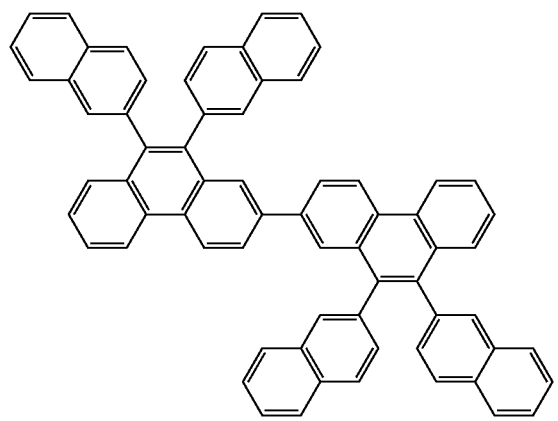
1-28
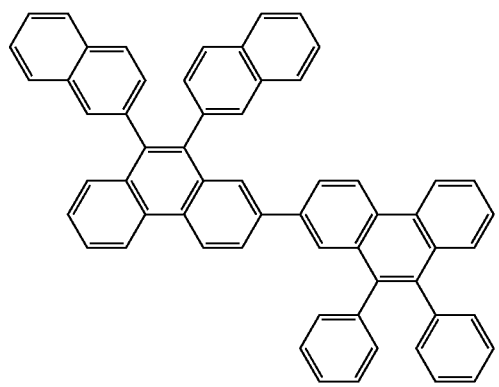
1-29
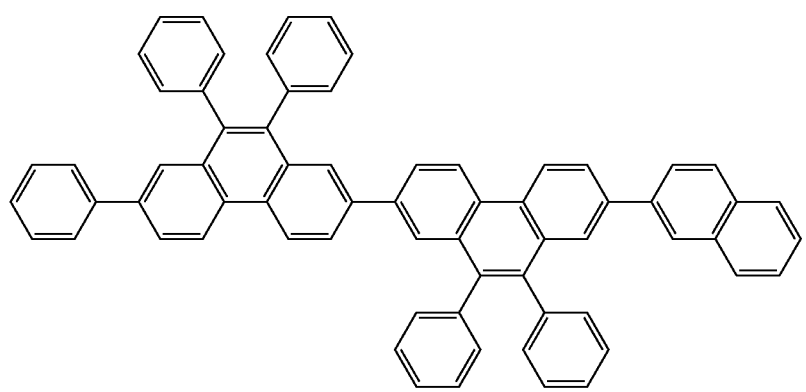

-continued
1-30
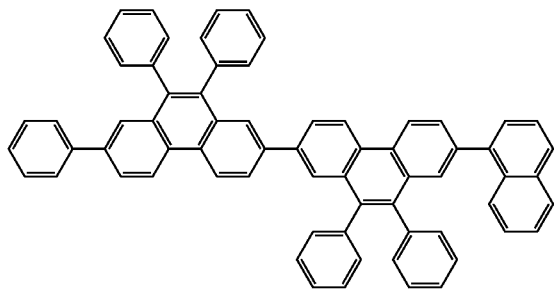
1-31
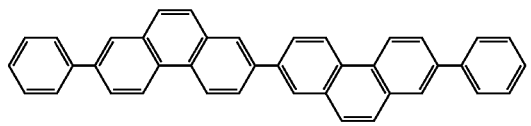
1-32
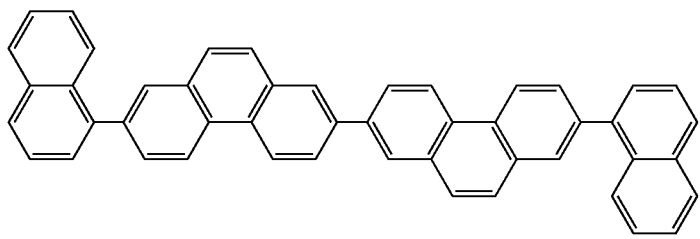
1-33
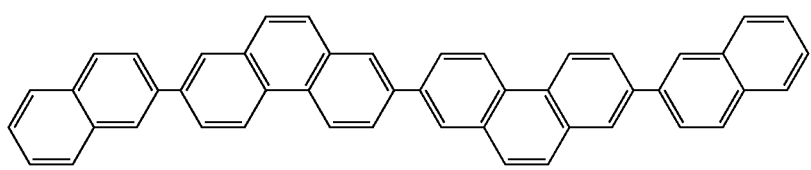
1-34
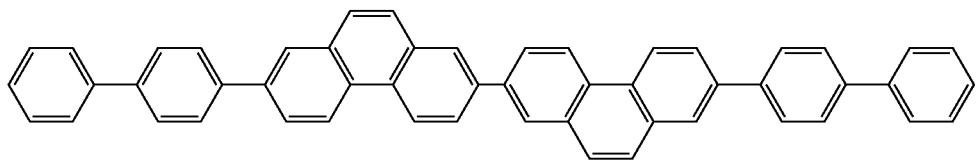
1-35
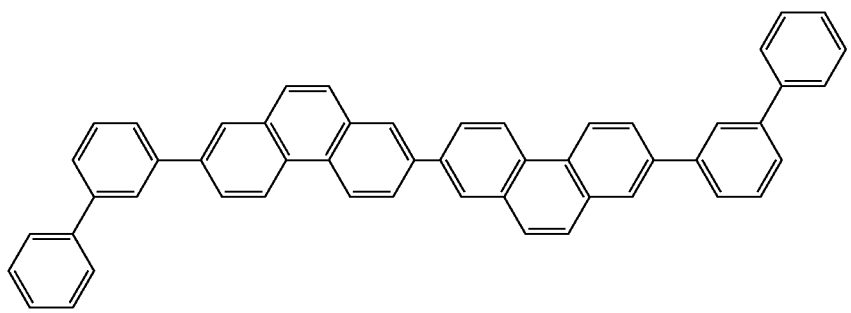
1-36
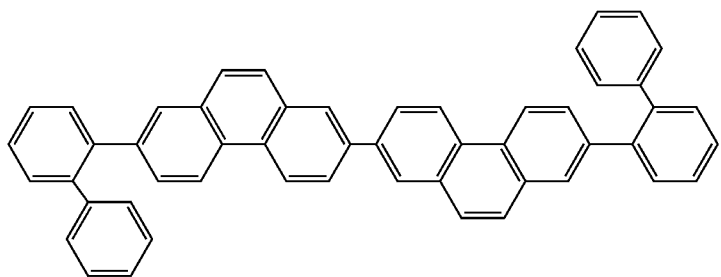

-continued
1-37
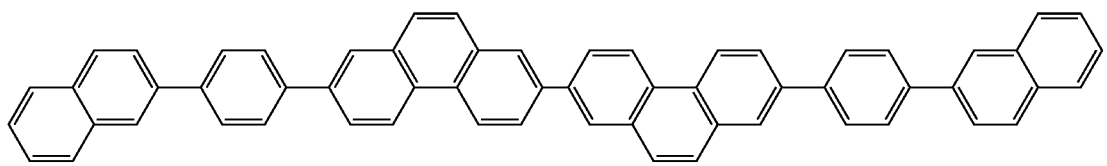
1-38
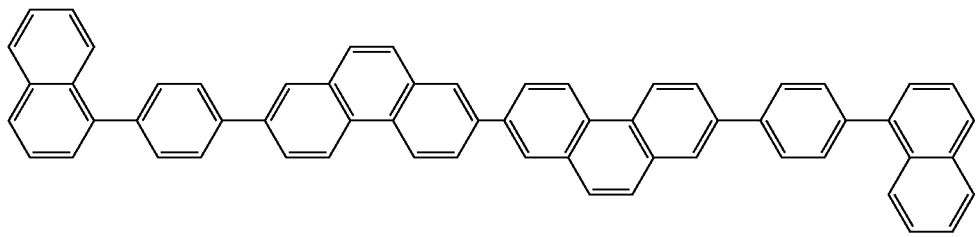
1-39 1-40
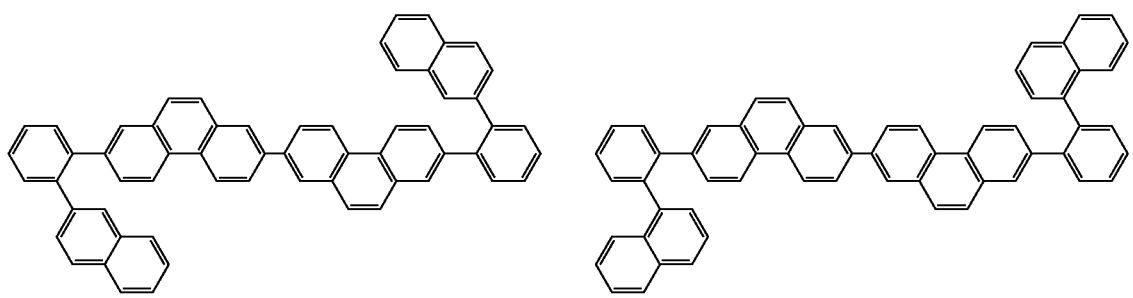
1-41
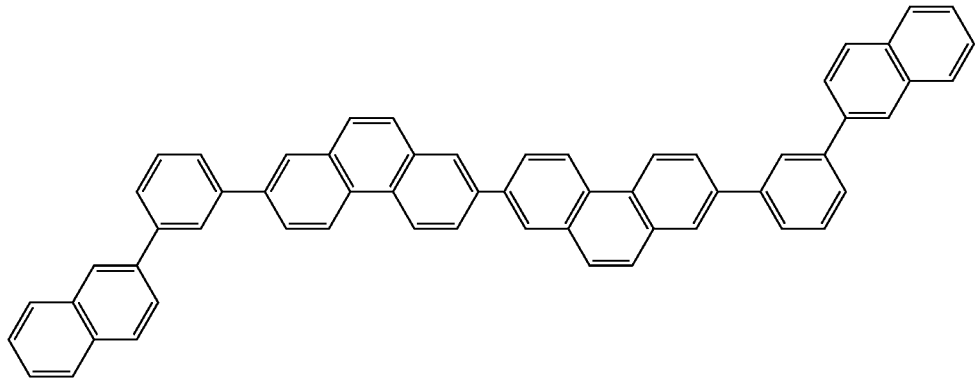
[Chemical Formula 9]
1-42
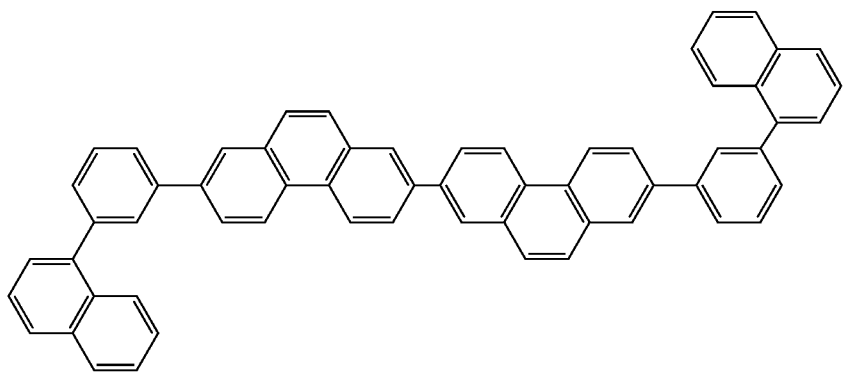

-continued
1-43
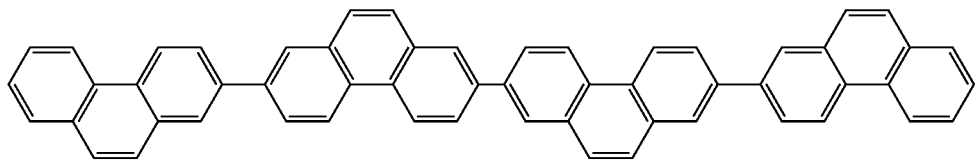
1-44
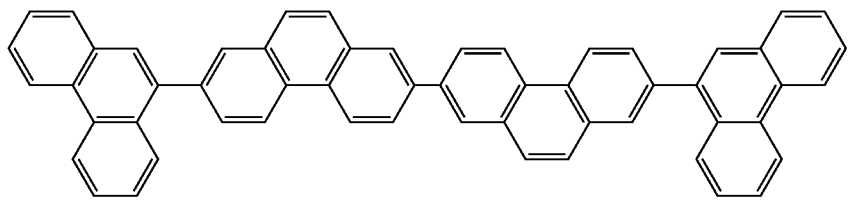
1-45
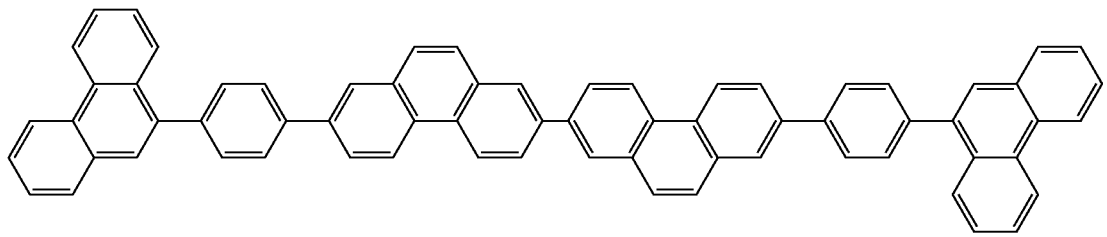
1-46
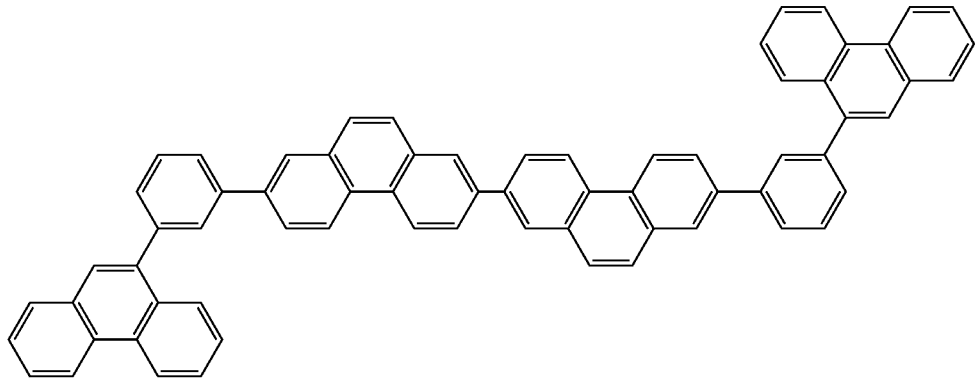
1-47
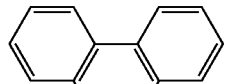
1-48
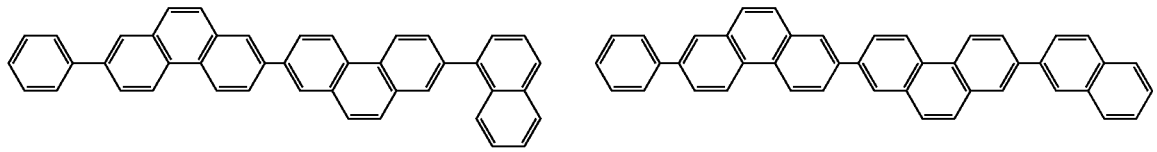
1-49
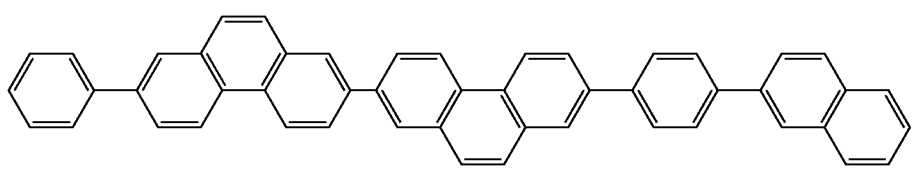
1-50
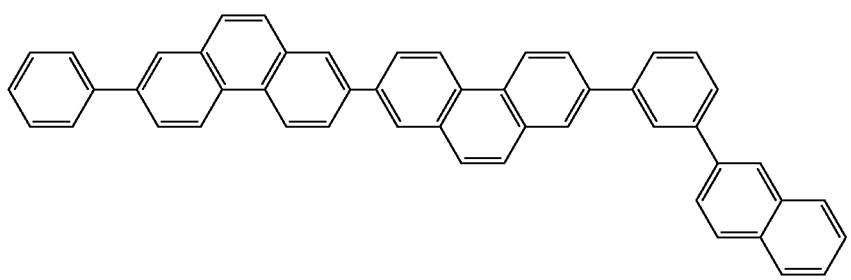

1-51
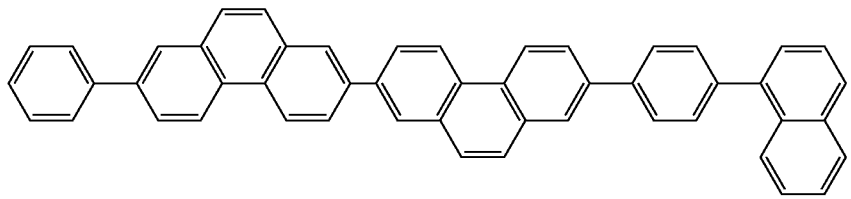
1-52
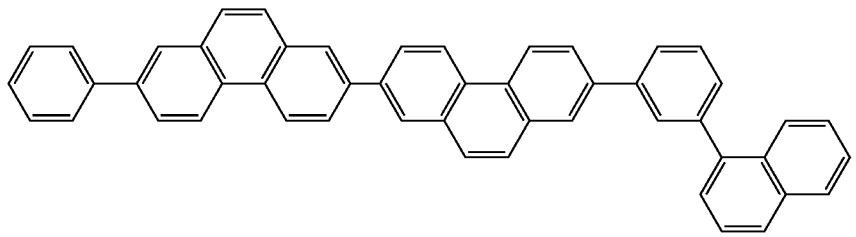
1-53
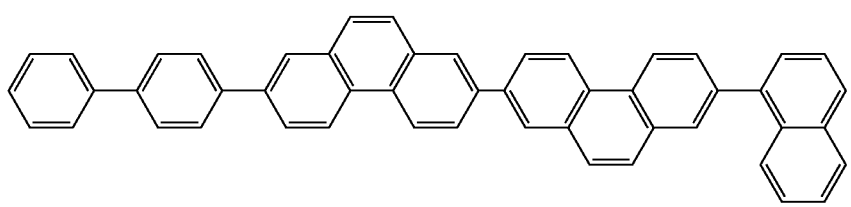
1-54
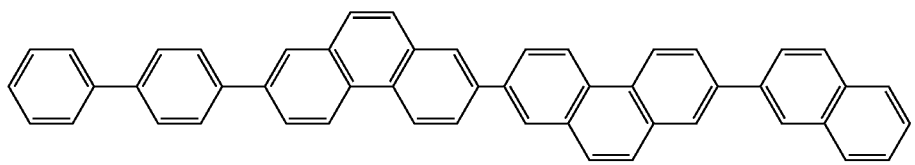
1-55
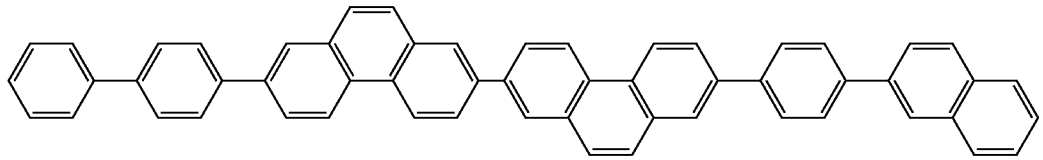
1-56
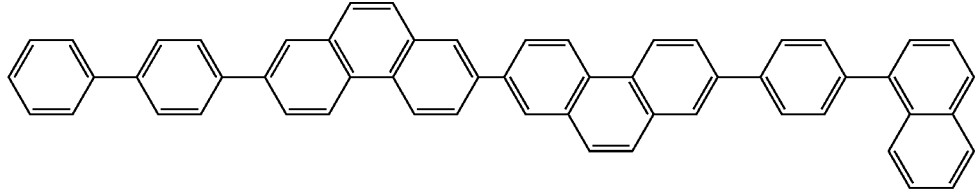
1-57
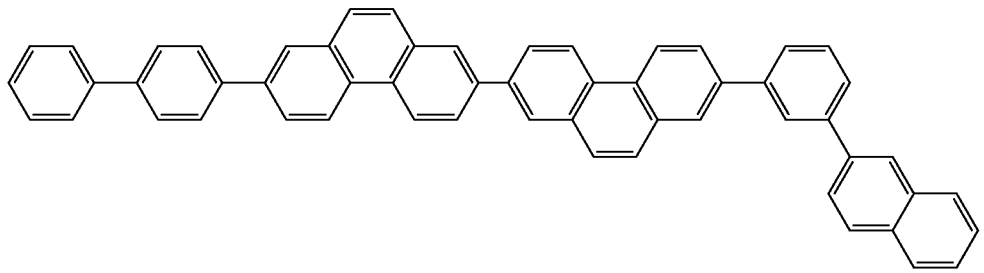

-continued
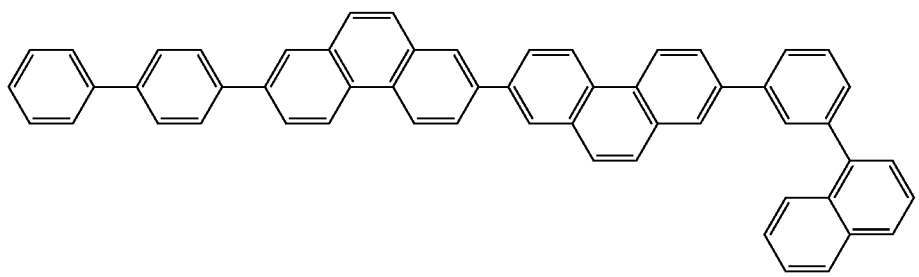
1-58
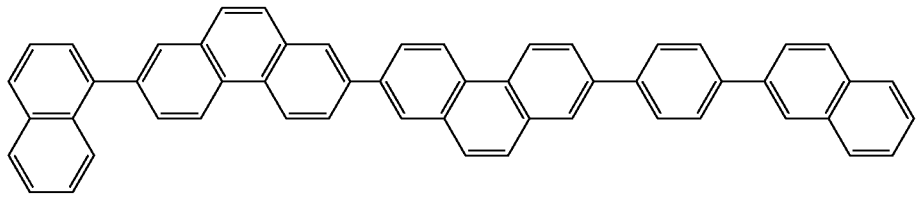
1-59
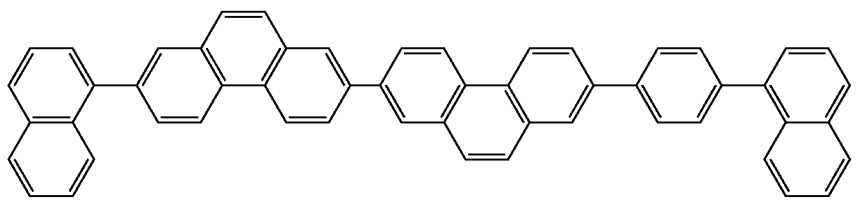
1-60
[Chemical Formula 10]
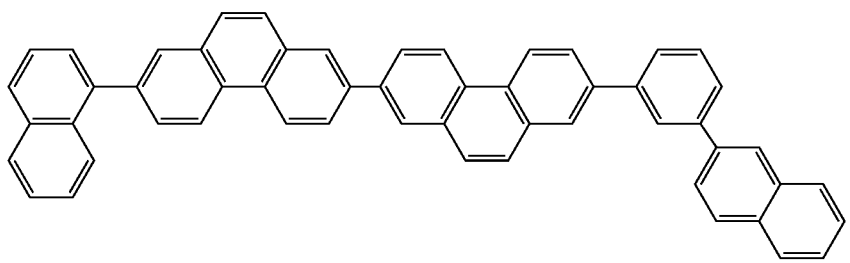
1-61
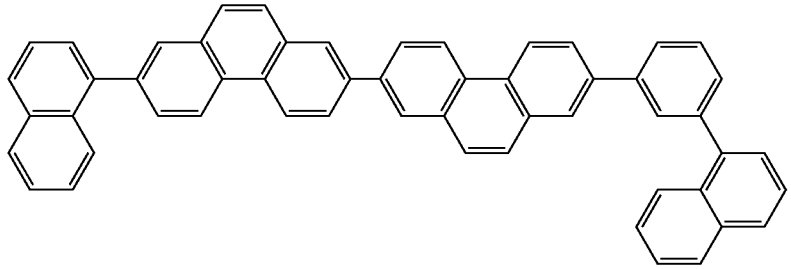
1-62
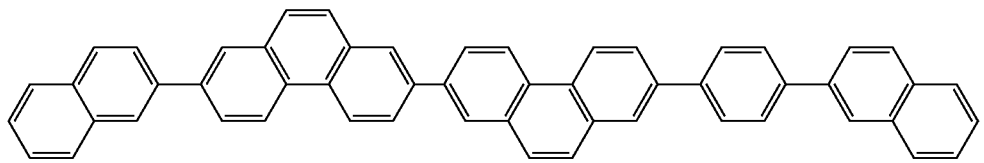
1-63
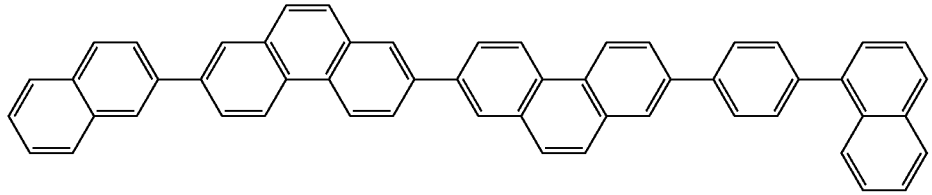
1-64

-continued
1-65
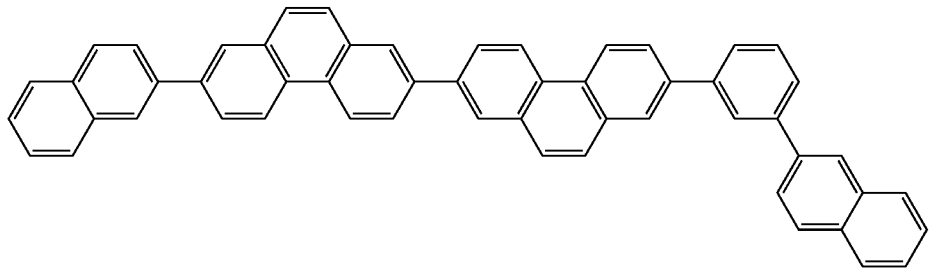
1-66
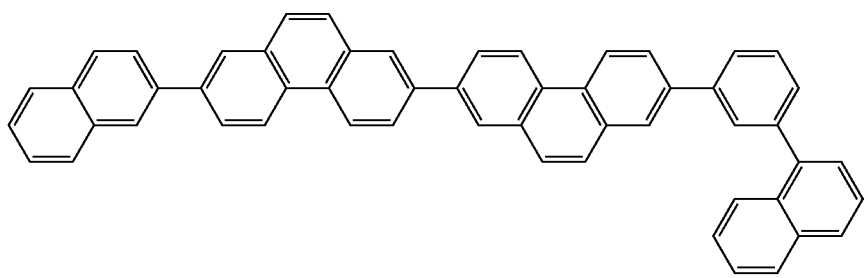
1-67
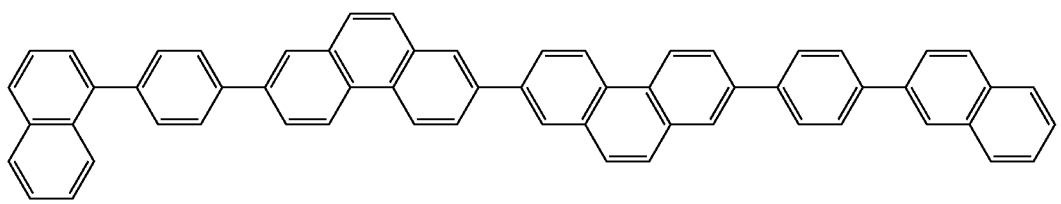
1-68
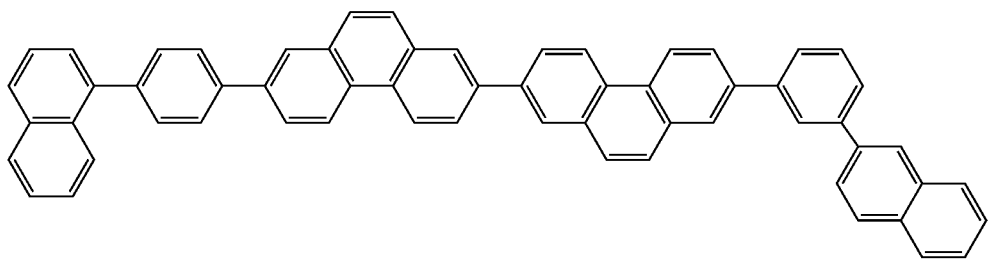
1-69
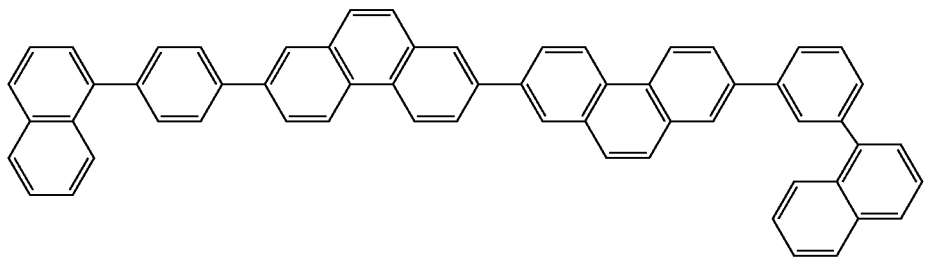
1-70
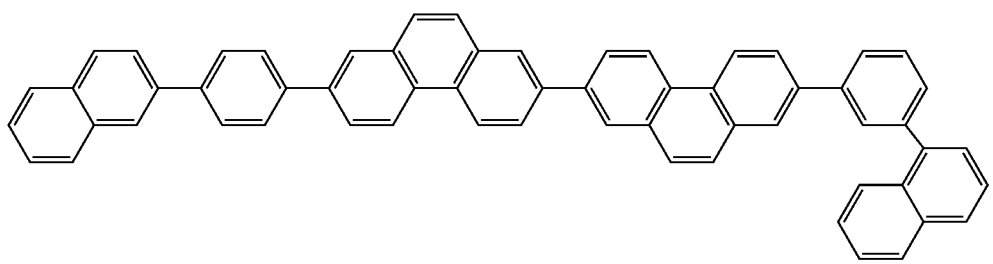

1-71
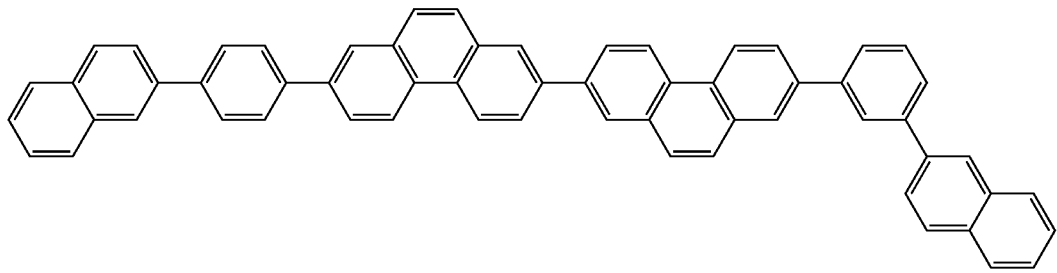
1-72
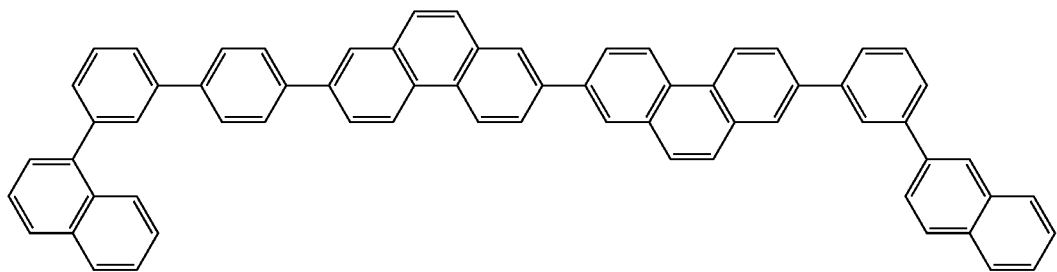
1-73
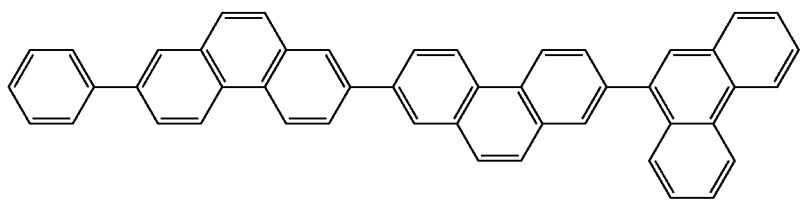
1-74
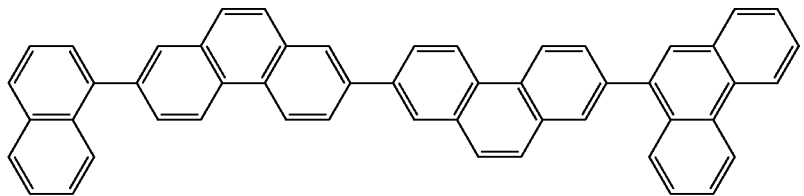
1-75
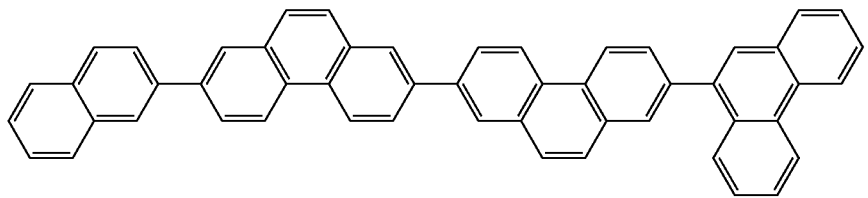
1-76
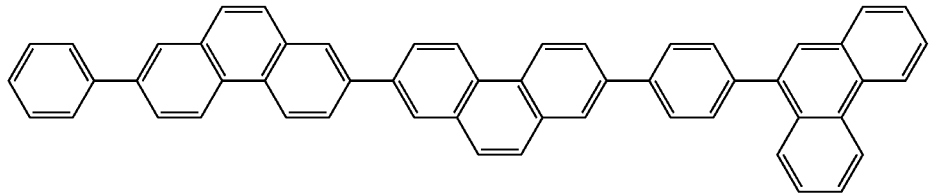
1-77
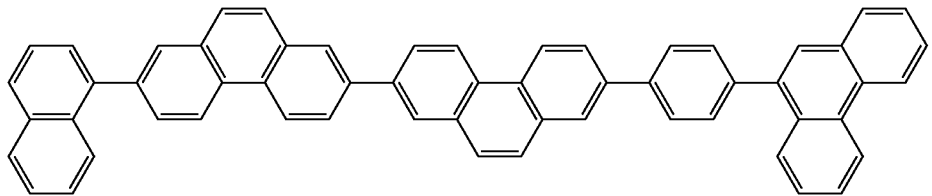

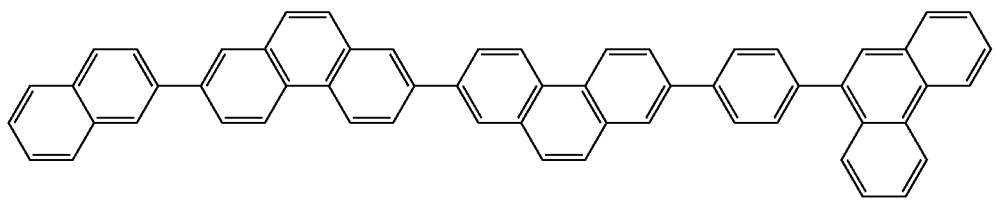
1-78
[Chemical Formula 11]
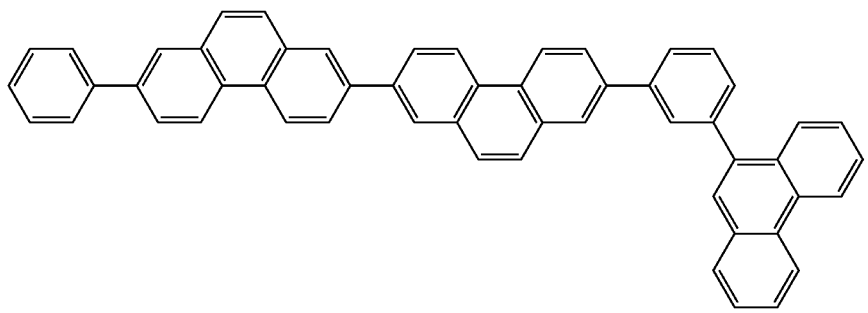
1-79
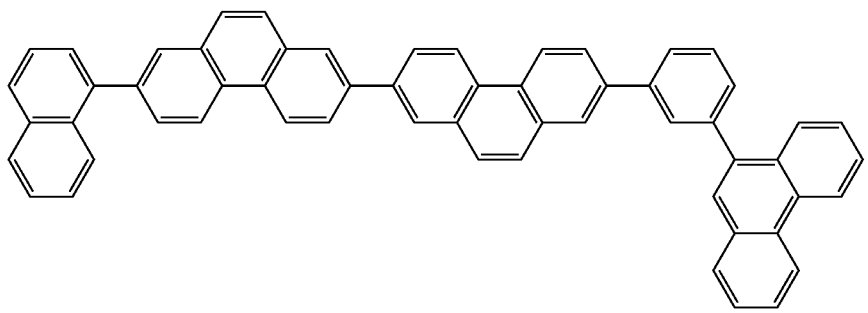
1-80
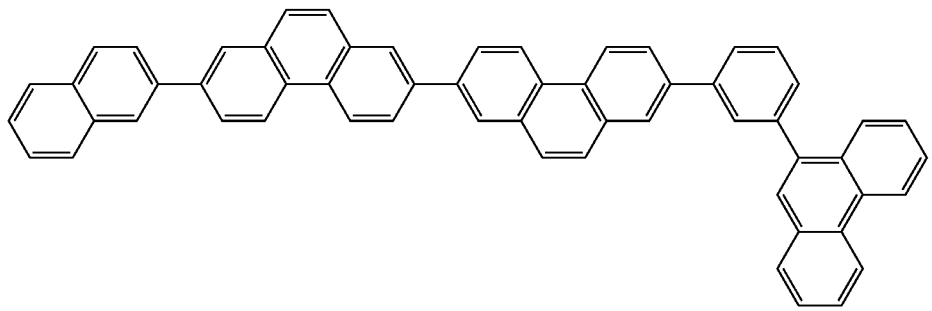
1-81
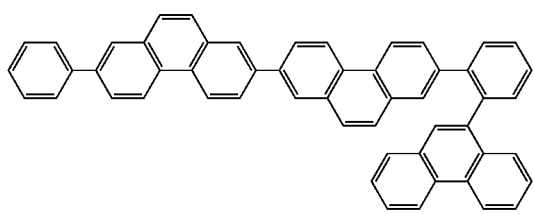
1-82
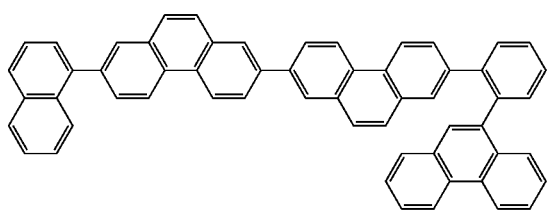
1-83

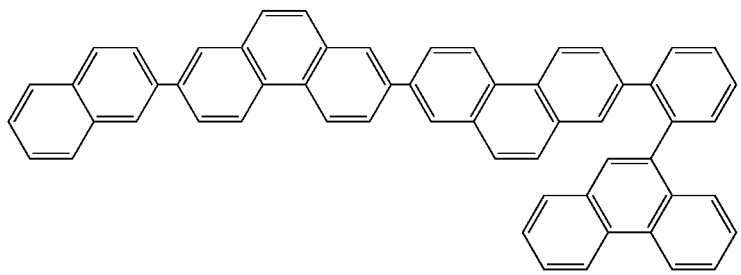
1-84
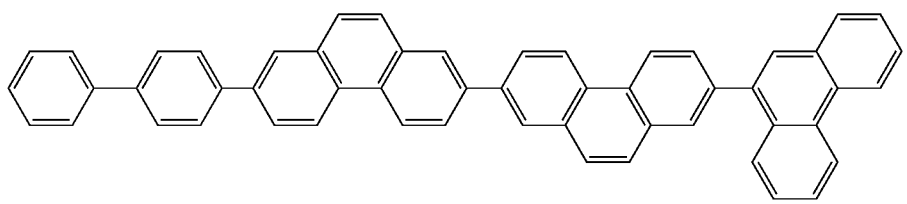
1-85
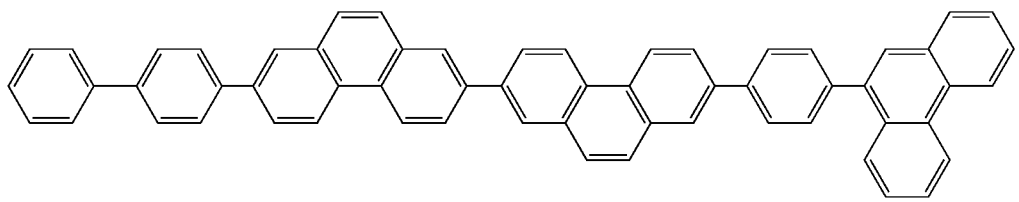
1-86
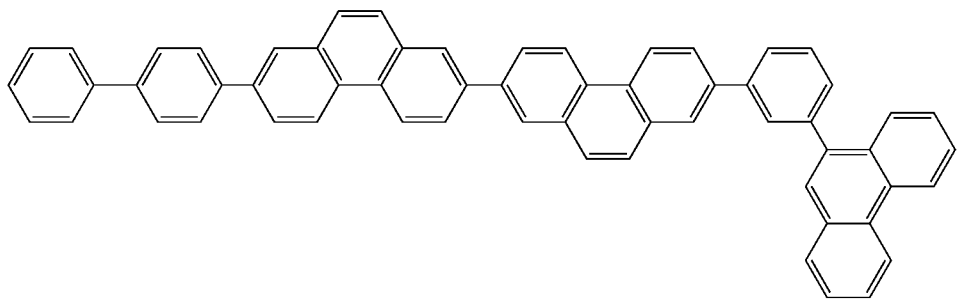
1-87
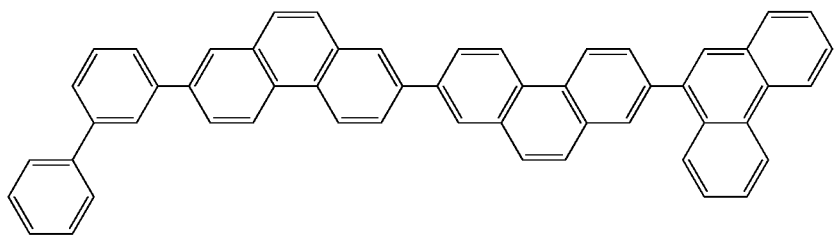
1-88
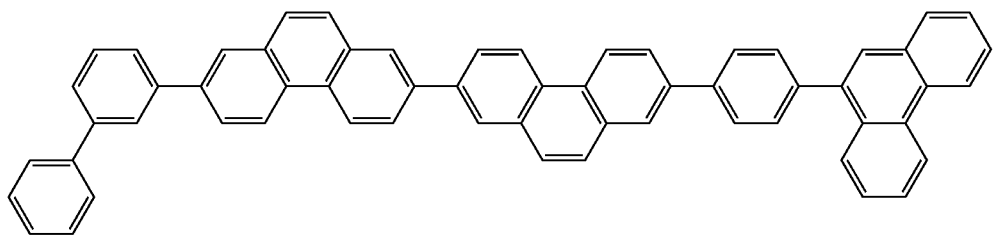
1-89

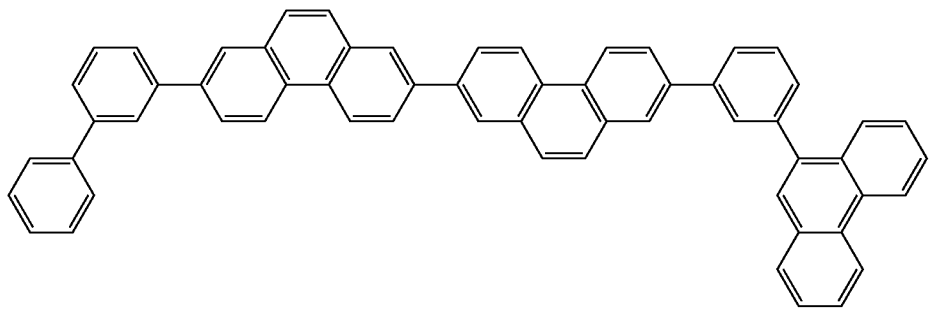
1-90
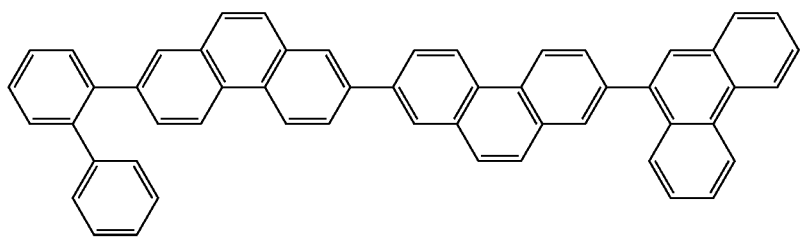
1-91
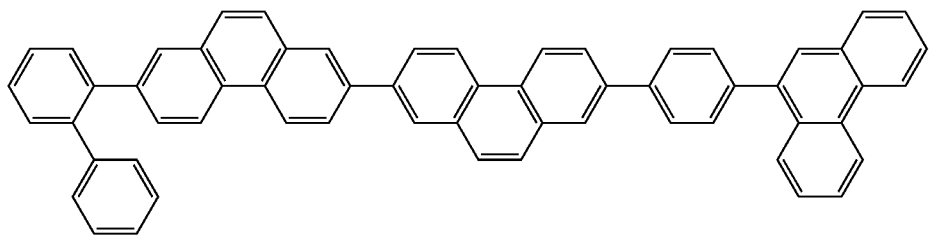
1-92
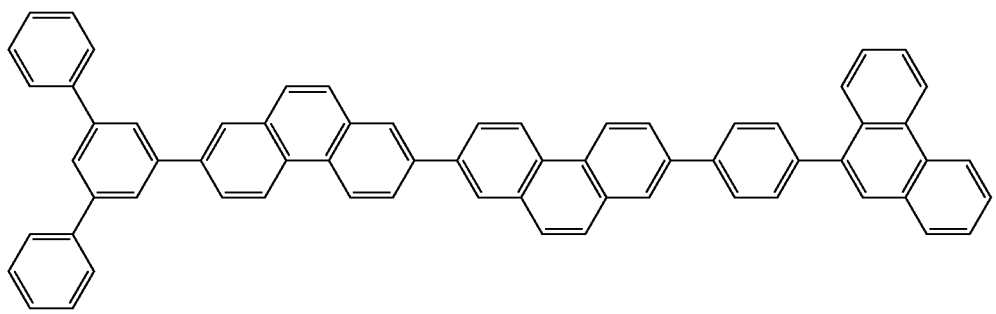
1-93
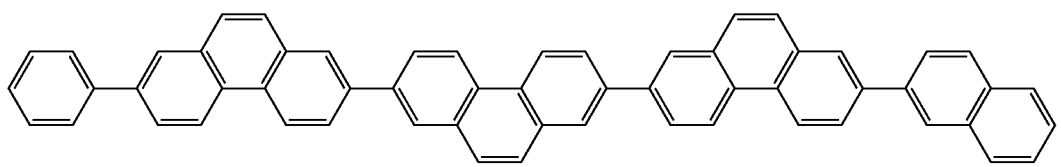
1-94
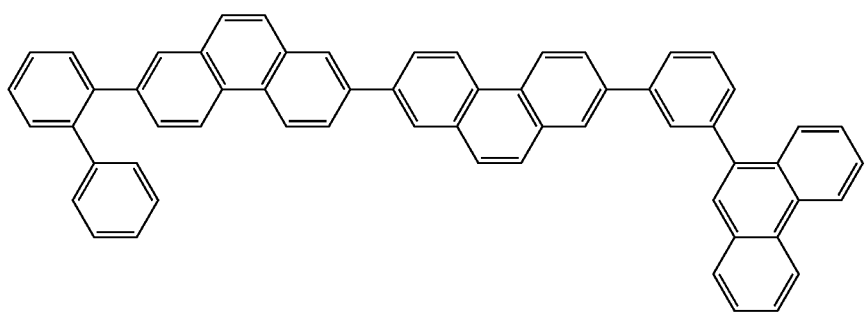
1-95

1-96
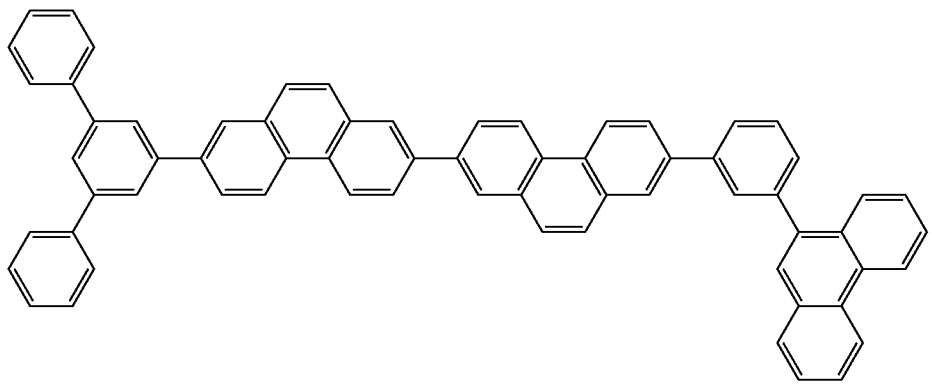
1-97
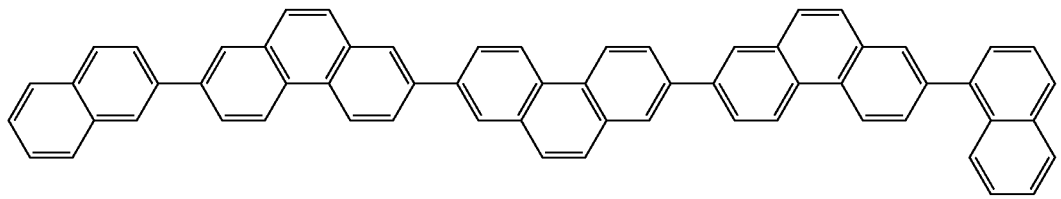
1-98
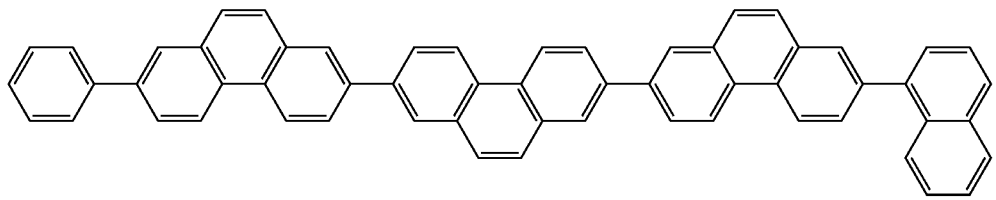
[Chemical Formula 12]
1-99
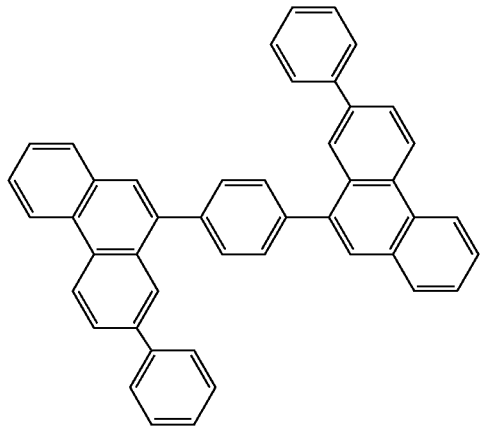
1-100
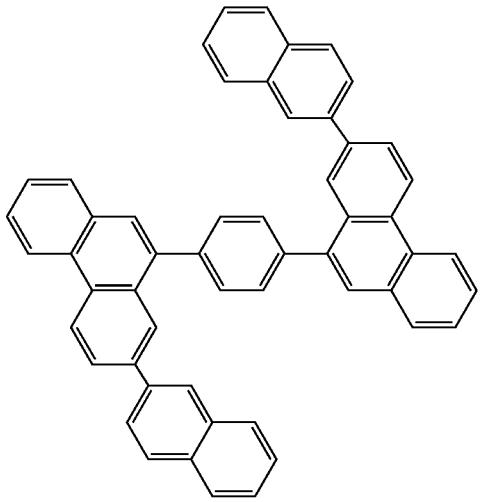

-continued
1-101
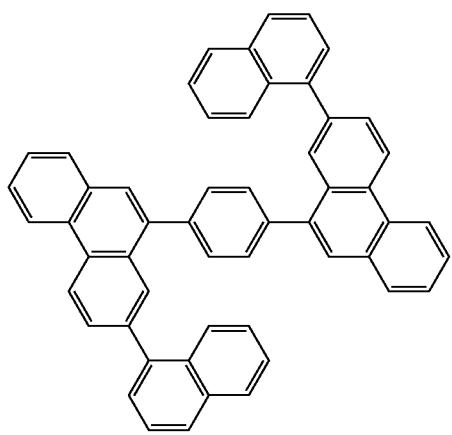
1-102
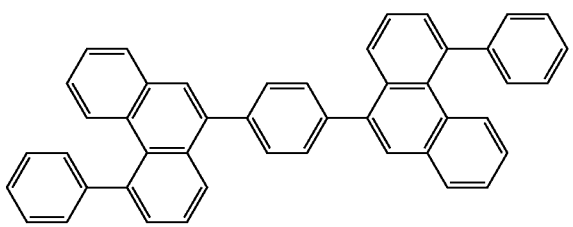
1-103
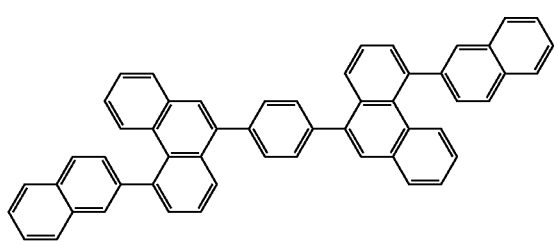
1-104
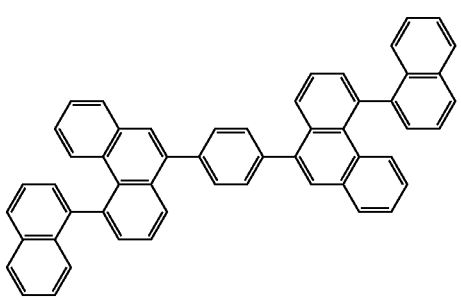
1-105
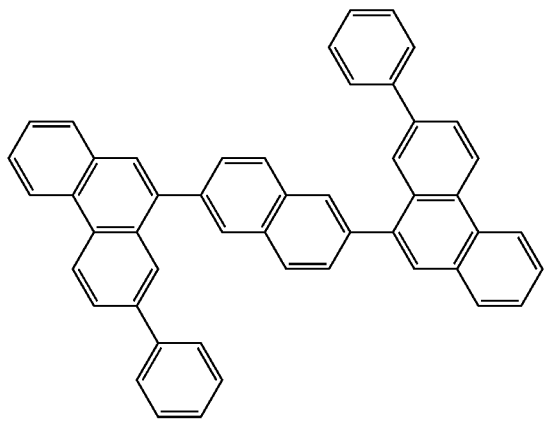
1-106
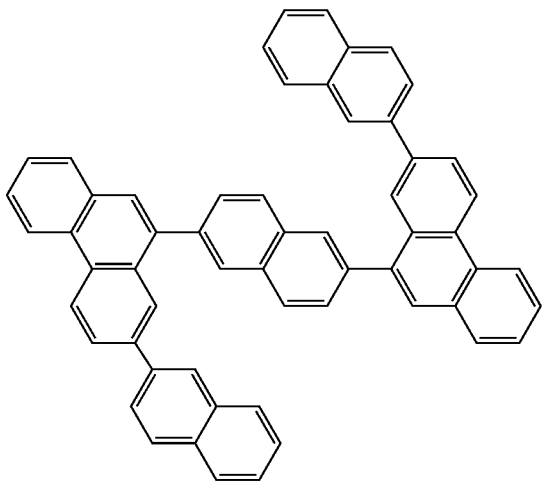
1-107
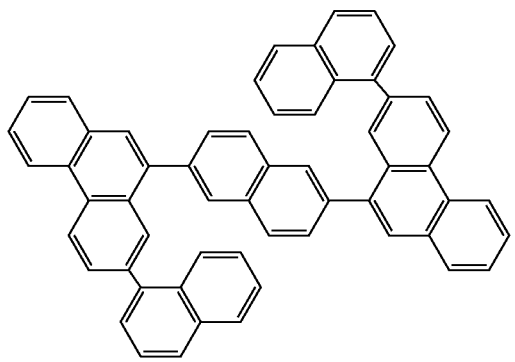
1-108
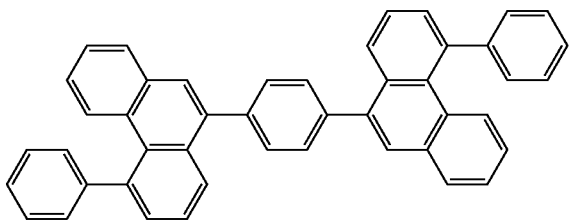

-continued
1-109
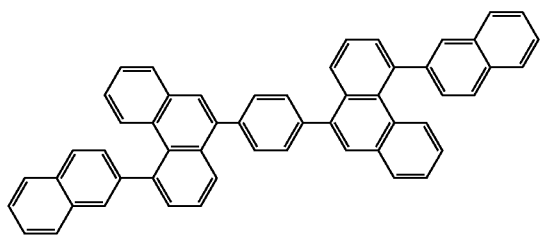
1-110
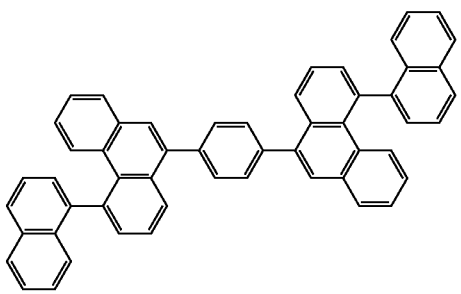
1-111
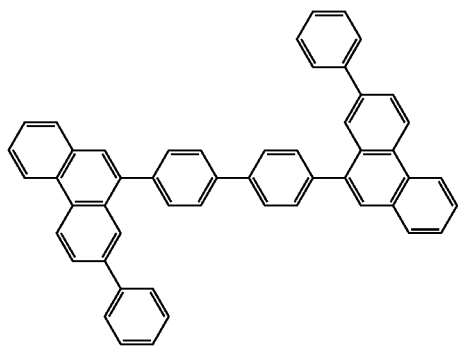
1-112
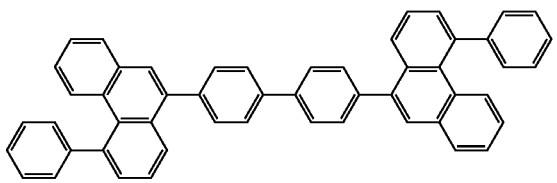
1-113
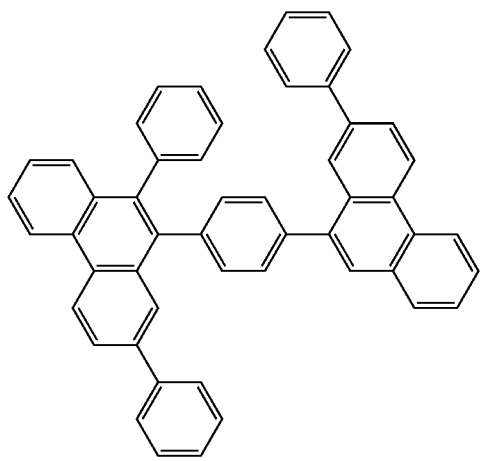
1-114
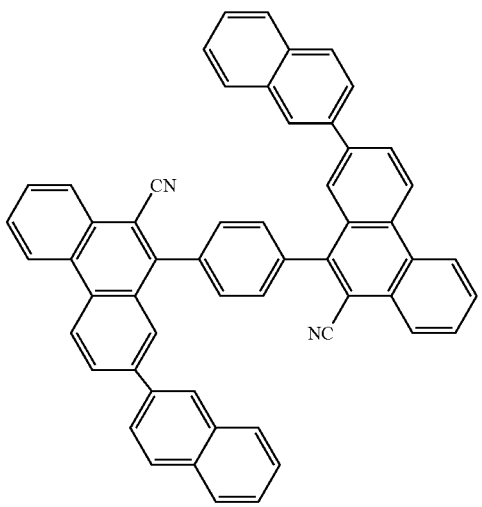

-continued
1-115
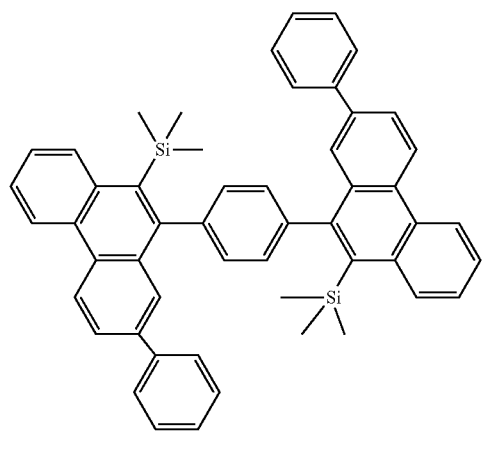
1-116
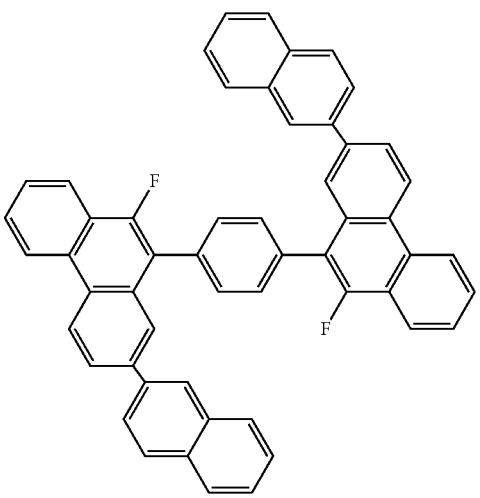
1-117
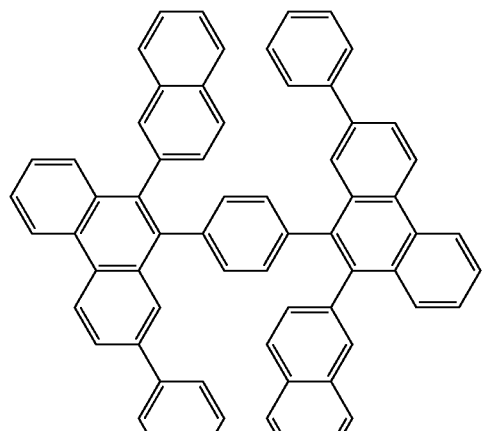
1-118
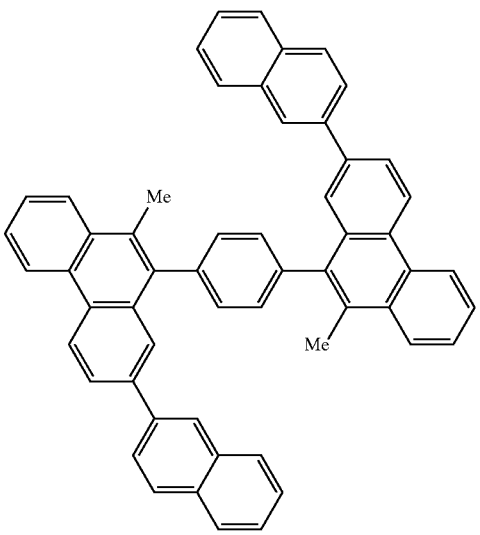
[Chemical Formula 13]
1-119
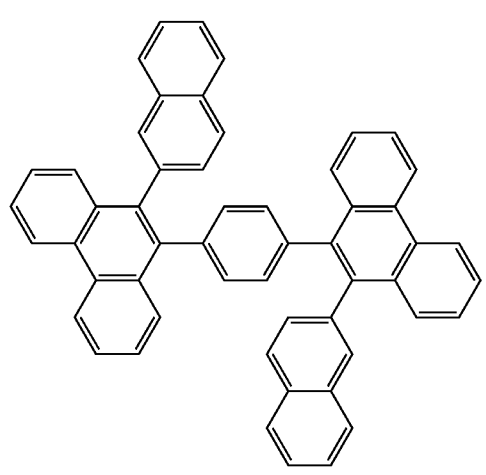
1-120
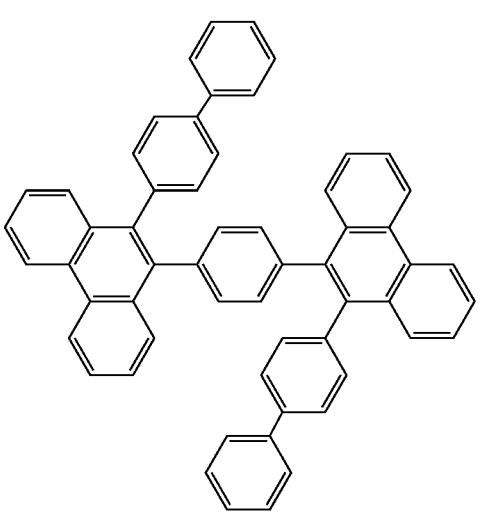

-continued
1-121
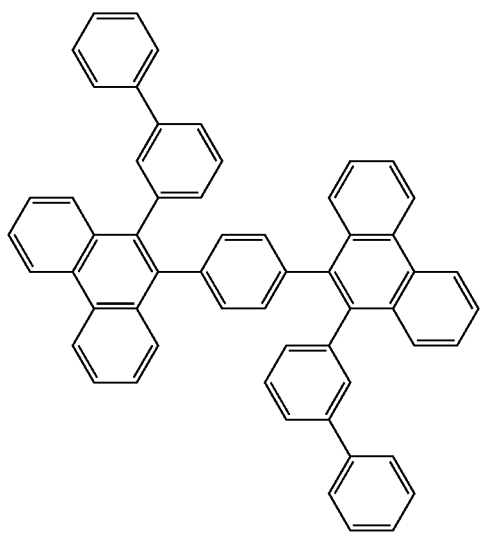
1-122
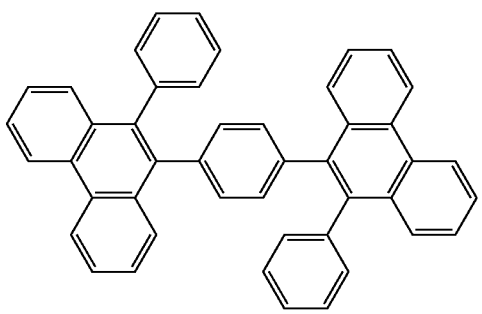
1-123
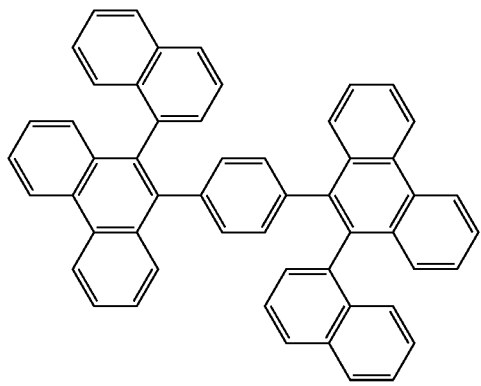
1-124
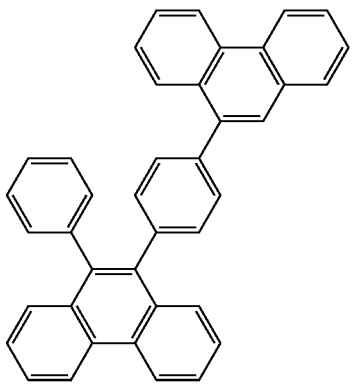
1-125
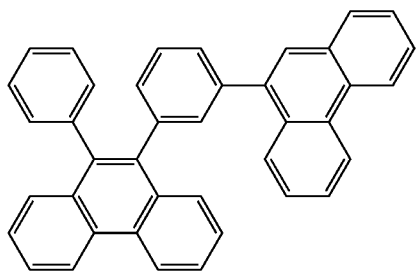
1-126
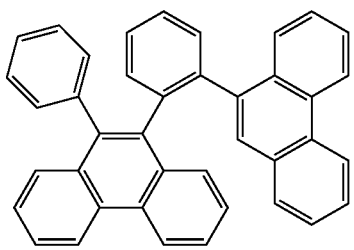
1-127
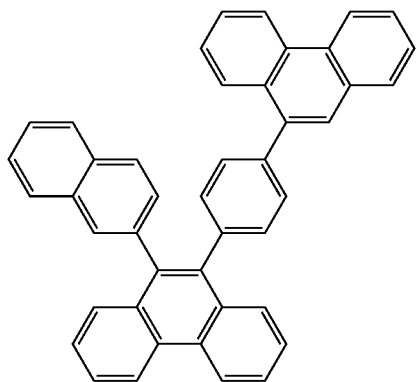
1-128
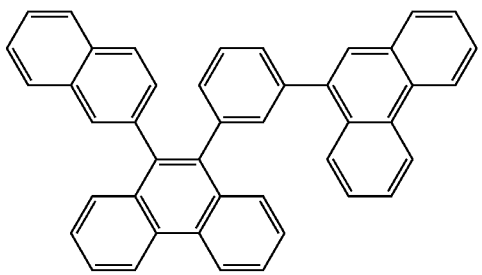

-continued
1-129
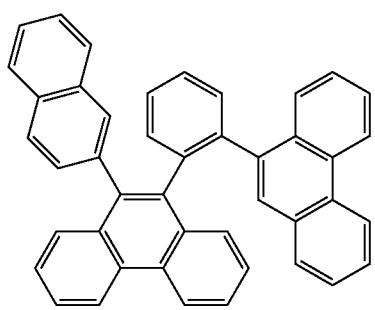
1-130
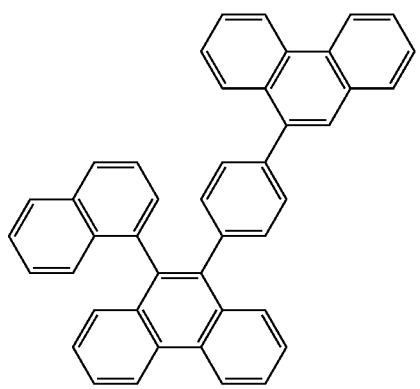
1-131
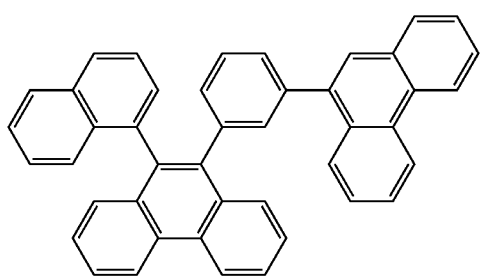
1-132
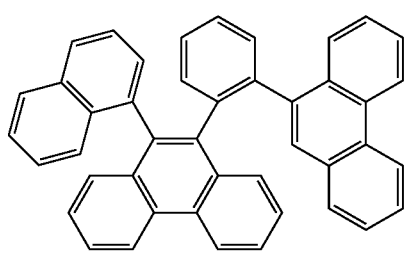
1-133
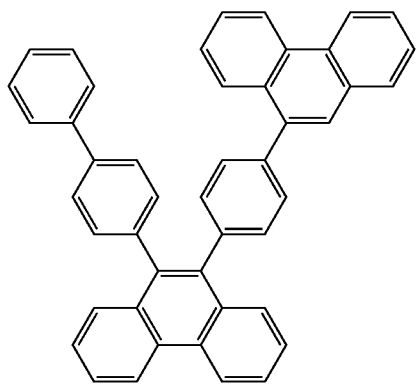
1-134
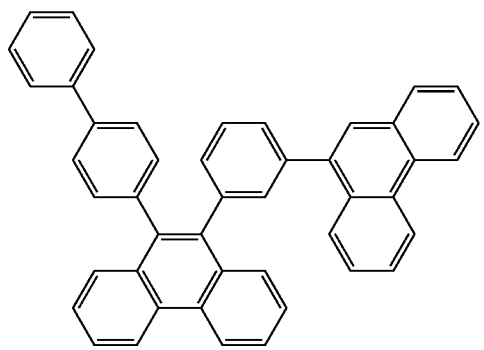
1-135
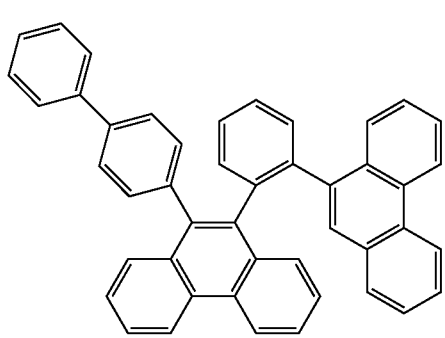
1-136
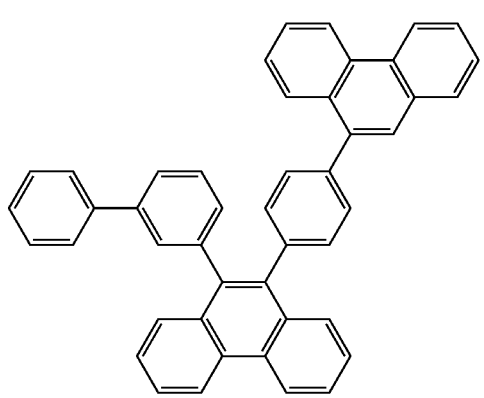

-continued
1-137
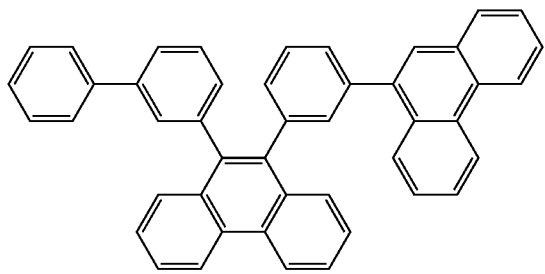
1-138
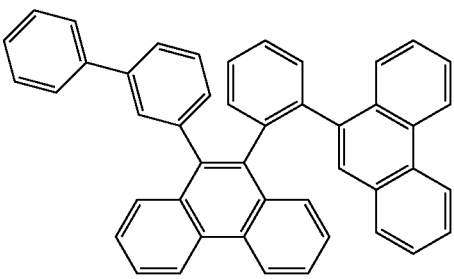
1-139
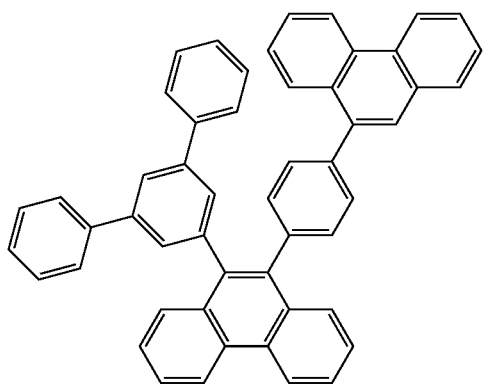
1-140
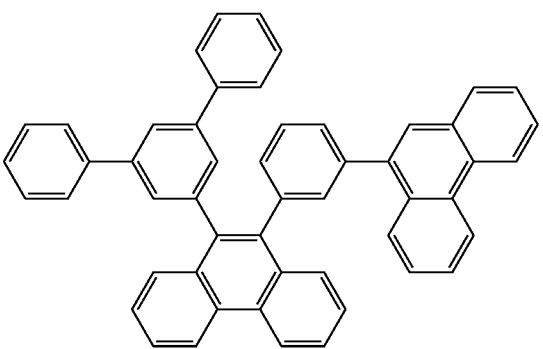
1-141
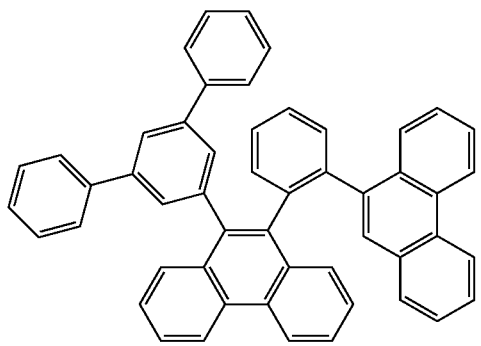
1-142
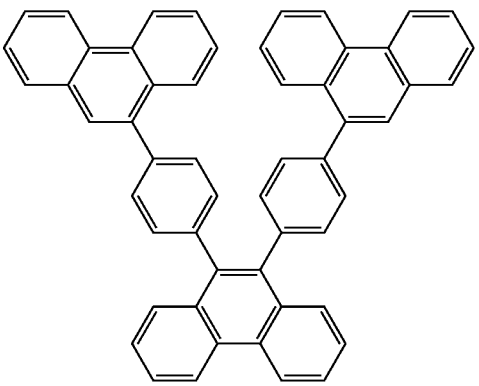
1-143
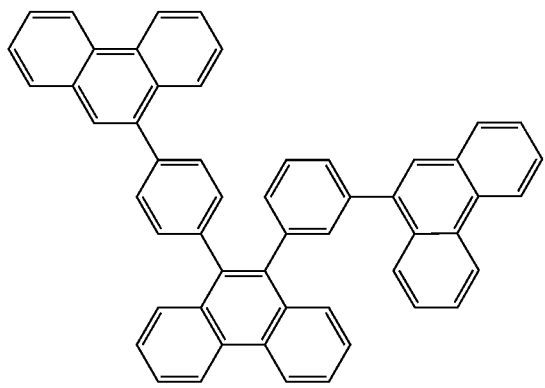
1-144
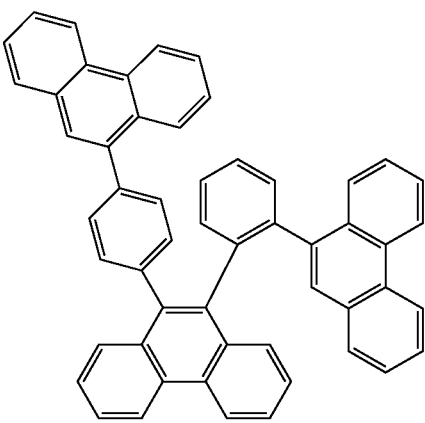

1-145
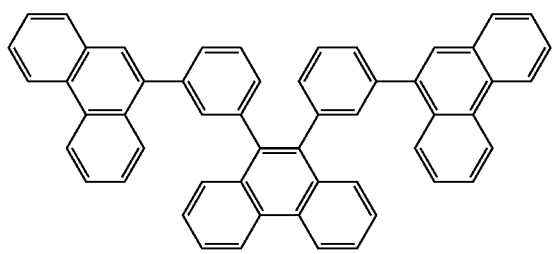
1-146
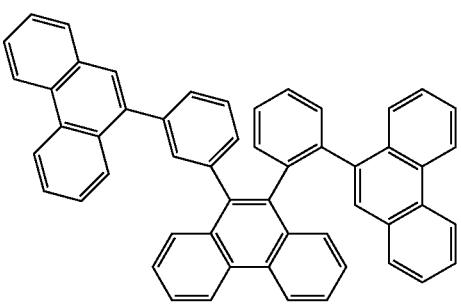
1-147
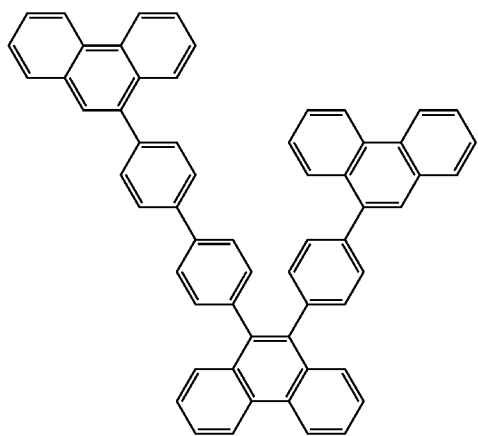
1-148
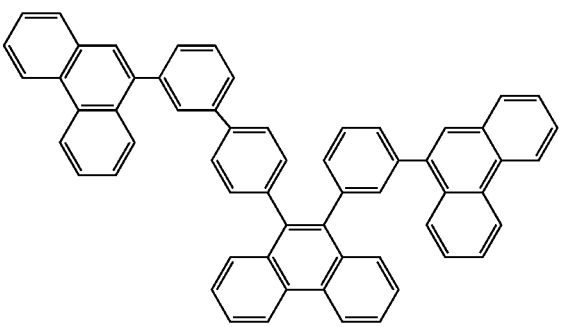
[Chemical Formula 14]
1-149
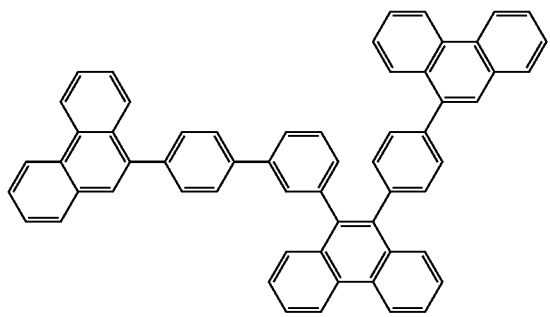
1-150
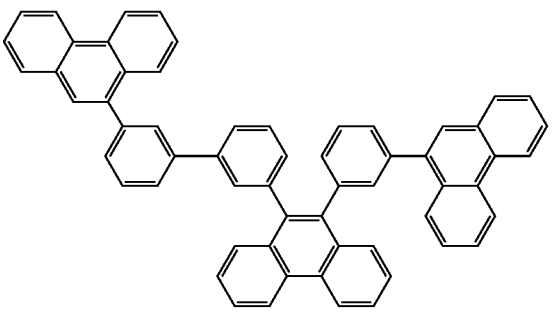
1-151
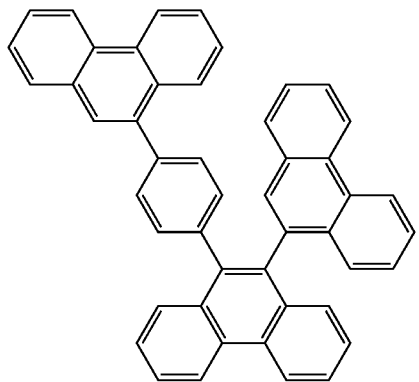
1-152
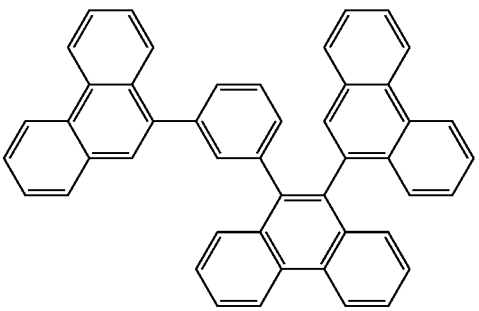

-continued
1-153
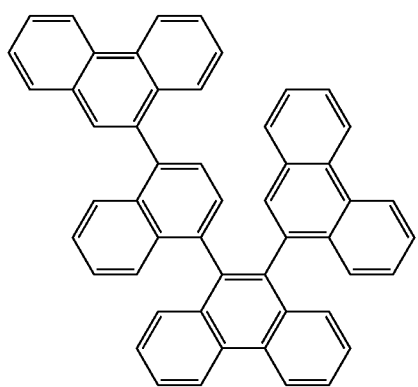
1-154
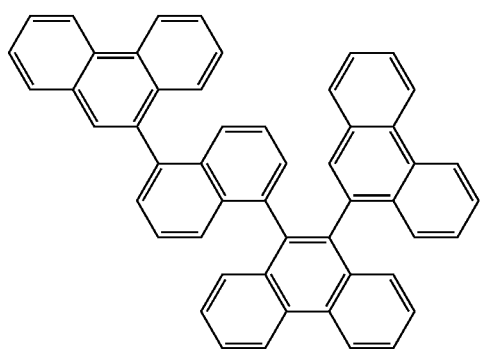
1-155
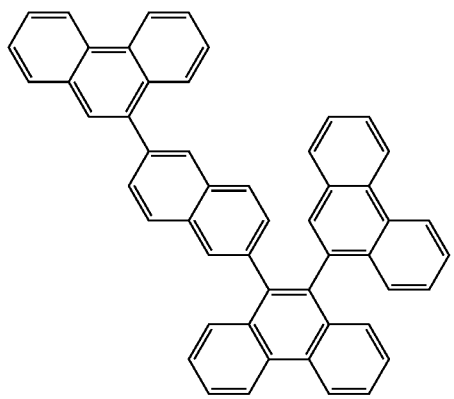
1-156
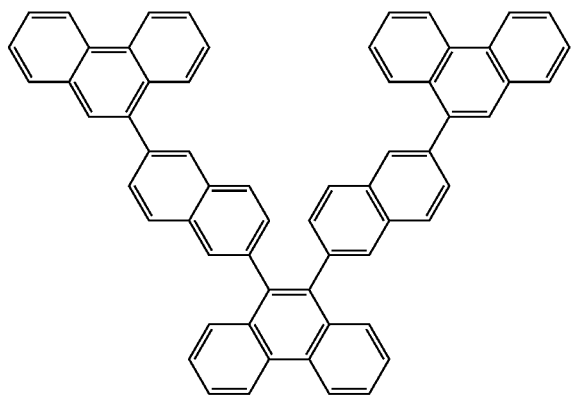
1-157
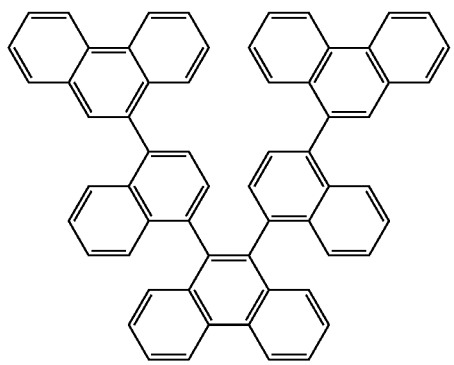
1-158
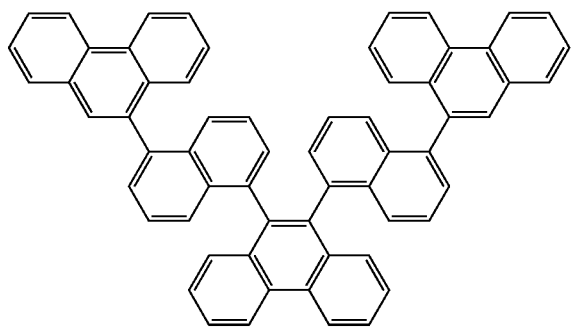
1-159
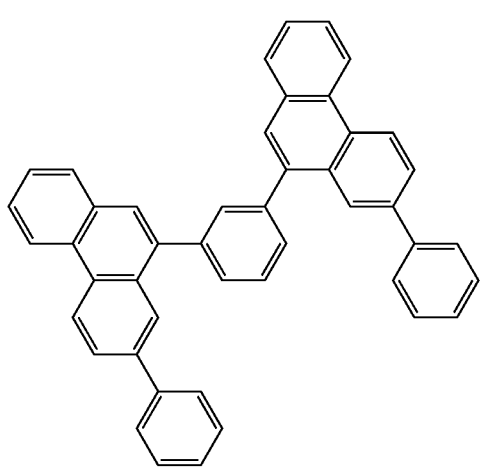
1-160
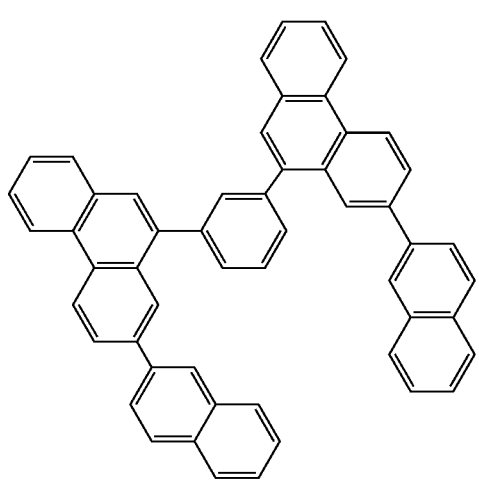

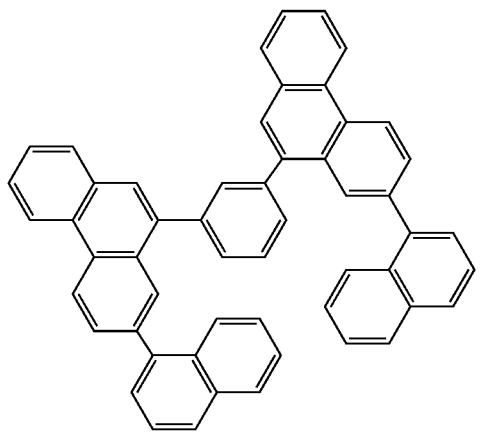

-continued
1-167
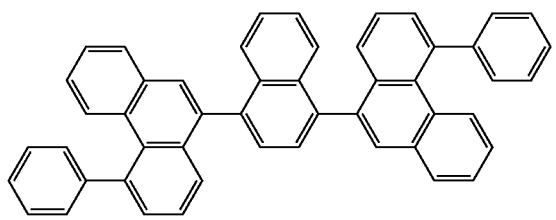
1-168
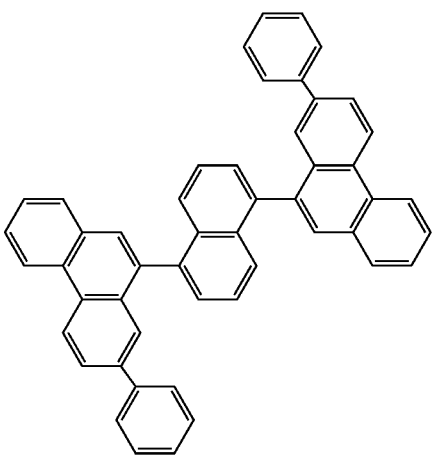
1-169
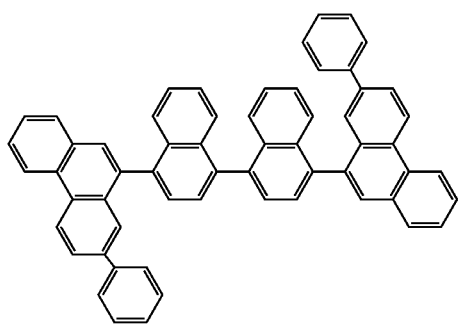
1-170
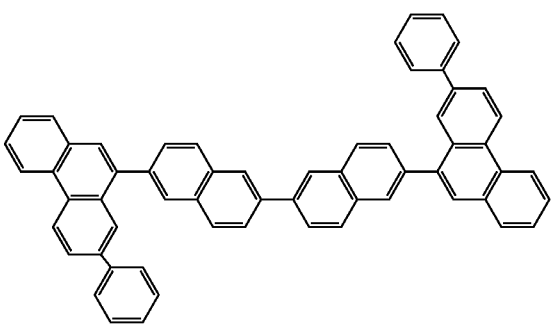
1-171
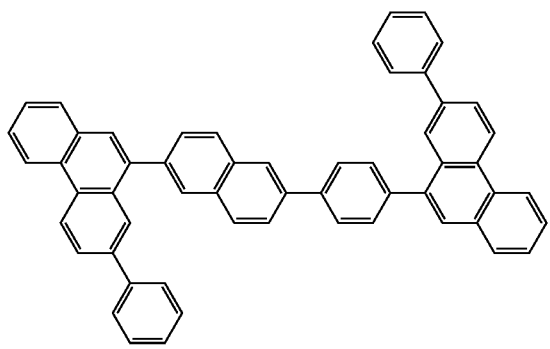
1-172
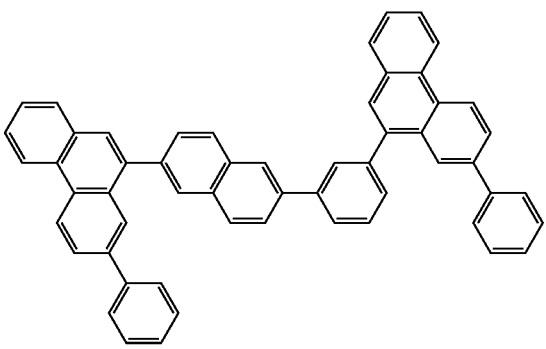
1-173
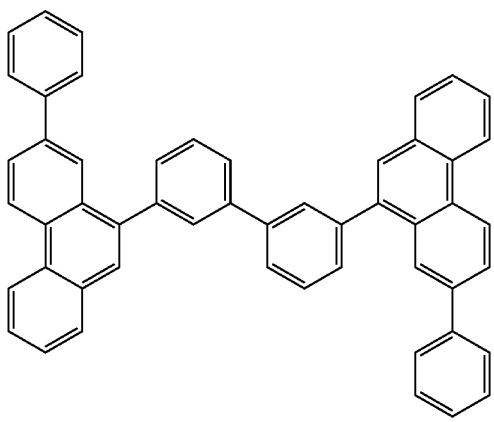

[Chemical Formula 15]
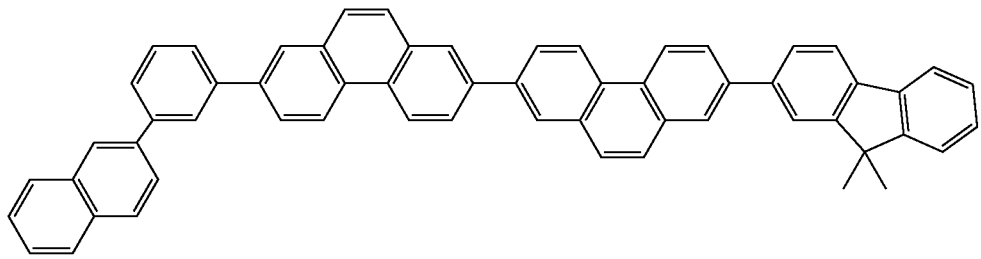
1-174
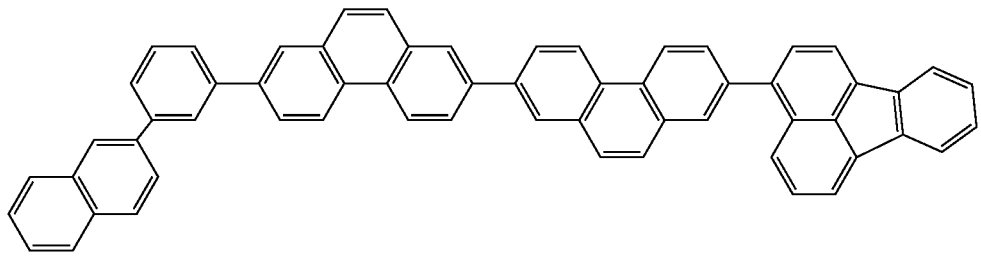
1-175
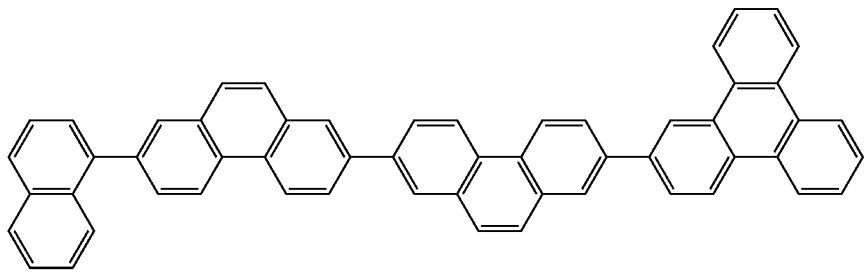
1-176
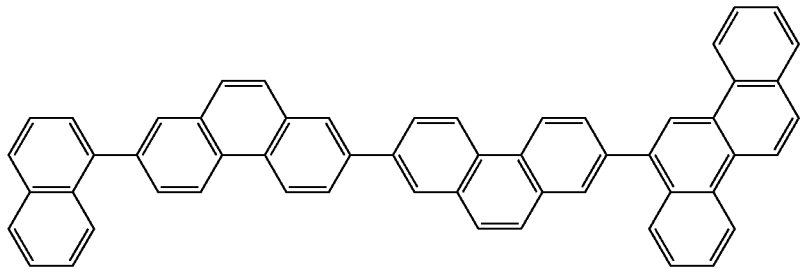
1-177
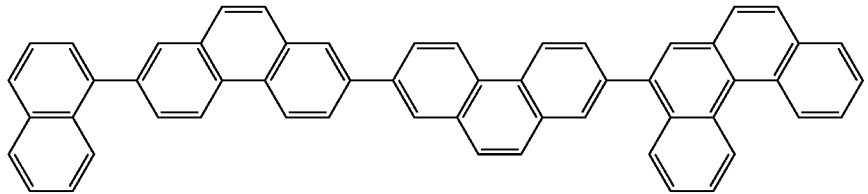
1-178
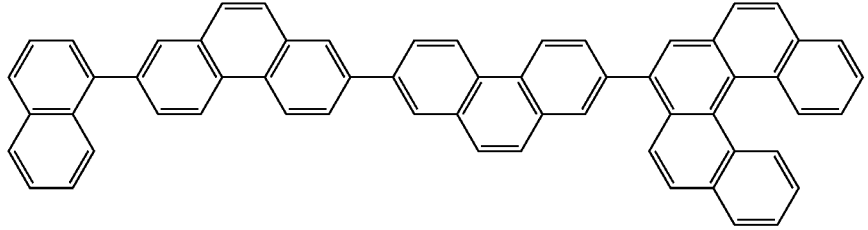
1-179

-continued
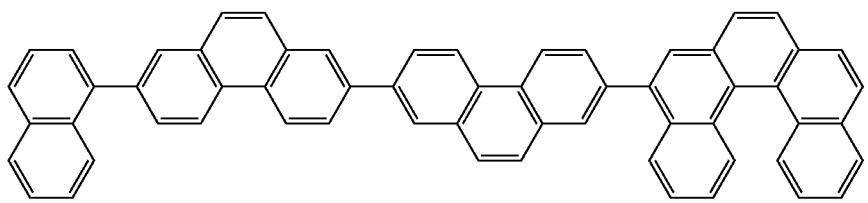
1-180
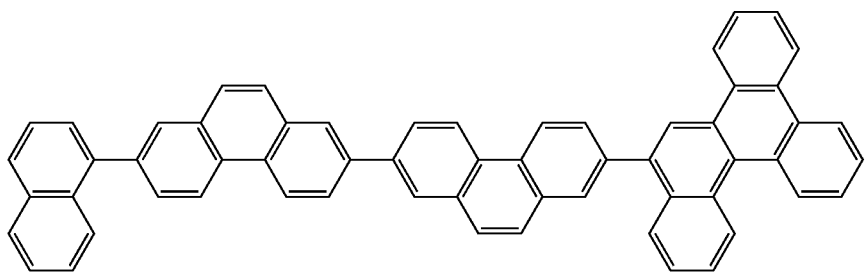
1-181
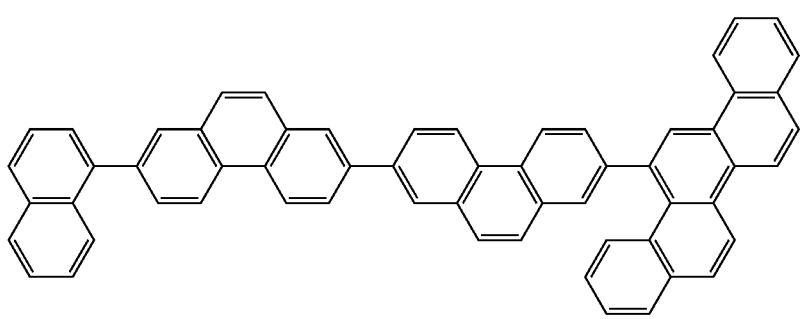
1-182
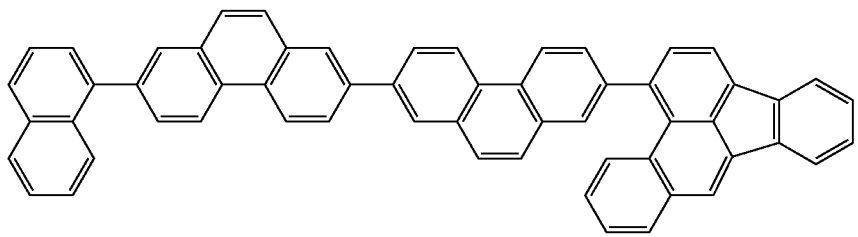
1-183
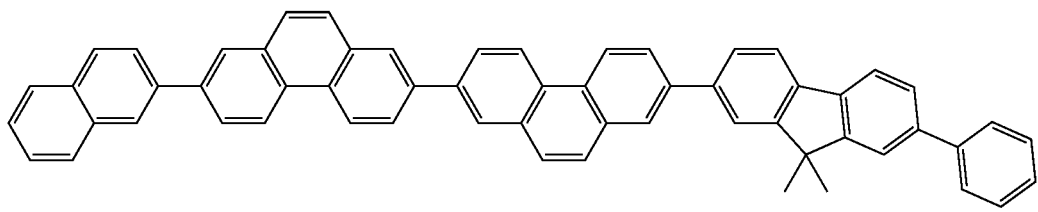
1-184
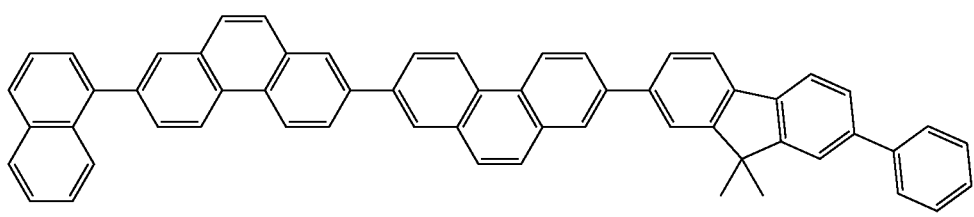
1-185

[Organic-EL-Device Material]

A material for organic EL devices according another aspect of the invention contains the phenanthrene derivative represented by the formula (1).

The material for organic EL devices according to the aspect of the invention is preferably used as the host material of the emitting layer.

By using the organic-EL-device material containing the phenanthrene derivative represented by the formula (1) as the host material of the emitting layer, an emitting layer of high efficiency and long lifetime is obtainable.

[Organic EL Device]

Next, an organic EL device according to a still further aspect of the invention will be described below.

The organic EL device according to the aspect of the invention includes a single-layered or multilayered organic thin-film layer provided between a cathode and an anode, and the organic thin-film layer includes an emitting layer. At least one layer of the organic thin-film layer contains the organic-EL-device material according to the aspect of the invention.

Structure examples of a multilayered organic EL device are structures that respectively include: an anode, hole transporting layer (hole injecting layer), emitting layer and cathode; an anode, emitting layer, electron transporting layer (electron injecting layer) and cathode; an anode, hole transporting layer (hole injecting layer), emitting layer, electron transporting layer (electron injecting layer) and cathode; and an anode, hole transporting layer (hole injecting layer), emitting layer, hole blocking layer, electron transporting layer (electron injecting layer) and cathode.

The organic EL device 1 includes a transparent substrate 2, an anode 3, a cathode 4 and an organic thin-film layer 10 positioned between the anode 3 and the cathode 4.

The organic thin-film layer 10 includes a phosphorescent-emitting layer 5 containing host and phosphorescent dopant. A layer such as a hole injecting/transporting layer 6 may be provided between the phosphorescent-emitting layer 5 and the anode 3 while a layer such as an electron injecting/transporting layer 7 may be provided between the phosphorescent-emitting layer 5 and the cathode 4.

In addition, an electron blocking layer may be provided to the phosphorescent-emitting layer 5 adjacently to the anode 3 while a hole blocking layer may be provided to the phosphorescent-emitting layer 5 adjacently to the cathode 4.

With this arrangement, electrons and holes can be trapped in the phosphorescent-emitting layer 5, thereby enhancing probability of exciton generation in the phosphorescent-emitting layer 5.

It should be noted that the "hole injecting/transporting layer" herein means "at least either one of a hole injecting layer and a hole transporting layer" while the "electron injecting/transporting layer" herein means "at least either one of an electron injecting layer and an electron transporting layer."

In the organic EL device according to the aspect of the invention, the emitting layer preferably contains the organic-EL-device material according to the aspect of the invention as the host material. Further, the emitting layer preferably contains the host material and a phosphorescent-emitting material, and the host material is preferably the organic-EL-device material.

Examples of the phosphorescent-emitting material are metal complexes that contain: a metal selected from Ir, Pt, Os, Au, Cu, Re and Ru; and a ligand. The phosphorescent-emitting material is preferably a compound containing a metal selected from iridium (Ir), osmium (Os) and platinum (Pt) because such a compound, which exhibits high phosphorescence quantum yield, can further enhance external quantum efficiency of the emitting device. The phosphorescent-emitting material is more preferably a metal complex such as an iridium complex, osmium complex or platinum complex, among which an iridium complex and platinum complex are more preferable and ortho metalation of an iridium complex is the most preferable. Further preferable examples of the ortho metalation of the metal complex are iridium complexes and the like shown below.

[Chemical Formula 16]

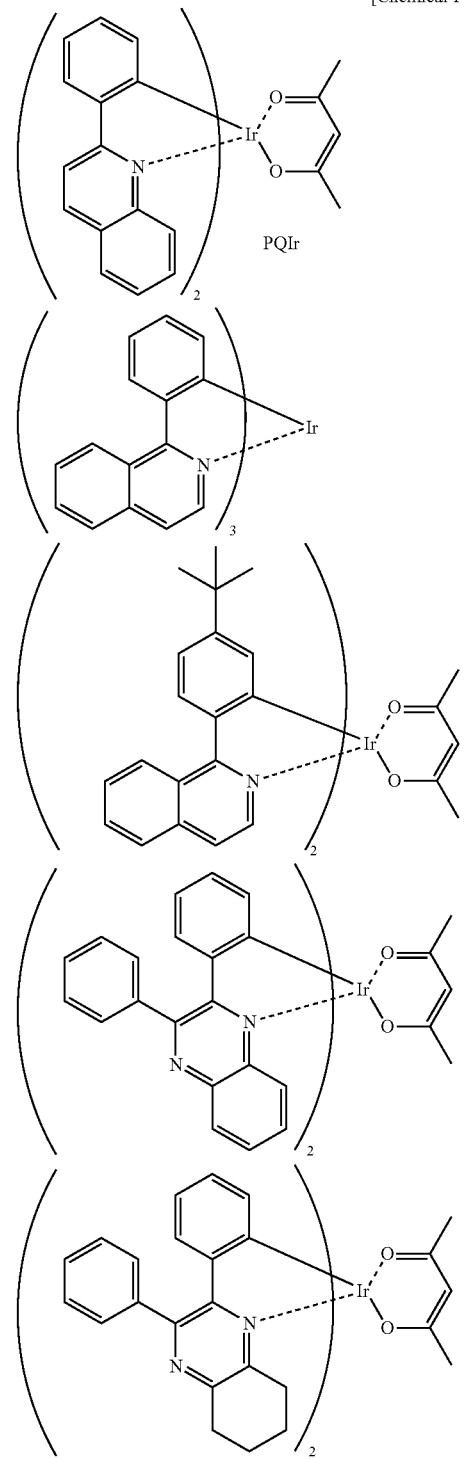

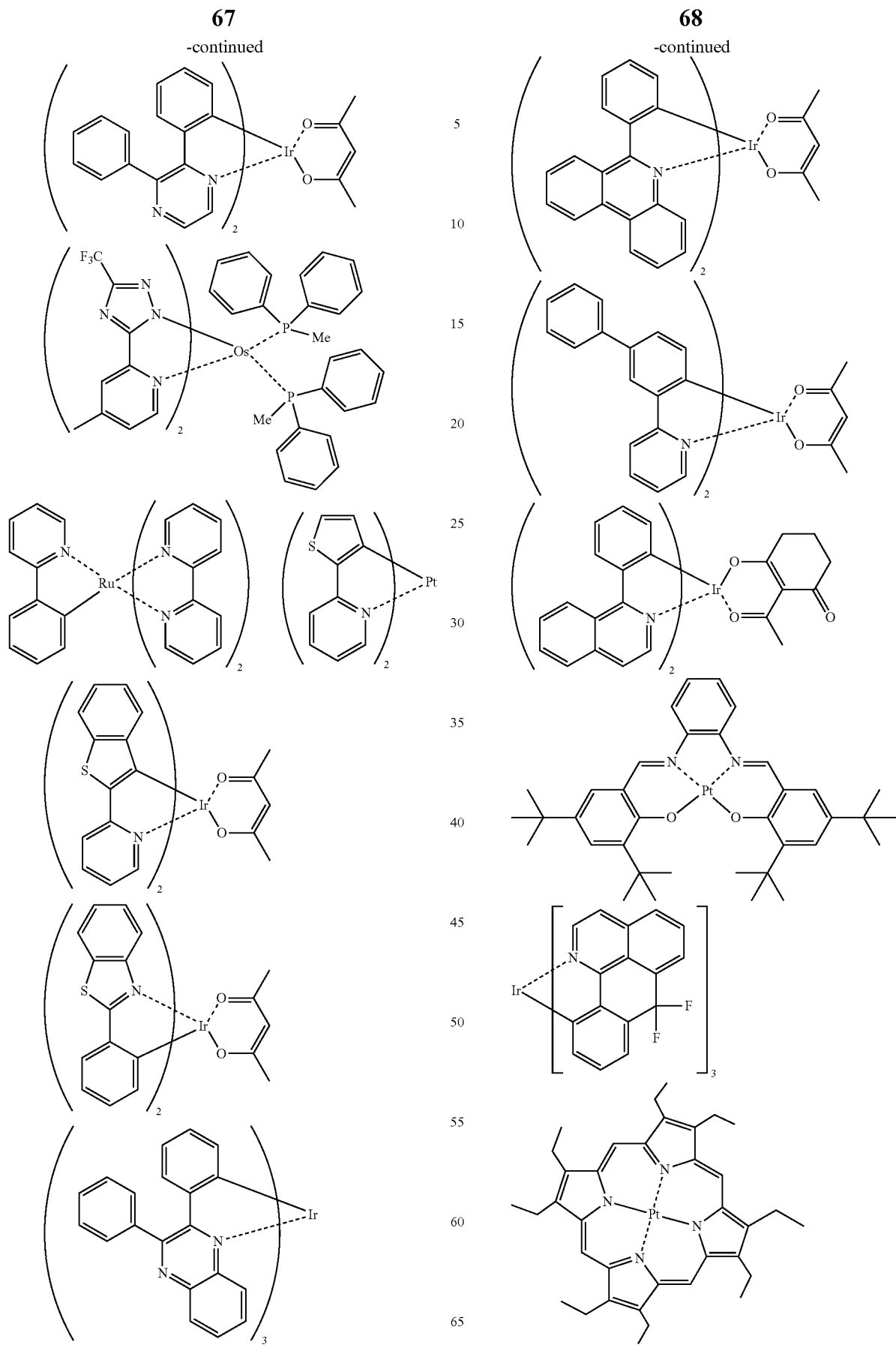

[Chemical Formula 17]
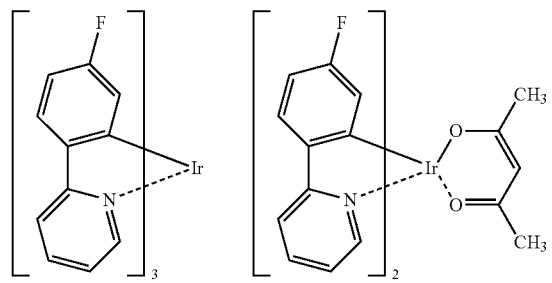
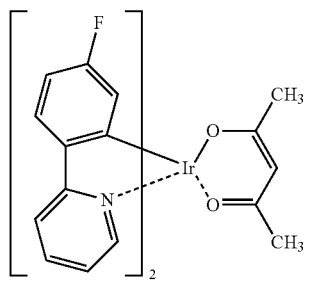
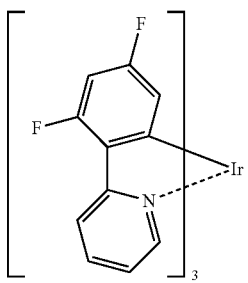
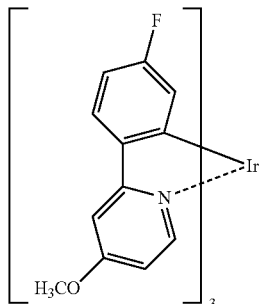
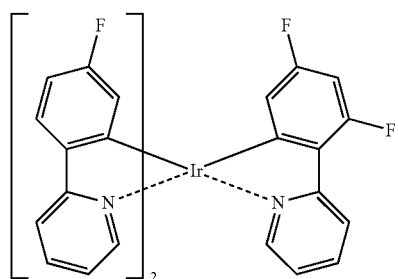
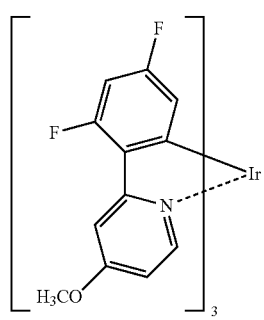
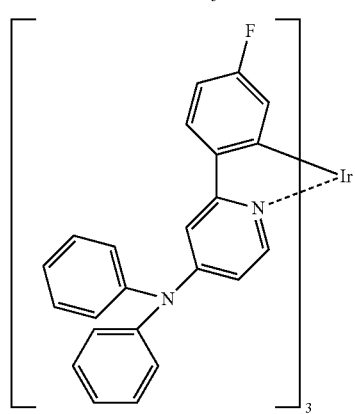
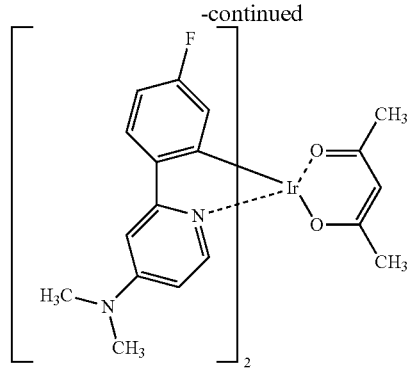
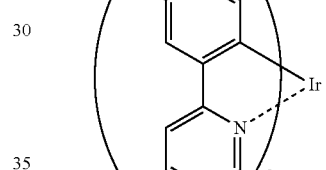
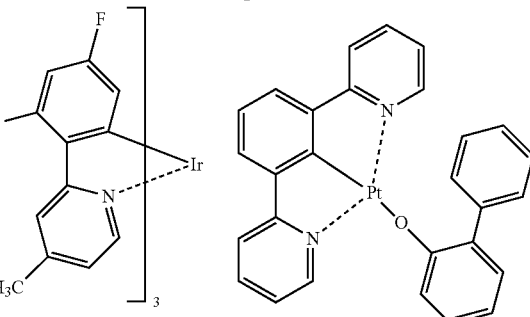
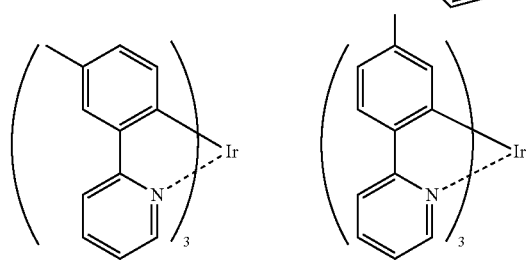
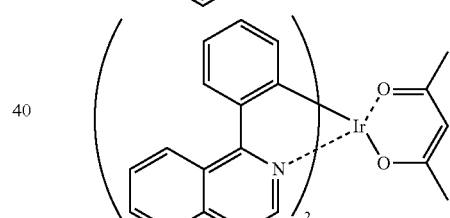
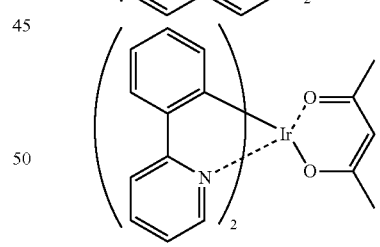
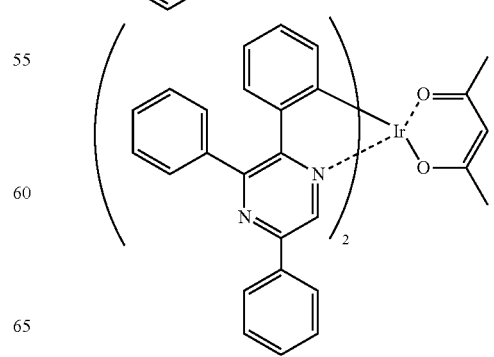

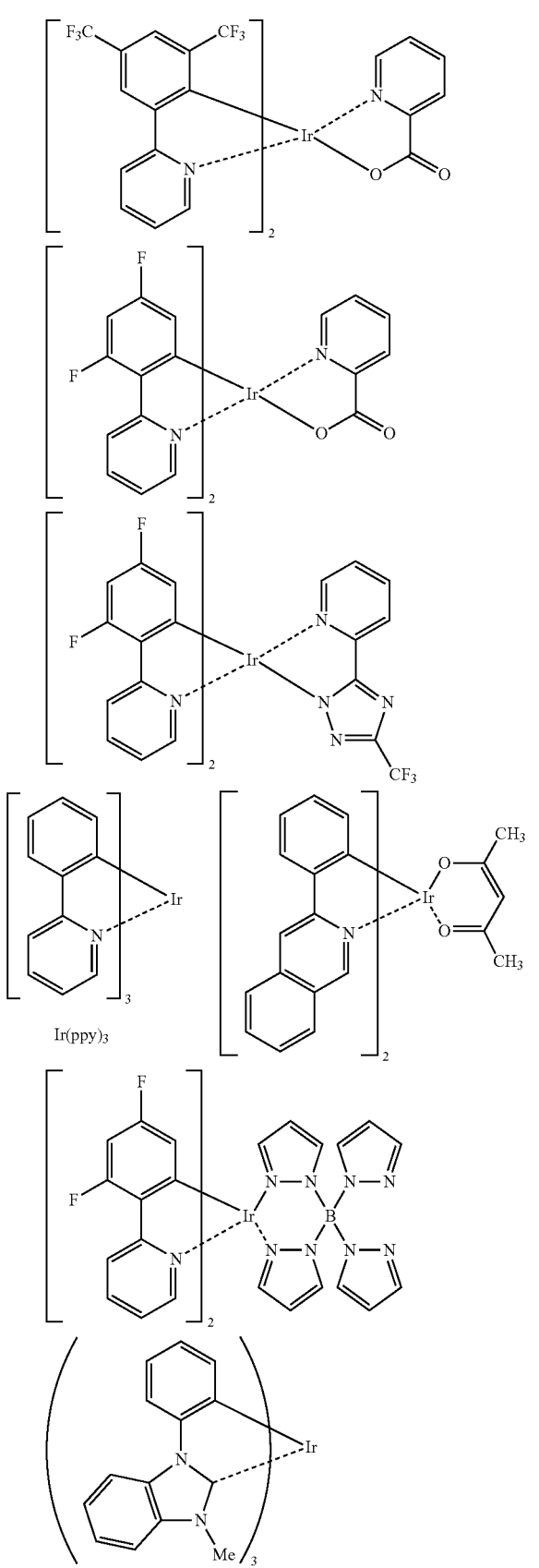
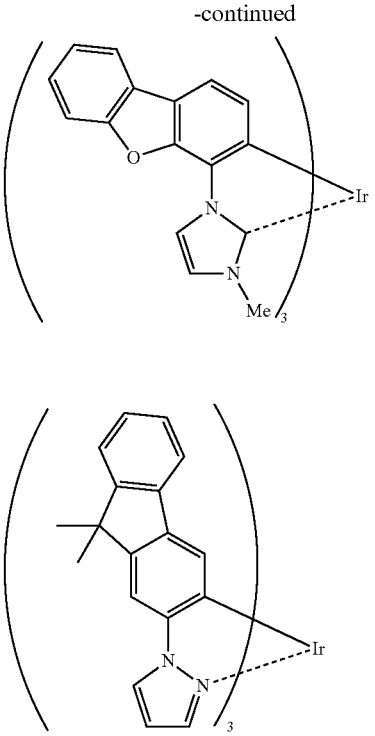

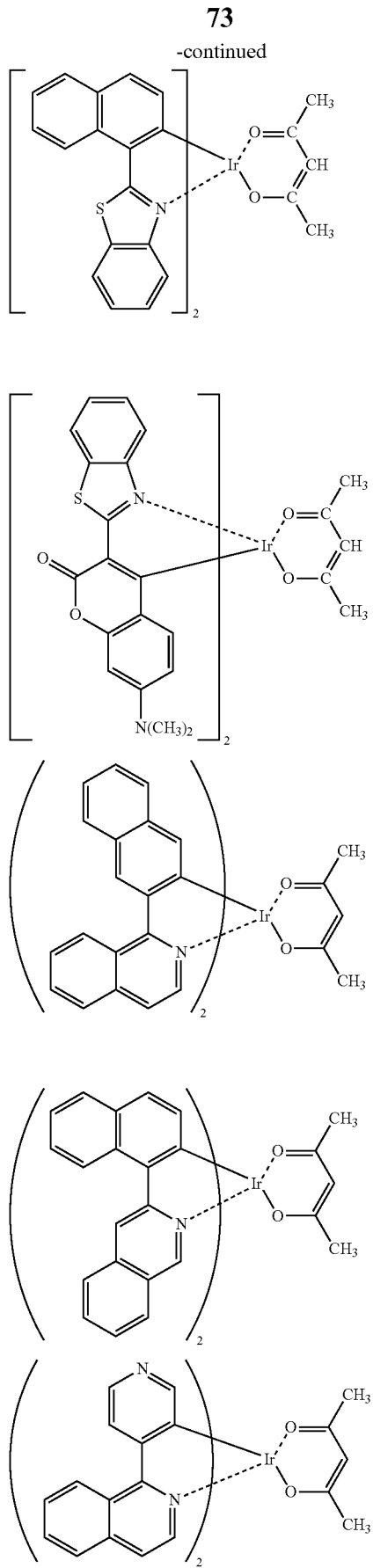

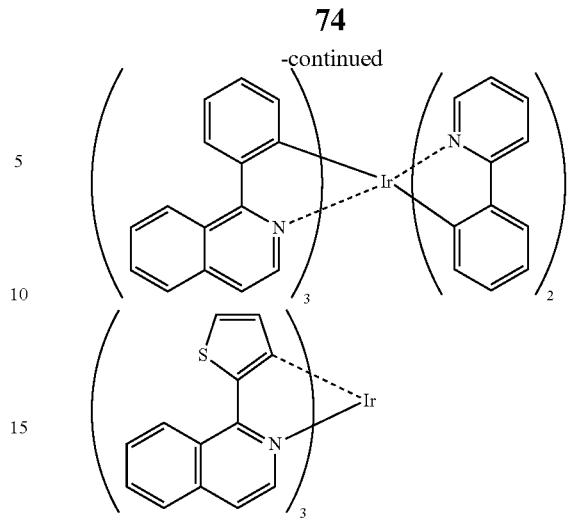

In the organic EL device according to the aspect of the invention, the emitting layer contains the host material and the phosphorescent-emitting material, and the above iridium complex is used as the phosphorescent-emitting material.

In the aspect of the invention, the maximum wavelength of the emission by the phosphorescent-emitting material is preferably 520 nm to 700 nm, more preferably 590 nm to 700 nm.

By doping the phosphorescent-emitting material (phosphorescent dopant) having such an emission wavelength to the organic-EL-device material according to the aspect of the invention so as to form the emitting layer, the organic EL device can exhibit high efficiency.

The organic EL device according to the aspect of the invention may include the hole transporting layer (or the hole injecting layer). The hole transporting layer (or the hole injecting layer) may preferably contain the organic-EL-device material according to the aspect of the invention. Alternatively, when the organic EL device according to the aspect of the invention includes at least either one of the electron transporting layer and the hole blocking layer, the at least either one of the electron transporting layer and the hole blocking layer may preferably contain the organic-EL-device material according to the aspect of the invention.

In the organic EL device according to the aspect of the invention, a reduction-causing dopant may be preferably contained in an interfacial region between the cathode and the organic thin-film layer.

With this arrangement, the organic EL device can emit light with enhanced luminance intensity and have a longer lifetime.

The reduction-causing dopant may be at least one compound selected from an alkali metal, alkali metal complex, alkali metal compound, alkali earth metal, alkali earth metal complex, alkali earth metal compound, rare-earth metal, rare-earth metal complex, rare-earth metal compound and the like.

Examples of the alkali metal are Na (work function: 2.36 eV), K (work function: 2.28 eV), Rb (work function: 2.16 eV), Cs (work function: 1.95 eV) and the like, among which a substance having a work function of 2.9 eV or less is particularly preferable. Among the above, the reduction-causing dopant is preferably K, Rb or Cs, more preferably Rb or Cs, the most preferably Cs.

Examples of the alkali earth metal are Ca (work function: 2.9 eV), Sr (work function: 2.0 to 2.5 eV), Ba (work function: 2.52 eV) and the like, among which a substance having a work function of 2.9 eV or less is particularly preferable.

Examples of the rare-earth metal are Sc, Y, Ce, Tb, Yb and the like, among which a substance having a work function of 2.9 eV or less is particularly preferable.

Since the above preferable metals have particularly high reducibility, addition of a relatively small amount of the metals to an electron injecting zone can enhance luminance intensity and lifetime of the organic EL device.

Examples of the alkali metal compound include an alkali oxide such as $Li_2O$, $Cs_2O$ and $K_2O$, and an alkali halide such as LiF, NaF, CsF and KF. LiF, $Li_2O$, and NaF are preferable.

Examples of the alkali earth metal compound include BaO, SrO, CaO and their mixture such as $Ba_xSr_{1-x}O$ (0<x<1) and $Ba_xCa_{1-x}O$ (0 (0<x<1). BaO, SrO, and CaO are preferable.

Examples of the rare earth metal compound include $YbF_3$, $ScF_3$, $ScO_3$, $Y_2O_3$, $Ce_2O_3$, $GdF_3$ and $TbF_3$. $YbF_3$, $ScF_3$, and $TbF_3$ are preferable.

The alkali metal complex, alkali earth metal complex and rare earth metal complex are not specifically limited as long as they contain at least one metal ion of an alkali metal ion, an alkali earth metal ion and a rare earth metal ion. In addition, the ligand is preferably quinolynol, benzoquinolynol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzoimidazole, hydroxybenzotriazole, hydroxyfluboran, bipyridyl, phenanthroline, phthalocyanin, porphyrin, cyclopentadiene, β-diketones, azomethines, and derivatives thereof. However, the ligand is not limited thereto.

The reduction-causing dopant is added to preferably form a layer or an island pattern in the interfacial region. The layer of the reduction-causing dopant or the island pattern of the reduction-causing dopant is preferably formed by depositing the reduction-causing dopant by resistance heating deposition while an emitting material for forming the interfacial region or an organic substance as an electron-injecting material are simultaneously deposited, so that the reduction-causing dopant is dispersed in the organic substance. Dispersion concentration at which the reduction-causing dopant is dispersed in the organic substance is a mole ratio (organic substance to reduction-causing dopant) of 100:1 to 1:100, preferably 5:1 to 1:5.

When the reduction-causing dopant forms the layer, the emitting material or the electron injecting material for forming the organic layer of the interfacial region is initially layered, and the reduction-causing dopant is subsequently deposited singularly thereon by resistance heating deposition to form a preferably 0.1 to 15 nm-thick layer.

When the reduction-causing dopant forms the island pattern, the emitting material or the electron injecting material for forming the organic layer of the interfacial region is initially formed in an island shape, and the reduction-causing dopant is subsequently deposited singularly thereon by resistance heating deposition to form a preferably 0.05 to 1 nm-thick island shape.

A ratio of the main component to the reduction-causing dopant in the organic EL device according to the aspect of the invention is preferably a mole ratio (main component to reduction-causing dopant) of 5:1 to 1:5, more preferably 2:1 to 1:2.

The organic EL device according to the aspect of the invention preferably includes the electron injecting layer between the emitting layer and the cathode, and the electron injecting layer preferably contains a nitrogen-containing cyclic derivative as the main component.

It should be noted that "as the main component" means that the nitrogen-containing cyclic derivative is contained in the electron injecting layer at a content of 50 mass % or more.

The electron injecting layer or the electron transporting layer, which aids injection of the electrons into the emitting layer, has a high electron mobility. The electron injecting layer is provided for adjusting energy level, by which, for instance, sudden changes of the energy level can be reduced.

A preferable example of an electron transporting material for forming the electron injecting layer is an aromatic heterocyclic compound having in the molecule at least one heteroatom. Particularly, a nitrogen-containing cyclic derivative is preferable.

A preferable example of the nitrogen-containing cyclic derivative is a nitrogen-containing cyclic metal chelate complex represented by the following formula (A).

[Chemical Formula 20]

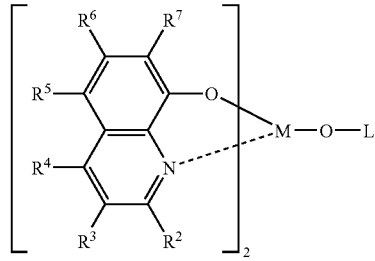

(A)

$R^2$ to $R^7$ each independently represent a hydrogen atom, a halogen atom, an oxy group, an amino group, a hydrocarbon group having 1 to 40 carbon atoms, an alkoxy group, an aryloxy group, an alkoxycarbonyl group, or a heterocyclic group. These groups may be substituted or unsubstituted.

Examples of the halogen atom include fluorine, chlorine, bromine, and iodine. In addition, examples of the substituted or unsubstituted amino group include an alkylamino group, an arylamino group, and an aralkylamino group.

Examples of the hydrocarbon group having 1 to 40 carbon atoms include a substituted or unsubstituted alkyl group, an alkenyl group, a cycloalkyl group, an aryl group, and an aralkyl group.

Examples of the alkyl group include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a 2-methylpentyl group, a 1-pentylhexyl group, a 1-butylpentyl group, a 1-heptyloctyl group, a 3-methylpentyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 1,2-dinitroethyl group, a 2,3-dinitro-t-butyl group, and a 1,2,3-trinitropropyl group.

Among these, preferred are a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a 1-pentylhexyl group, a 1-butylpentyl group, and a 1-heptyloctyl group.

Examples of the alkenyl group include a vinyl group, an allyl group, a 1-butenyl group, a 2-butenyl group, a 3-butenyl group, a 1,3-butanedienyl group, a 1-methylvinyl group, a styryl group, a 2,2-diphenylvinyl group, a 1,2-diphenylvinyl group, a 1-methylallyl group, a 1,1-dimethylallyl group, a 2-methylallyl group, a 1-phenylallyl group, a 2-phenylallyl group, a 3-phenylallyl group, a 3,3-diphenylallyl group, a 1,2-dimethylallyl group, a 1-phenyl-1-butenyl group, and a 3-phenyl-1-butenyl group. A styryl group, a 2,2-diphenylvinyl group, and a 1,2-diphenylvinyl group are preferred.

Examples of the cycloalkyl group include a cyclopentyl group, a cyclohexyl group, a cyclooctyl group, and a 3,5-tetramethylcyclohexyl group. A cyclohexyl group, a cyclooctyl group, and a 3,5-tetramethylcyclohexyl group are preferable.

The alkoxy group is a group represented by —OY. Example of Y are the same as those described above for the alkyl group. The preferred examples are also the same.

Examples of the non-fused aryl group include a phenyl group, a biphenyl-2-yl group, a biphenyl-3-yl group, a biphenyl-4-yl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 4'-methylbiphenylyl group, a 4"-t-butyl-p-terphenyl-4-yl group, an o-cumenyl group, an m-cumenyl group, a p-cumenyl group, a 2,3-xylyl group, a 3,4-xylyl group, a 2,5-xylyl group, a mesityl group, and an m-quarterphenyl group.

Among these, preferred are a phenyl group, a biphenyl-2-yl group, a biphenyl-3-yl group, a biphenyl-4-yl group, an m-terphenyl-4-yl group, an m-terphenyl-3-yl group, an m-terphenyl-2-yl group, a p-tolyl group, a 3,4-xylyl group, and an m-quarterphenyl-2-yl group.

Examples of the fused aryl group include a 1-naphthyl group and a 2-naphthyl group.

The heterocyclic group is a mono ring or a fused ring. The heterocyclic group preferably has 1 to 20 ring carbon atoms, more preferably 1 to 12 ring carbon atoms, and still more preferably 2 to 10 ring carbon atoms. An example thereof is an aromatic heterocyclic group having at least one hetero atom selected from a nitrogen atom, an oxygen atom, a sulfur atom and a selenium atom. Examples of the heterocyclic group include groups that are derived from pyrrolidine, piperidine, piperazine, morpholine, thiophene, selenophene, furan, pyrrol, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthridine, quinoxaline, quinazoline, cinnoline, pteridine, acridine, phenanthroline, phenazine, tetrazole, benzimidazole, benzoxazole, benzothiazole, benzotriazole, tetrazaindene, carbazole, and azepine. Preferably, the heterocyclic group is derived from furan, thiophene, pyridine, pyrazine, pyrimidine, pyridazine, triazine, quinoline, phthalazine, naphthiridine, quinoxaline and quinazoline. More preferably, the heterocyclic group is a group derived from furan, thiophene, pyridine and quinoline, and still more preferably a quinolinyl group.

Examples of the aralkyl group include a benzyl group, a 1-phenylethyl group, a 2-phenylethyl group, a 1-phenylisopropyl group, a 2-phenylisopropyl group, a phenyl-t-butyl group, a α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a p-methylbenzyl group, an m-methylbenzyl group, an o-methylbenzyl group, a p-chlorobenzyl group, an m-chlorobenzyl group, an o-chlorobenzyl group, a p-bromobenzyl group, an m-bromobenzyl group, an o-bromobenzyl group, a p-iodobenzyl group, an m-iodobenzyl group, an o-iodobenzyl group, a p-hydroxybenzyl group, an m-hydroxybenzyl group, an o-hydroxybenzyl group, a p-aminobenzyl group, an m-aminobenzyl group, an o-aminobenzyl group, a p-nitrobenzyl group, an m-nitrobenzyl group, an o-nitrobenzyl group, a p-cyanobenzyl group, an m-cyanobenzyl group, an o-cyanobenzyl group, a 1-hydroxy-2-phenylisopropyl group, and a 1-chloro-2-phenylisopropyl group.

Among these, preferred are a benzyl group, a p-cyanobenzyl group, an m-cyanobenzyl group, an o-cyanobenzyl group, a 1-phenylethyl group, a 2-phenylethyl group, a 1-phenylisopropyl group, and a 2-phenylisopropyl group.

The aryloxy group is represented by —OY'. Examples of Y' include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, and a 4'-t-butyl-p-terphenyl-4-yl group.

The heteroaryloxy group in the aryloxy group is represented by —OZ'. Examples of Z' include a 2-pyrrolyl group, a 3-pyrrolyl group, a pyrazinyl group, a 2-pyrizinyl group, a 3-pyrizinyl group, a 4-pyrizinyl group, a 2-indolyl group, a 3-indolyl group, a 4-indolyl group, a 5-indolyl group, a 6-indolyl group, a 7-indolyl group, a 1-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, a 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthroline-2-yl group, a 1,7-phenanthroline-3-yl group, a 1,7-phenanthroline-4-yl group, a 1,7-phenanthroline-5-yl group, a 1,7-phenanthroline-6-yl group, a 1,7-phenanthroline-8-yl group, a 1,7-phenanthroline-9-yl group, a 1,7-phenanthroline-10-yl group, a 1,8-phenanthroline-2-yl group, a 1,8-phenanthroline-3-yl group, a 1,8-phenanthroline-4-yl group, a 1,8-phenanthroline-5-yl group, a 1,8-phenanthroline-6-yl group, a 1,8-phenanthroline-7-yl group, a 1,8-phenanthroline-9-yl group, a 1,8-phenanthroline-10-yl group, a 1,9-phenanthroline-2-yl group, a 1,9-phenanthroline-3-yl group, a 1,9-phenanthroline-4-yl group, a 1,9-phenanthroline-5-yl group, a 1,9-phenanthrolin-6-yl group, a 1,9-phenanthrolin-7-yl group, a 1,9-phenanthroline-8-yl group, a 1,9-phenanthroline-10-yl group, a 1,10-phenanthroline-2-yl group, a 1,10-phenanthroline-3-yl group, a 1,10-phenanthroline-4-yl group, a 1,10-phenanthroline-5-yl group, a 2,9-phenanthroline-1-yl group, a 2,9-phenanthroline-3-yl group, a 2,9-phenanthroline-4-yl group, a 2,9-phenanthroline-5-yl group, a 2,9-phenanthroline-6-yl group, a 2,9-phenanthroline-7-yl group, a 2,9-phenanthroline-8-yl group, a 2,9-phenanthroline-10-yl group, a 2,8-phenanthroline-1-yl group, a 2,8-phenanthroline-3-yl group, a 2,8-phenanthroline-4-yl group, a 2,8-phenanthroline-5-yl group, a 2,8-phenanthroline-6-yl group, a 2,8-phenanthroline-7-yl group, a 2,8-phenanthroline-9-yl group, a 2,8-phenanthroline-10-yl group, a 2,7-phenanthroline-1-yl group, a 2,7-phenanthroline-3-yl group, a 2,7-phenanthroline-4-yl group, a 2,7-phenanthroline-5-yl group, a 2,7-phenanthroline-6-yl group, a 2,7-phenanthroline-8-yl group, a 2,7-phenanthroline-9-yl group, a 2,7-phenanthroline-10-yl group, a 1-phenazinyl group, a 2-phenazinyl group, a 1-phenothiazinyl group, a 2-phenothiazinyl group, a 3-phenothiazinyl group, a 4-phenothiazinyl group, a 1-phenoxazinyl group, a 2-phenoxazinyl group, a 3-phenoxazinyl group, a 4-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl 1-indolyl group, a 4-t-butyl 1-indolyl group, a 2-t-butyl 3-indolyl group, and a 4-t-butyl 3-indolyl group.

The alkoxycarbonyl group is represented by —COOY'. Examples of Y' are the same as the examples of the alkyl group.

The alkylamino group and the aralkylamino group are represented by —NQ$^1$Q$^2$. Examples for each of Q$^1$ and Q$^2$ are the same as the examples described in relation to the alkyl group and the aralkyl group, and preferable examples for each of Q$^1$ and Q$^2$ are also the same as those described in relation to the alkyl group and the aralkyl group. Either one of Q$^1$ and Q$^2$ may be a hydrogen atom.

The arylamino group is represented by —NAr$^1$Ar$^2$. Examples for each of Ar$^1$ and Ar$^2$ are the same as the examples described in relation to the non-fused aryl group and the fused aryl group. Either one of Ar$^1$ and Ar$^2$ may be a hydrogen atom.

M represents aluminum (Al), gallium (Ga) or indium (In), among which In is preferable.

L in the formula (A) represents a group represented by the following formula (A') or the following formula (A").

[Chemical Formula 21]

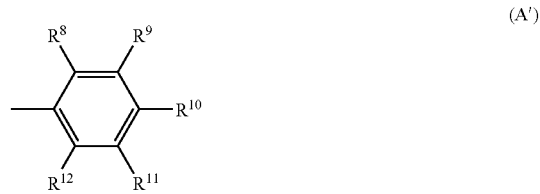

(A')

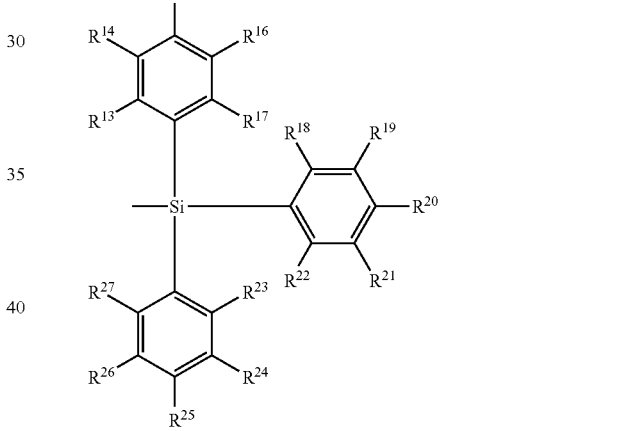

(A")

In the formula, $R^8$ to $R^{12}$ each independently represent a hydrogen atom or a substituted or unsubstituted hydrocarbon group having 1 to 40 carbon atoms. Adjacent groups may form a cyclic structure. In the formula, $R^{13}$ to $R^{27}$ each independently represent a hydrogen atom or a substituted or unsubstituted hydrocarbon group having 1 to 40 carbon atoms. Adjacent groups may form a cyclic structure.

Examples of the hydrocarbon group having 1 to 40 carbon atoms represented by each of $R^8$ to $R^{12}$ and $R^{13}$ to $R^{27}$ in the formulae (A') and (A") are the same as those of $R^2$ to $R^7$.

Examples of a divalent group formed when an adjacent set of $R^8$ to $R^{12}$ and $R^{13}$ to $R^{27}$ forms a cyclic structure are a tetramethylene group, a pentamethylene group, a hexamethylene group, a diphenylmethane-2,2'-diyl group, a diphenylethane-3,3'-diyl group, a diphenylpropane-4,4'-diyl group and the like.

Examples of the nitrogen-containing cyclic metal chelate complex represented by the formula (A) will be shown below. However, the nitrogen-containing cyclic metal chelate complex is not limited to the exemplary compounds shown below.

[Chemical Formula 22]
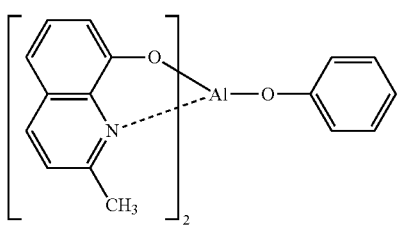 (A-1)
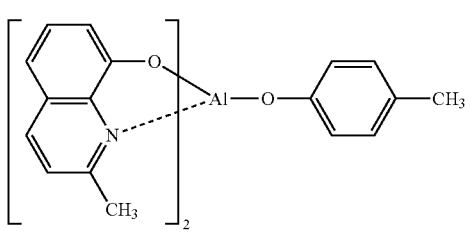 (A-2)
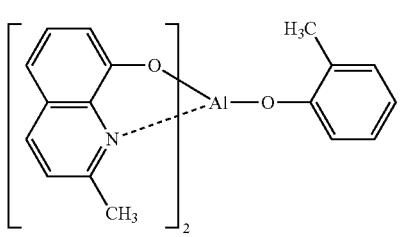 (A-3)
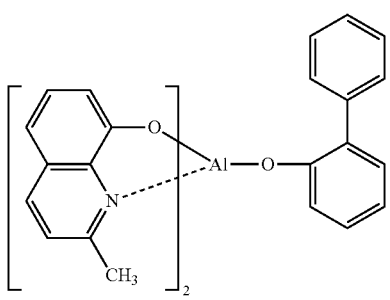 (A-4)
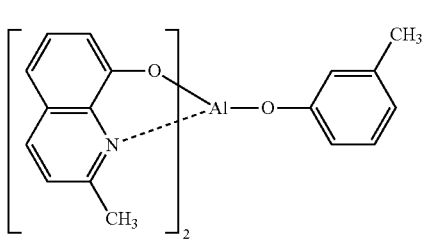 (A-5)
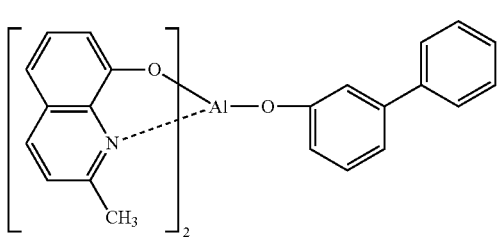 (A-6)
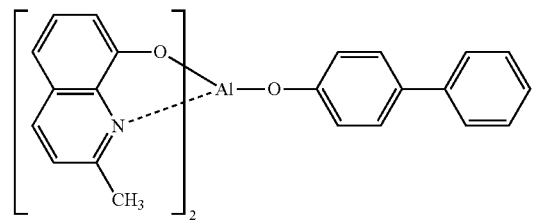 (A-7)
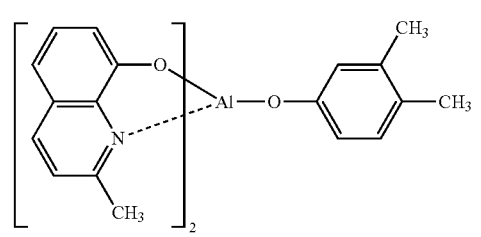 (A-8)
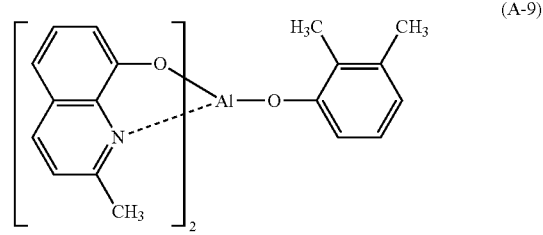 (A-9)
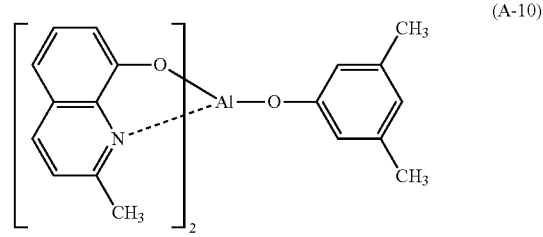 (A-10)
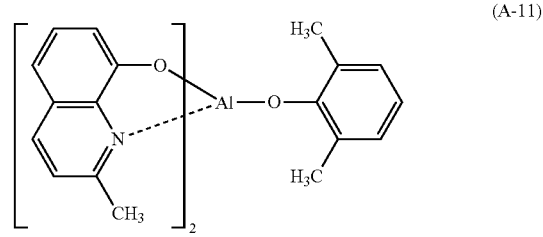 (A-11)
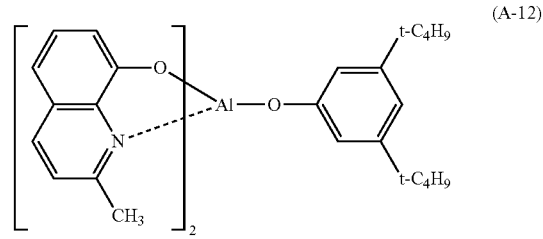 (A-12)
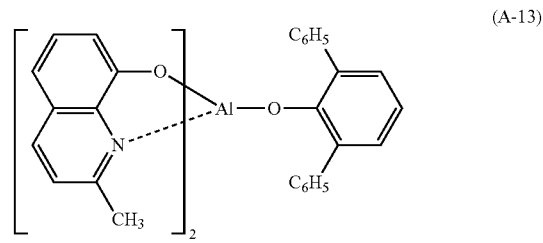 (A-13)

(A-14)
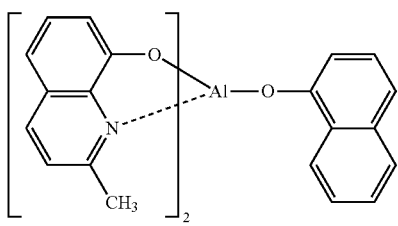
(A-15)
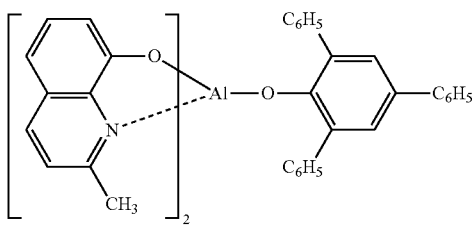
(A-16)
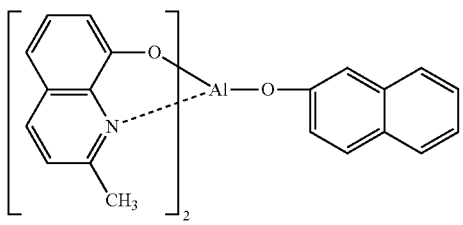
[Chemical Formula 23]
(A-17)
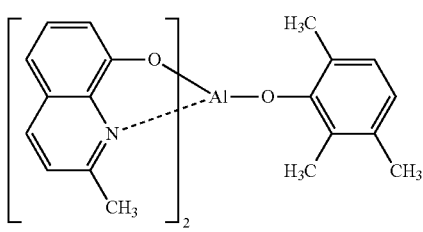
(A-18)
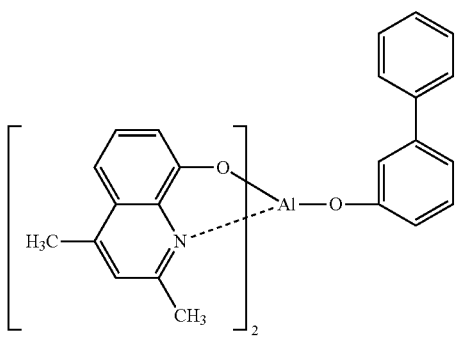
(A-19)
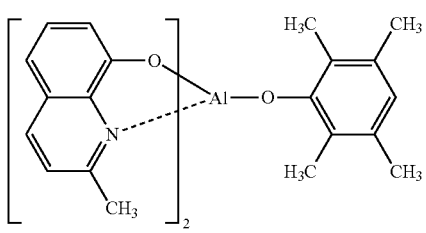
(A-20)
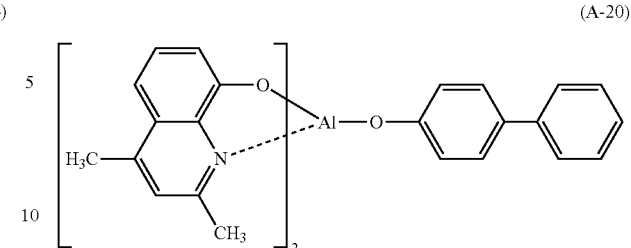
(A-21)
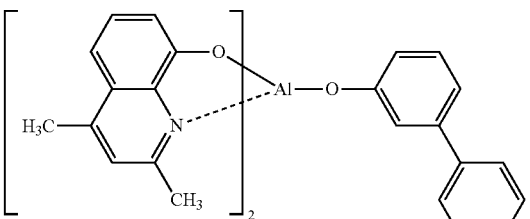
(A-22)
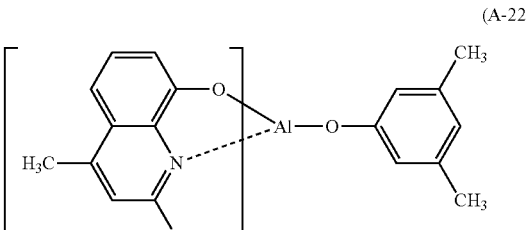
(A-25)
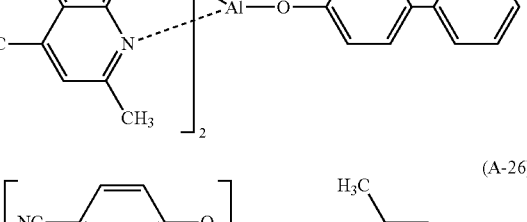
(A-26)
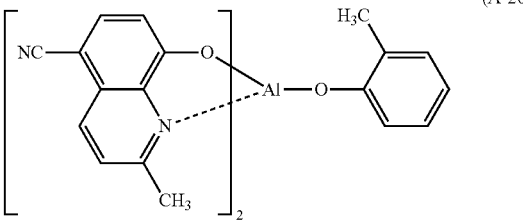
(A-27)
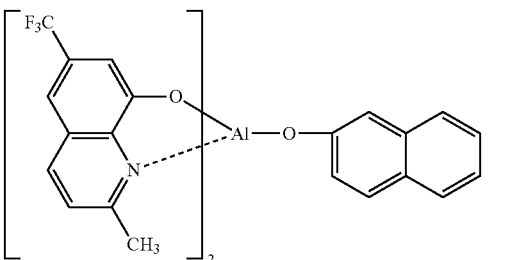

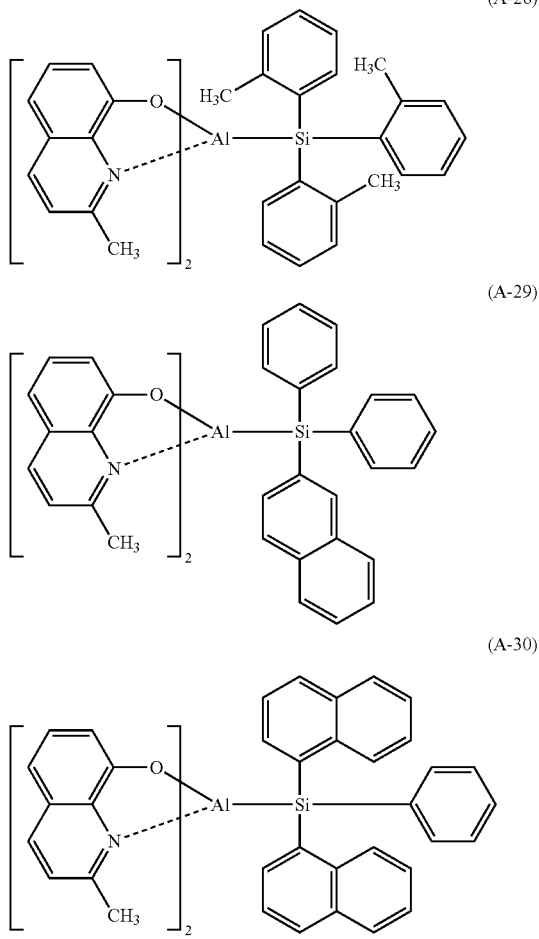
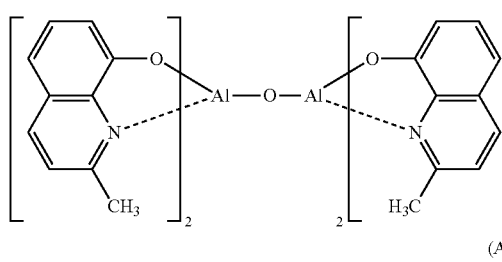
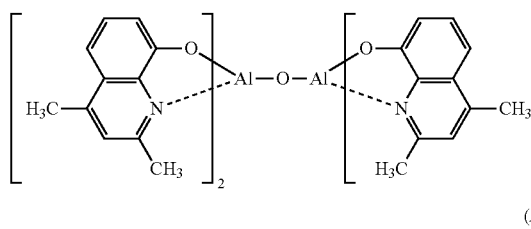
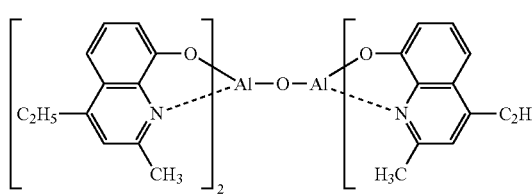
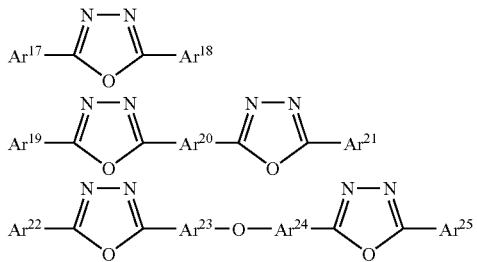

According to the aspect of the invention, the electron injecting layer preferably contains a nitrogen-containing heterocyclic derivative.

The electron injecting layer or the electron transporting layer, which aids injection of the electrons into the emitting layer, has a high electron mobility. The electron injecting layer is provided for adjusting energy level, by which, for instance, sudden changes of the energy level can be reduced. As a material for the electron injecting layer or the electron transporting layer, 8-hydroxyquinoline or a metal complex of its derivative, an oxadiazole derivative and a nitrogen-containing heterocyclic derivative are preferable. An example of the 8-hydroxyquinoline or the metal complex of its derivative is a metal chelate oxinoid compound containing a chelate of oxine (typically 8-quinolinol or 8-hydroxyquinoline). For instance, tris(8-quinolinol) aluminum can be used. Examples of the oxadiazole derivative are as follows.

[Chemical Formula 25]

In the formula, $Ar^{17}$, $Ar^{18}$, $Ar^{19}$, $Ar^{21}$, $Ar^{22}$ and $Ar^{25}$ each represent a substituted or unsubstituted aryl group. $Ar^{17}$, $Ar^{19}$ and $Ar^{22}$ may be the same as or different from $Ar^{18}$, $Ar^{21}$ and $Ar^{25}$ respectively. $Ar^{20}$, $Ar^{23}$ and $Ar^{24}$ each represents a substituted or unsubstituted arylene group. $Ar^{23}$ and $Ar^{24}$ may be mutually the same or different.

Examples of the arylene group are a phenylene group, naphthylene group, biphenylene group, anthranylene group, perylenylene group and pyrenylene group. Examples of the substituent therefor are an alkyl group having 1 to 10 carbon atoms, alkoxy group having 1 to 10 carbon atoms and cyano group. Such an electron transport compound is preferably an electron transport compound that can be favorably formed into a thin film(s). Examples of the electron transport compounds are as follows.

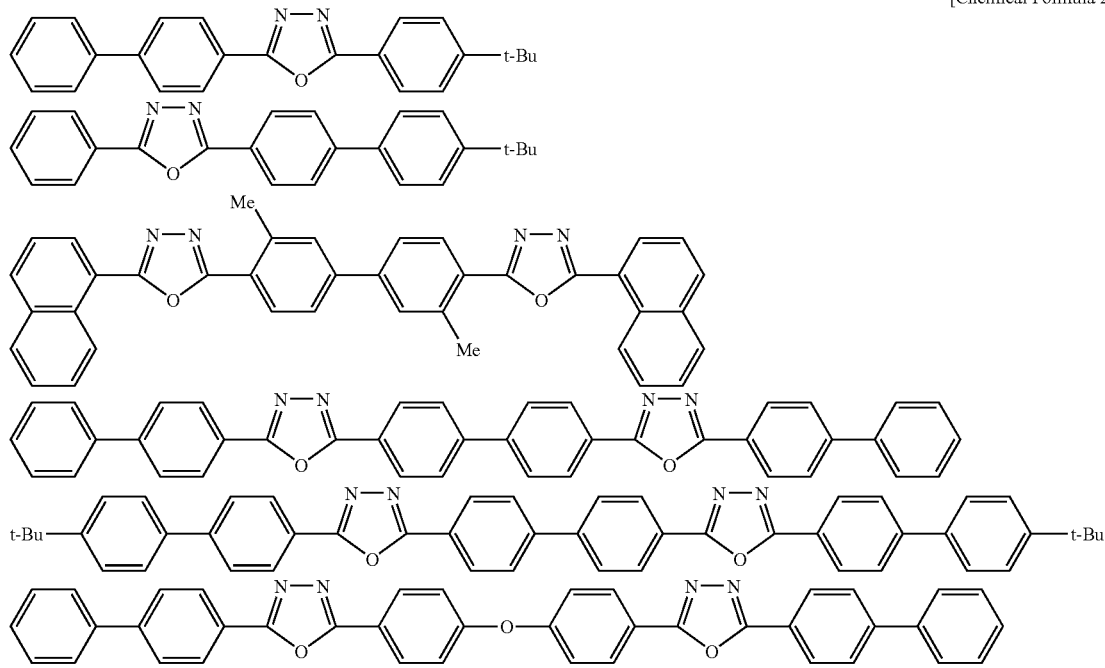

An example of the nitrogen-containing heterocyclic derivative is a nitrogen-containing compound that is not a metal complex, the derivative being formed of an organic compound represented by one of the following general formulae. Examples of the nitrogen-containing heterocyclic derivative are five-membered ring or six-membered ring derivative having a skeleton represented by the formula (A) and a derivative having a structure represented by the formula (B).

[Chemical Formula 27]

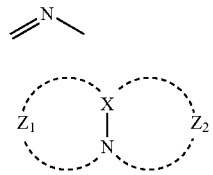

(A)

(B)

In the formula (B), X represents a carbon atom or nitrogen atom. $Z_1$ and $Z_2$ each independently represent an atom group capable of forming a nitrogen-containing heterocycle.

[Chemical Formula 28]

(C)

Preferably, the nitrogen-containing heterocyclic derivative is an organic compound having nitrogen-containing aromatic polycyclic series having a five-membered ring or six-membered ring. When the nitrogen-containing heterocyclic derivative includes such nitrogen-containing aromatic polycyclic series having plural nitrogen atoms, the nitrogen-containing heterocyclic derivative may be a nitrogen-containing aromatic polycyclic organic compound having a skeleton formed by a combination of the skeletons respectively represented by the formulae (A) and (B), or by a combination of the skeletons respectively represented by the formulae (A) and (C).

A nitrogen-containing group of the nitrogen-containing organic compound is selected from nitrogen-containing heterocyclic groups respectively represented by the following general formulae.

[Chemical Formula 29]

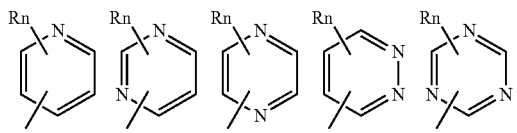

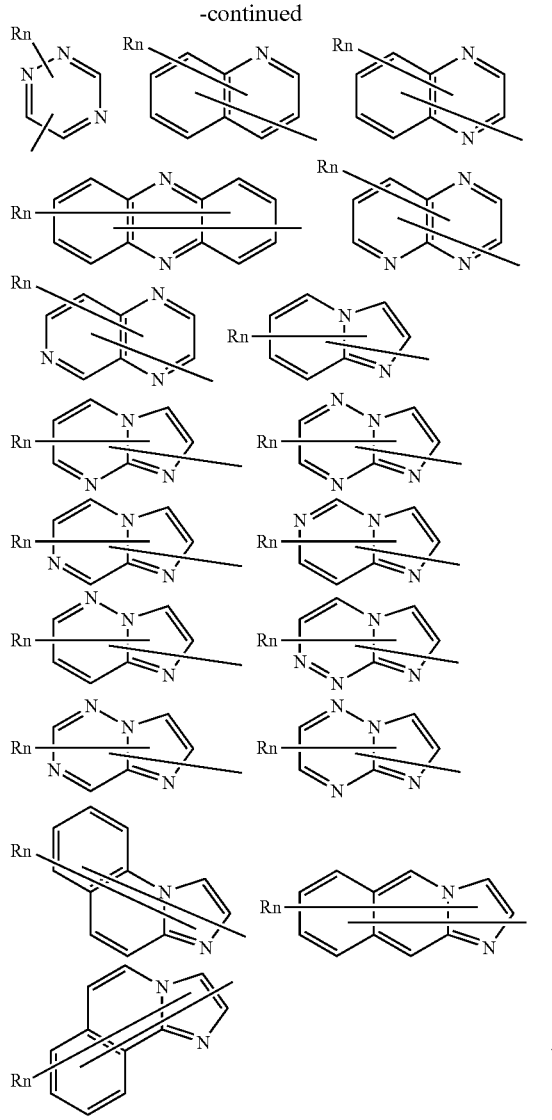

In the formulae: R represents an aryl group having 6 to 40 carbon atoms, heteroaryl group having 3 to 40 carbon atoms, alkyl group having 1 to 20 carbon atoms or alkoxy group having 1 to 20 carbon atoms; and n represents an integer of 0 to 5. When n is an integer of 2 or more, plural R may be mutually the same or different.

A preferable specific compound is a nitrogen-containing heterocyclic derivative represented by the following formula.

HAr-L$^1$-Ar$^1$—Ar$^2$  [Chemical Formula 30]

In the formula, HAr represents a substituted or unsubstituted nitrogen-containing heterocycle having 3 to 40 carbon atoms; L$^1$ represents a single bond, substituted or unsubstituted arylene group having 6 to 40 carbon atoms or substituted or unsubstituted heteroarylene group having 3 to 40 carbon atoms; Ar$^1$ represents a substituted or unsubstituted divalent aromatic hydrocarbon group having 6 to 40 carbon atoms; and Ar$^2$ represents a substituted or unsubstituted aryl group having 6 to 40 carbon atoms or substituted or unsubstituted heteroaryl group having 3 to 40 carbon atoms.

HAr is exemplarily selected from the following group.

[Chemical Formula 31]

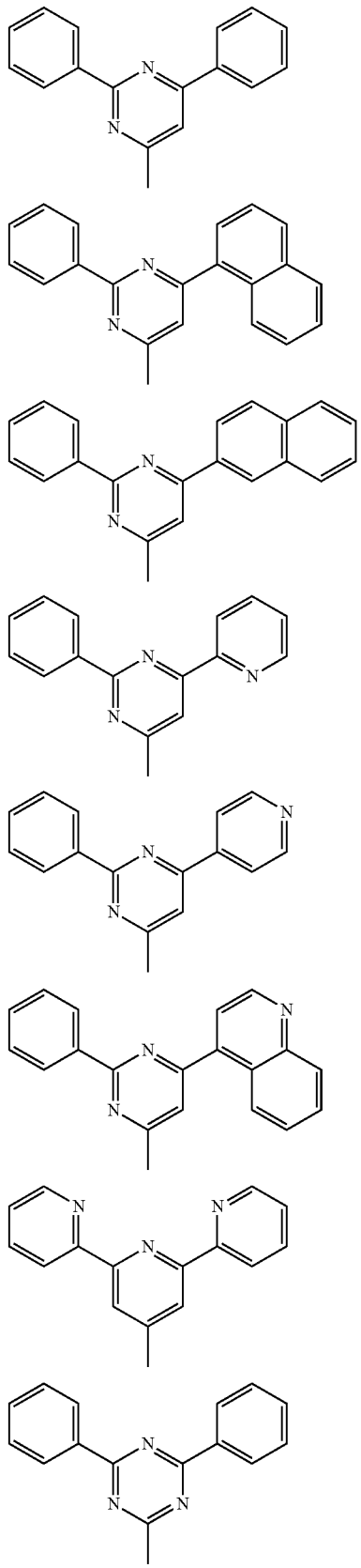

-continued
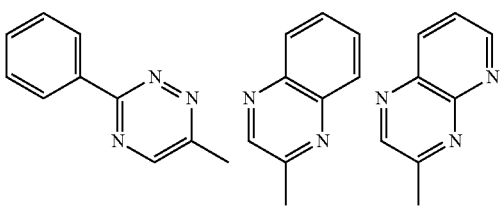 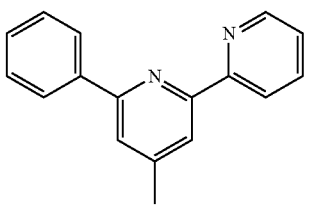
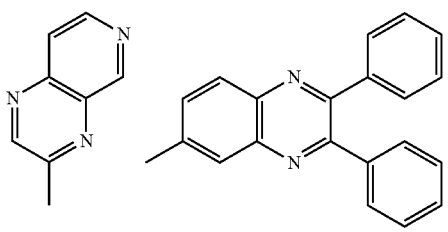
$L^1$ is exemplarily selected from the following group.
[Chemical Formula 32]
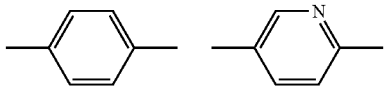
$Ar^2$ is exemplarily selected from the following group.
[Chemical Formula 33]
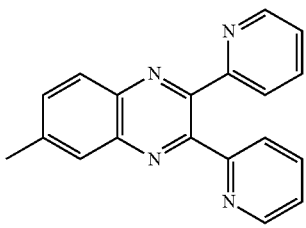
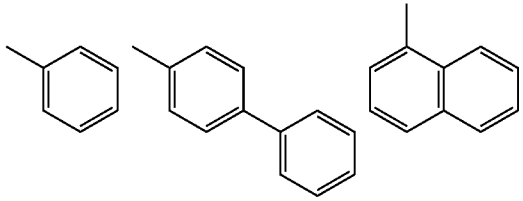
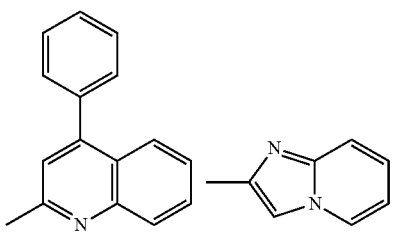 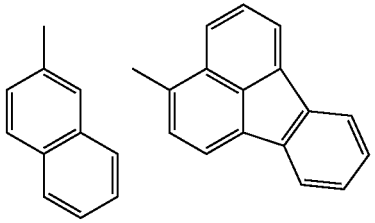
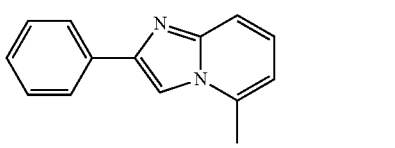 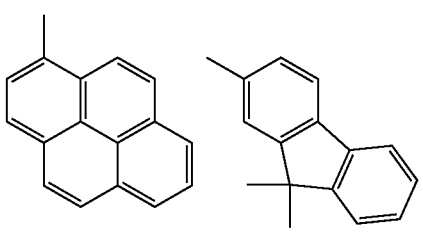
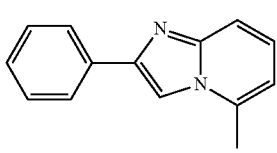
$Ar^1$ is exemplarily selected from the following arylanthranil groups.
[Chemical Formula 34]
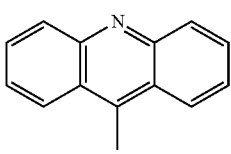 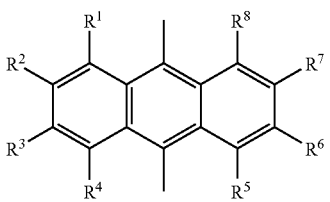

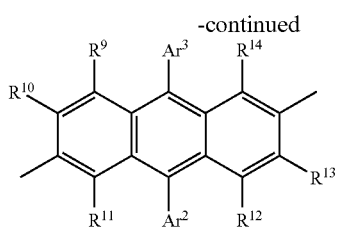

In the formula, $R^1$ to $R^{14}$ each independently represent a hydrogen atom, a halogen atom, an alkyl group having 1 to 20 carbon atoms, an alkoxy group having 1 to 20 carbon atoms, an aryloxy group having 6 to 40 carbon atoms, a substituted or unsubstituted aryl group having 6 to 40 carbon atoms, or a heteroaryl group having 3 to 40 carbon atoms. $Ar^3$ represents a substituted or unsubstituted aryl group having 6 to 40 carbon atoms, or a heteroaryl group having 3 to 40 carbon atoms.

The nitrogen-containing heterocyclic derivative may be a nitrogen-containing heterocyclic derivative in which $R^1$ to $R^8$ in the structure of $Ar^1$ represented by the above formula each represent a hydrogen atom.

Other than the above, the following compound (see JP-A-9-3448) can be favorably used.

[Chemical Formula 35]

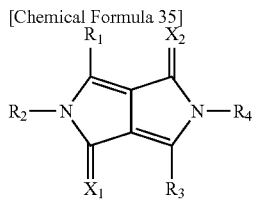

In the formula, $R_1$ to $R_4$ each independently represent a hydrogen atom, a substituted or unsubstituted aliphatic group, a substituted or unsubstituted alicyclic group, a substituted or unsubstituted carbocyclic aromatic ring group, or substituted or unsubstituted heterocyclic group. $X_1$ and $X_2$ each independently represent an oxygen atom, a sulfur atom or a dicyanomethylene group.

Alternatively, the following compound (see JP-A-2000-173774) can also be favorably used.

[Chemical Formula 36]

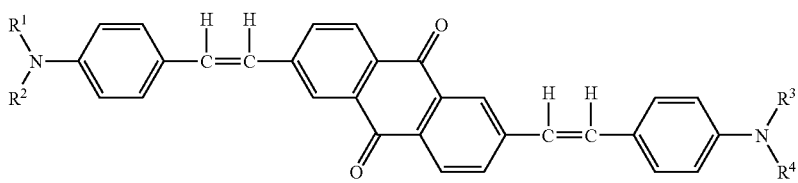

In the formula, $R^1$, $R^2$, $R^3$ and $R^4$, which may be mutually the same or different, each represent an aryl group represented by the following formula.

[Chemical Formula 37]

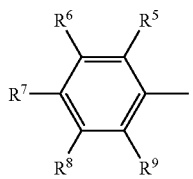

In the formula, $R^5$, $R^6$, $R^7$, $R^8$ and $R^9$, which may be mutually the same or different, each represent a hydrogen atom, a saturated or unsaturated alkoxyl group, alkyl group, amino group or alkylamino group. At least one of $R^5$, $R^6$, $R^7$, $R^8$ and $R^9$ represents a saturated or unsaturated alkoxyl group, alkyl group, amino group or alkylamino group.

A polymer compound containing the nitrogen-containing heterocyclic group or a nitrogen-containing heterocyclic derivative may be used.

The electron transporting layer preferably contains at least one of nitrogen-containing heterocycle derivatives respectively represented by the following formulae (201) to (203).

[Chemical Formula 38]

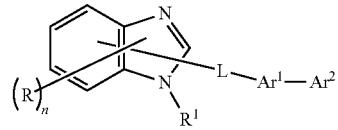  (201)

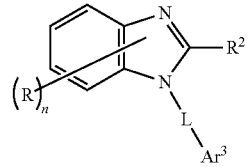  (202)

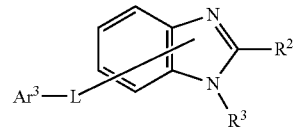  (203)

In the formulae (201) to (203): R represents a hydrogen atom, substituted or unsubstituted aryl group having 6 to 60 carbon atoms, substituted or unsubstituted pyridyl group, substituted or unsubstituted quinolyl group, substituted or unsubstituted alkyl group having 1 to 20 carbon atoms or substituted or unsubstituted alkoxy group having 1 to 20 carbon atoms; n represents an integer of 0 to 4; $R^1$ represents a substituted or unsubstituted aryl group having 6 to 60 carbon atoms, substituted or unsubstituted pyridyl group, substituted or unsubstituted quinolyl group, substituted or unsubstituted alkyl group having 1 to 20 carbon atoms or alkoxy group having 1 to 20 carbon atoms; $R^2$ and $R^3$ each independently represent a hydrogen atom, substituted or unsubstituted aryl group having 6 to 60 carbon atoms, substituted or unsubstituted pyrydyl group, substituted or unsubstituted quinolyl group, substituted or unsubstituted alkyl group having 1 to 20 carbon atoms or substituted or unsubstituted alkoxy group having 1 to 20 carbon atoms; L represents a substituted or unsubstituted arylene group having 6 to 60 carbon atoms, substituted or unsubstituted pyridinylene group, substituted or unsubstituted quinolinylene group or substituted or unsubstituted fluorenylene group; $Ar^1$ represents a substituted or unsubstituted arylene group having 6 to 60 carbon atoms, substituted or unsubstituted pyridinylene group or substituted or unsubstituted quinolinylene group; $Ar^2$ represents a substituted or unsubstituted aryl group having 6 to 60 carbon atoms, substituted or unsubstituted pyridyl group, substituted or unsubstituted quinolyl group, substituted or unsubstituted alkyl group having 1 to 20 carbon atoms or substituted or unsubstituted alkoxy group having 1 to 20 carbon atoms.

$Ar^3$ represents a substituted or unsubstituted aryl group having 6 to 60 carbon atoms, substituted or unsubstituted pyridyl group, substituted or unsubstituted quinolyl group, substituted or unsubstituted alkyl group having 1 to 20 carbon atoms, substituted or unsubstituted alkoxy group having 1 to 20 carbon atoms or a group represented by —$Ar^1$—$Ar^2$ ($Ar^1$ and $Ar^2$ may be the same as the above).

In the formulae (201) to (203), R represents a hydrogen atom, a substituted or unsubstituted aryl group having 6 to 60 carbon atoms, a substituted or unsubstituted pyridyl group, substituted or unsubstituted quinolyl group, a substituted or unsubstituted alkyl group having 1 to 20 carbon atoms, or a substituted or unsubstituted alkoxy group having 1 to 20 carbon atoms.

The aryl group having 6 to 60 carbon atom is preferably an aryl group having 6 to 40 carbon atoms, more preferably an aryl group having 6 to 20 carbon atoms. Examples of such an aryl group are a phenyl group, naphthyl group, anthryl group, phenanthryl group, naphthacenyl group, chrysenyl group, pyrenyl group, biphenyl group, terphenyl group, tolyl group, t-butylphenyl group, (2-phenylpropyl)phenyl group, fluoranthenyl group, fluorenyl group, a monovalent group formed of spirobifluorene, perfluorophenyl group, perfluoronaphthyl group, perfluoroanthryl group, perfluorobiphenyl group, a monovalent group formed of 9-phenylanthracene, a monovalent group formed of 9-(1'naphthyl)anthracene, a monovalent group formed of 9-(2'-naphthyl)anthracene, a monovalent group formed of 6-phenylchrysene, and a monovalent group formed of 9-[4-(diphenylamine)phenyl]anthracene, among which a phenyl group, naphthyl group, biphenyl group, terphenyl group, 9-(10-phenyl)anthryl group, 9-[10-(1'-naphthyl)]anthryl group and 9-[10-(2'-naphthyl)]anthryl group are preferable.

The alkyl group having 1 to 20 carbon atoms is preferably an alkyl group having 1 to 6 carbon atoms. Examples of such an alkyl group are a methyl group, ethyl group, propyl group, butyl group, pentyl group, hexyl group, and a haloalkyl group such as trifluoromethyl group. When such an alkyl group has 3 or more carbon atoms, the alkyl group may be linear, cyclic or branched.

The alkoxy group having 1 to 20 carbon atoms is preferably an alkoxy group having 1 to 6 carbon atoms. Examples of such an alkoxy group are a methoxy group, ethoxy group, propoxy group, butoxy group, pentyloxy group, and hexyloxy group. When such an alkoxy group has 3 or more carbon atoms, the alkoxy group may be linear, cyclic or branched.

Examples of a substituent for the group represented by R are a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms, or a substituted or unsubstituted heteroaryl group having 3 to 40 carbon atoms.

Examples of the halogen atom are fluorine, chlorine, bromine, iodine and the like.

Examples for each of the alkyl group having 1 to 20 carbon atoms, the alkoxy group having 1 to 20 carbon atoms, and an aryl group having 6 to 40 carbon atoms may be the same as the above examples.

Examples of the aryloxy group having 6 to 40 carbon atoms are a phenoxy group and a biphenyloxy group.

Examples of the heteroaryl group having 3 to 40 carbon atoms are a pyrrolyl group, furyl group, thienyl group, silolyl group, pyridyl group, quinolyl group, isoquinolyl group, benzofuryl group, imidazolyl group, pyrimidyl group, carbazolyl group, selenophenyl group, oxadiazolyl group and triazolyl group.

n is an integer in a range of 0 to 4, preferably 0 to 2.

In the formulae (201), $R^1$ represents a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or an alkoxy group having 1 to 20 carbon atoms.

Examples for each of the groups, the preferable number of carbon atoms contained in each of the groups, and preferable examples of the substituent for each of the groups are the same as those described in relation to R.

In the formulae (202) and (203), $R^2$ and $R^3$ each independently represent a hydrogen atom, a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms.

Examples for each of the groups, the preferable number of carbon atoms contained in each of the groups, and preferable examples of the substituent for each of the groups are the same as those described in relation to R.

In the formulae (201) to (203), L represents a substituted or unsubstituted arylene group having 6 to 60 carbon atoms, a substituted or unsubstituted pyridinylene group, a substituted or unsubstituted quinolinylene group, or a substituted or unsubstituted fluorenylene group.

The arylene group having 6 to 60 carbon atoms is preferably an arylene group having 6 to 40 carbon atoms, more preferably an arylene group having 6 to 20 carbon atoms. An example of such an arylene group is a divalent group formed by removing one hydrogen atom from the aryl group having been described in relation to R. Examples of a substituent for the group represented by L are the same as those described in relation to R.

Alternatively, L is preferably a group selected from groups represented by the following formulae.

[Chemical Formula 39]

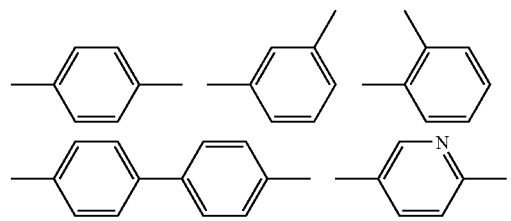

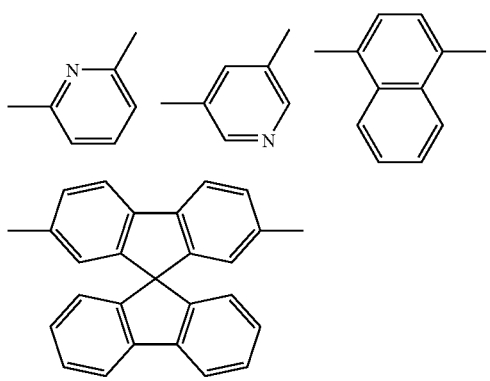

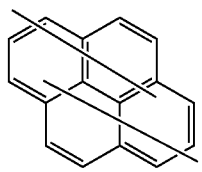
(107)

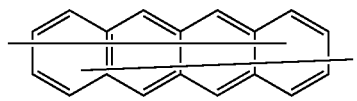
(108)

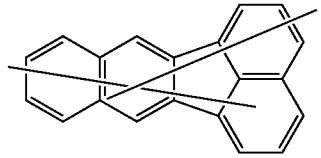
(109)

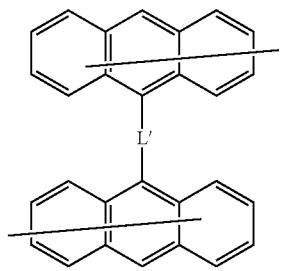
(110)

In the formulae (201), Ar¹ represents a substituted or unsubstituted arylene group having 6 to 60 carbon atoms, a substituted or unsubstituted pyridinylene group, or a substituted or unsubstituted quinolinylene group. Examples of a substituent for the groups represented by Ar¹ and Ar³ are the same as those described in relation to R.

Alternatively, Ar¹ is preferably selected from fused ring groups respectively represented by the following formulae (101) to (110).

[Chemical Formula 40]

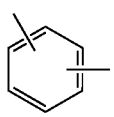
(101)

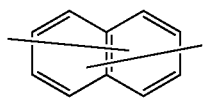
(102)

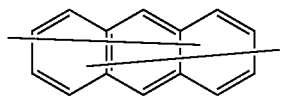
(103)

(104)

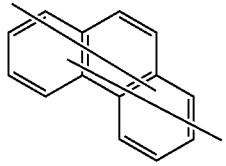
(105)

(106)

In the formulae (101) to (110), the fused rings each may be linked with a link group formed of a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms or a substituted or unsubstituted heteroaryl group having 3 to 40 carbon atoms. When the rings each are linked with plural link groups, the plural link groups may be mutually the same or different. Examples for each of the groups are the same as those described above.

In the formula (110), L' represents a single bond or a group selected from groups represented by the following formulae.

[Chemical Formula 41]

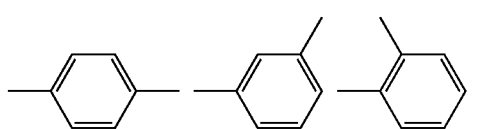

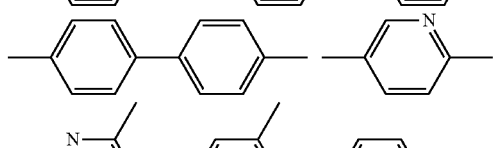

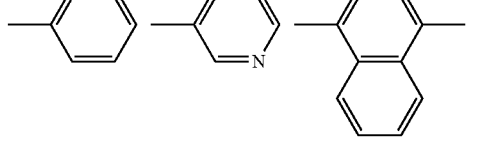

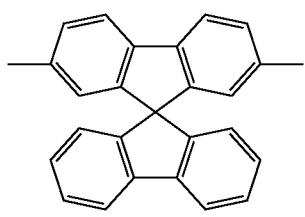
The structure of Ar¹ represented by the formula (103) is preferably a fused ring group represented by any one of the following formulae (111) to (125).
[Chemical Formula 42]
(111)
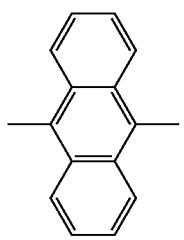
(112)
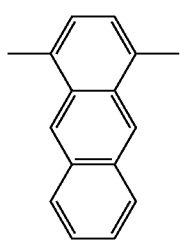
(113)
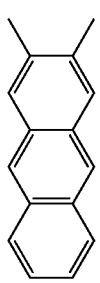
(114)
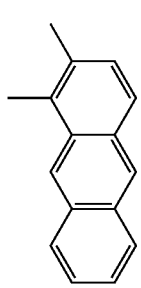
(115)
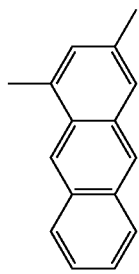
(116)
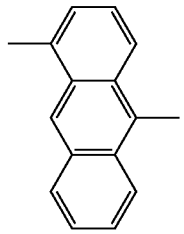
(117)
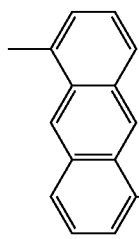
(118)
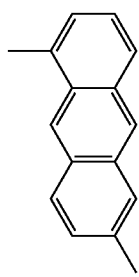
(119)
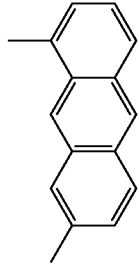
(120)
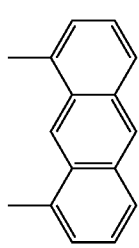

-continued (121)
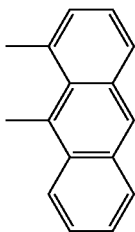

(122)
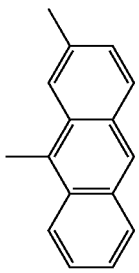

(123)
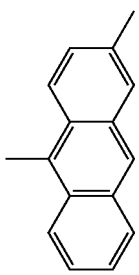

(124)
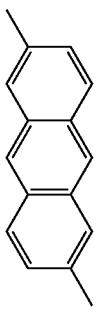

(125)
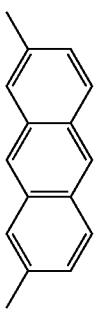

In the formulae (11) to (125), the fused rings each may be linked with a link group formed of a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms or a substituted or unsubstituted heteroaryl group having 3 to 40 carbon atoms. When the rings each are linked with plural link groups, the plural link groups may be mutually the same or different. Examples for each of the groups are the same as those described above.

In the formula (201), $Ar^2$ represents a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms.

Examples for each of the groups, the preferable number of carbon atoms contained in each of the groups, and preferable examples of the substituent for each of the groups are the same as those described in relation to R.

In the formulae (202) and (203), $Ar^3$ represents a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, a substituted or unsubstituted alkoxy group having 1 to 20 carbon atoms, or a group represented by —$Ar^1$—$Ar^2$ ($Ar^1$ and $Ar^2$ are the same as the above).

Examples for each of the groups, the preferable number of carbon atoms contained in each of the groups, and preferable examples of the substituent for each of the groups are the same as those described in relation to R.

Alternatively, $Ar^3$ is preferably selected from fused ring groups respectively represented by the following formulae (126) to (135).

[Chemical Formula 43]

(126)
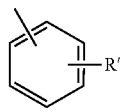

(127)
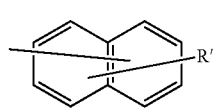

(128)
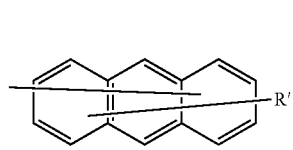

(129)
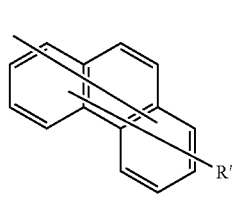

(130)
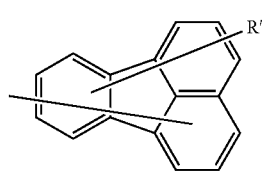

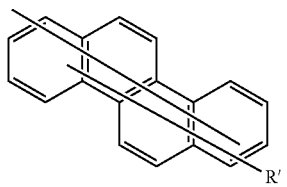
(131)

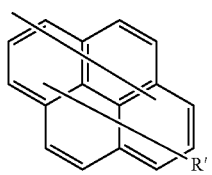
(132)

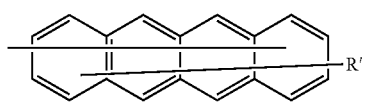
(133)

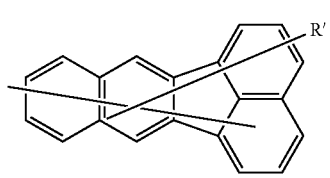
(134)

(135)

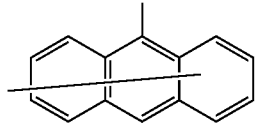

[Chemical Formula 44]

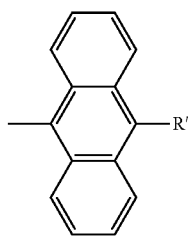
(136)

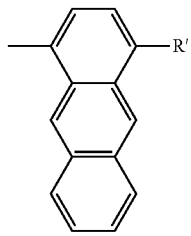
(137)

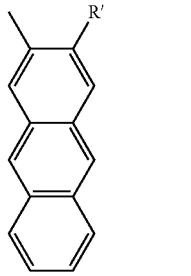
(138)

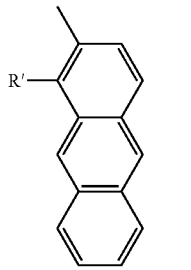
(139)

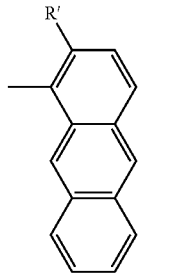
(140)

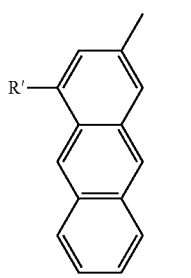
(141)

In the formulae (126) to (135), the fused rings each may be linked with a link group formed of a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms or a substituted or unsubstituted heteroaryl group having 3 to 40 carbon atoms. When the rings each are linked with plural link groups, the plural link groups may be mutually the same or different. Examples for each of the groups are the same as those described above.

In the formula (135), L' represents the same as the above.

In the formulae (126) to (135), R' represents a hydrogen atom, a substituted or unsubstituted alkyl group having 1 to 20 carbon atoms, a substituted or unsubstituted aryl group having 6 to 40 carbon atoms, or a substituted or unsubstituted heteroaryl group having 3 to 40 carbon atoms. Examples for each of the groups are the same as those described above.

The structure of $Ar^3$ represented by the formula (128) is preferably a fused ring group represented by any one of the following formulae (136) to (158).

(142) 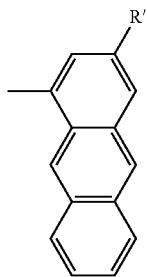
(143) 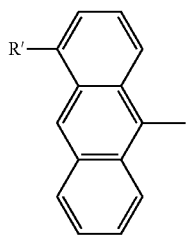
(144) 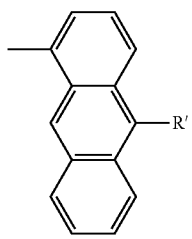
(145) 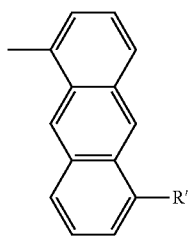
(146) 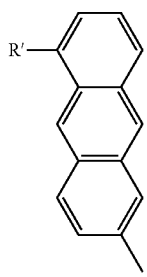
(147) 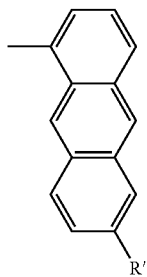
(148) 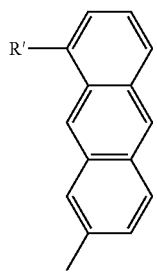
(149) 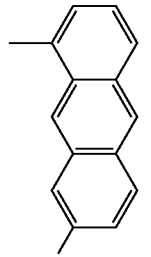
(150) 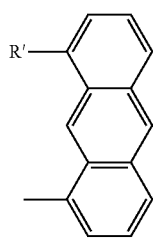
(151) 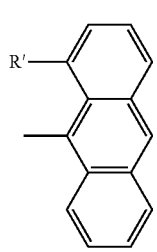
(152) 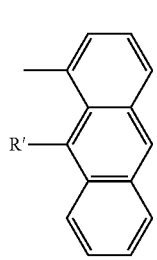
(153) 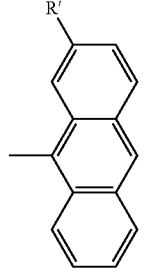

(154) 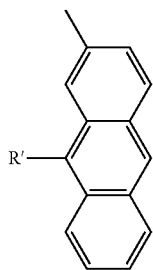

(155) 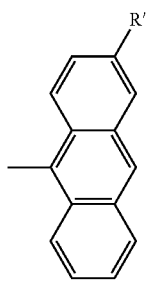

(156) 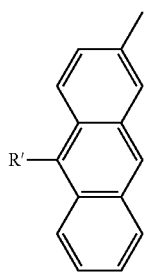

(157) 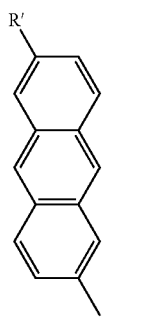

(158) 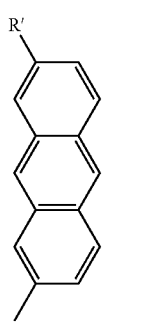

In the formulae (136) to (158), the fused rings each may be linked with a link group formed of a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms or a substituted or unsubstituted heteroaryl group having 3 to 40 carbon atoms. When the rings each are linked with plural link groups, the plural link groups may be mutually the same or different. Examples for each of the groups are the same as those described above. R' is the same as the above.

Alternatively, $Ar^2$ and $Ar^3$ each independently are preferably a group selected from groups represented by the following formulae.

[Chemical Formula 45]

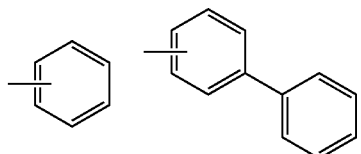

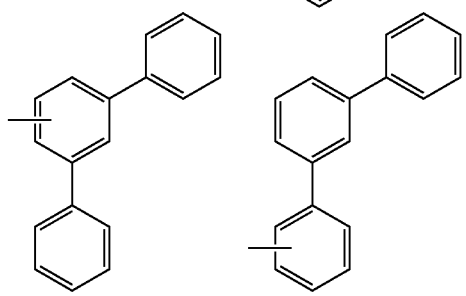

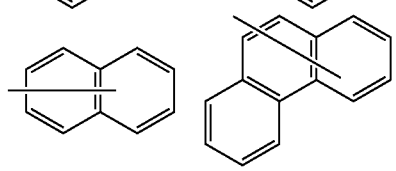

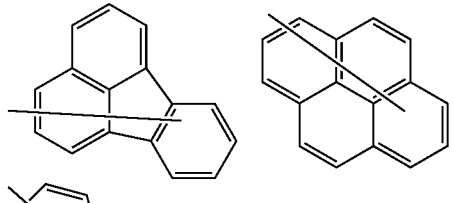

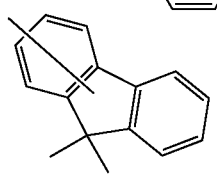

Examples of the nitrogen-containing heterocyclic derivative represented by any one of the formulae (201) to (203) according to the aspect of the invention will be shown below. However, the invention is not limited to the exemplary compounds shown below.

In the chart shown below, HAr represents any one of the following structures respectively in the structures represented by the formulae (201) to (203).

[Chemical Formula 46]

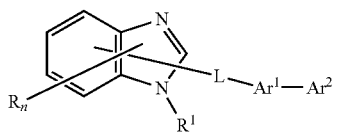

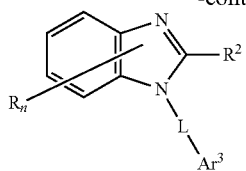
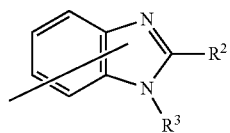

-continued
[Chemical Formula 47]
| | HAr | L | HAr—L—Ar¹—Ar² Ar¹ | Ar² |
|---|---|---|---|---|
| 6 | 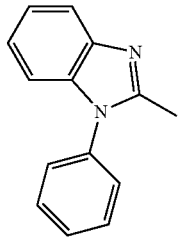 | 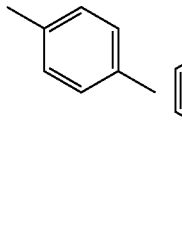 | 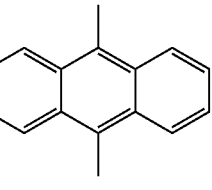 | 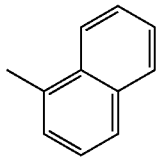 |
| 7 | 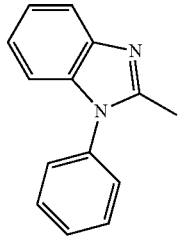 | 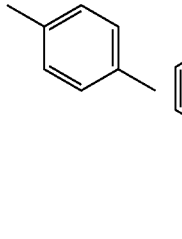 | 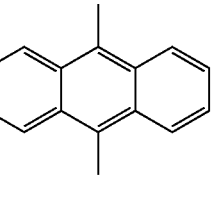 | 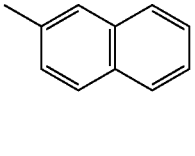 |
| 8 | 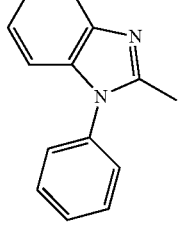 | 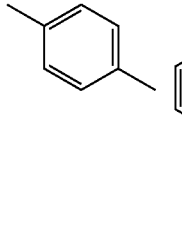 | 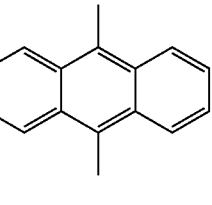 | 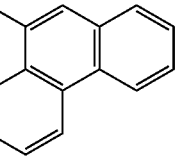 |
| 9 | 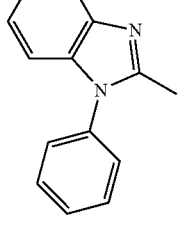 | 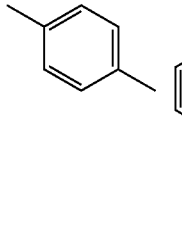 | 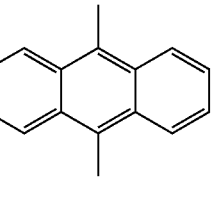 | 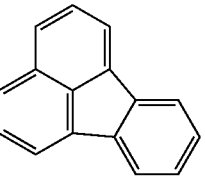 |
| 10 | 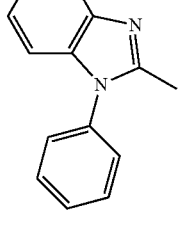 | 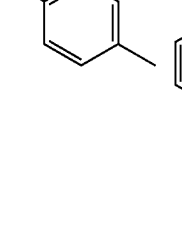 | 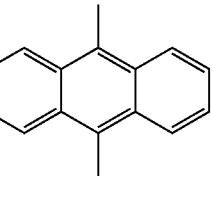 | 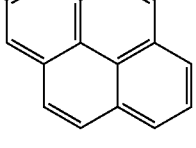 |
| 11 | 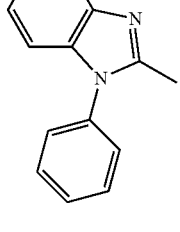 | 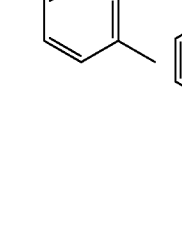 | 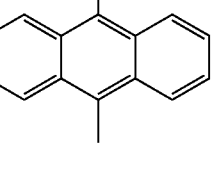 | 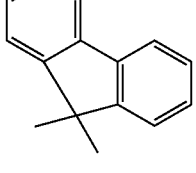 |

[Chemical Formula 47]
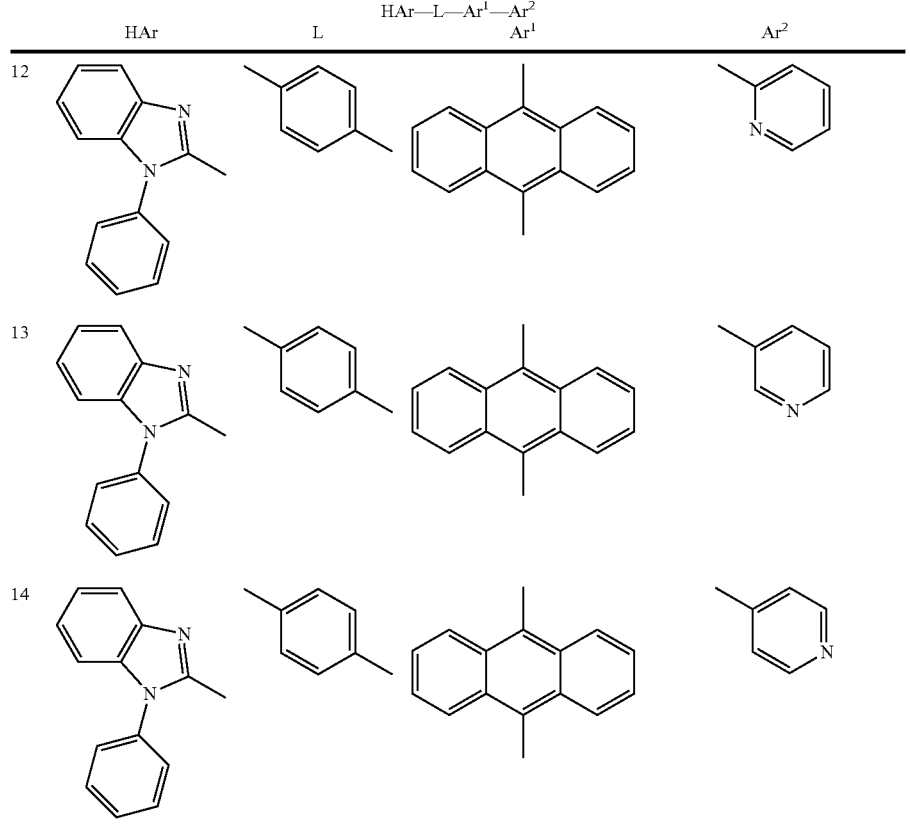
[Chemical Formula 48]
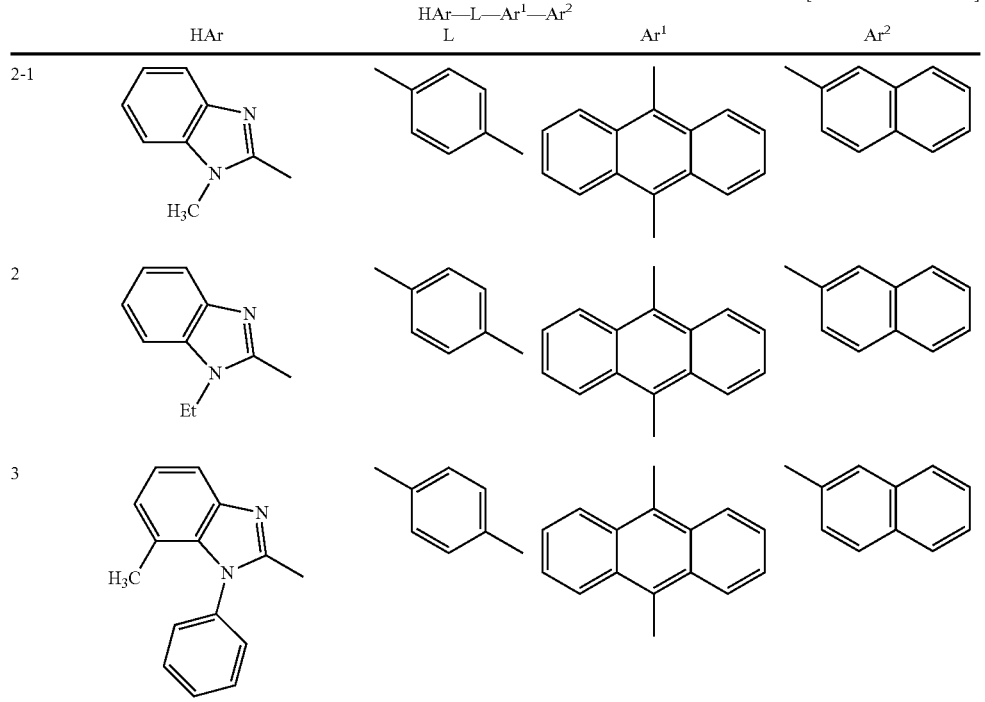

-continued

[Chemical Formula 48]

HAr—L—Ar¹—Ar²

| | HAr | L | Ar¹ | Ar² |
|---|---|---|---|---|
| 4 | | | | |
| 5 | | | | |
| 6 | | | | |
| 7 | | | | |
| 8 | | | | |

[Chemical Formula 48]
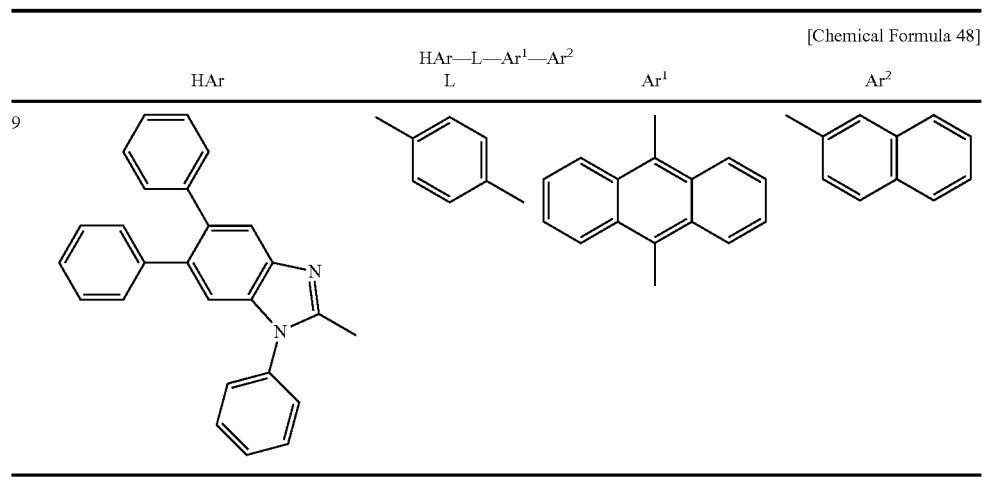
[Chemical Formula 49]
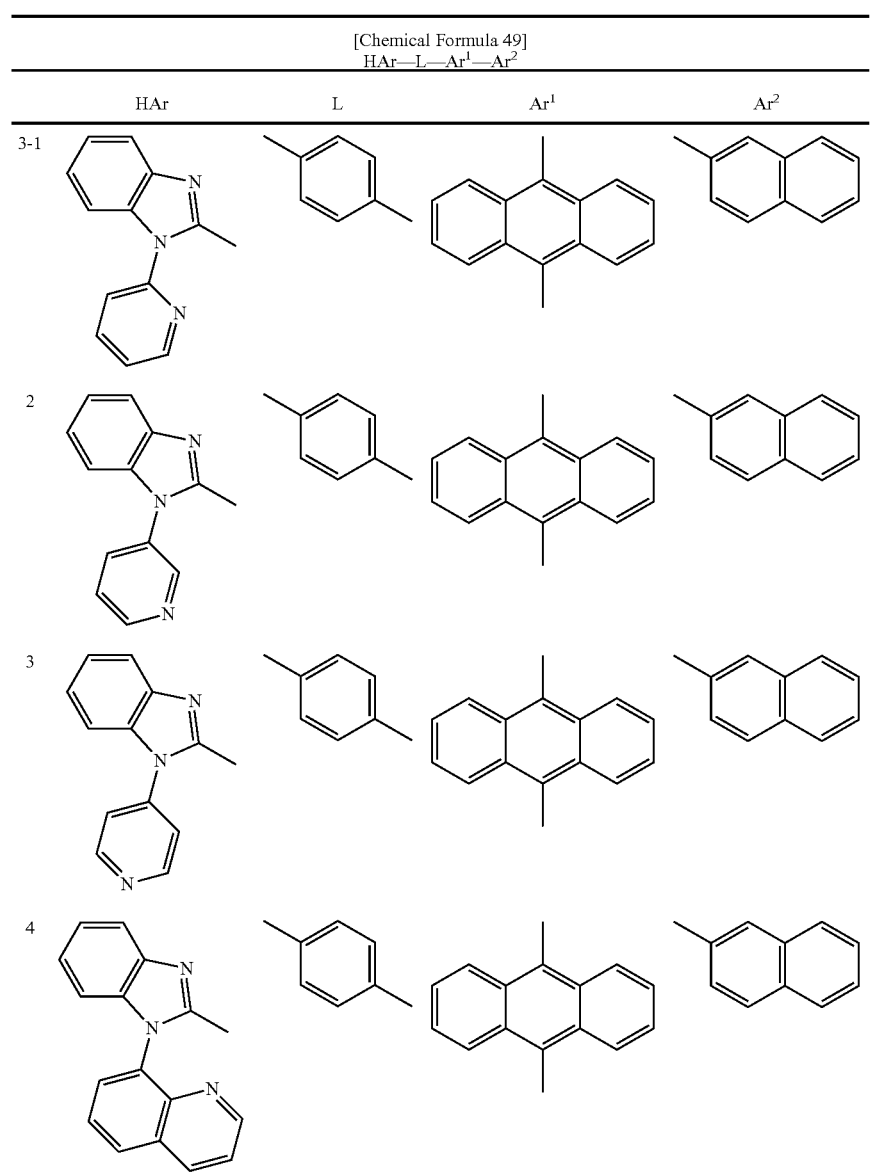

-continued
[Chemical Formula 49]
HAr—L—Ar¹—Ar²
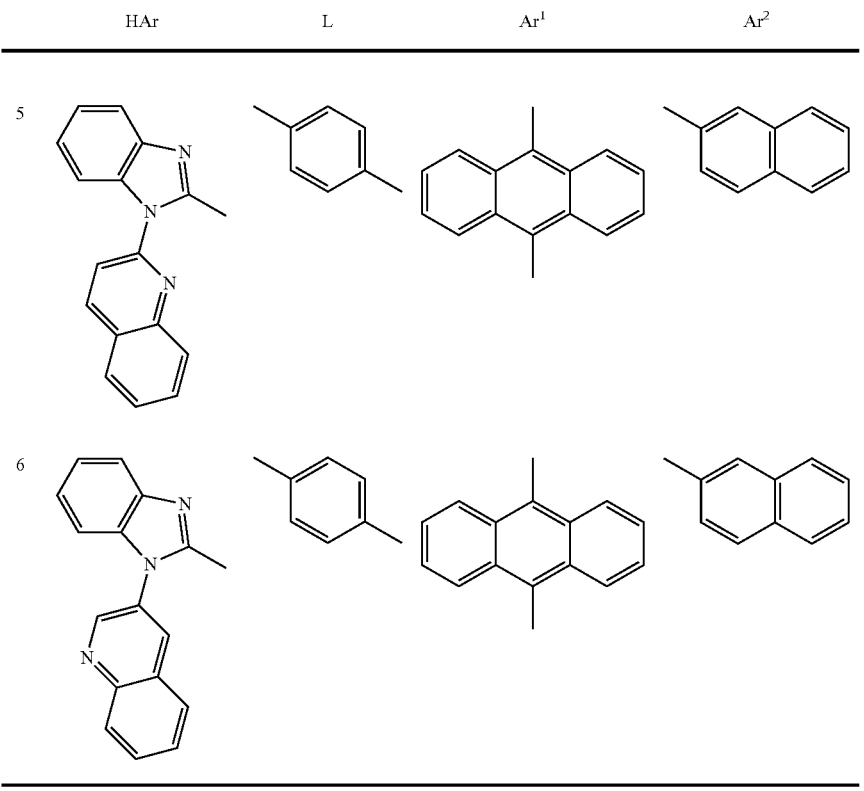
[Chemical Formula 50]
HAr—L—Ar¹—Ar²
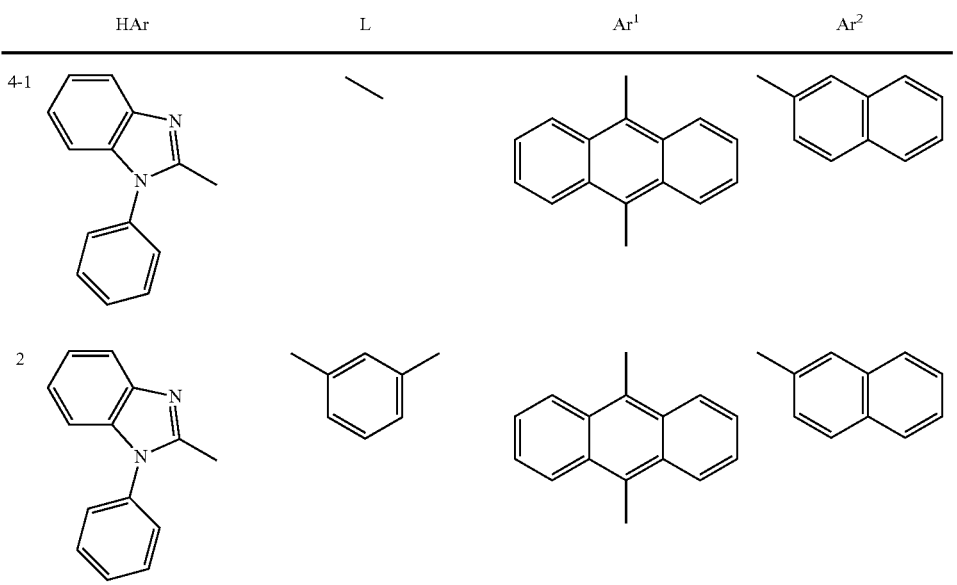

-continued
[Chemical Formula 50]
HAr—L—Ar¹—Ar²
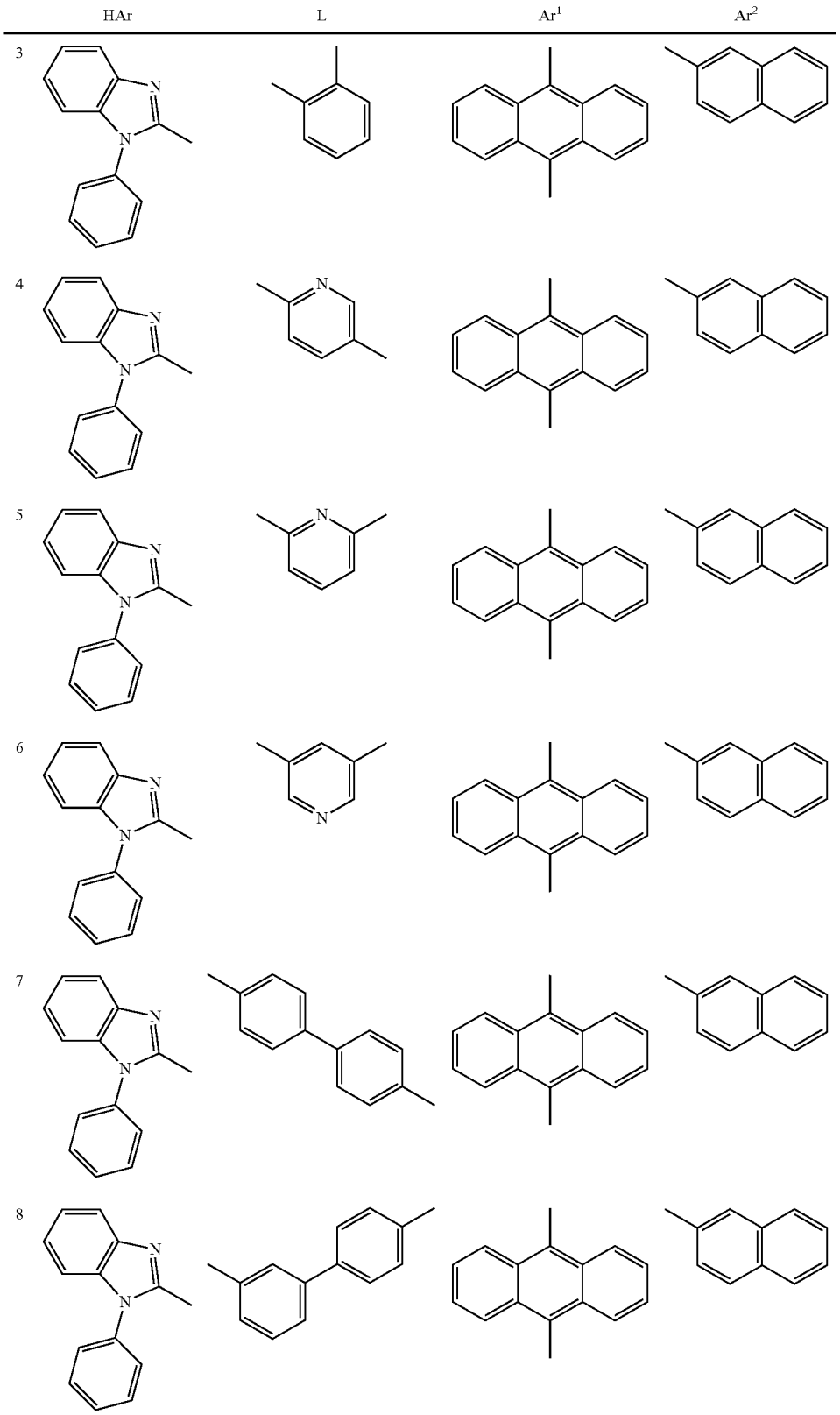

[Chemical Formula 50]
HAr—L—Ar¹—Ar²
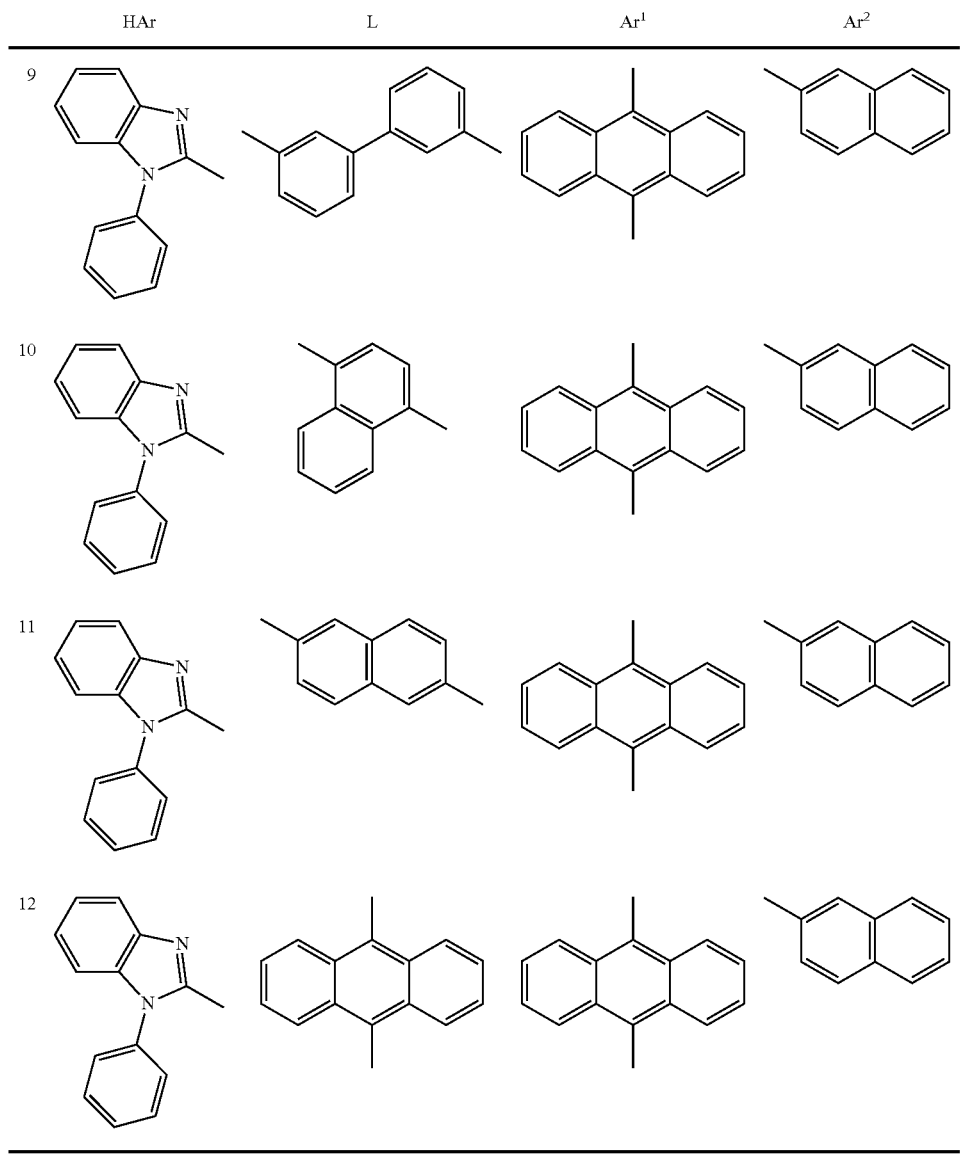
[Chemical Formula 51]
HAr—L—Ar¹—Ar²
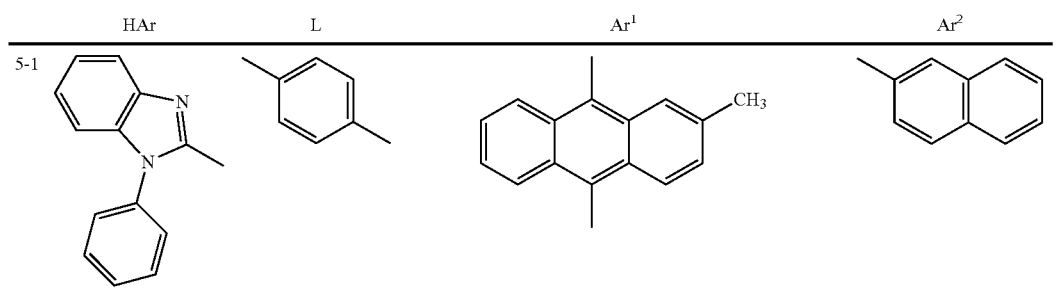

-continued
[Chemical Formula 51]
HAr—L—Ar¹—Ar²
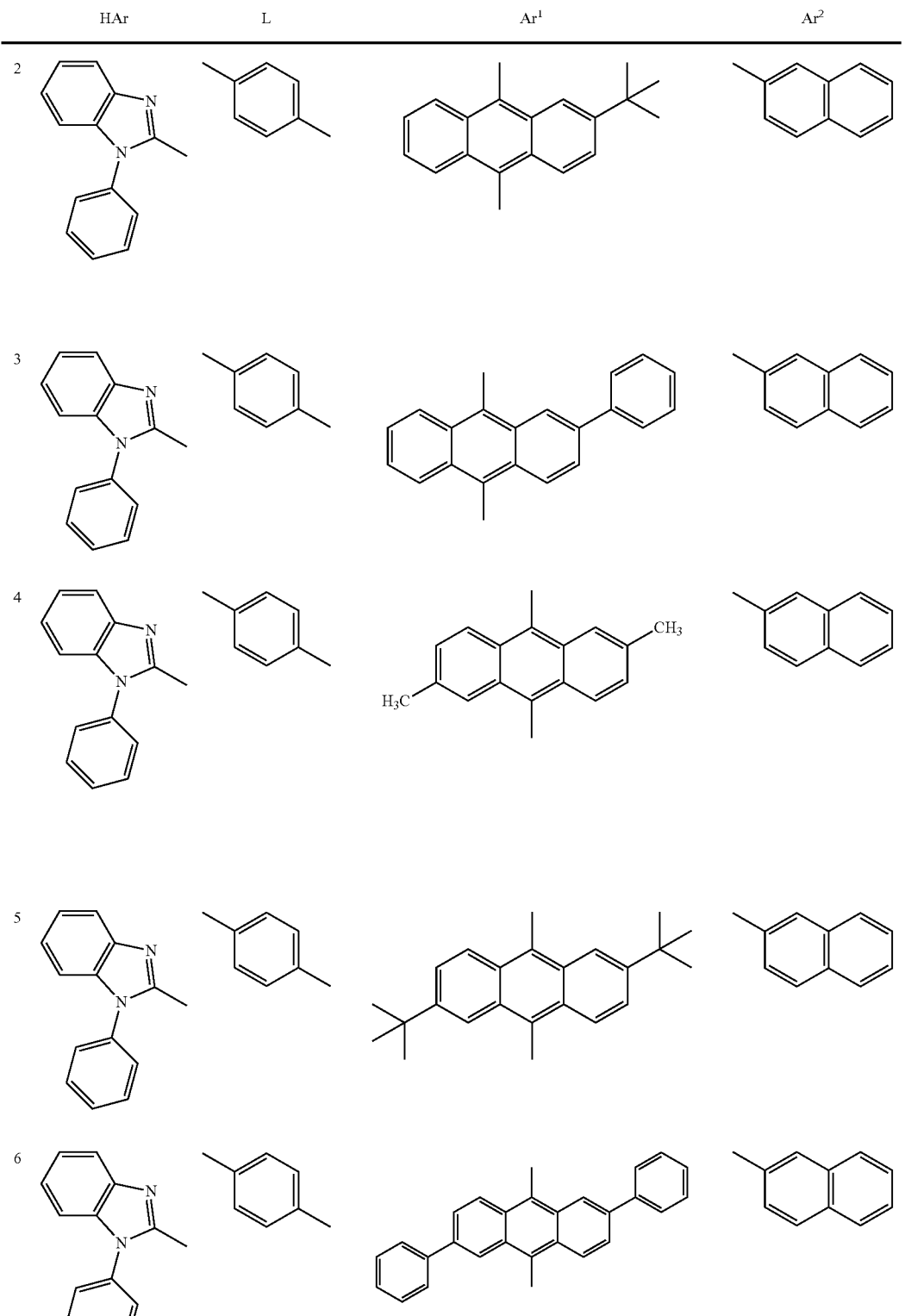

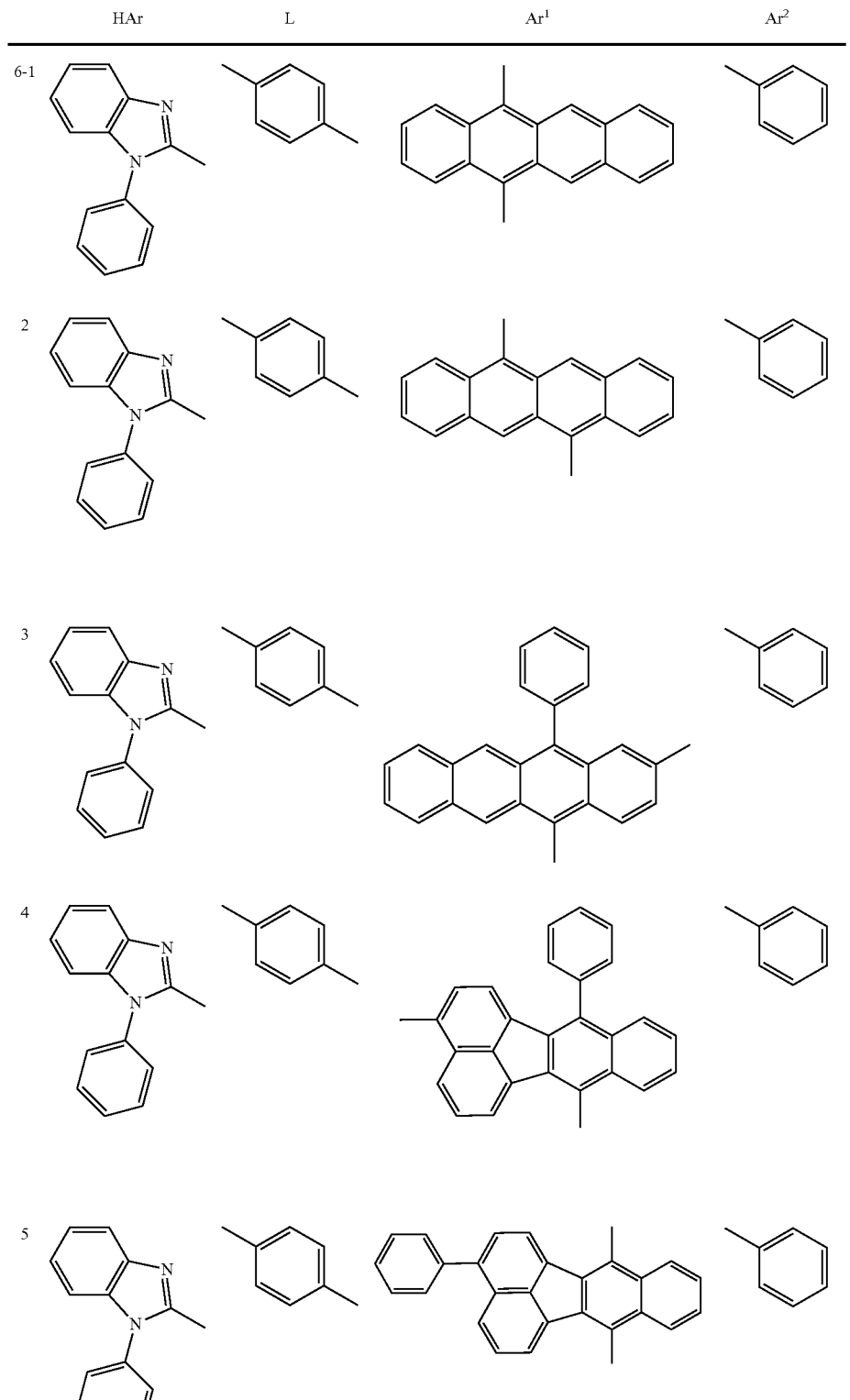

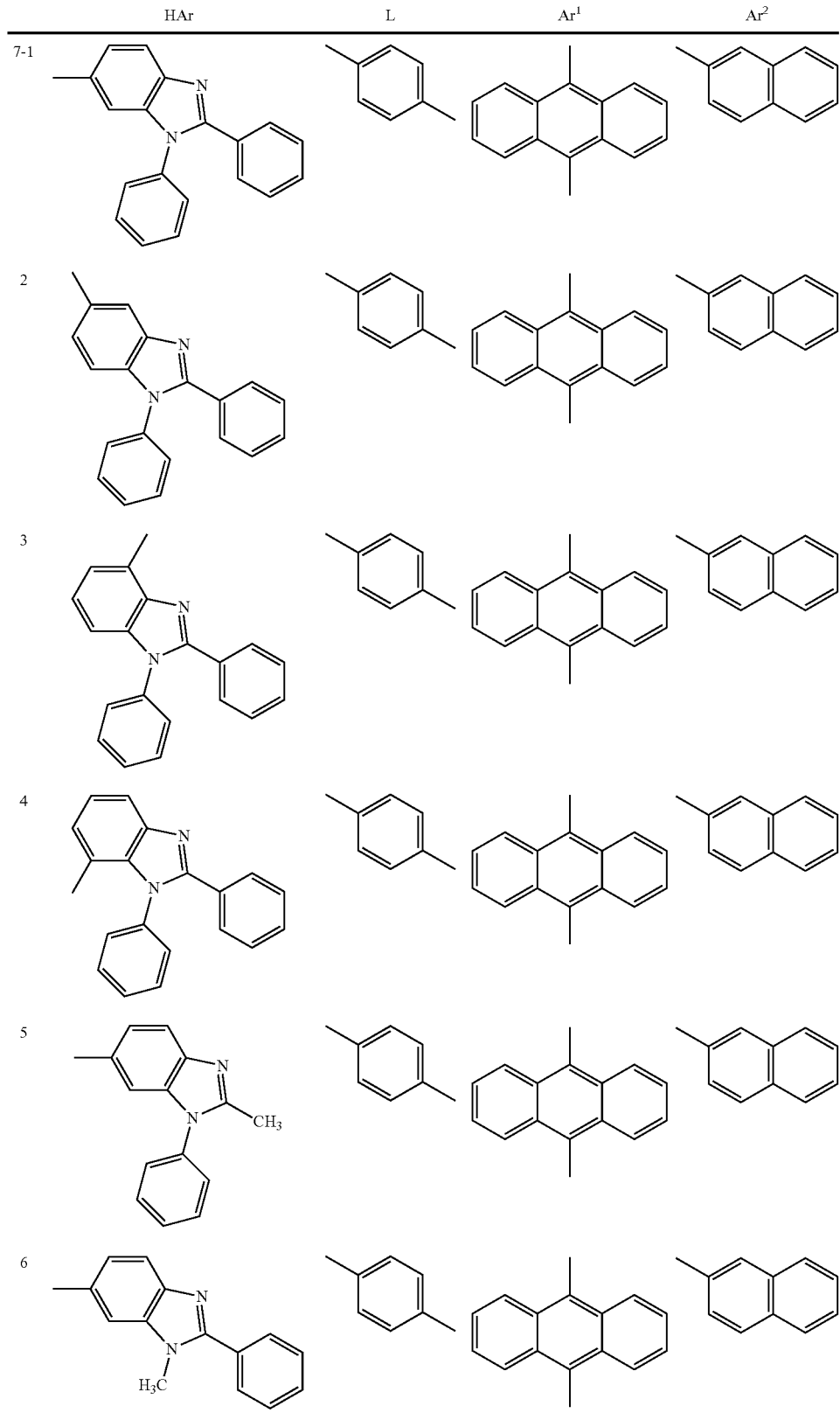

-continued
[Chemical Formula 53]
HAr—L—Ar¹—Ar²
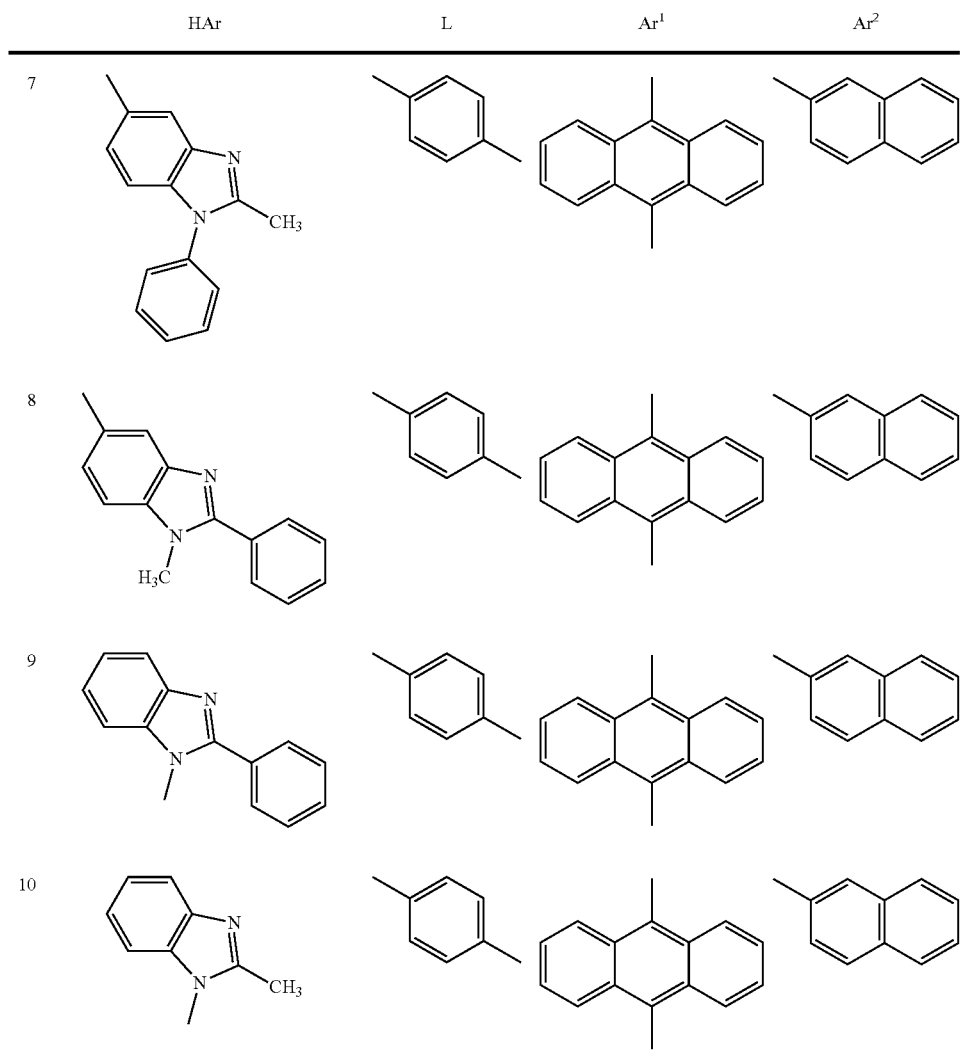
[Chemical Formula 54]
HAr—L—Ar¹—Ar²
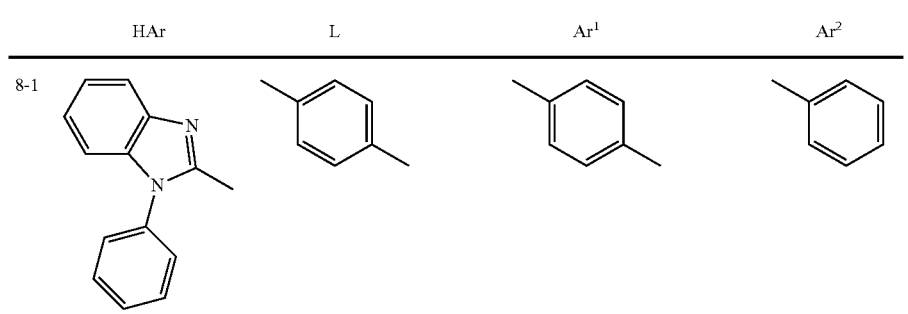

-continued

[Chemical Formula 54]
HAr—L—Ar¹—Ar²

| | HAr | L | Ar¹ | Ar² |
|---|---|---|---|---|
| 2 | 1-phenyl-2-methylbenzimidazole | 1,4-phenylene | 1,3-phenylene | phenyl |
| 3 | 1-phenyl-2-methylbenzimidazole | 1,4-phenylene | 1,4-naphthylene | phenyl |
| 4 | 1-phenyl-2-methylbenzimidazole | 1,4-phenylene | 2,6-naphthylene | phenyl |
| 5 | 1-phenyl-2-methylbenzimidazole | 1,4-phenylene | 9,10-phenanthrylene | phenyl |
| 6 | 1-phenyl-2-methylbenzimidazole | 1,4-phenylene | 2,7-phenanthrylene | phenyl |
| 7 | 1-phenyl-2-methylbenzimidazole | 1,4-phenylene | 9-phenanthryl | H |

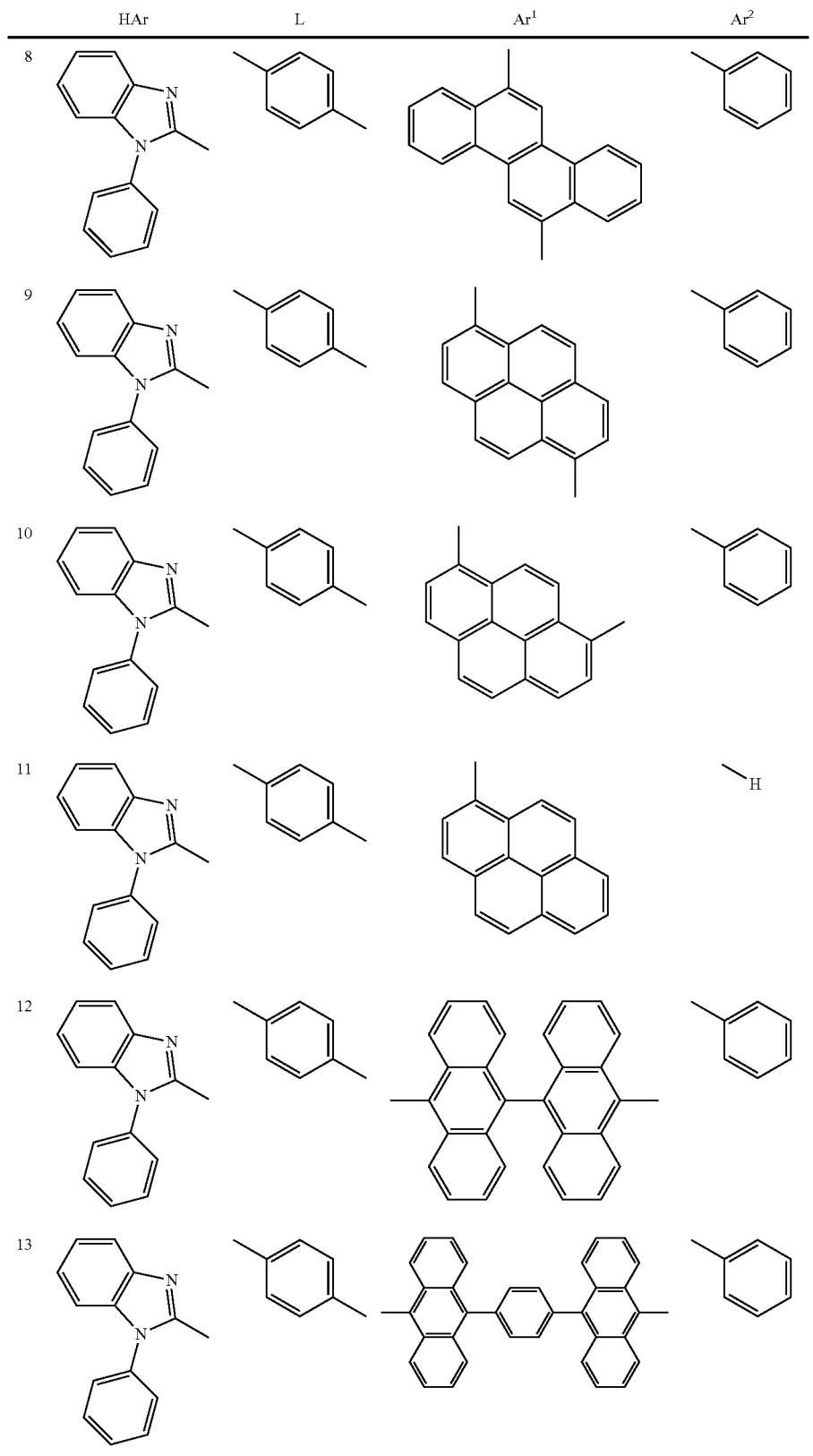

[Chemical Formula 55]
HAr—L—Ar¹—Ar²

[Chemical Formula 55]
HAr—L—Ar¹—Ar²
| | HAr | L | Ar¹ | Ar² |
|---|---|---|---|---|
| 8 | 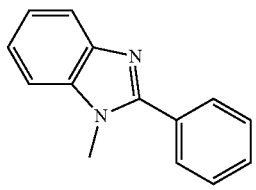 | 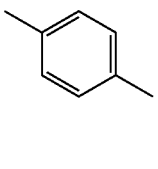 | 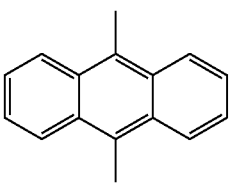 | 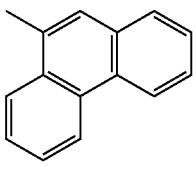 |
| 9 | 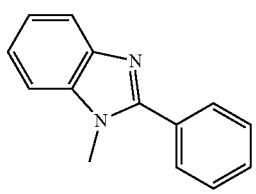 | 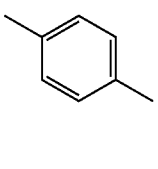 | 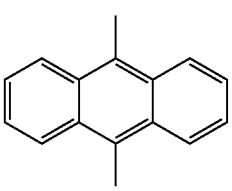 | 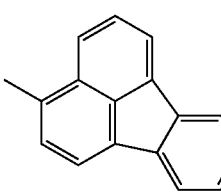 |
| 10 | 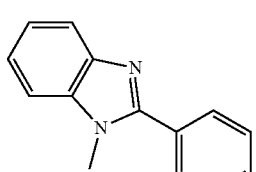 | 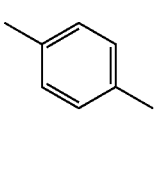 | 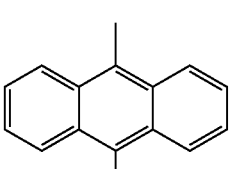 | 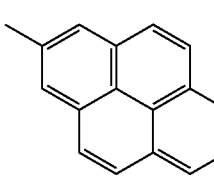 |
| 11 | 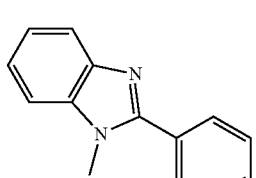 | 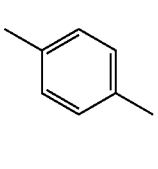 | 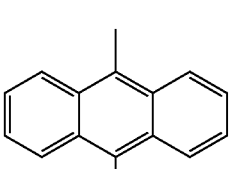 | 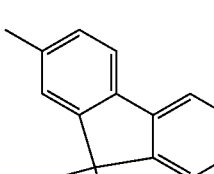 |
| 12 | 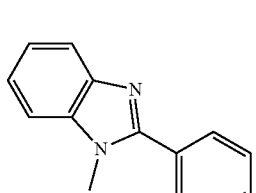 | 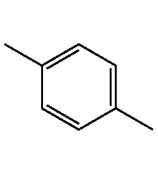 | 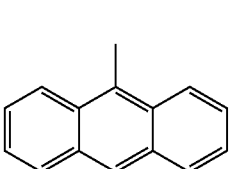 | 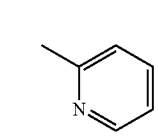 |
| 13 | 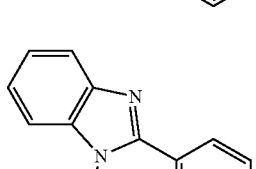 | 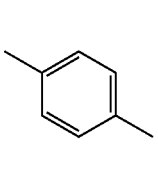 | 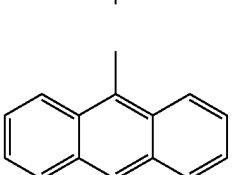 | 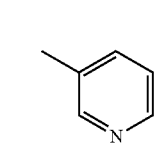 |
| 14 | 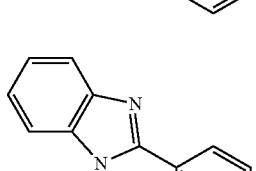 | 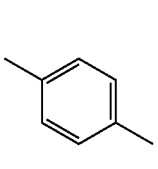 | 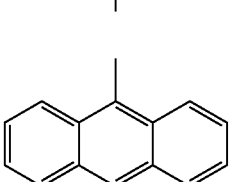 | 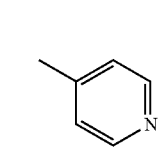 |

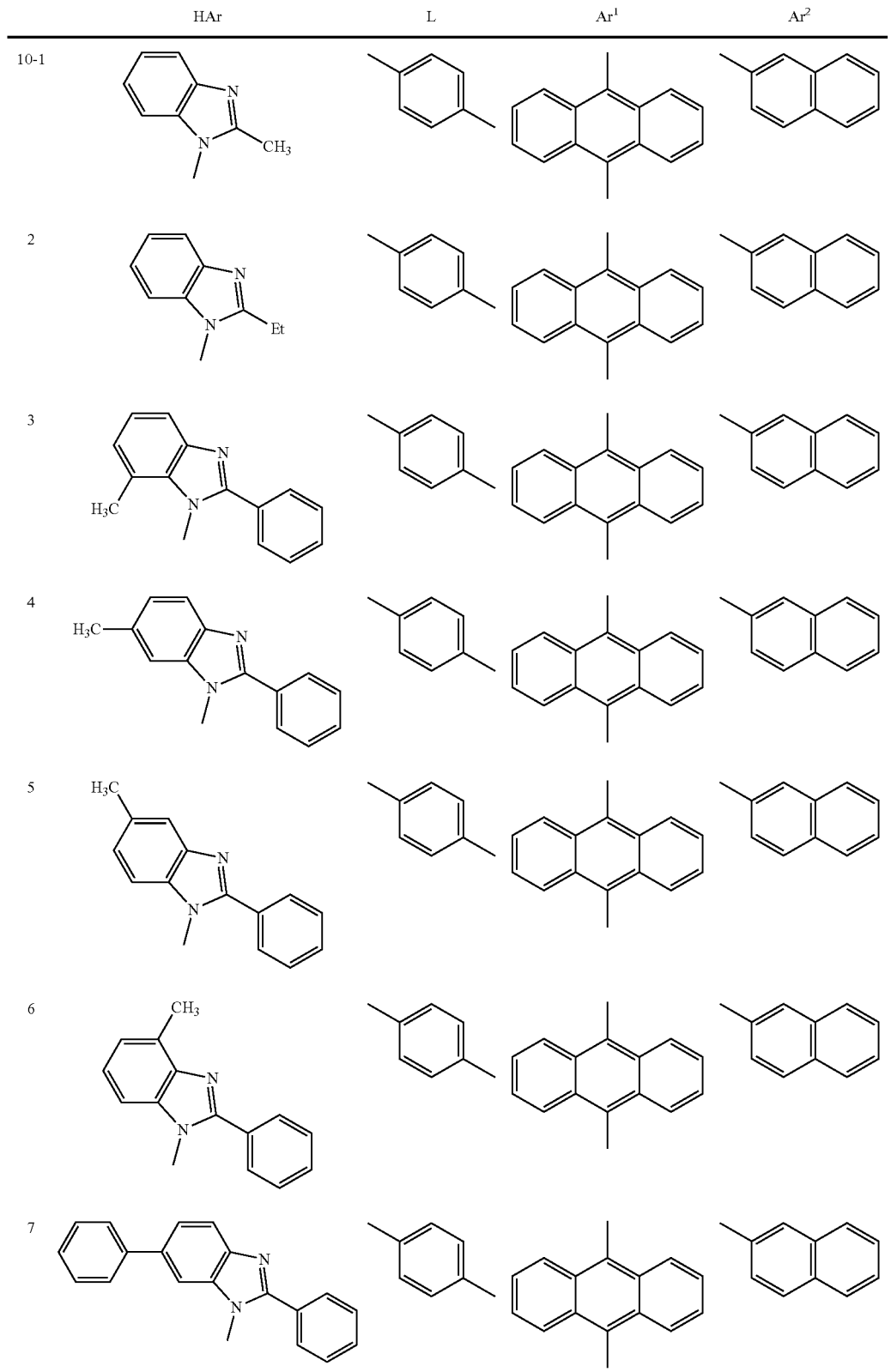

-continued
[Chemical Formula 56]
HAr—L—Ar¹—Ar²
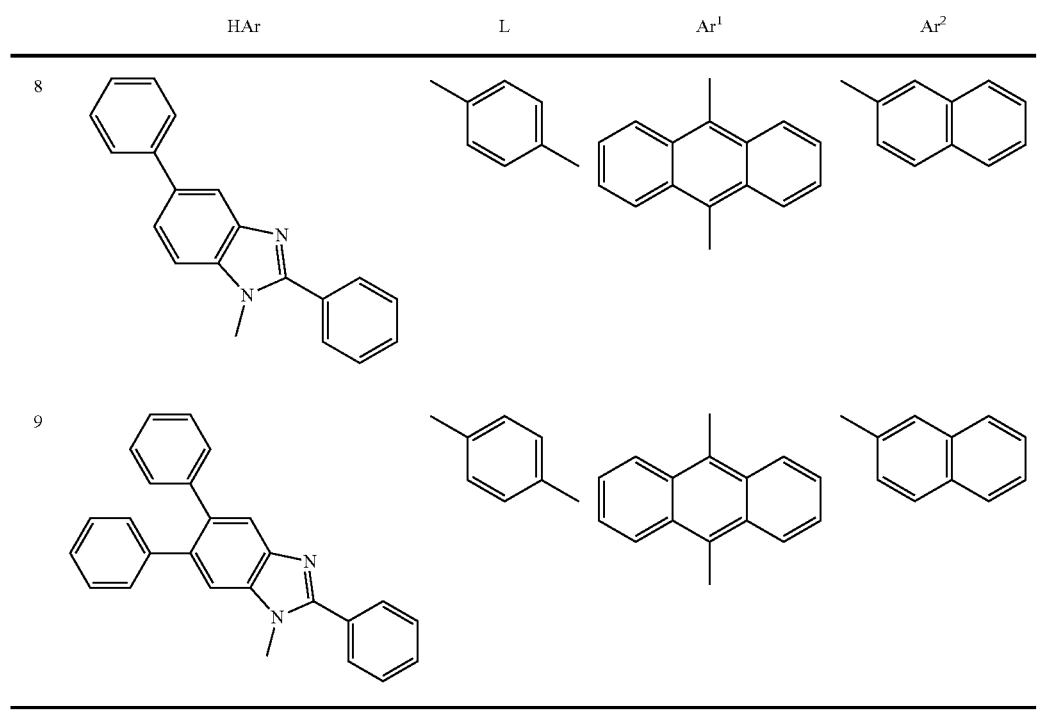
[Chemical Formula 57]
HAr—L—Ar¹—Ar²
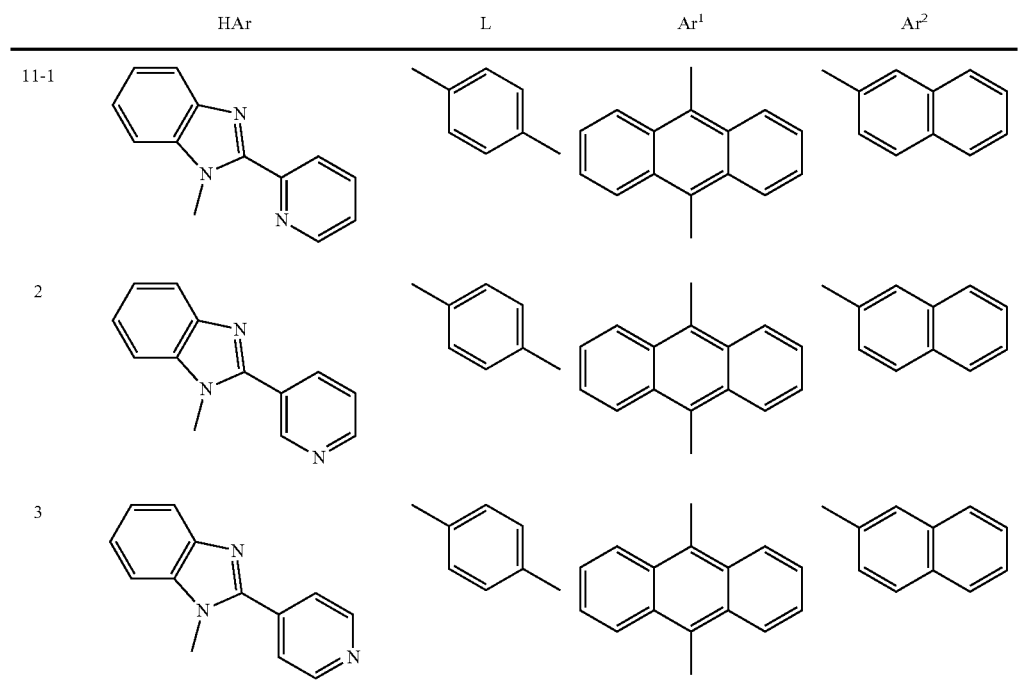

-continued
[Chemical Formula 57]
HAr—L—Ar¹—Ar²
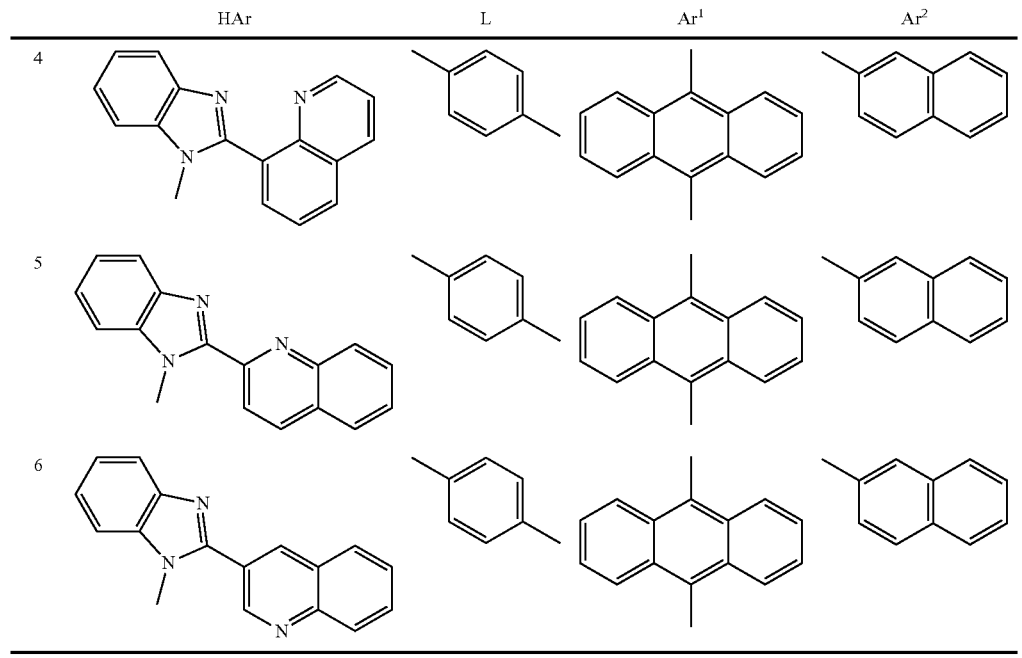
[Chemical Formula 58]
HAr—L—Ar¹—Ar²
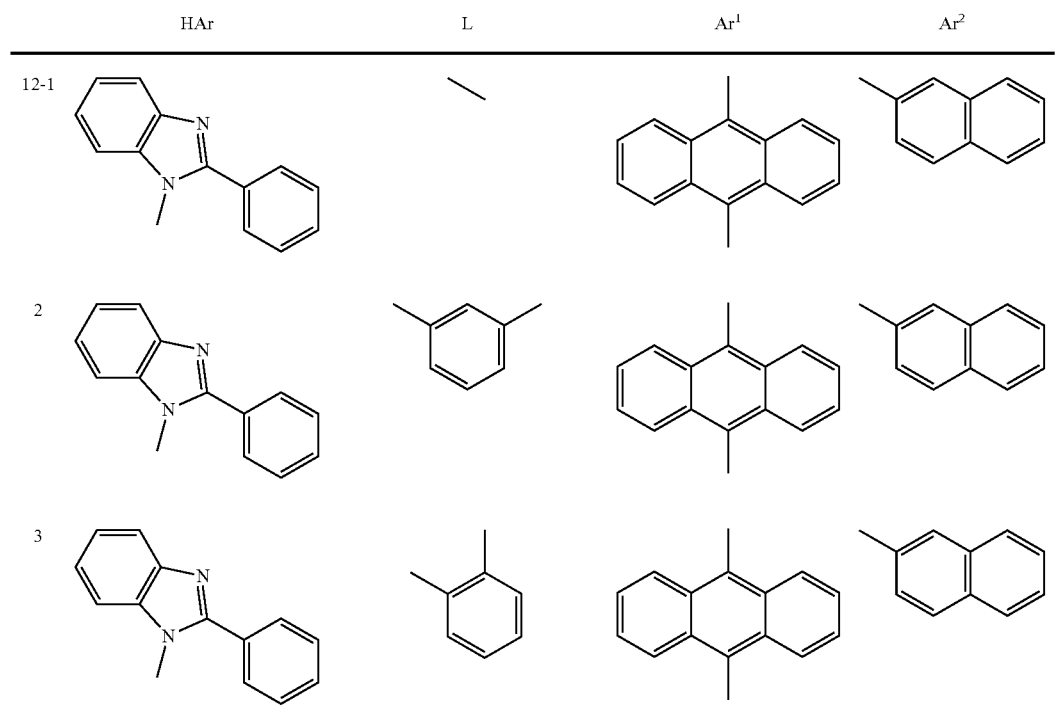

-continued
[Chemical Formula 58]
HAr—L—Ar¹—Ar²
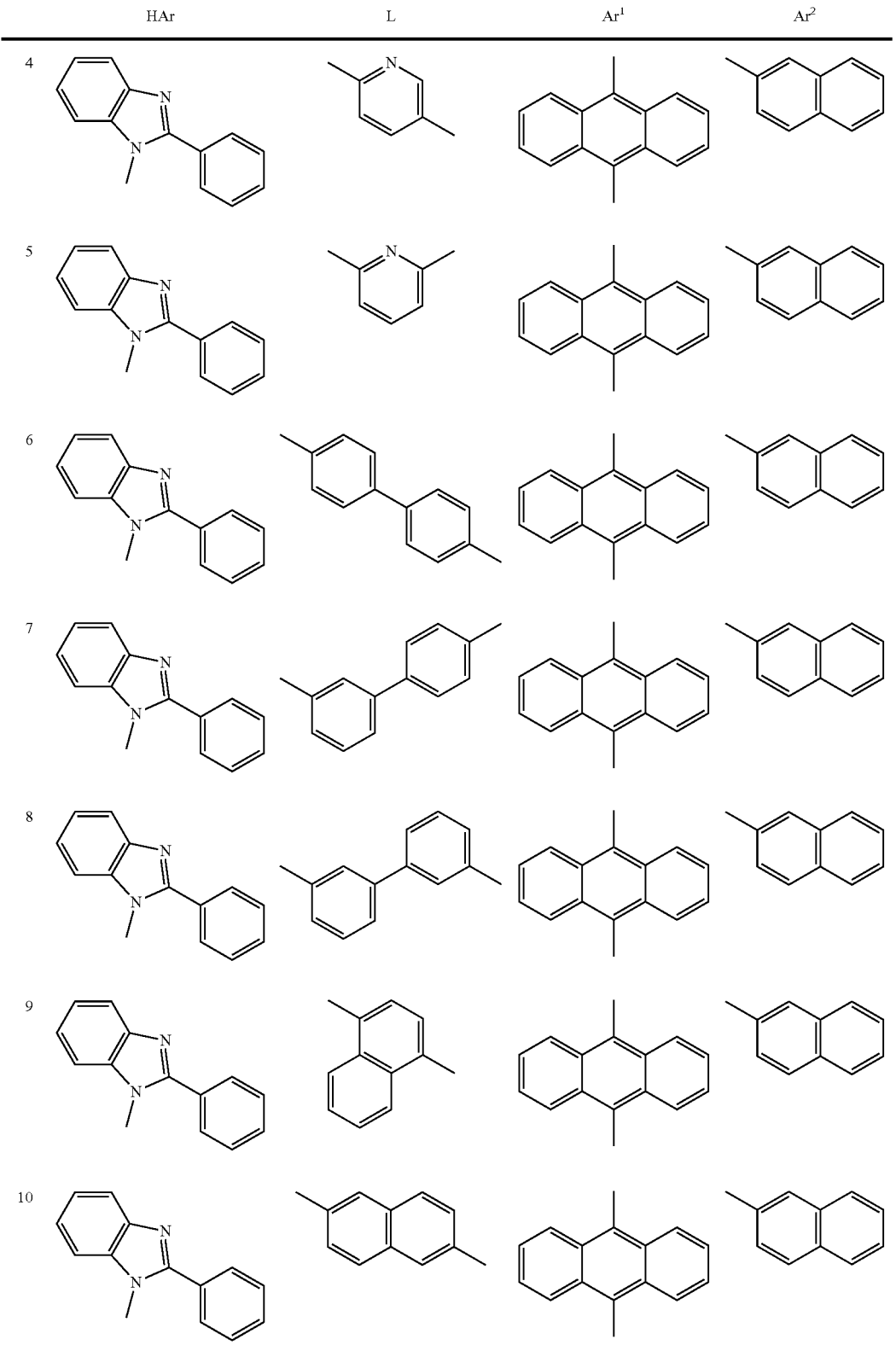

-continued
[Chemical Formula 58]
HAr—L—Ar¹—Ar²
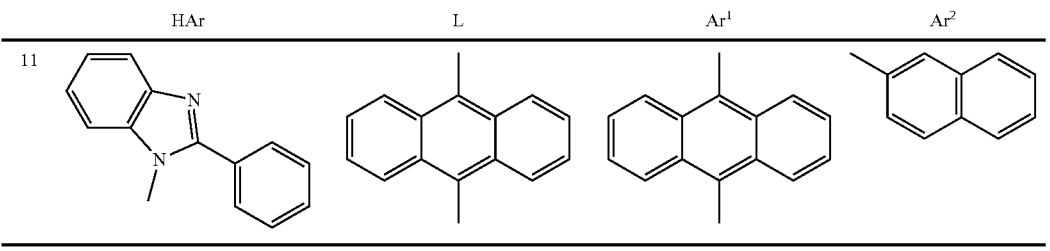
[Chemical Formula 59]
HAr—L—Ar¹—Ar²
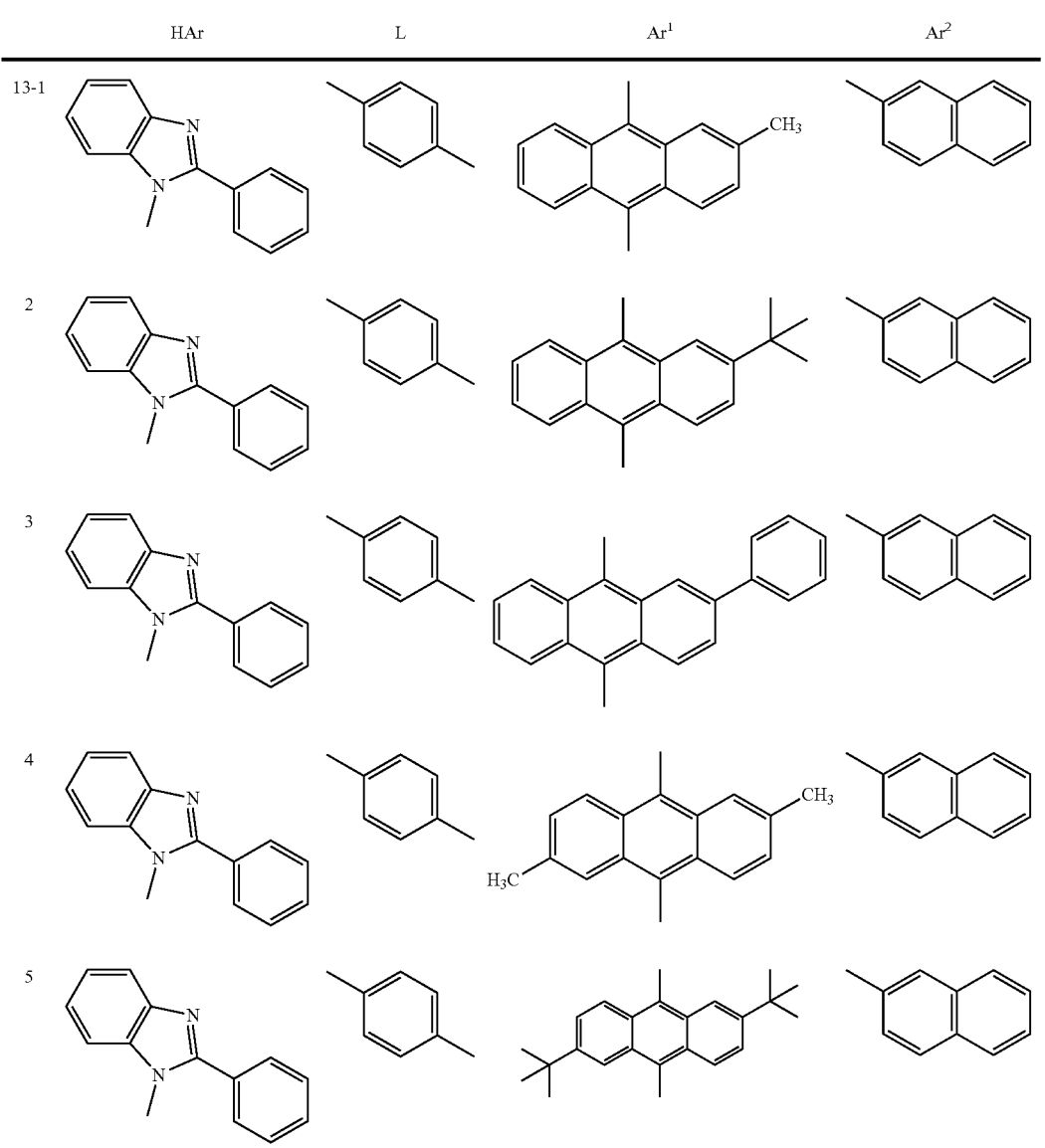

-continued
[Chemical Formula 59]
HAr—L—Ar¹—Ar²
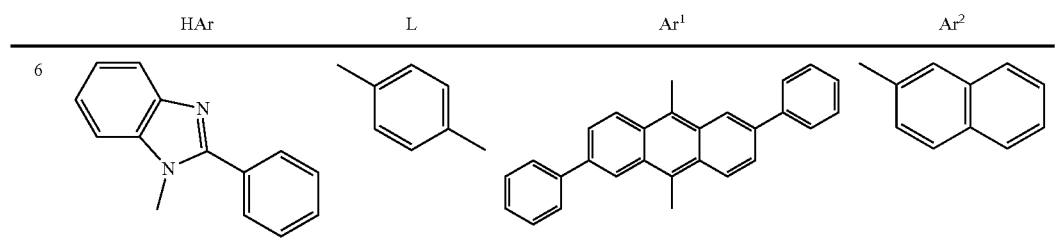
[Chemical Formula 60]
HAr—L—Ar¹—Ar²
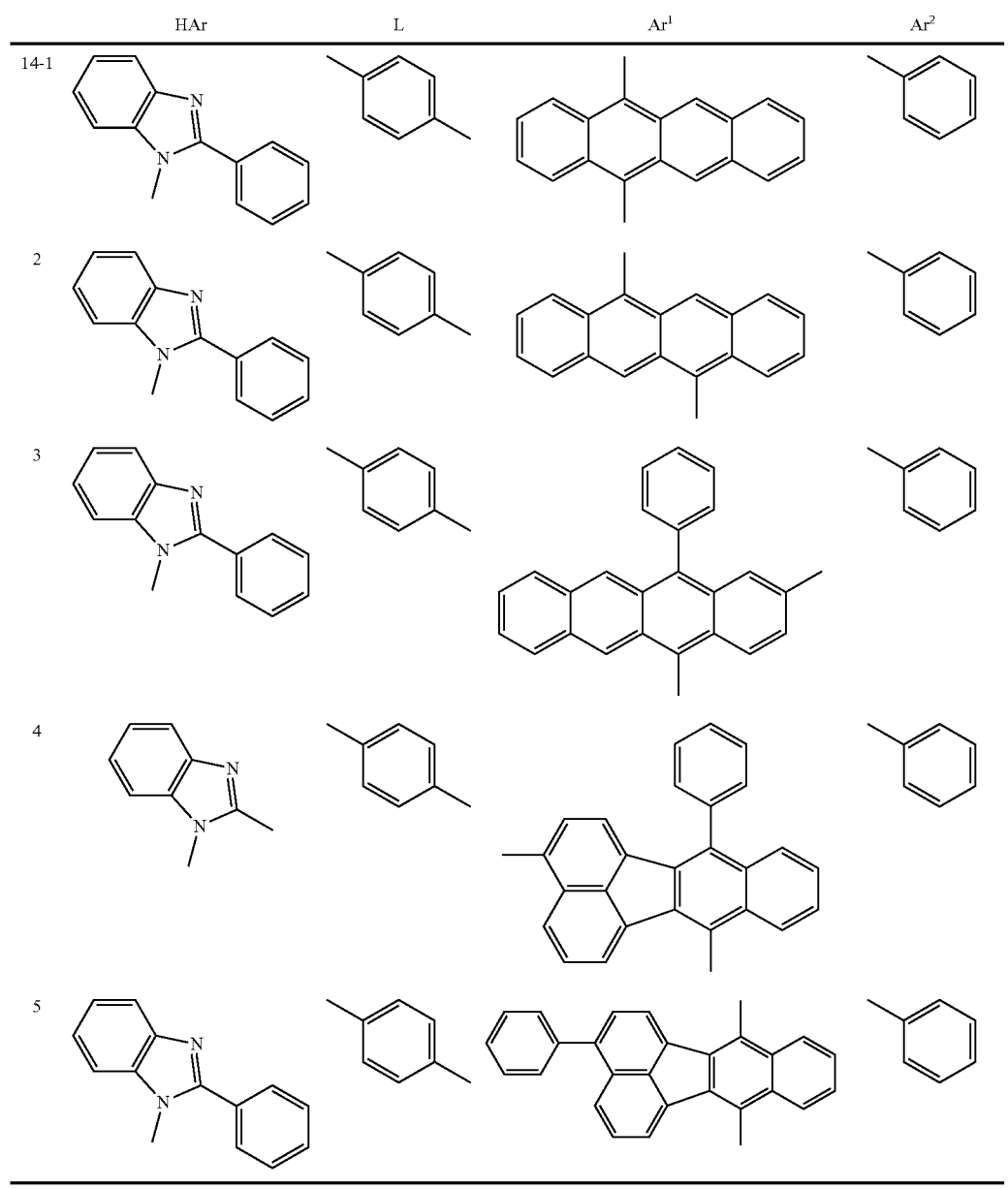

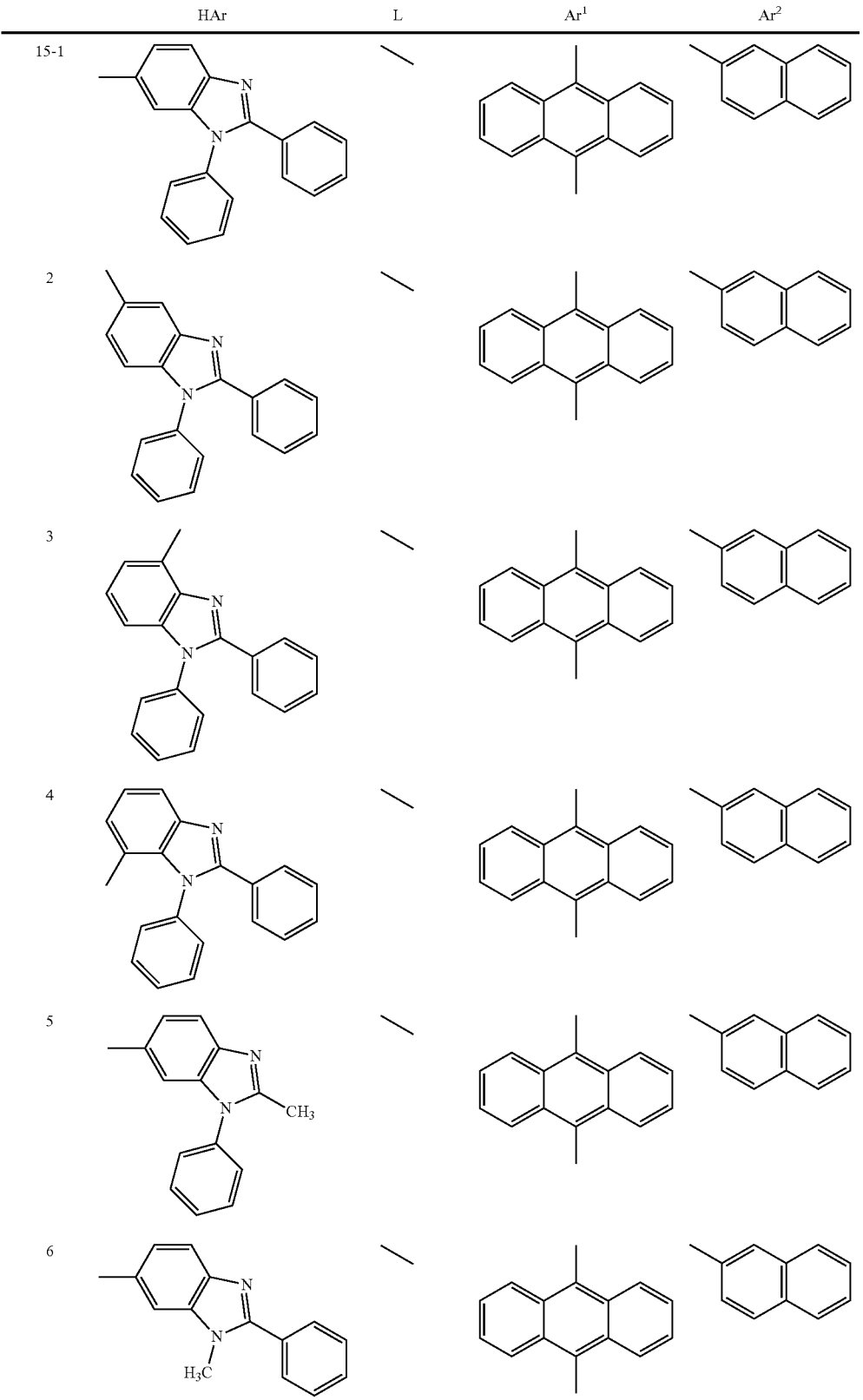

-continued
[Chemical Formula 61]
HAr—L—Ar¹—Ar²
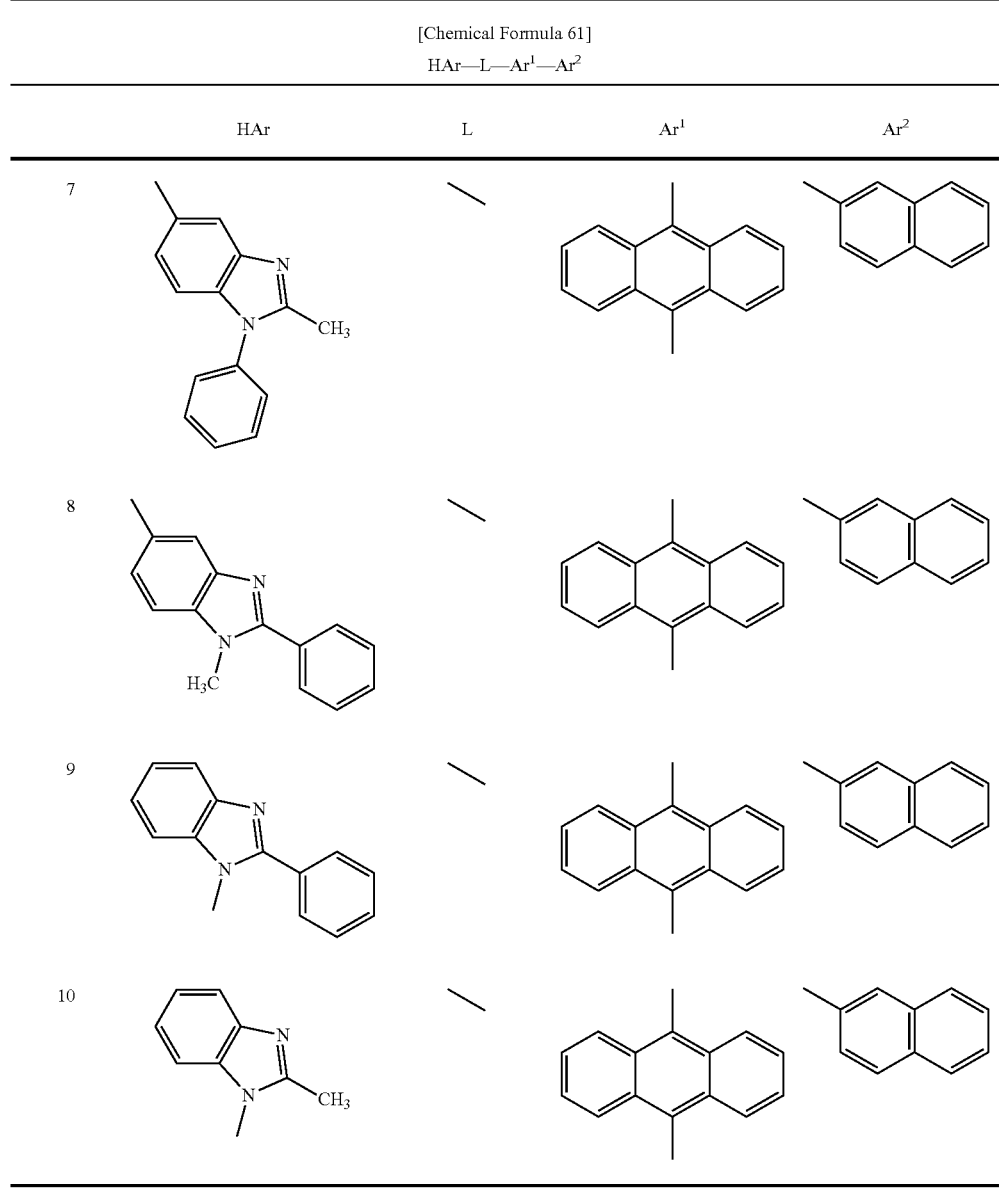
[Chemical Formula 62]
HAr—L—Ar¹—Ar²
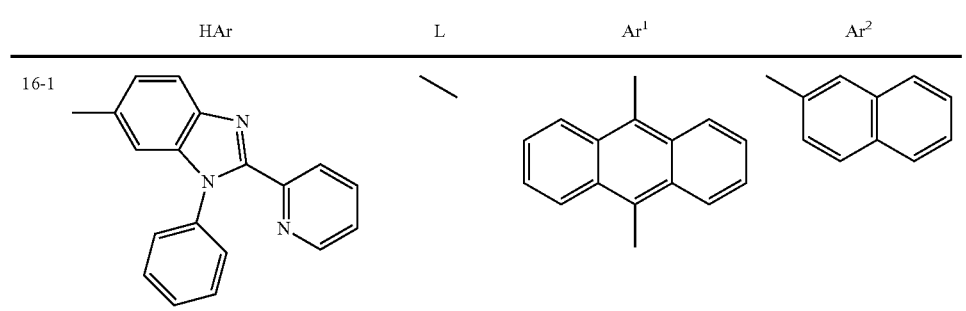

-continued
[Chemical Formula 62]
HAr—L—Ar¹—Ar²
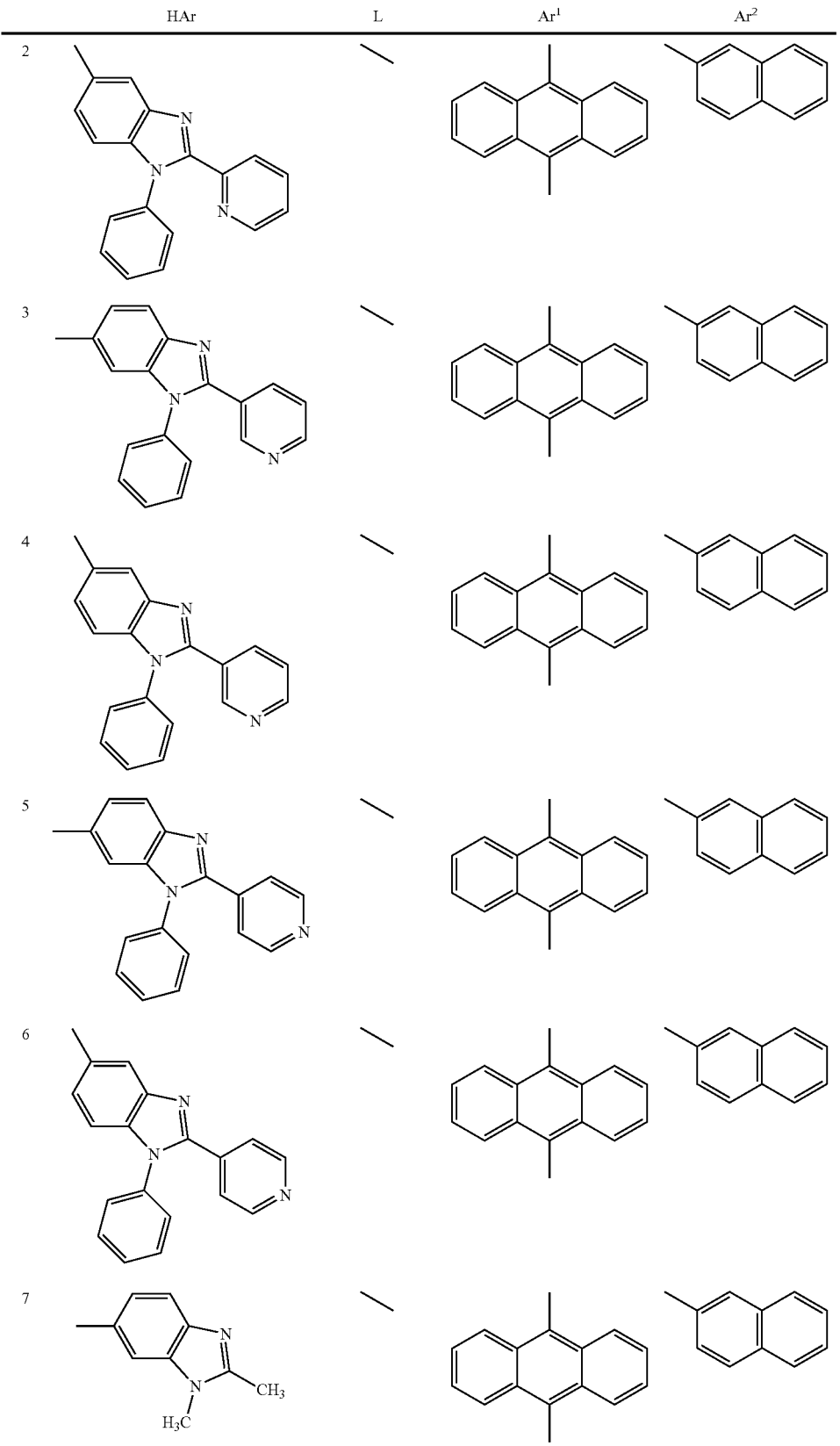

-continued
[Chemical Formula 62]
HAr—L—Ar¹—Ar²
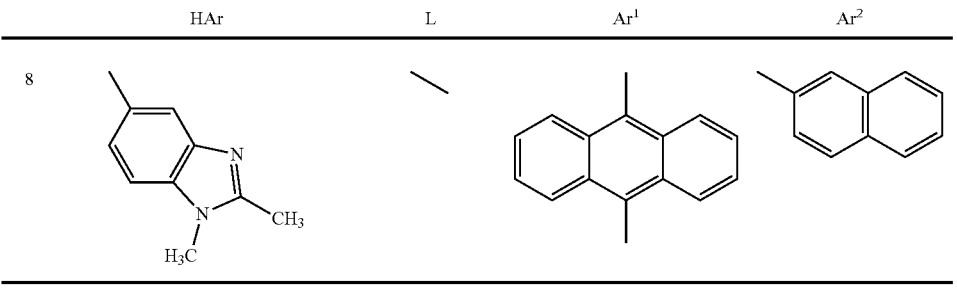
[Chemical Formula 63]
HAr—L—Ar¹—Ar²
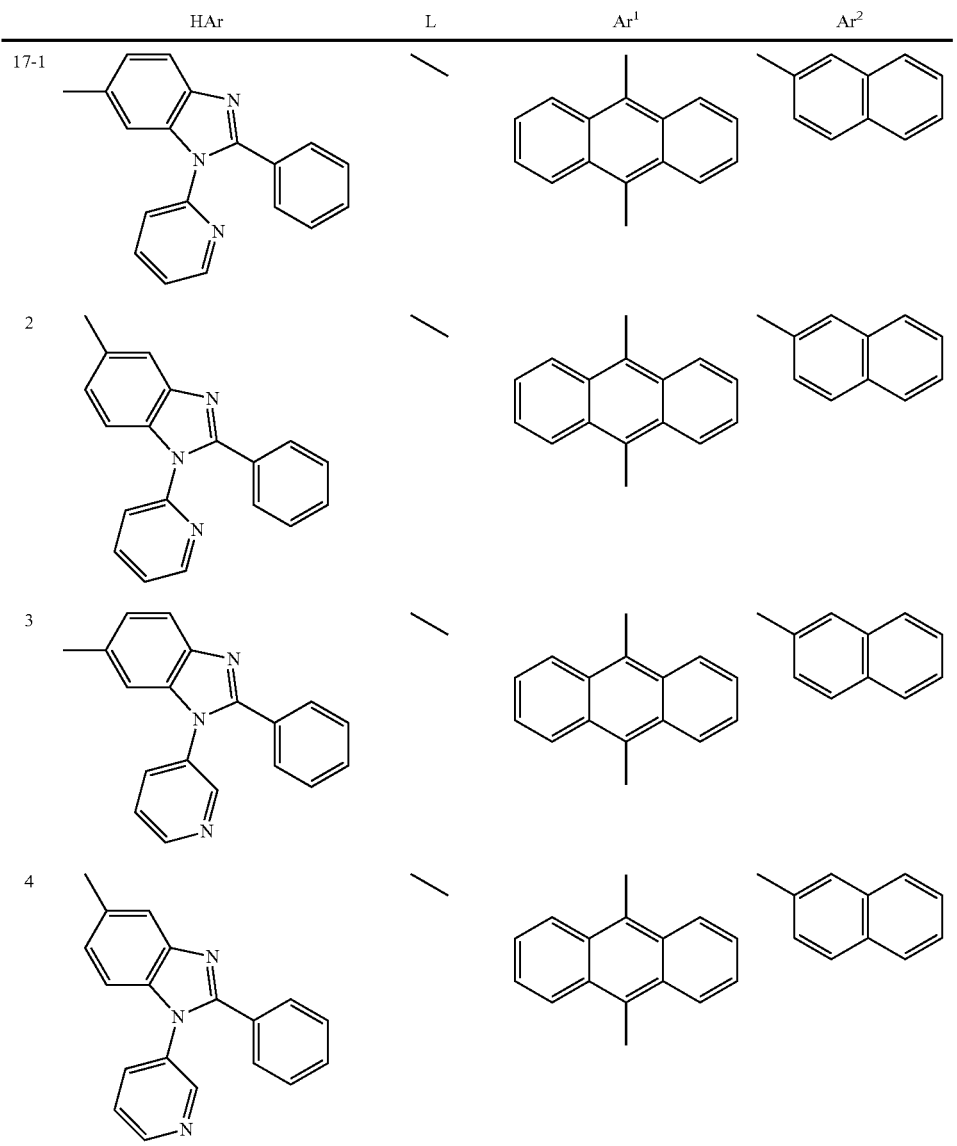

[Chemical Formula 63]
HAr—L—Ar¹—Ar²

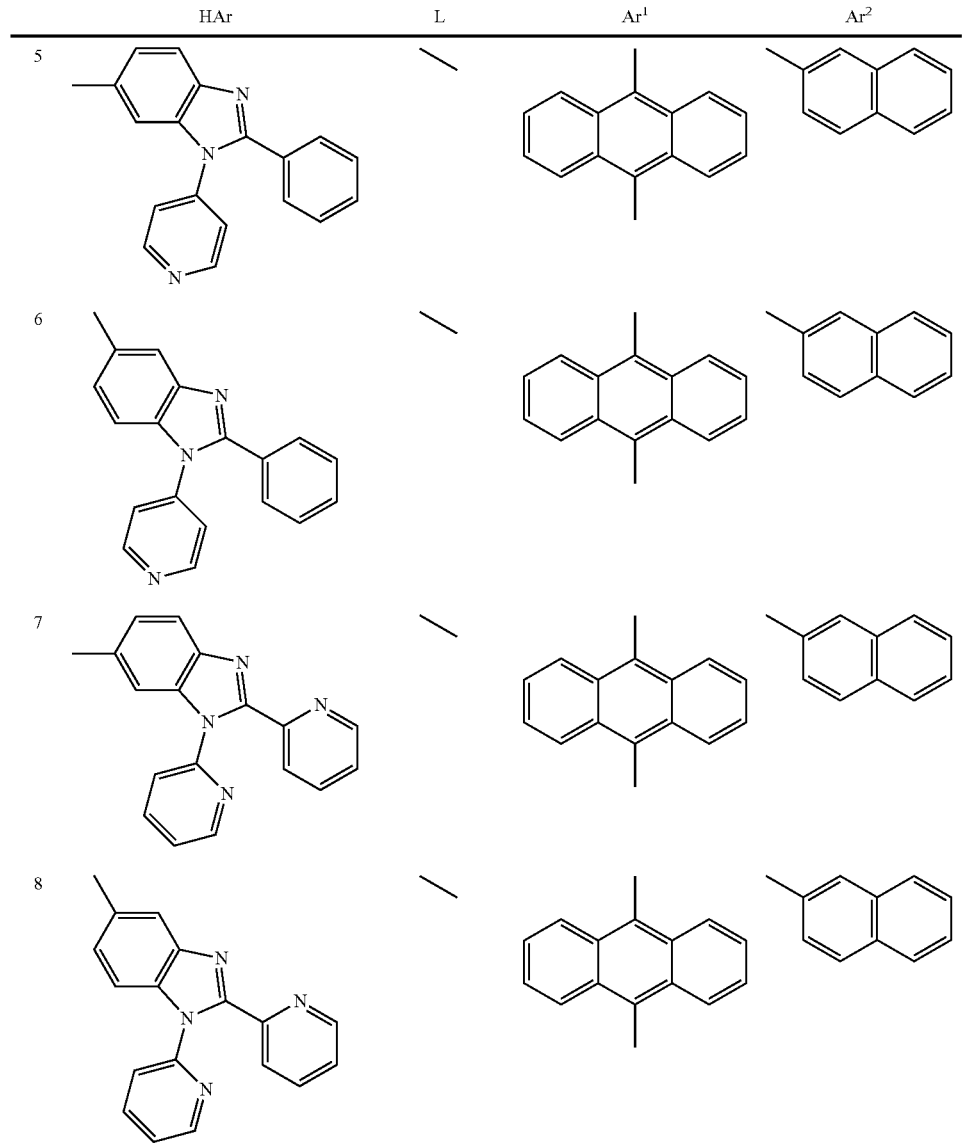

Among the above examples, the compounds (1-1), (1-5), (1-7), (2-1), (3-1), (4-2), (4-6), (7-2), (7-7), (7-8), (7-9) and (9-7) are particularly preferred.

Although thickness of the electron injecting layer or the electron transporting layer is not specifically limited, the thickness is preferably 1 to 100 nm.

The electron injecting layer preferably contains an inorganic compound such as an insulator or a semiconductor in addition to the nitrogen-containing cyclic derivative. Such an insulator or a semiconductor, when contained in the electron injecting layer, can effectively prevent a current leak, thereby enhancing electron injectability of the electron injecting layer.

As the insulator, it is preferable to use at least one metal compound selected from a group consisting of an alkali metal chalcogenide, an alkali earth metal chalcogenide, a halogenide of alkali metal and a halogenide of alkali earth metal. By forming the electron injecting layer from the alkali metal chalcogenide or the like, the electron injecting capability can preferably be further enhanced. Specifically, preferable examples of the alkali metal chalcogenide are $Li_2O$, $K_2O$, $Na_2S$, $Na_2Se$ and $Na_2O$, while preferable example of the alkali earth metal chalcogenide are CaO, BaO, SrO, BeO, BaS and CaSe. Preferable examples of the halogenide of the alkali metal are LiF, NaF, KF, LiCl, KCl and NaCl. Preferable examples of the halogenide of the alkali earth metal are fluorides such as $CaF_2$, $BaF_2$, $SrF_2$, $MgF_2$ and $BeF_2$, and halogenides other than the fluoride.

Examples of the semiconductor are one of or a combination of two or more of an oxide, a nitride or an oxidized nitride containing at least one element selected from Ba, Ca, Sr, Yb, Al, Ga, In, Li, Na, Cd, Mg, Si, Ta, Sb and Zn. An inorganic compound for forming the electron injecting layer is preferably a microcrystalline or amorphous semiconductor film.

When the electron injecting layer is formed of such semiconductor film, more uniform thin film can be formed, thereby reducing pixel defects such as a dark spot. Examples of such an inorganic compound are the above-described alkali metal chalcogenide, alkali earth metal chalcogenide, halogenide of the alkali metal and halogenide of the alkali earth metal.

The electron injecting layer in the aspect of the invention may preferably contain the above-described reduction-causing dopant.

The hole injecting layer or the hole transporting layer (including the hole injecting/transporting layer) may contain an aromatic amine compound such as an aromatic amine derivative represented by the following (I).

[Chemical Formula 64]

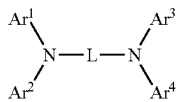

(I)

In the above formula (I), $Ar^1$ to $Ar^4$ represent a substituted or unsubstituted aryl group having 6 to 50 ring carbon atoms or a substituted or unsubstituted heteroaryl group having 5 to 50 ring atoms.

Examples of the substituted or unsubstituted aryl group having 6 to 50 ring carbon atoms include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4'-t-butyl-p-terphenyl-4-yl group, a fluoranthenyl group, and a fluorenyl group.

Examples of the substituted or unsubstituted heteroaryl group having 5 to 50 ring atoms include a 1-pyrrolyl group, a 2-pyrrolyl group, a 3-pyrrolyl group, a pyrazinyl group, a 2-pyrizinyl group, a 3-pyrizinyl group, a 4-pyrizinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, a 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthroline-2-yl group, a 1,7-phenanthroline-3-yl group, a 1,7-phenanthroline-4-yl group, a 1,7-phenanthroline-5-yl group, a 1,7-phenanthroline-6-yl group, a 1,7-phenanthroline-8-yl group, a 1,7-phenanthroline-9-yl group, a 1,7-phenanthroline-10-yl group, a 1,8-phenanthroline-2-yl group, a 1,8-phenanthroline-3-yl group, a 1,8-phenanthroline-4-yl group, a 1,8-phenanthroline-5-yl group, a 1,8-phenanthroline-6-yl group, a 1,8-phenanthroline-7-yl group, a 1,8-phenanthroline-9-yl group, a 1,8-phenanthroline-10-yl group, a 1,9-phenanthroline-2-yl group, a 1,9-phenanthroline-3-yl group, a 1,9-phenanthroline-4-yl group, a 1,9-phenanthroline-5-yl group, a 1,9-phenanthroline-6-yl group, a 1,9-phenanthroline-7-yl group, a 1,9-phenanthroline-8-yl group, a 1,9-phenanthroline-10-yl group, a 1,10-phenanthroline-2-yl group, a 1,10-phenanthroline-3-yl group, a 1,10-phenanthroline-4-yl group, a 1,10-phenanthroline-5-yl group, a 2,9-phenanthroline-1-yl group, a 2,9-phenanthroline-3-yl group, a 2,9-phenanthroline-4-yl group, a 2,9-phenanthroline-5-yl group, a 2,9-phenanthroline-6-yl group, a 2,9-phenanthroline-7-yl group, a 2,9-phenanthroline-8-yl group, a 2,9-phenanthroline-10-yl group, a 2,8-phenanthroline-1-yl group, a 2,8-phenanthroline-3-yl group, a 2,8-phenanthroline-4-yl group, a 2,8-phenanthroline-5-yl group, a 2,8-phenanthroline-6-yl group, a 2,8-phenanthroline-7-yl group, a 2,8-phenanthroline-9-yl group, a 2,8-phenanthroline-10-yl group, a 2,7-phenanthroline-1-yl group, a 2,7-phenanthroline-3-yl group, a 2,7-phenanthroline-4-yl group, a 2,7-phenanthroline-5-yl group, a 2,7-phenanthroline-6-yl group, a 2,7-phenanthroline-8-yl group, a 2,7-phenanthroline-9-yl group, a 2,7-phenanthroline-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl 1-indolyl group, a 4-t-butyl 1-indolyl group, a 2-t-butyl 3-indolyl group, and a 4-t-butyl 3-indolyl group. Preferable are phenyl group, a naphthyl group, a biphenyl group, an anthranil group, a phenanthryl group, a pyrenyl group, a chrysenyl group, a fluoranthenyl group, a fluorenyl group and the like.

L indicates a linking group. The examples are a divalent group obtained by linking a substituted or unsubstituted arylene group having 6 to 50 ring carbon atoms, a substituted or unsubstituted heteroarylene group having 5 to 50 ring atoms, or at least two arylene groups or heteroarylene groups via a single bond, an ether bond, a thioether bond, an alkylene group having 1 to 20 carbon atoms, an alkenylene group having 2 to 20 carbon atoms, or an amino group. Examples of the arylene group having 6 to 50 ring carbon atoms include a 1,4-phenylene group, a 1,2-phenylene group, a 1,3-phenylene group, a 1,4-naphthylene group, a 2,6-naphthylene group, a 1,5-naphthylene group, a 9,10-anthranylene group, a 9,10-phenanthrenylene group, a 3,6-phenanthrenylene group, a 1,6-pyrenylene group, a 2,7-pyrenylene group, a 6,12-chrysenylene group, a 4,4'-biphenylene group, a 3,3'-biphenylene group, a 2,2'-biphenylene group, and a 2,7-fluorenylene group. Examples of the arylene group having 5 to 50 ring atoms include a 2,5-thiophenylene group, a 2,5-silolylene group, and a 2,5-oxadiazolylene group. Preferably, the arylene group is 1,4-phenylene group, a 1,2-phenylene group, a 1,3-phenylene group, a 1,4-naphthylene group, a 9,10-anthranylene group, a 6,12-chrysenylene group, a 4,4'-biphenylene group, a 3,3'-biphenylene group, a 2,2'-biphenylene group, or a 2,7-fluorenylene group.

When L is a linking group consisting of two or more arylene groups or heteroarylene groups, the arylene groups or heteroarylene groups adjacent to each other may form a new ring by bonding to each other via a divalent group. Examples of the divalent group for forming a ring include a tetramethylene group, a pentamethylene group, a hexamethylene group, a diphenylmethane-2,2'-diyl group, a diphenylethane-3,3'-diyl group, and a diphenylpropane-4,4'-diyl group.

Examples of the substituent group of $Ar^1$ to $Ar^4$ and L include a substituted or unsubstituted aryl group having 6 to 50 ring carbon atoms, a substituted or unsubstituted heteroaryl group having 5 to 50 ring atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted heteroaryloxy group having 5 to 50 ring atoms, a substituted or unsubstituted arylthio group having 6 to 50 ring carbon atoms, a substituted or unsubstituted heteroarylthio group having 5 to 50 ring atoms, a substituted or unsubstituted alkoxycarbonyl group having 2 to 50 carbon atoms, an amino group which is substituted with a substituted or unsubstituted aryl group having 6 to 50 ring carbon atoms or a heteroaryl group having 5 to 50 ring atoms, a halogen atom, cyano group, a nitro group, and a hydroxy group.

Examples of the substituted or unsubstituted aryl group having 6 to 50 ring carbon atoms include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4'-t-butyl-p-terphenyl-4-yl group, a fluoranthenyl group, and a fluorenyl group.

Examples of the substituted or unsubstituted heteroaryl group having 5 to 50 ring atoms include a 1-pyrrolyl group, a 2-pyrrolyl group, a 3-pyrrolyl group, a pyrazinyl group, a 2-pyrizinyl group, a 3-pyrizinyl group, a 4-pyrizinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, a 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthroline-2-yl group, a 1,7-phenanthroline-3-yl group, a 1,7-phenanthroline-4-yl group, a 1,7-phenanthroline-5-yl group, a 1,7-phenanthroline-6-yl group, a 1,7-phenanthroline-8-yl group, a 1,7-phenanthroline-9-yl group, a 1,7-phenanthroline-10-yl group, a 1,8-phenanthroline-2-yl group, a 1,8-phenanthroline-3-yl group, a 1,8-phenanthroline-4-yl group, a 1,8-phenanthroline-5-yl group, a 1,8-phenanthroline-6-yl group, a 1,8-phenanthroline-7-yl group, a 1,8-phenanthroline-9-yl group, a 1,8-phenanthroline-10-yl group, a 1,9-phenanthroline-2-yl group, a 1,9-phenanthroline-3-yl group, a 1,9-phenanthroline-4-yl group, a 1,9-phenanthroline-5-yl group, a 1,9-phenanthroline-6-yl group, a 1,9-phenanthroline-7-yl group, a 1,9-phenanthroline-8-yl group, a 1,9-phenanthroline-10-yl group, a 1,10-phenanthroline-2-yl group, a 1,10-phenanthroline-3-yl group, a 1,10-phenanthroline-4-yl group, a 1,10-phenanthroline-5-yl group, a 2,9-phenanthroline-1-yl group, a 2,9-phenanthroline-3-yl group, a 2,9-phenanthroline-4-yl group, a 2,9-phenanthroline-5-yl group, a 2,9-phenanthroline-6-yl group, a 2,9-phenanthroline-7-yl group, a 2,9-phenanthroline-8-yl group, a 2,9-phenanthroline-10-yl group, a 2,8-phenanthroline-1-yl group, a 2,8-phenanthroline-3-yl group, a 2,8-phenanthroline-4-yl group, a 2,8-phenanthroline-5-yl group, a 2,8-phenanthroline-6-yl group, a 2,8-phenanthroline-7-yl group, a 2,8-phenanthroline-9-yl group, a 2,8-phenanthroline-10-yl group, a 2,7-phenanthroline-1-yl group, a 2,7-phenanthroline-3-yl group, a 2,7-phenanthroline-4-yl group, a 2,7-phenanthroline-5-yl group, a 2,7-phenanthroline-6-yl group, a 2,7-phenanthroline-8-yl group, a 2,7-phenanthroline-9-yl group, a 2,7-phenanthroline-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl 1-indolyl group, a 4-t-butyl 1-indolyl group, a 2-t-butyl 3-indolyl group, and a 4-t-butyl 3-indolyl group.

Examples of the substituted or unsubstituted alkyl group having 1 to 50 carbon atoms include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and a 1,2,3-trinitropropyl group.

Examples of the substituted or unsubstituted cycloalkyl group having 3 to 50 carbon atoms include a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group.

The substituted or unsubstituted alkoxy group having 1 to 50 carbon atoms is a group represented by —OY. Examples of Y include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and a 1,2,3-trinitropropyl group.

Examples of the substituted or unsubstituted aralkyl group having 7 to 50 carbon atoms include a benzyl group, a 1-phenylethyl group, a 2-phenylethyl group, a 1-phenylisopropyl group, a 2-phenylisopropyl group, a phenyl-t-butyl group, a α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrrolylmethyl group, a 2-(1-pyrrolyl)ethyl group, a p-methylbenzyl group, an m-methylbenzyl group, an o-methylbenzyl group, a p-chlorobenzyl group, an m-chlorobenzyl group, an o-chlorobenzyl group, a p-bromobenzyl group, an m-bromobenzyl group, an o-bromobenzyl group, a p-iodobenzyl group, an m-iodobenzyl group, an o-iodobenzyl group, a p-hydroxybenzyl group, an m-hydroxybenzyl group, an o-hydroxybenzyl group, a p-aminobenzyl group, an m-aminobenzyl group, an o-aminobenzyl group, a p-nitrobenzyl group, an m-nitrobenzyl group, an o-nitrobenzyl group, a p-cyanobenzyl group, an m-cyanobenzyl group, an o-cyanobenzyl group, a 1-hydroxy-2-phenylisopropyl group, and a 1-chloro-2-phenylisopropyl group.

The substituted or unsubstituted aryloxy group having 6 to 50 ring carbon atoms is represented by —OY'. Examples of Y' include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, and a 4'-t-butyl-p-terphenyl-4-yl group.

The substituted or unsubstituted heteroaryloxy group having 5 to 50 ring atoms is represented by —OZ'. Examples of Z' include a 2-pyrrolyl group, a 3-pyrrolyl group, a pyrazinyl group, a 2-pyrizinyl group, a 3-pyrizinyl group, a 4-pyrizinyl group, a 2-indolyl group, a 3-indolyl group, a 4-indolyl group, a 5-indolyl group, a 6-indolyl group, a 7-indolyl group, a 1-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, a 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthroline-2-yl group, a 1,7-phenanthroline-3-yl group, a 1,7-phenanthroline-4-yl group, a 1,7-phenanthroline-5-yl group, a 1,7-phenanthroline-6-yl group, a 1,7-phenanthroline-8-yl group, a 1,7-phenanthroline-9-yl group, a 1,7-phenanthroline-10-yl group, a 1,8-phenanthroline-2-yl group, a 1,8-phenanthroline-3-yl group, a 1,8-phenanthroline-4-yl group, a 1,8-phenanthroline-5-yl group, a 1,8-phenanthroline-6-yl group, a 1,8-phenanthroline-7-yl group, a 1,8-phenanthroline-9-yl group, a 1,8-phenanthroline-10-yl group, a 1,9-phenanthroline-2-yl group, a 1,9-phenanthroline-3-yl group, a 1,9-phenanthroline-4-yl group, a 1,9-phenanthroline-5-yl group, a 1,9-phenanthroline-6-yl group, a 1,9-phenanthroline-7-yl group, a 1,9-phenanthroline-8-yl group, a 1,9-phenanthroline-10-yl group, a 1,10-phenanthroline-2-yl group, a 1,10-phenanthroline-3-yl group, a 1,10-phenanthroline-4-yl group, a 1,10-phenanthroline-5-yl group, a 2,9-phenanthroline-1-yl group, a 2,9-phenanthroline-3-yl group, a 2,9-phenanthroline-4-yl group, a 2,9-phenanthroline-5-yl group, a 2,9-phenanthroline-6-yl group, a 2,9-phenanthroline-7-yl group, a 2,9-phenanthroline-8-yl group, a 2,9-phenanthroline-10-yl group, a 2,8-phenanthroline-1-yl group, a 2,8-phenanthroline-3-yl group, a 2,8-phenanthroline-4-yl group, a 2,8-phenanthroline-5-yl group, a 2,8-phenanthroline-6-yl group, a 2,8-phenanthroline-7-yl group, a 2,8-phenanthroline-9-yl group, a 2,8-phenanthroline-10-yl group, a 2,7-phenanthroline-1-yl group, a 2,7-phenanthroline-3-yl group, a 2,7-phenanthroline-4-yl group, a 2,7-phenanthroline-5-yl group, a 2,7-phenanthroline-6-yl group, a 2,7-phenanthroline-8-yl group, a 2,7-phenanthroline-9-yl group, a 2,7-phenanthroline-10-yl group, a 1-phenazinyl group, a 2-phenazinyl group, a 1-phenothiazinyl group, a 2-phenothiazinyl group, a 3-phenothiazinyl group, a 4-phenothiazinyl group, a 1-phenoxazinyl group, a 2-phenoxazinyl group, a 3-phenoxazinyl group, a 4-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl 1-indolyl group, a 4-t-butyl 1-indolyl group, a 2-t-butyl 3-indolyl group, and a 4-t-butyl 3-indolyl group.

The substituted or unsubstituted arylthio group having 6 to 50 ring carbon atoms is represented by —SY". Examples of Y" include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, and a 4'-t-butyl-p-terphenyl-4-yl group.

The substituted or unsubstituted heteroarylthio group having 5 to 50 ring atoms is represented by —SZ", and examples of Z" include a 2-pyrrolyl group, a 3-pyrrolyl group, a pyrazinyl group, a 2-pyrizinyl group, a 3-pyrizinyl group, a 4-pyrizinyl group, a 2-indolyl group, a 3-indolyl group, a 4-indolyl group, a 5-indolyl group, a 6-indolyl group, a 7-indolyl group, a 1-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, a 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthroline-2-yl group, a 1,7-phenanthroline-3-yl group, a 1,7-phenanthroline-4-yl group, a 1,7-phenanthroline-5-yl group, a 1,7-phenanthroline-6-yl group, a 1,7-phenanthroline-8-yl group, a 1,7-phenanthroline-9-yl group, a 1,7-phenanthroline-10-yl group, a 1,8-phenanthroline-2-yl group, a 1,8-phenanthroline-3-yl group, a 1,8-phenanthroline-4-yl group, a 1,8-phenanthroline-5-yl group, a 1,8-phenanthroline-6-yl group, a 1,8-phenanthroline-7-yl group, a 1,8-phenanthroline-9-yl group, a 1,8-phenanthroline-10-yl group, a 1,9-phenanthroline-2-yl group, a 1,9-phenanthroline-3-yl group, a 1,9-phenanthroline-4-yl group, a 1,9-phenanthroline-5-yl group, a 1,9-phenanthroline-6-yl group, a 1,9-phenanthroline-7-yl group, a 1,9-phenanthroline-8-yl group, a 1,9-phenanthroline-10-yl group, a 1,10-phenanthroline-2-yl group, a 1,10-phenanthroline-3-yl group, a 1,10-phenanthroline-4-yl group, a 1,10-phenanthroline-5-yl group, a 2,9-phenanthroline-1-yl group, a 2,9-phenanthroline-3-yl group, a 2,9-phenanthroline-4-yl group, a 2,9-phenanthroline-5-yl group, a 2,9-phenanthroline-6-yl group, a 2,9-phenanthroline-7-yl group, a 2,9-phenanthroline-8-yl group, a 2,9-phenanthroline-10-yl group, a 2,8-phenanthroline-1-yl group, a 2,8-phenanthroline-3-yl group, a 2,8-phenanthroline-4-yl group, a 2,8-phenanthroline-5-yl group, a 2,8-phenanthroline-6-yl group, a 2,8-phenanthroline-7-yl group, a 2,8-phenanthroline-9-yl group, a 2,8-phenanthroline-10-yl group, a 2,7-phenanthroline-1-yl group, a 2,7-phenanthroline-3-yl group, a 2,7-phenanthroline-4-yl group, a 2,7-phenanthroline-5-yl group, a 2,7-phenanthroline-6-yl group, a 2,7-phenanthroline-8-yl group, a 2,7-phenanthroline-9-yl group, a 2,7-phenanthroline-10-yl group, a 1-phenazinyl group, a 2-phenazinyl group, a 1-phenothiazinyl group, a 2-phenothiazinyl group, a 3-phenothiazinyl group, a 4-phenothiazinyl group, a 1-phenoxazinyl group, a 2-phenoxazinyl group, a 3-phenoxazinyl group, a 4-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl 1-indolyl group, a 4-t-butyl 1-indolyl group, a 2-t-butyl 3-indolyl group, and a 4-t-butyl 3-indolyl group.

The substituted or unsubstituted alkoxycarbonyl group having 2 to 50 carbon atoms is represented by —COOZ. Examples of Z include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and a 1,2,3-trinitropropyl group.

The amino group which is substituted with a substituted or unsubstituted aryl group having 6 to 50 ring carbon atoms or with a substituted or unsubstituted heteroaryl group having 5 to 50 ring atoms is represented by —NPQ. Examples of P and Q include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4'-t-butyl-p-terphenyl-4-yl group, a 2-pyrrolyl group, a 3-pyrrolyl group, a pyrazinyl group, a 2-pyrizinyl group, a 3-pyrizinyl group, a 4-pyrizinyl group, a 2-indolyl group, a 3-indolyl group, a 4-indolyl group, a 5-indolyl group, a 6-indolyl group, a 7-indolyl group, a 1-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, a 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthroline-2-yl group, a 1,7-phenanthroline-3-yl group, a 1,7-phenanthroline-4-yl group, a 1,7-phenanthroline-5-yl group, a 1,7-phenanthroline-6-yl group, a 1,7-phenanthroline-8-yl group, a 1,7-phenanthroline-9-yl group, a 1,7-phenanthroline-10-yl group, a 1,8-phenanthroline-2-yl group, a 1,8-phenanthroline-3-yl group, a 1,8-phenanthroline-4-yl group, a 1,8-phenanthroline-5-yl group, a 1,8-phenanthroline-6-yl group, a 1,8-phenanthroline-7-yl group, a 1,8-phenanthroline-9-yl group, a 1,8-phenanthroline-10-yl group, a 1,9-phenanthroline-2-yl group, a 1,9-phenanthroline-3-yl group, a 1,9-phenanthroline-4-yl group, a 1,9-phenanthroline-5-yl group, a 1,9-phenanthroline-6-yl group, a 1,9-phenanthroline-7-yl group, a 1,9-phenanthroline-8-yl group, a 1,9-phenanthroline-10-yl group, a 1,10-phenanthroline-2-yl group, a 1,10-phenanthroline-3-yl group, a 1,10-phenanthroline-4-yl group, a 1,10-phenanthroline-5-yl group, a 2,9-phenanthroline-1-yl group, a 2,9-phenanthroline-3-yl group, a 2,9-phenanthroline-4-yl group, a 2,9-phenanthroline-5-yl group, a 2,9-phenanthroline-6-yl group, a 2,9-phenanthroline-7-yl group, a 2,9-phenanthroline-8-yl group, a 2,9-phenanthroline-10-yl group, a 2,8-phenanthroline-1-yl group, a 2,8-phenanthroline-3-yl group, a 2,8-phenanthroline-4-yl group, a 2,8-phenanthroline-5-yl group, a 2,8-phenanthroline-6-yl group, a 2,8-phenanthroline-7-yl group, a 2,8-phenanthroline-9-yl group, a 2,8-phenanthroline-10-yl group, a 2,7-phenanthroline-1-yl group, a 2,7-phenanthroline-3-yl group, a 2,7-phenanthroline-4-yl group, a 2,7-phenanthroline-5-yl group, a 2,7-phenanthroline-6-yl group, a 2,7-phenanthroline-8-yl group, a 2,7-phenanthroline-9-yl group, a 2,7-phenanthroline-10-yl group, a 1-phenazinyl group, a 2-phenazinyl group, a 1-phenothiazinyl group, a 2-phenothiazinyl group, a 3-phenothiazinyl group, a 4-phenothiazinyl group, a 1-phenoxazinyl group, a 2-phenoxazinyl group, a 3-phenoxazinyl group, a 4-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl 1-indolyl group, a 4-t-butyl 1-indolyl group, a 2-t-butyl 3-indolyl group, and a 4-t-butyl 3-indolyl group.

Examples of the compound represented by the formula (I) are shown below. However, the compound is not limited thereto.

[Chemical Formula 65]
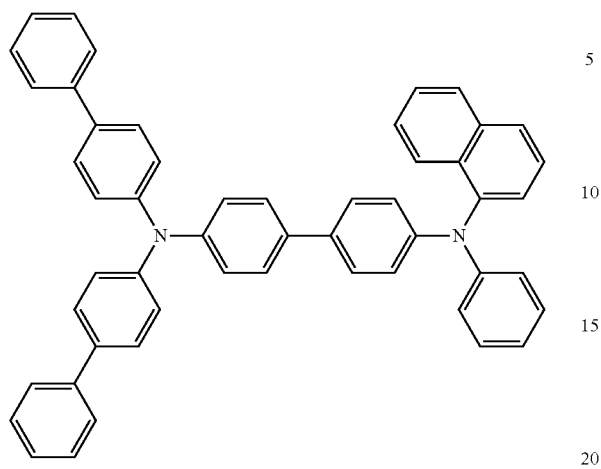
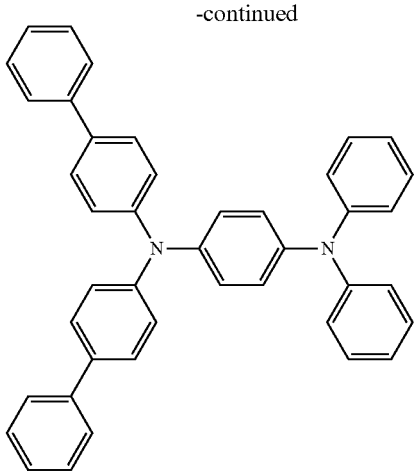
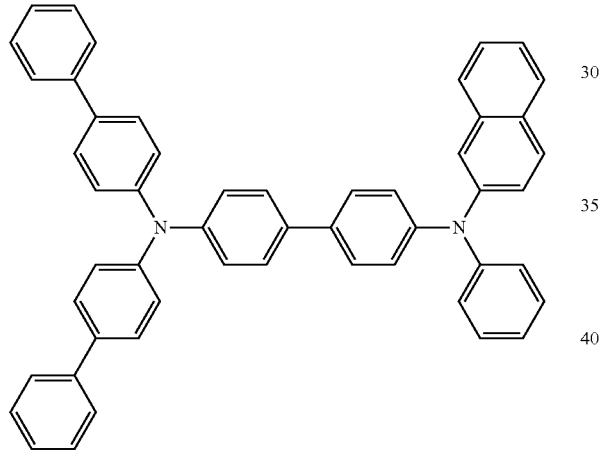
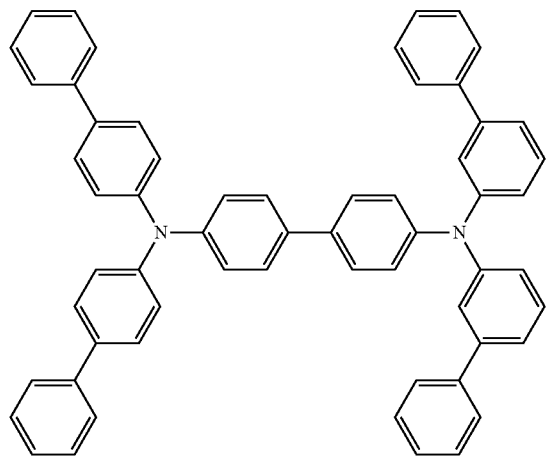
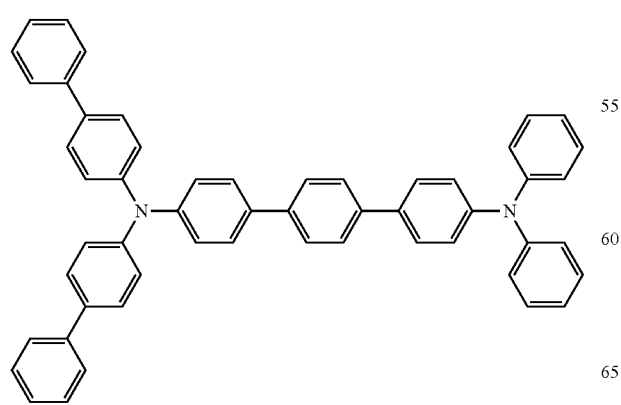
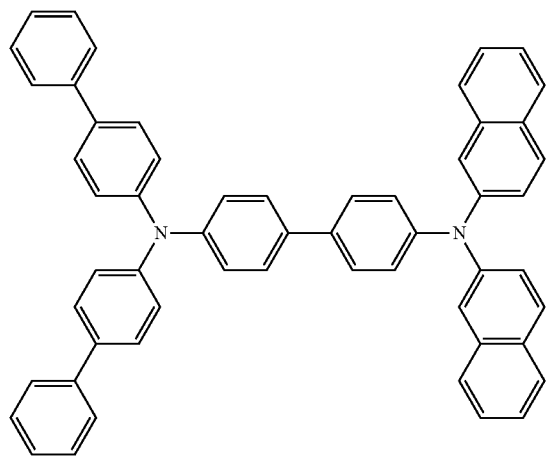

175
-continued
176
-continued
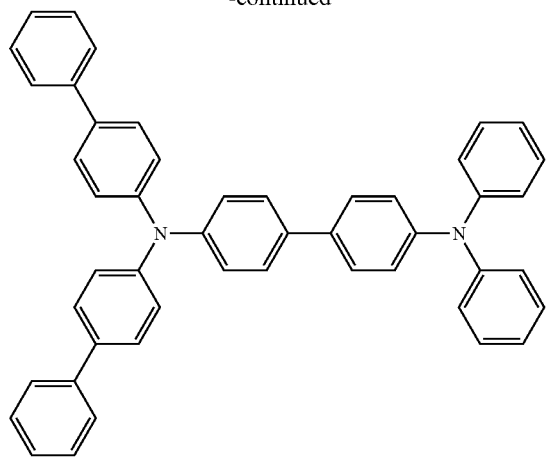
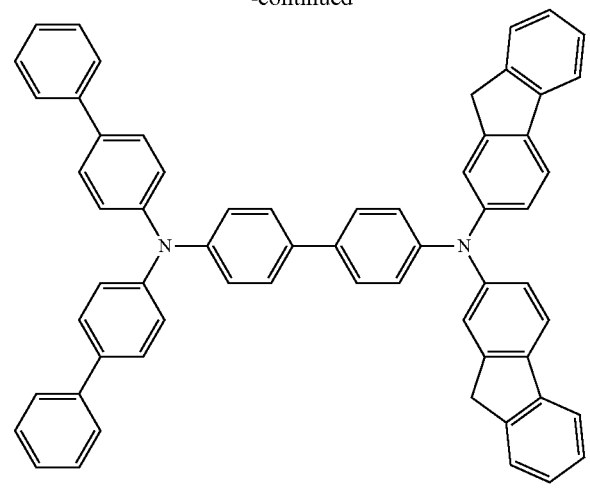
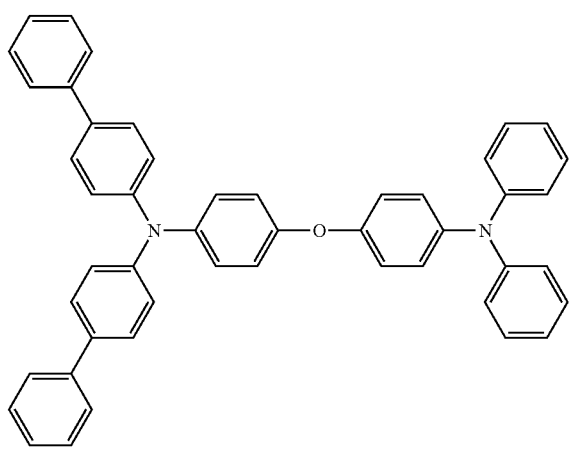
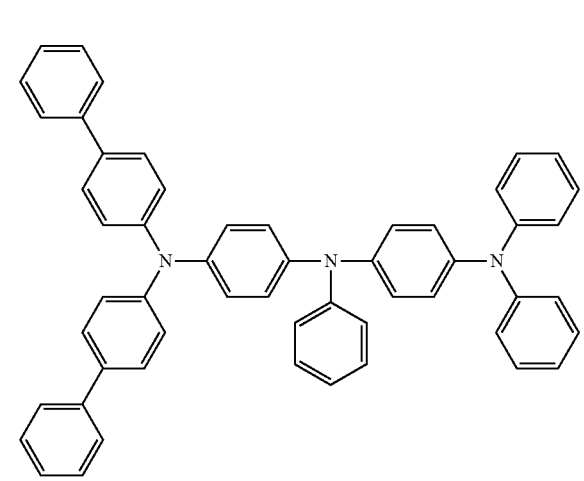
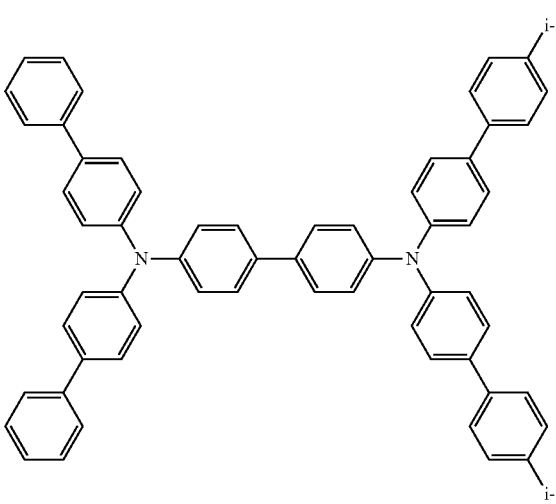
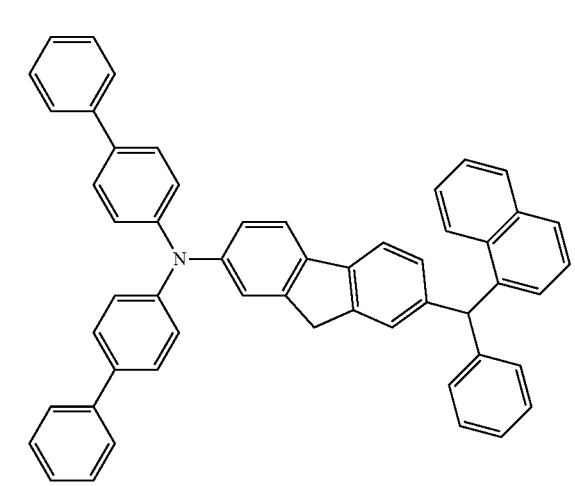

177
-continued
178
-continued
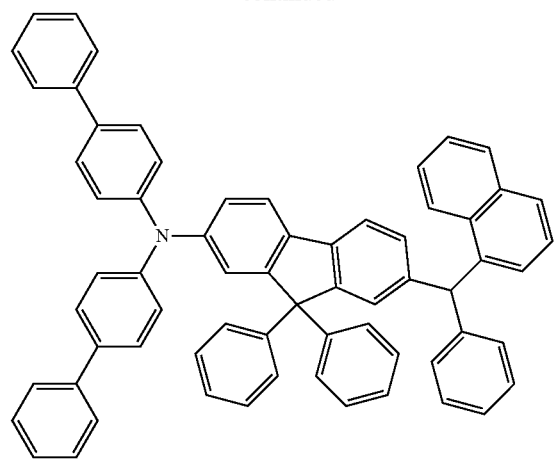
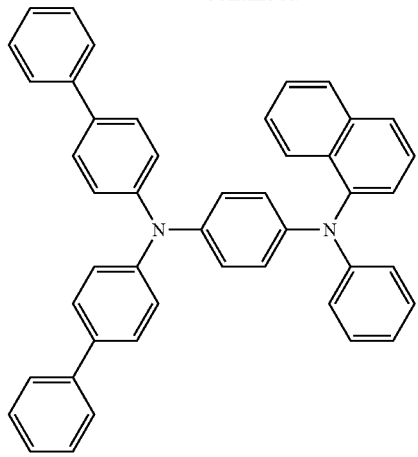
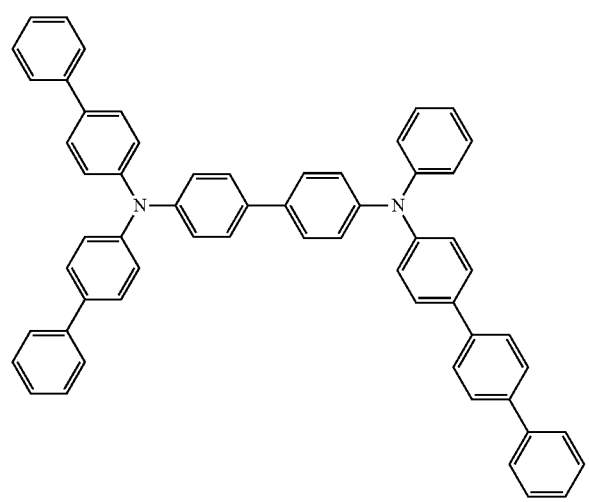
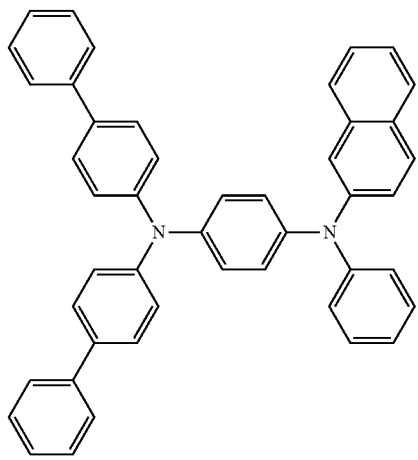
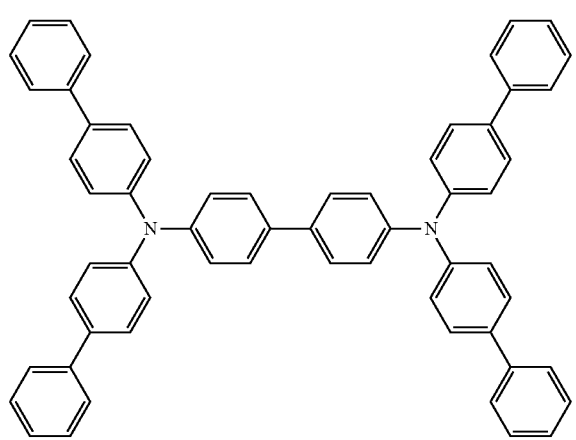
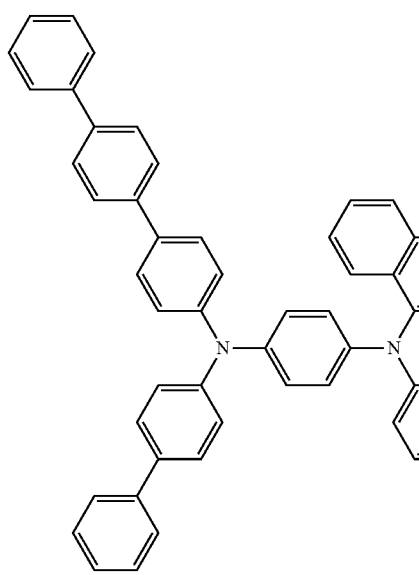

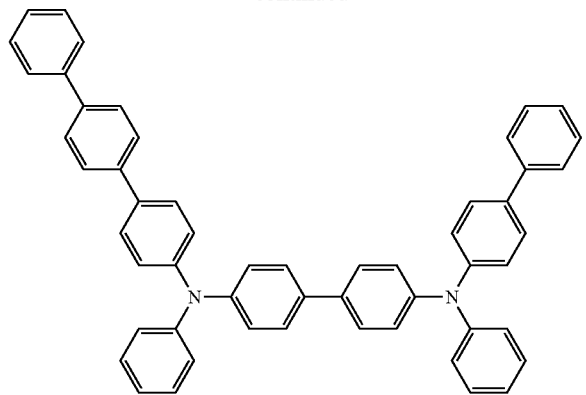

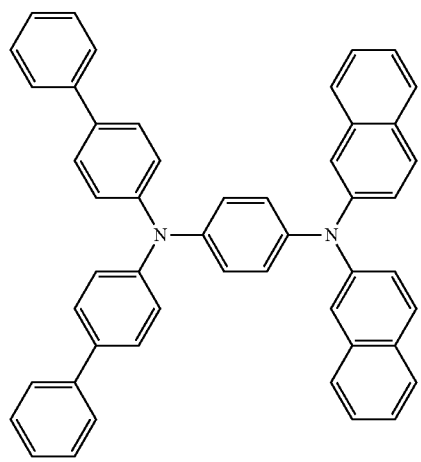

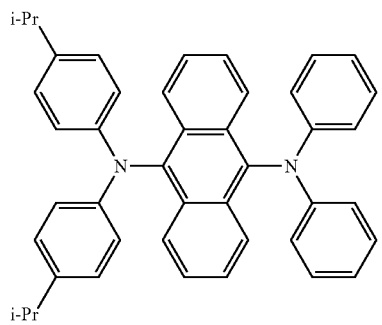

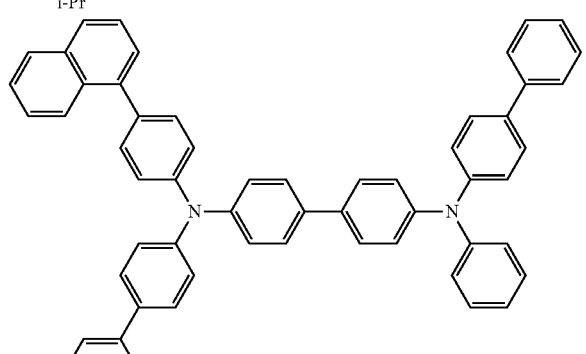

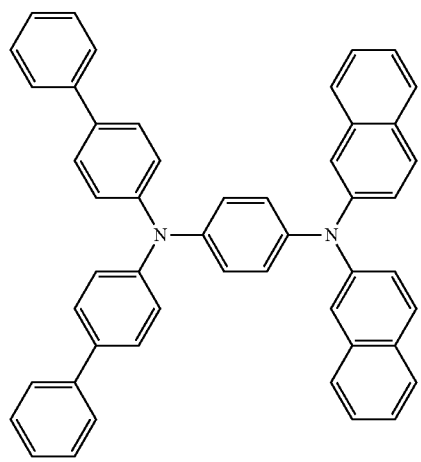

Aromatic amine represented by the following general formula (II) can also be preferably used for forming the hole injecting layer or the hole transporting layer.

[Chemical Formula 66]

In the formula (II), $Ar^1$ to $Ar^3$ each represent the same as those represented by $Ar^1$ to $Ar^4$ of the above formula (I). Examples of the compound represented by the general formula (II) are shown below. However, the compound represented by the formula (II) is not limited thereto.

[Chemical Formula 67]

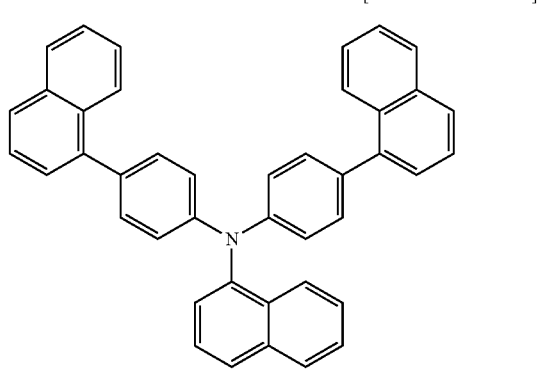

181
-continued
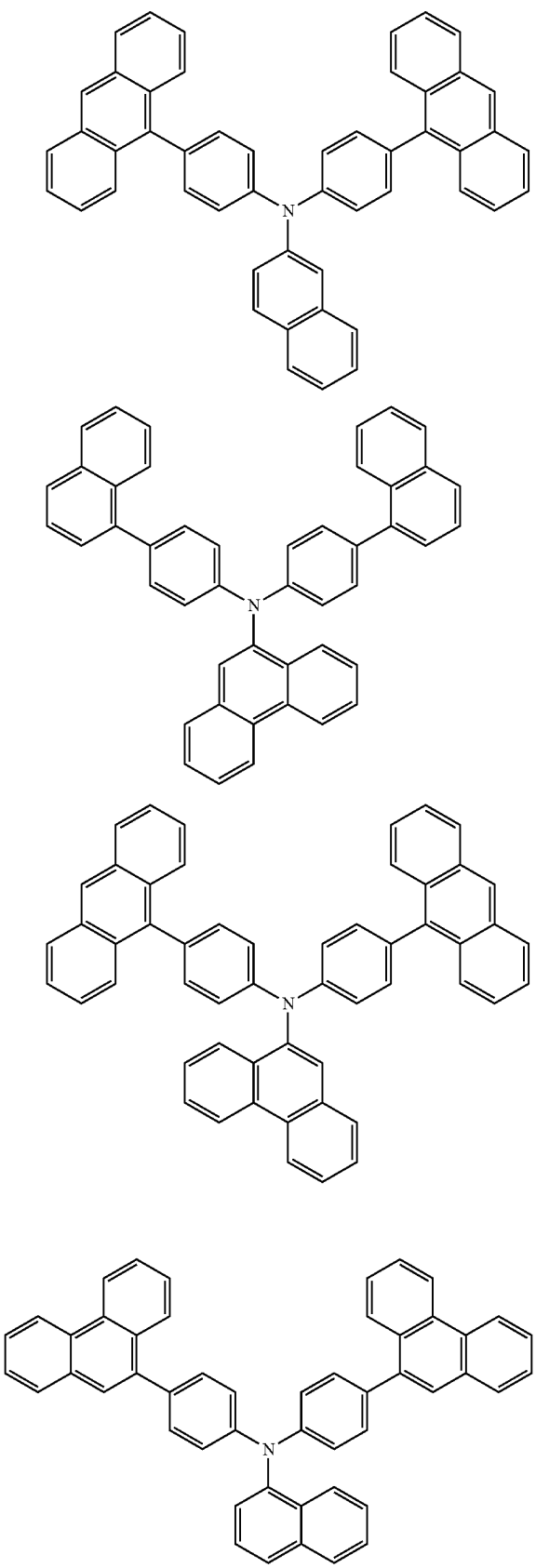
182
-continued
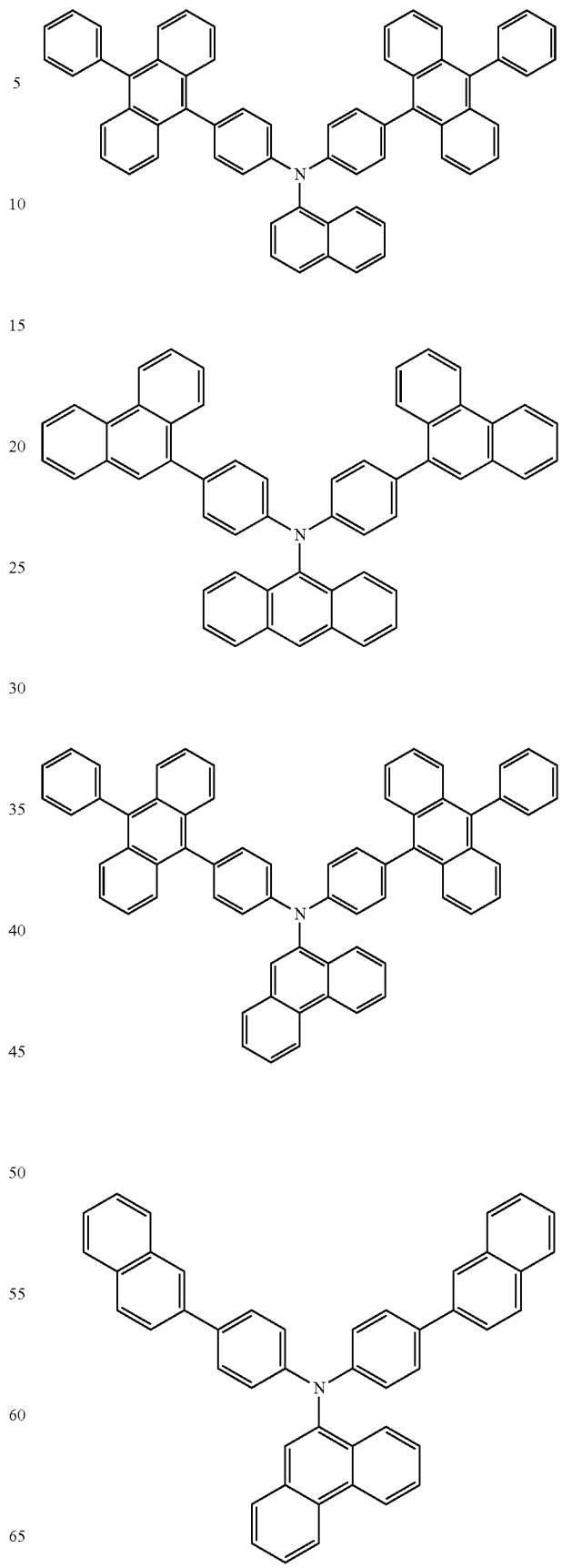

-continued

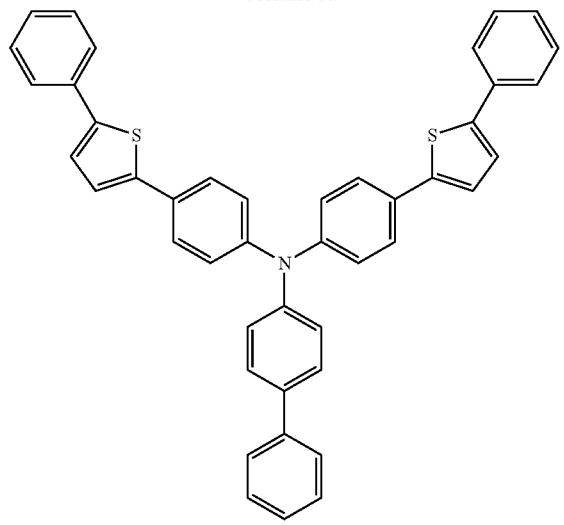

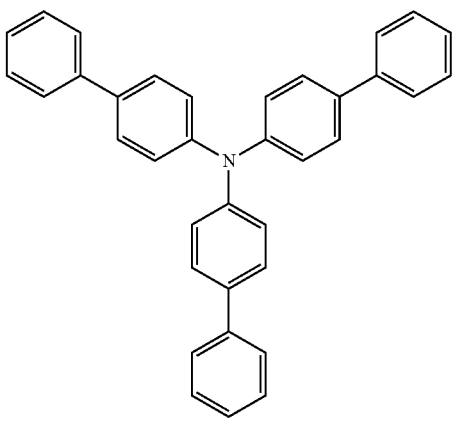 [SMILES: c1ccc(-c2ccc(N(c3ccc(-c4ccccc4)cc3)c3ccc(-c4ccccc4)cc3)cc2)cc1]

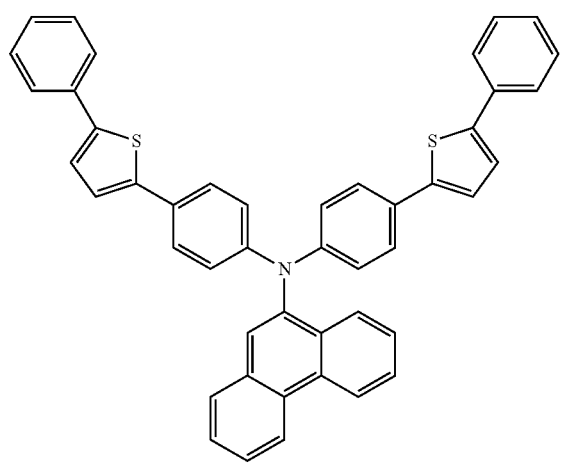

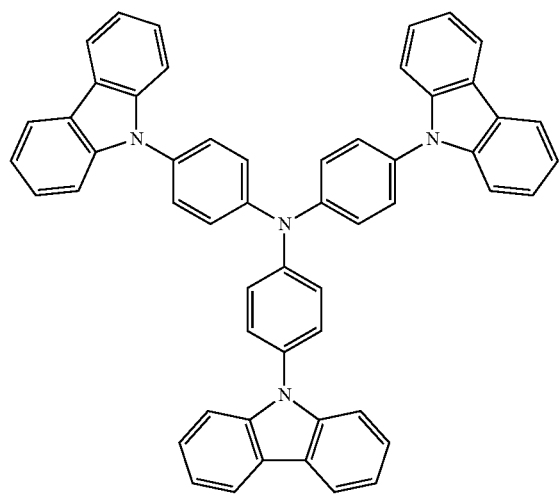

The anode of the organic EL device is used for injecting holes into the hole transporting layer or the emitting layer. It is effective that the anode has a work function of 4.5 eV or more. Exemplary materials for the anode for use in the aspect of the invention are indium-tin oxide (ITO), tin oxide (NESA), gold, silver, platinum and copper. The cathode is preferably formed of a material with smaller work function in order to inject electrons into the electron injecting layer or the emitting layer. Although a material for the cathode is subject to no specific limitation, examples of the material are indium, aluminum, magnesium, alloy of magnesium and indium, alloy of magnesium and aluminum, alloy of aluminum and lithium, alloy of aluminum, scandium and lithium, alloy of magnesium and silver and the like.

A method of forming each of the layers in the organic EL device according to the aspect of the invention is not particularly limited. A conventionally-known methods such as vacuum deposition or spin coating may be employed for forming the layers. The organic thin-film layer containing the compound represented by the formula (1), which is used in the organic EL device according to the aspect of the invention, may be formed by a conventional coating method such as vacuum deposition, molecular beam epitaxy (MBE method) and coating methods using a solution such as a dipping, spin coating, casting, bar coating, and roll coating.

Although the thickness of each organic layer of the organic EL device is not particularly limited, the thickness is generally preferably in a range of several nanometers to 1 μm because an excessively-thinned film likely entails defects such as a pin hole while an excessively-thickened film requires high voltage to be applied and deteriorates efficiency.

The organic EL device is formed on a light-transmissive substrate. The light-transmissive substrate, which supports the organic EL device, is preferably a smoothly-shaped substrate that transmits 50% or more of light in a visible region of 400 nm to 700 nm.

The light-transmissive substrate is exemplarily a glass plate, a polymer plate or the like.

For the glass plate, materials such as soda-lime glass, barium/strontium-containing glass, lead glass, aluminosilicate glass, borosilicate glass, barium borosilicate glass and quartz can be used.

185

For the polymer plate, materials such as polycarbonate, acryl, polyethylene terephthalate, polyether sulfide and polysulfone can be used.

SYNTHESIS EXAMPLE

Next, the invention will be described in further detail with reference to synthesis reference(s) and synthesis example(s). However, the invention is not limited to such synthesis examples.

[Synthesis Reference 1-1] Synthesis of 2-(3-bromophenyl)naphthalene

[Chemical Formula 68]

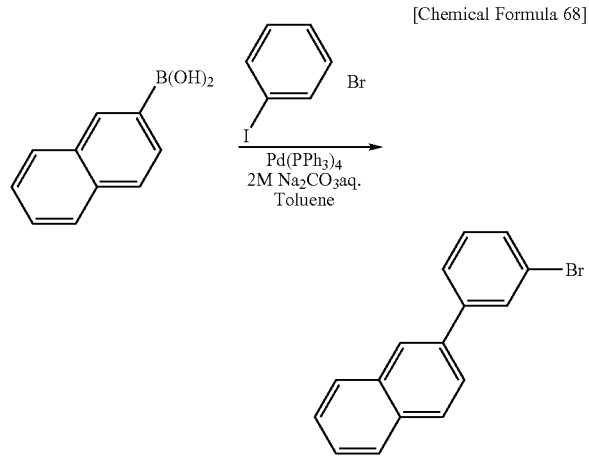

Under an argon gas atmosphere, 243 g (1.41 mol) of 2-naphthaleneboronic acid, 400 g (1.41 mol) of 3-bromoiodobenzene, 3.27 g (28.2 mmol) of tetrakis(triphenylphosphine)palladium(0), 6.4 L of toluene and 3.2 L of aqueous solution of 2M sodium carbonate were added together, and stirred while being refluxed for 24 hours. After the reaction was over, the mixture experienced filtration, through which aqueous phase thereof was eliminated. After organic phase thereof was washed by water and dried with magnesium sulfate, the toluene was distilled away under reduced pressure. Residue thereof was refined by silica-gel column chromatography, such that 303 g of 2-(3-bromophenyl)naphthalene was obtained at an yield of 76%.

[Synthesis Reference 1-2] Synthesis of 3-(2-naphthyl)phenylboronic acid

[Chemical Formula 69]

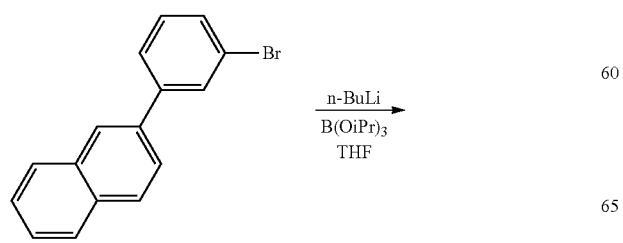

186

-continued

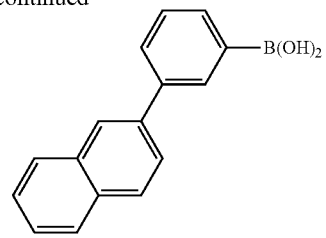

Under an argon gas atmosphere, a mixture of 212 g (748 mmol) of 2(3-bromophenyl)naphthalene and 3 L of dehydrated THF was cooled down to minus 10 degree C., and 600 ml (948 mmol) of hexane solution of 1.6M n-butyllithium was dropped into the mixture while the mixture was being stirred. Then, the mixture was stirred at 0 degree C. for 2 hours. The reaction solution was again cooled down to minus 78 degrees C., and 450 g (2.39 mol) of triisopropylborate was dropped into the solution. Then, the solution was stirred at room temperature for 17 hours. The reaction mixture was added with aqueous solution of hydrochloric acid and stirred at room temperature for 1 hour. The reaction mixture was added with 3 L of toluene, and aqueous phase thereof was eliminated. After organic phase thereof was dried with magnesium sulfate, the solvent was distilled away under reduced pressure. By recrystallizing the obtained solid by toluene, 126 g of 3-(2-naphthyl)phenylboronic acid was obtained at an yield of 67%.

[Synthesis Reference 2-1] Synthesis of 2-(3-bromophenyl)naphthalene

[Chemical Formula 70]

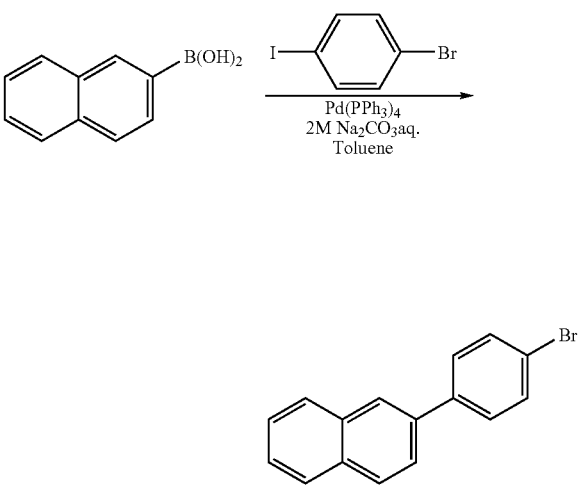

Under an argon gas atmosphere, 70.0 g (407 mmol) of 2-naphthaleneboronic acid, 115.10 g (407 mmol) of 4-bromoiodobenzene, 9.40 g (8.14 mmol) of tetrakis(triphenylphosphine)palladium(0), 1.2 L of toluene and 600 mL of aqueous solution of 2M sodium carbonate were added together, and stirred at 90 degrees C. for 20 hours. After the reaction was over, toluene was distilled away and methanol was added. Then, the precipitated solid was separated by filtration. The obtained solid was recrystallized with acetic ether and methanol and dried. 77.2 g of 2-(4-bromophenyl)naphthalene was obtained at an yield of 67%.

[Synthesis Reference 2-2] Synthesis of 4-(2-naphthyl)phenylboronic acid

[Chemical Formula 71]

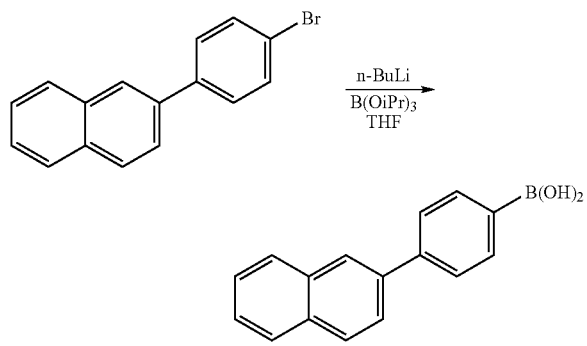

Under an argon gas atmosphere, a mixture of 50.0 g (177 mmol) of 2(4-bromophenyl)naphthalene and 500 mL of dehydrated THF was cooled down to minus 60 degree C. Then, 136 ml (212 mmol) of hexane solution of 1.56M n-butyllithium was dropped into the mixture while the mixture was being stirred. The reaction mixture was further stirred at minus 60 degrees for 1 hour. 99.6 g (529 mmol) of triisopropylborate was dropped into the reaction mixture at minus 60 degrees C. Subsequently, the reaction mixture was warmed up to room temperature, and stirred for 18 hours. The reaction mixture was added with aqueous solution of hydrochloric acid and stirred at room temperature for 1 hour. After the reaction, the reaction mixture was added with toluene, and aqueous phase thereof was eliminated. Then, organic phase thereof was dried with magnesium sulfate, and the solvent was distilled away under reduced pressure. By recrystallizing the obtained solid by toluene, 33.6 g of 4-(2-naphthyl)phenylboronic acid was obtained at an yield of 84%.

[Synthesis Reference 3-1] Synthesis of 1-(3-bromophenyl)naphthalene

[Chemical Formula 72]

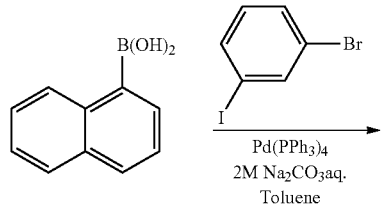

-continued

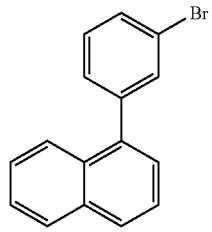

Under an argon gas atmosphere, 200.0 g (1.163 mol) of 1-naphthaleneboronic acid, 329.0 g (1.163 mol) of 3-bromoiodobenzene, 26.9 g (23.3 mmol) of tetrakis(triphenylphosphine)palladium(0), 3.7 L of toluene and 1.74 L of aqueous solution of 2M sodium carbonate were added together, and stirred while being refluxed for 24 hours. After the reaction was over, the mixture experienced filtration, through which aqueous phase thereof was eliminated. After organic phase thereof was washed by water and dried with magnesium sulfate, the toluene was distilled away under reduced pressure. Residue thereof was refined by silica-gel column chromatography, such that 250 g of 1-(3-bromophenyl)naphthalene was obtained at an yield of 76%.

[Synthesis Reference 3-2] Synthesis of 3-(1-naphthyl)phenylboronic acid

[Chemical Formula 73]

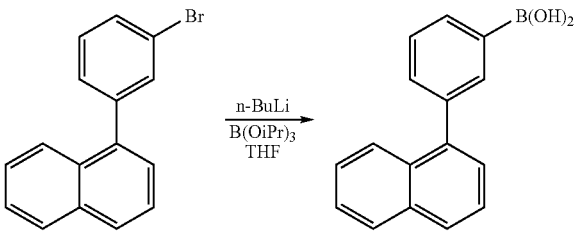

Under an argon gas atmosphere, a mixture of 200.0 g (706.3 mmol) of 1-(3-bromophenyl)naphthalene and 2.1 L of dehydrated THF was cooled down to minus 60 degree C. Then, 543 ml (847 mmol) of hexane solution of 1.56M n-butyllithium was dropped into the mixture while the mixture was being stirred. The reaction mixture was further stirred at minus 60 degrees for 2 hour. The reaction solution was again cooled down to minus 60 degrees C., and 398.5 g (2.119 mol) of triisopropylborate was dropped into the solution. Subsequently, the reaction mixture was warmed up to room temperature, and stirred for 17 hours. The reaction mixture was added with aqueous solution of hydrochloric acid and stirred at room temperature for 1 hour. After the reaction, the reaction mixture was added with toluene, and aqueous phase thereof was eliminated. Then, organic phase thereof was dried with magnesium sulfate, and the solvent was distilled away under reduced pressure. By recrystallizing the obtained solid by toluene, 126 g of 3-(1-naphthyl)phenylboronic acid was obtained at an yield of 67%.

[Synthesis Reference 4-1] Synthesis of 1-(4-bromophenyl)naphthalene

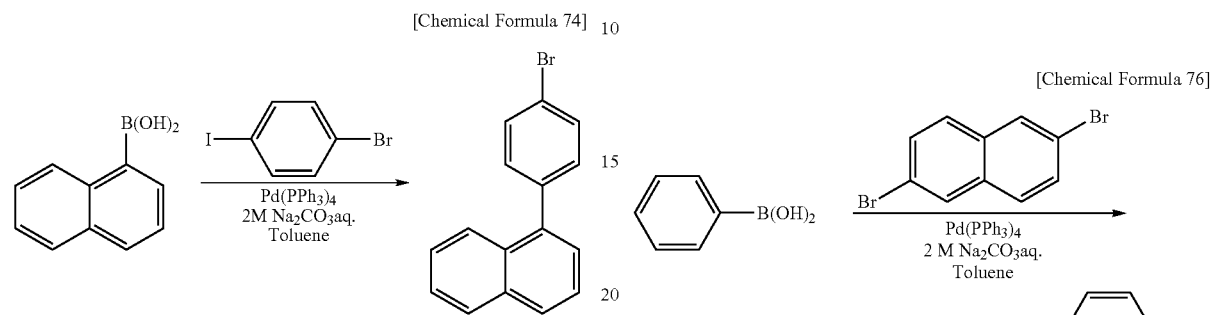

[Chemical Formula 74]

Under an argon gas atmosphere, 200.0 g (1.163 mol) of 1-naphthaleneboronic acid, 329.0 g (1.163 mol) of 4-bromoiodobenzene, 26.9 g (23.3 mmol) of tetrakis(triphenylphosphine)palladium(0), 3.7 L of toluene and 1.74 L of aqueous solution of 2M sodium carbonate were added together, and stirred at 90 degrees C. for 24 hours. After the reaction was over, the mixture experienced filtration, through which aqueous phase thereof was eliminated. After organic phase thereof was washed by water and dried with magnesium sulfate, the toluene was distilled away under reduced pressure. Residue thereof was refined by silica-gel column chromatography, such that 268 g of 1-(4-bromophenyl)naphthalene was obtained at an yield of 81%.

[Synthesis Reference 4-2] Synthesis of 4-(1-naphthyl)phenylboronic acid

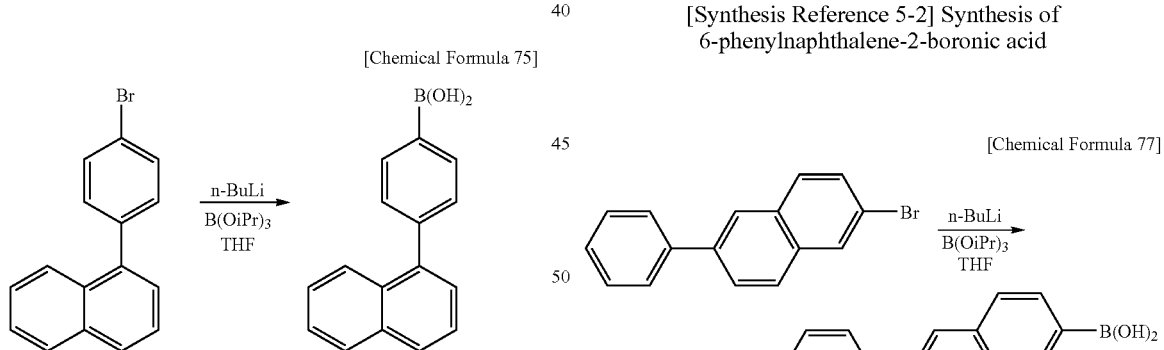

[Chemical Formula 75]

Under an argon gas atmosphere, a mixture of 208.8 g (737.4 mmol) of 1-(4-bromophenyl)naphthalene and 2.1 L of dehydrated THF was cooled down to minus 60 degree C. Then, 567 ml (884.9 mmol) of hexane solution of 1.56M n-butyllithium was dropped into the mixture while the mixture was being stirred. The reaction mixture was further stirred at minus 60 degrees for 2 hours. 416 g (2.21 mol) of triisopropylborate was dropped into the reaction mixture at minus 60 degrees C. The reaction mixture was then stirred at room temperature for 17 hours. The reaction mixture was added with aqueous solution of hydrochloric acid and stirred at room temperature for 1 hour. After the reaction, the reaction mixture was added with toluene, and aqueous phase thereof was eliminated. Then, organic phase thereof was dried with magnesium sulfate, and the solvent was distilled away under reduced pressure. By recrystallizing the obtained solid by toluene, 126 g of 4-(1-naphthyl)phenylboronic acid was obtained at an yield of 67%.

[Synthesis Reference 5-1] Synthesis of 2-bromo-6-phenylnaphthalene

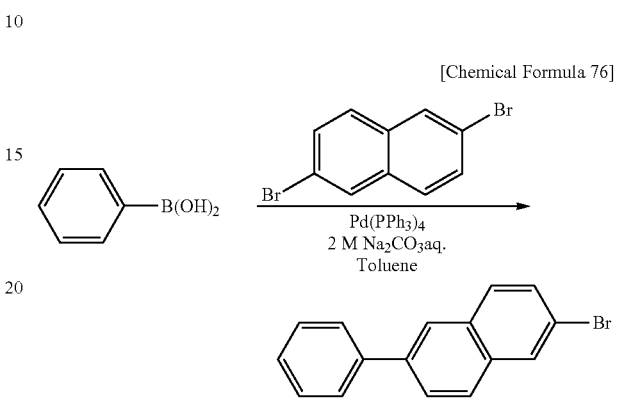

[Chemical Formula 76]

Under an argon gas atmosphere, 128.0 g (1.049 mol) of phenylboronic acid, 300.0 g (1.163 mol) of 2,6-dibromonaphthalene, 24.2 g (21.0 mmol) of tetrakis(triphenylphosphine)palladium(0), 4.3 L of dimethoxyethane and 1.60 L of aqueous solution of 2M sodium carbonate were added together, and stirred at 78 degrees C. for 24 hours. The reaction mixture was added with toluene and water, and aqueous phase thereof was eliminated. After organic phase thereof was washed by water and dried with magnesium sulfate, the toluene was distilled away under reduced pressure. Residue thereof was refined by silica-gel column chromatography and recrystallized with hexane such that 108 g of 2-bromo-6-phenylnaphthalene was obtained at an yield of 36%.

[Synthesis Reference 5-2] Synthesis of 6-phenylnaphthalene-2-boronic acid

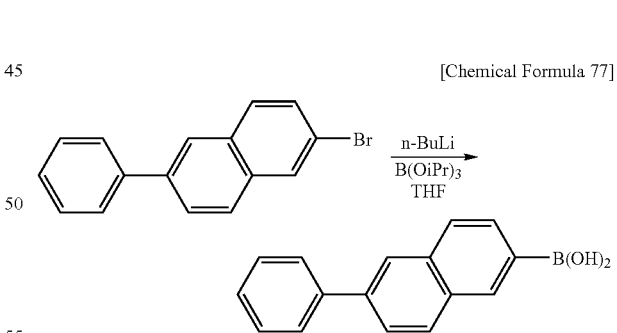

[Chemical Formula 77]

Under an argon gas atmosphere, a mixture of 100.0 g (353.1 mmol) of 2-bromo-6-phenylnaphthalene, 1.2 L of dehydrated THF and 1.2 L of dehydrated diethyl ether was cooled down to minus 20 degree C. Then, 280 ml (437 mmol) of hexane solution of 1.56M n-butyllithium was dropped into the mixture while the mixture was being stirred. The reaction mixture was further stirred at minus 20 degrees for 1 hour. The reaction mixture was cooled down to minus 60 degrees C., and 199.3 g (1.06 mol) of triisopropylborate was dropped into the mixture. The reaction mixture was warmed up and then stirred at room temperature for 16 hours. The reaction mixture was added with aqueous solution of hydrochloric acid and stirred at room temperature for 1 hour. After the reaction, the reaction mixture was added with toluene, and aqueous phase thereof was eliminated. Then, organic phase thereof was washed with water and dried with magnesium sulfate, and the solvent was distilled away under reduced pressure. By recrystallizing the obtained solid with hexane, 58.0 g of 6-phenylnaphthalene-2-boronic acid was obtained at an yield of 55%.

[Synthesis Example 1-1] Synthesis of Compound 1-2

[Chemical Formula 78]

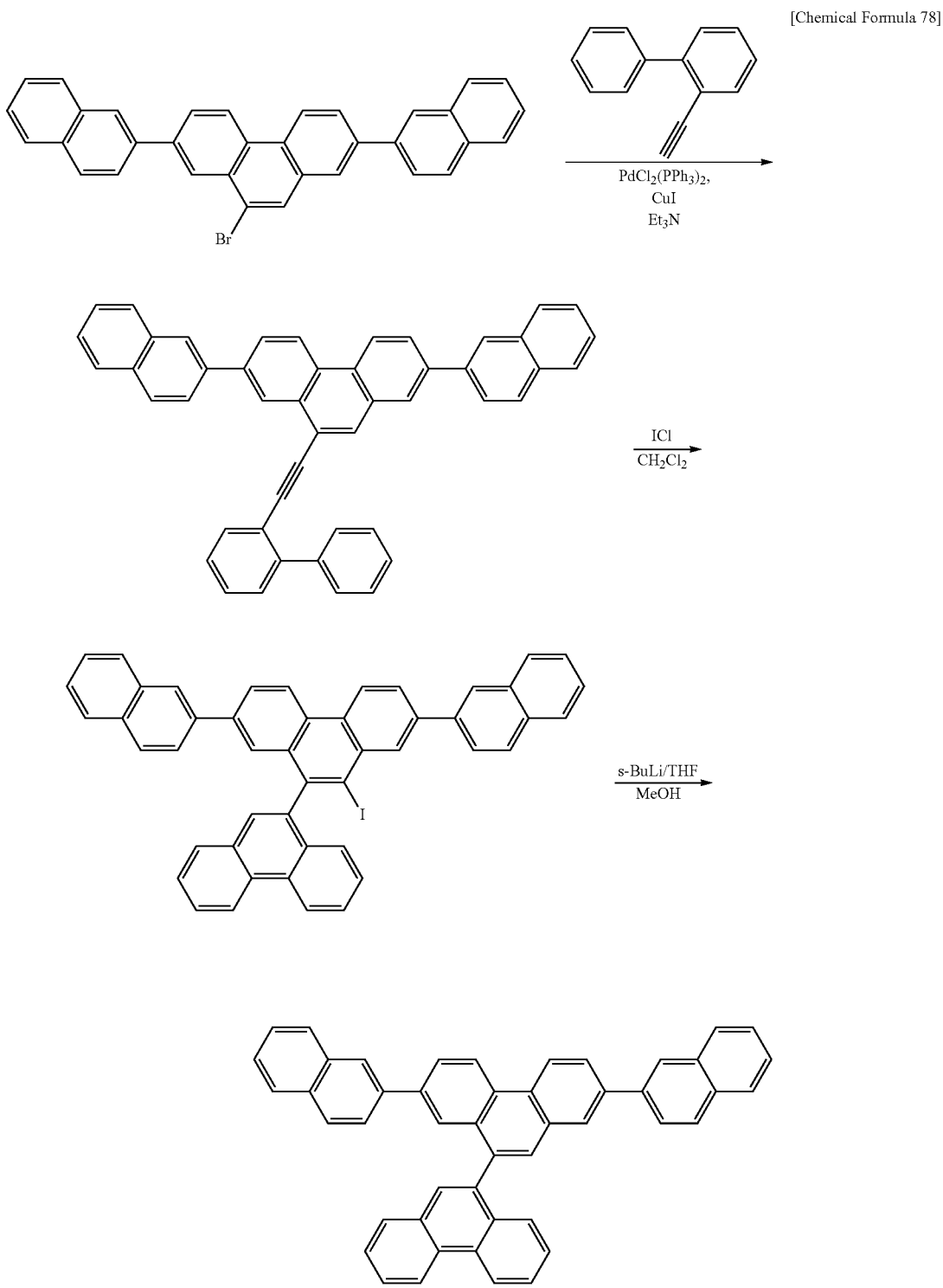

Under an argon gas atmosphere, a mixture of 10.0 g (19.6 mmol) of 9-bromo-2,7-di(naphthalene-2-yl)phenanthrene, 3.85 g (21.59 mmol) of 2-(1-ethynyl)biphenyl and 60 mL of triethylamine was added with 0.48 g (0.39 mmol) of PdCl$_2$(PPh$_3$)$_2$ and 0.15 g (0.79 mmol) of CuI. Then, the mixture was stirred at 60 degrees C. for 4 hours. After the reaction was over, insoluble matters were removed by filtration, and the solvent was distilled away. Then, the mixture was added with aqueous solution of hydrochloric acid, and extracted with toluene. Organic phase thereof was washed with aqueous solution of sodium hydrogencarbonate, and subsequently washed with saturated sodium chloride solution. After liquid separation, the organic phase was dried with anhydrous sodium sulfate and followed by filtration, and the solvent was distilled away. Then, the residue was refined by column chromatography, so that 8.4 g of 9-(2-(2-biphenyl)ethynyl)-2,7-di(naphthalene-2-yl)phenanthrene was obtained at an yield of 70%.

Under an argon gas atmosphere, a mixture of 5.00 g (8.24 mmol) of 9-(2-(2-biphenyl)ethynyl)-2,7-di(naphthalene-2-yl)phenanthrene and 85 mL of dichloromethane was cooled down to minus 78 degree C., and added with a mixture containing 1.61 g (9.89 mmol) of ICl and 15 mL of dichloromethane. The mixture was stirred at minus 78 degrees C. for 1 hour. The reaction mixture was added with aqueous solution of sodium bisulfite, and extracted with dichloromethane. The organic phase was washed with saturated sodium chloride solution. The organic phase was dried with anhydrous sodium sulfate. After filtration, the solvent was distilled away. Then, the residue was refined by flash column chromatography, so that 4.5 g of 9-(10-iodo-2,7-di(naphthalene-2-yl)phenanthrene was obtained at an yield of 80%.

Under an argon gas atmosphere, a mixture of 2.5 g (3.4 mmol) of 9-(10-iodo-2,7-di(naphthalene-2-yl)phenanthrene and 50 mL of dehydrated THF was cooled down to minus 70 degree C. Then, 4.09 ml (4.09 mmol) of hexane solution of 1.00M s-butyllithium was dropped into the mixture while the mixture was being stirred. The mixture was stirred at minus 70 degrees C. for 2 hours. The reaction mixture was added with MeOH, warmed up to room temperature and stirred for 1 hour. The reaction mixture was added with aqueous solution of hydrochloric acid, and extracted with toluene. The organic phase was washed with saturated sodium chloride solution. The organic phase was dried with anhydrous sodium sulfate. After filtration, the solvent was distilled away. Then, the residue was refined by flash column chromatography, so that 1.54 g of the compound 1-2 was obtained at an yield of 74%.

Mass-spectrum analysis consequently showed that m/e was equal to 606 while a calculated molecular weight was 606.23.

[Synthesis Example 1-2] Synthesis of Compound 1-7

[Chemical Formula 79]

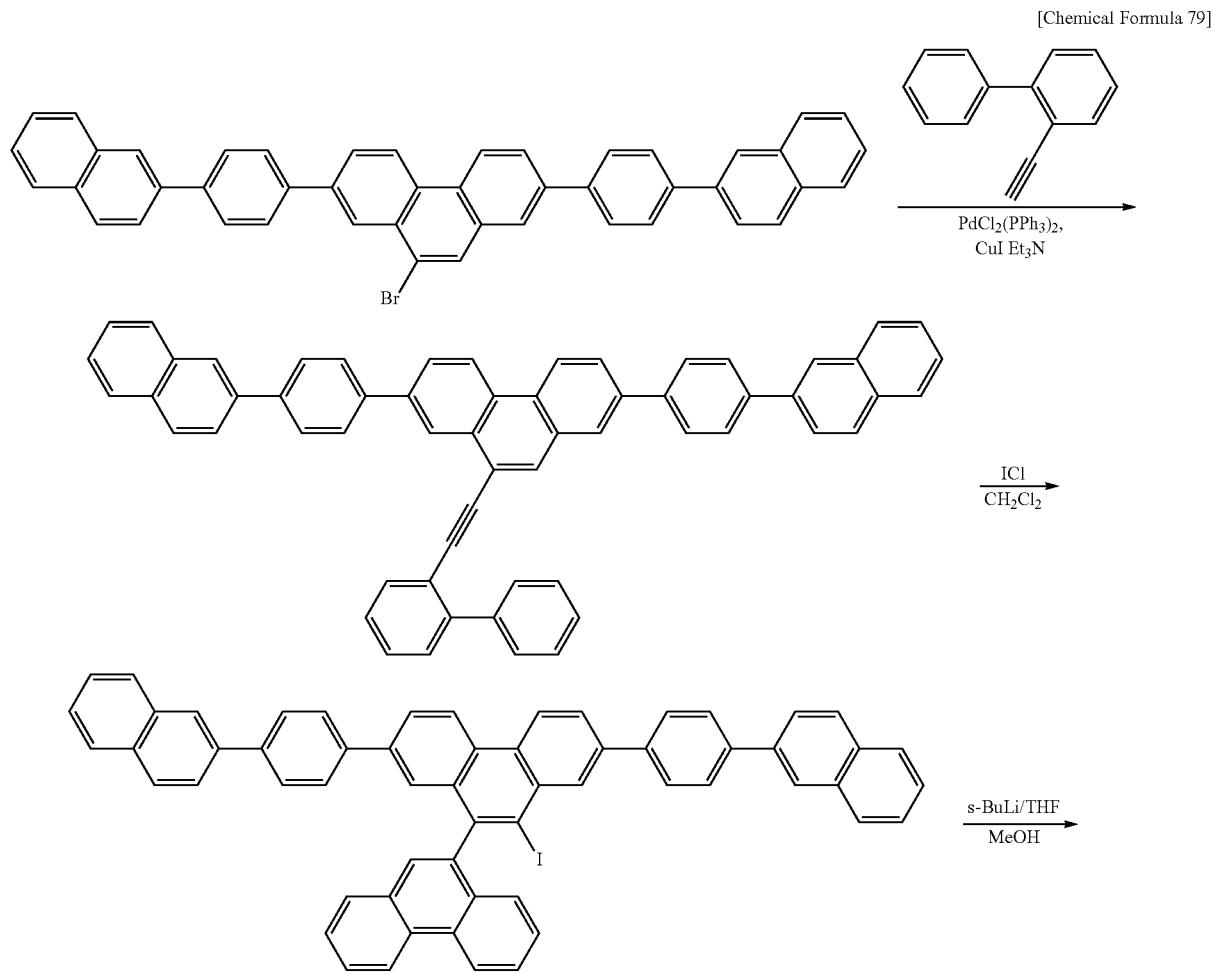

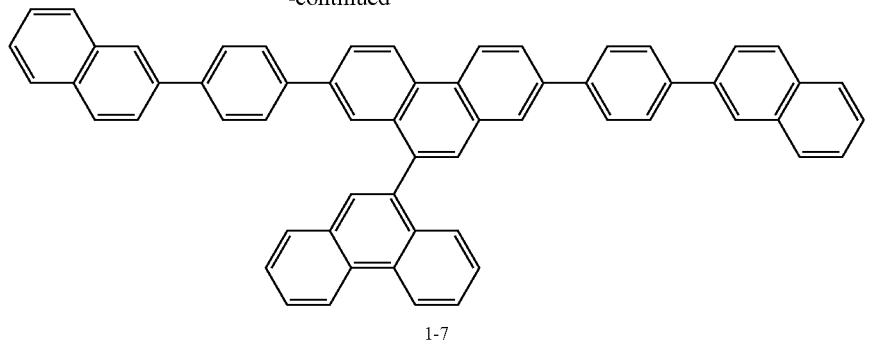
1-7
The compound 1-7 was synthesized in the same manner as the compound 1-2, except that 9-bromo-2,7-bis(4-(naphthalene-2-yl)phenyl)phenanthrene was used in place of 9-bromo-2,7-di(naphthalene-2-yl)phenanthrene.
Mass-spectrum analysis consequently showed that m/e was equal to 758 while a calculated molecular weight was 758.3.
[Synthesis Example 1-3] Synthesis of Compound 1-8
[Chemical Formula 80]
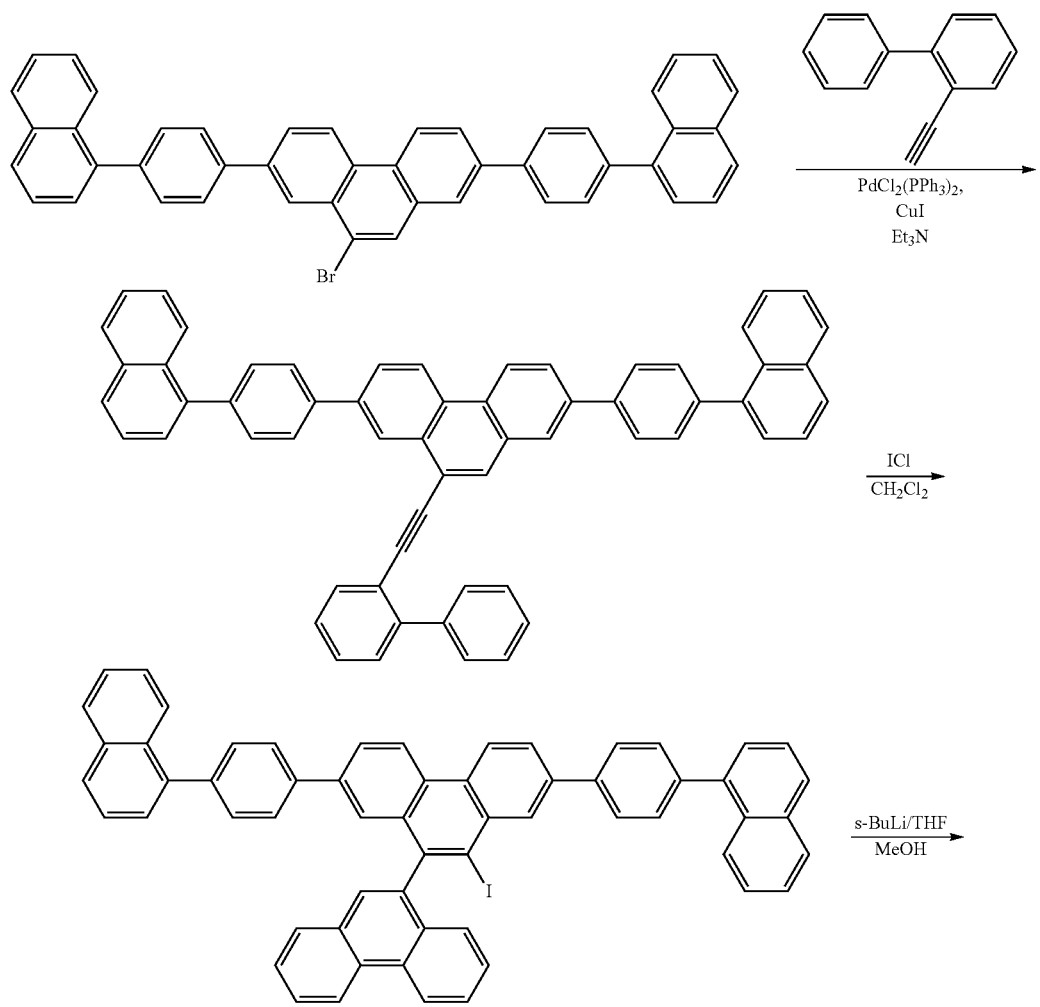

-continued
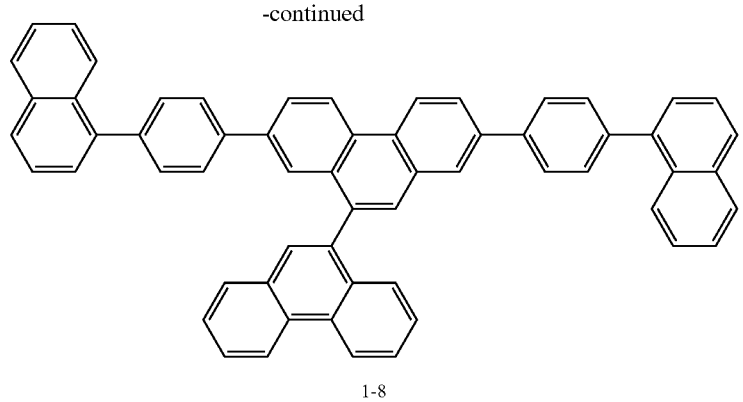
1-8
The compound 1-8 was synthesized in the same manner as the compound 1-2, except that 9-bromo-2,7-bis(4-(naphthalene-1-yl)phenyl)phenanthrene was used in place of 9-bromo-2,7-di(naphthalene-2-yl)phenanthrene.
Mass-spectrum analysis consequently showed that m/e was equal to 758 while a calculated molecular weight was 758.3.
[Synthesis Example 1-4] Synthesis of Compound 1-9
[Chemical Formula 81]
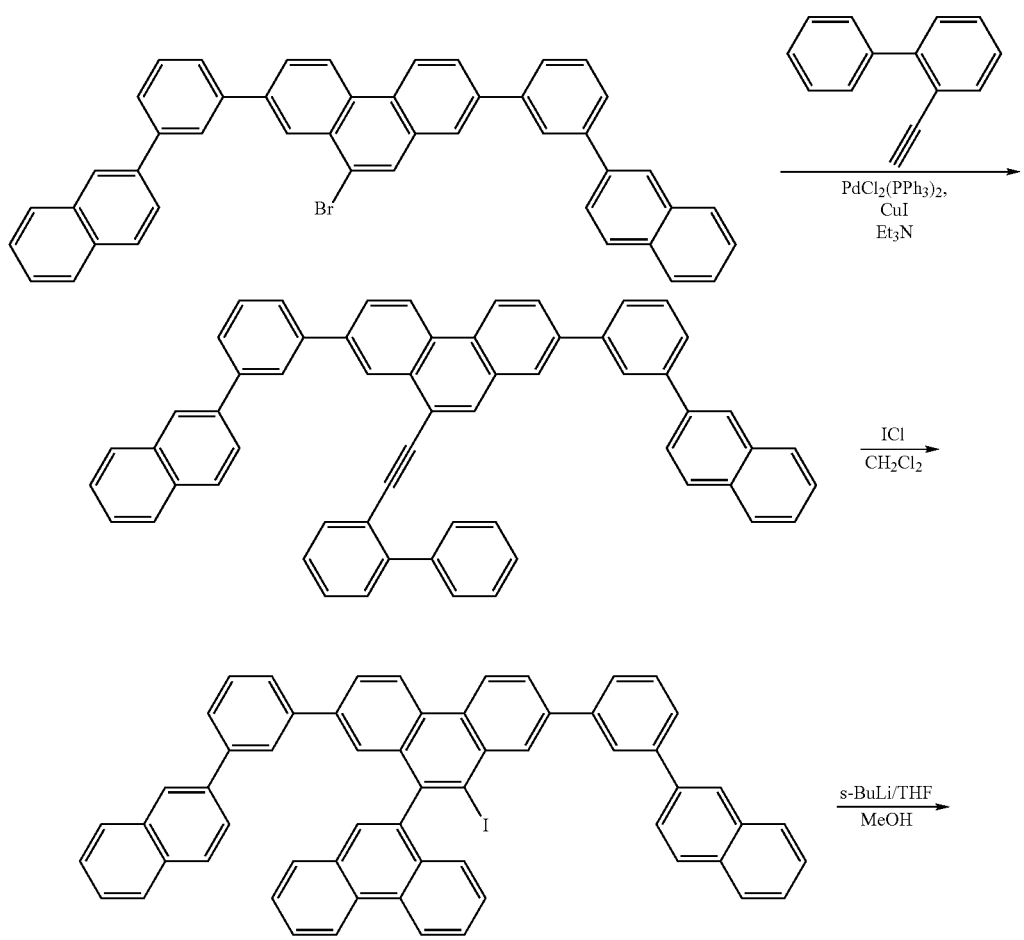

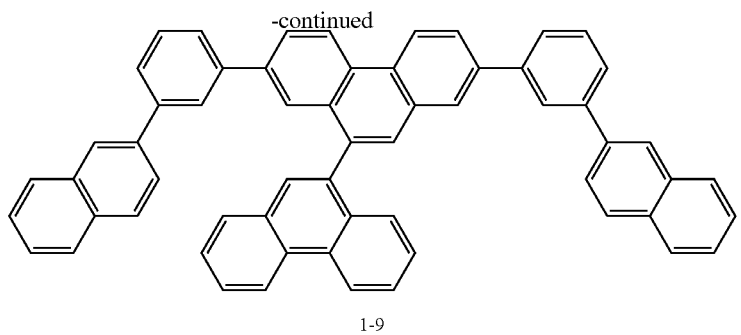

1-9

The compound 1-9 was synthesized in the same manner as the compound 1-2, except that 9-bromo-2,7-bis(3-(naphthalene-2-yl)phenyl)phenanthrene was used in place of 9-bromo-2,7-di(naphthalene-2-yl)phenanthrene.

Mass-spectrum analysis consequently showed that m/e was equal to 758 while a calculated molecular weight was 758.3.

[Synthesis Example 1-5] Synthesis of Compound 1-37

[Chemical Formula 82]

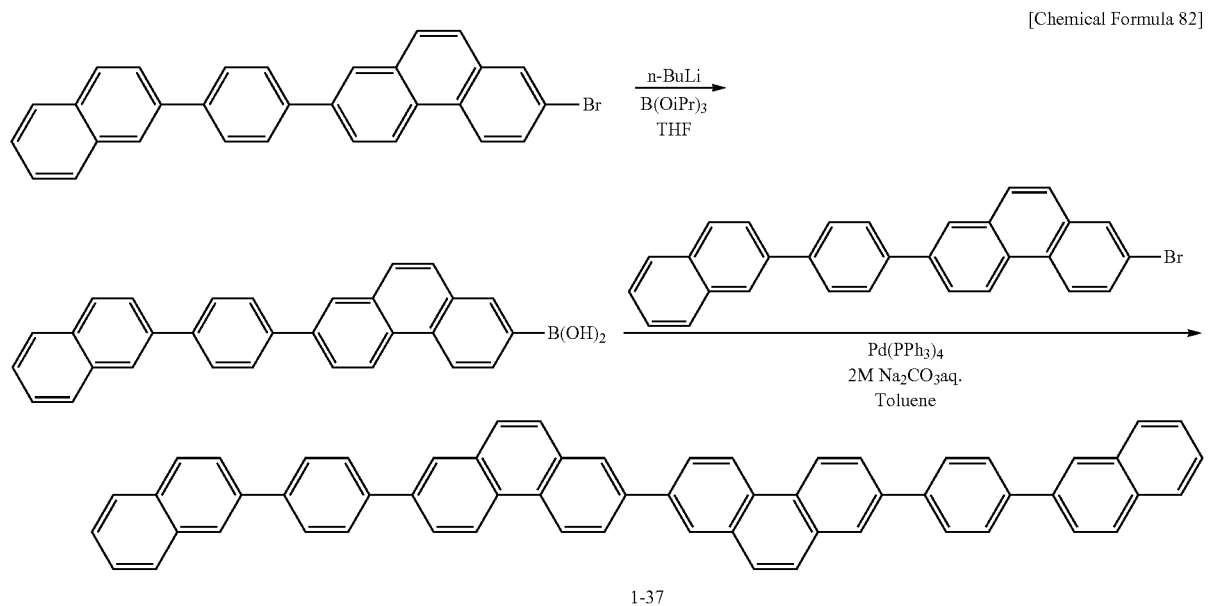

1-37

Under an argon gas atmosphere, a mixture of 15.0 g (32.7 mmol) of 2-bromo-7-(4-(naphthalene-2-yl)phenyl)phenanthrene and 150 mL of dehydrated THF was cooled down to minus 60 degree C. Then, 25.3 ml (39.2 mmol) of hexane solution of 1.55M n-butyllithium was dropped into the mixture while the mixture was being stirred. The reaction mixture was further stirred at minus 60 degrees for 2 hours. The reaction solution was again cooled down to minus 70 degrees C., and 18.4 g (98.0 mmol) of triisopropylborate was dropped into the solution. The reaction mixture was warmed back to room temperature, stirred for 2 hours and left unattended for one night. Subsequently, the reaction mixture was added with aqueous solution of hydrochloric acid while being cooled on an ice bath, and stirred for 1 hour at room temperature. The reaction mixture was added with toluene, and aqueous phase thereof was eliminated. After organic phase thereof was dried with magnesium sulfate, the solvent was distilled away under reduced pressure. By recrystallizing the obtained solid with toluene-hexane, 9.5 g of 7-(4-(naphthalene-2-yl)phenyl)phenanthrene-2-ylboronic acid was obtained at an yield of 69%.

Under an argon gas atmosphere, 3.00 g (6.53 mmol) of 2-bromo-7-(4-(naphthalene-2-yl)phenyl)phenanthrene, 2.77 g (6.53 mmol) of 7-(4-(naphthalene-2-yl)phenyl)phenanthrene-2-ylboronic acid, 0.15 g (0.13 mmol) of tetrakis (triphenylphosphine)palladium(0), 100 mL of toluene and 9.79 g of aqueous solution of 2M sodium carbonate were mixed, and stirred at 100 degrees C. for 7 hours. Subsequently, the reaction mixture was cooled down to room temperature, added with water and stirred for 1 hour. Then, the reaction mixture was added with methanole, and the solid was filtrated. The solid was washed with methanol, DME and toluene. The obtained solid was refined by silica-gel column chromatography and recrystallized by toluene-hexane, such that 2.30 g of the compound 1-37 was obtained at an yield of 46%.

Mass-spectrum analysis consequently showed that m/e was equal to 758 while a calculated molecular weight was 758.3.

[Synthesis Example 1-6] Synthesis of Compound 1-38

[Chemical Formula 83]

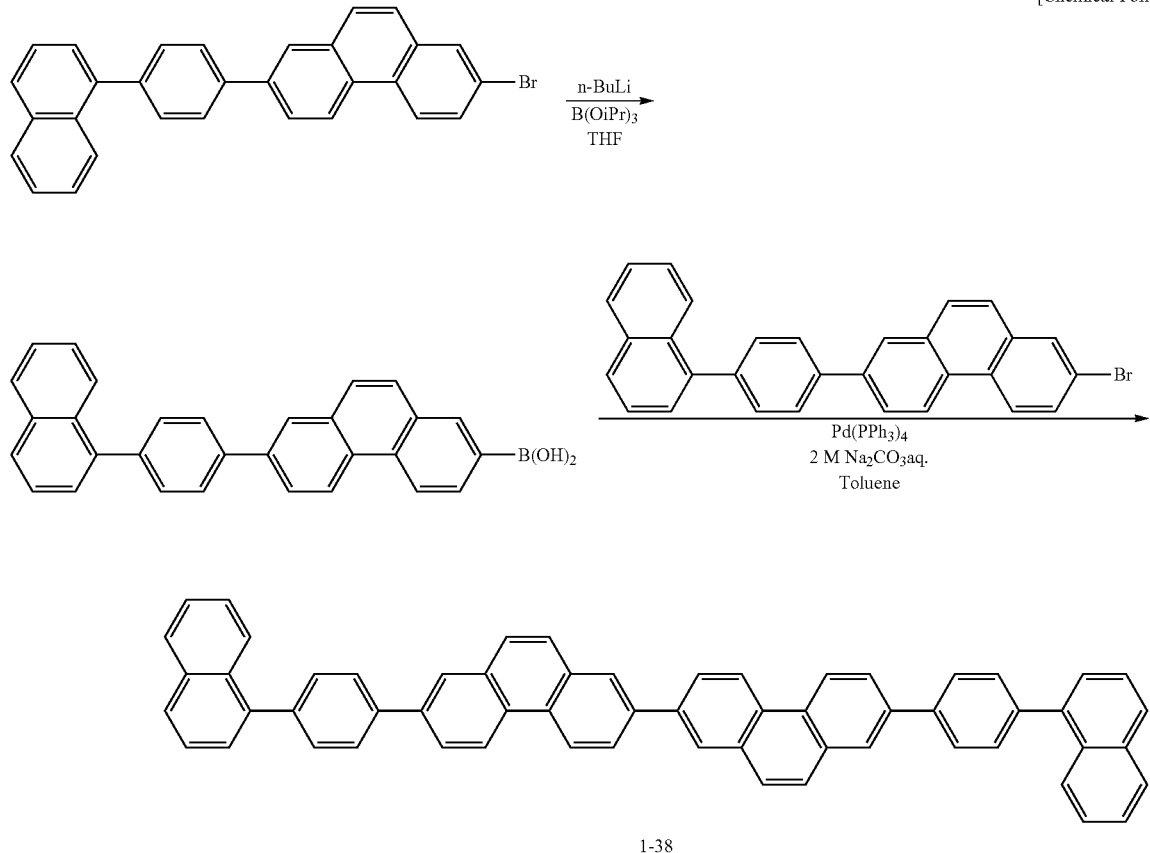

1-38

The compound 1-38 was synthesized in the same manner as the compound 1-37, except that 2-bromo-7-(4-(naphthalene-1-yl)phenyl)phenanthrene was used in place of 2-bromo-7-(4-(naphthalene-2-yl)phenyl)phenanthrene.

Mass-spectrum analysis consequently showed that m/e was equal to 758 while a calculated molecular weight was 758.3.

[Synthesis Example 1-7] Synthesis of Compound 1-41

[Chemical Formula 84]

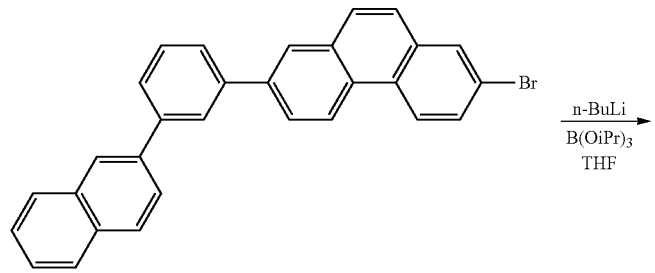

-continued
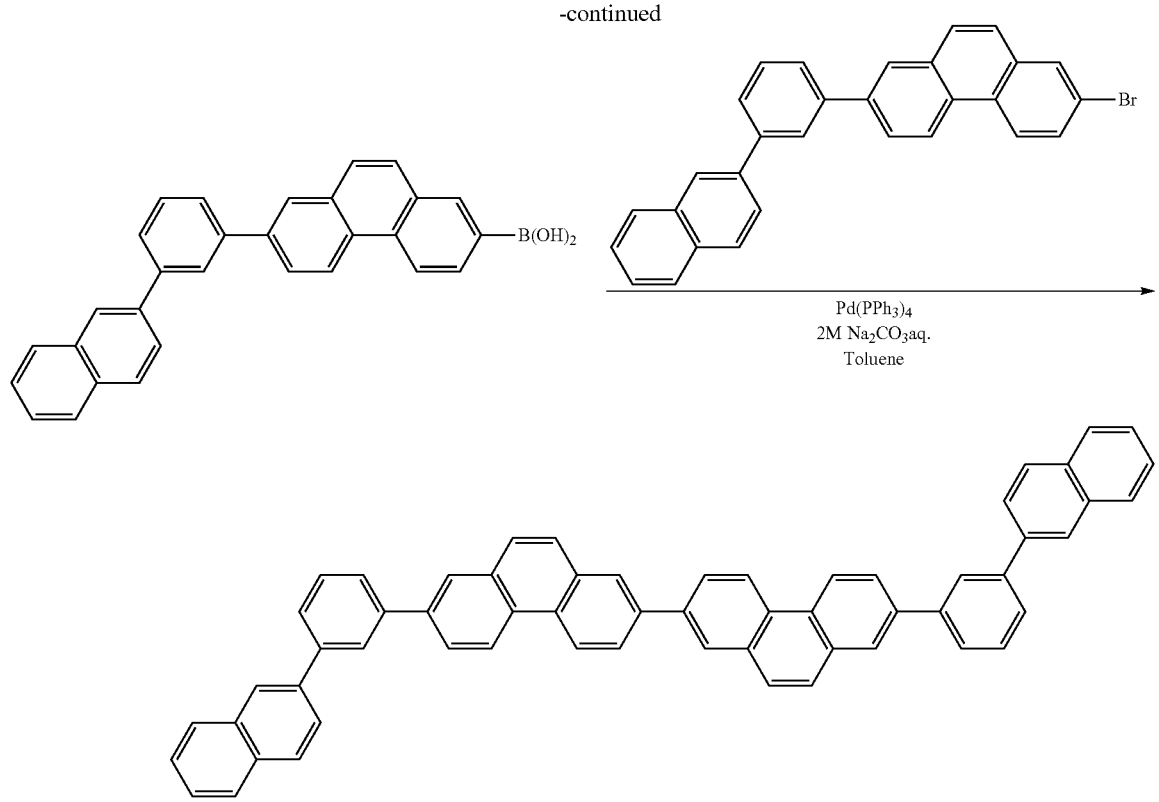
1-41
The compound 1-41 was synthesized in the same manner as the compound 1-37, except that 2-bromo-7-(3-(naphthalene-2-yl)phenyl)phenanthrene was used in place of 2-bromo-7-(4-(naphthalene-2-yl)phenyl)phenanthrene.
Mass-spectrum analysis consequently showed that m/e was equal to 758 while a calculated molecular weight was 758.3.
[Synthesis Example 1-8] Synthesis of Compound 1-63
[Chemical Formula 85]
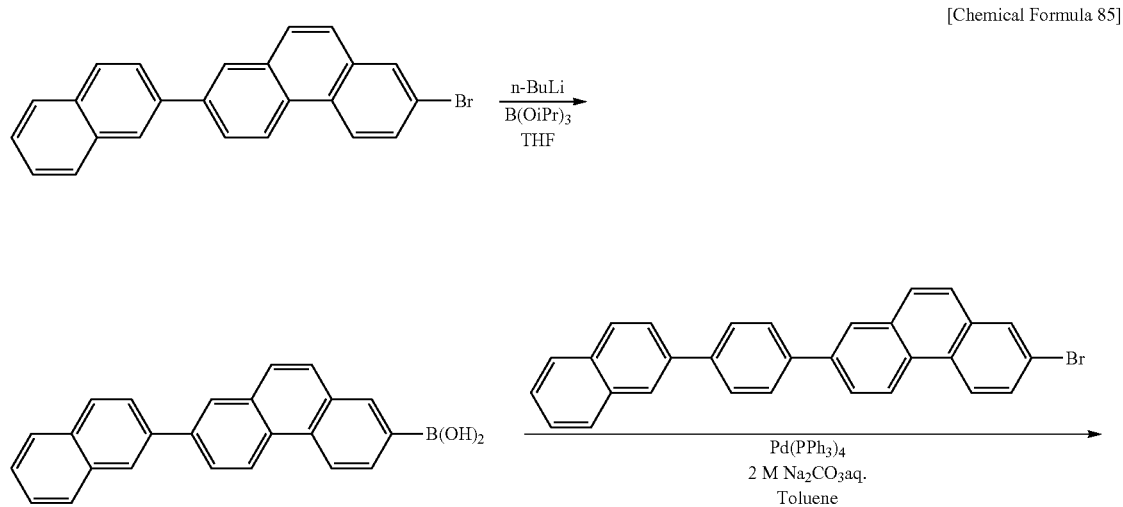

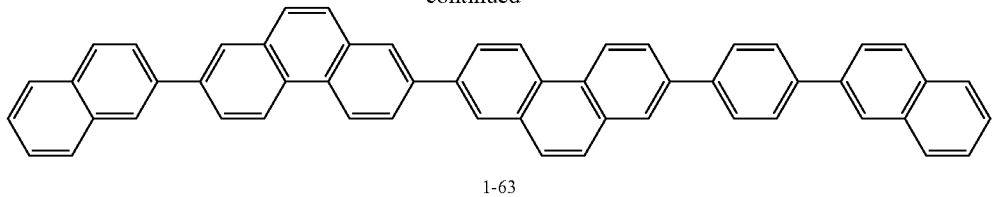

1-63

Under an argon gas atmosphere, a mixture of 15.0 g (39.1 mmol) of 2-bromo-7-(naphthalene-2-yl)phenanthrene and 150 mL of dehydrated THF was cooled down to minus 60 degree C. Then, 30.3 ml (46.7 mmol) of hexane solution of 1.55M n-butyllithium was dropped into the mixture while the mixture was being stirred. The reaction mixture was further stirred at minus 60 degrees for 2 hours. The reaction solution was again cooled down to minus 70 degrees C., and 22.08 g (117.4 mmol) of triisopropylborate was dropped into the solution. The reaction mixture was warmed back to room temperature, stirred for 2 hours and left unattended for one night. Subsequently, the reaction mixture was added with aqueous solution of hydrochloric acid while being cooled on an ice bath, and stirred for 1 hour at room temperature. The reaction mixture was added with toluene, and aqueous phase thereof was eliminated. After organic phase thereof was dried with magnesium sulfate, the solvent was distilled away under reduced pressure. By recrystallizing the obtained solid with toluene-hexane, 8.4 g of 7-(naphthalene-2-yl)phenanthrene-2-ylboronic acid was obtained at an yield of 62%.

Under an argon gas atmosphere, 3.96 g (8.62 mmol) of 2-bromo-7-(4-(naphthalene-2-yl)phenyl)phenanthrene, 3.00 g (8.62 mmol) of 7-(naphthalene-2-yl)phenanthrene-2-ylboronic acid, 0.20 g (0.17 mmol) of tetrakis(triphenylphosphine)palladium(0), 100 mL of toluene and 12.9 g of aqueous solution of 2M sodium carbonate were mixed, and stirred at 100 degrees C. for 7 hours. Subsequently, the reaction mixture was cooled down to room temperature, added with water and stirred for 1 hour. Then, the reaction mixture was added with methanole, and the solid was filtrated. The solid was washed with methanol, DME and toluene. The obtained solid was refined by silica-gel column chromatography and recrystallized by toluene-hexane, such that 2.70 g of the compound 1-63 was obtained at an yield of 42%.

Mass-spectrum analysis consequently showed that m/e was equal to 682 while a calculated molecular weight was 682.27.

[Synthesis Example 1-9] Synthesis of Compound 1-64

[Chemical Formula 86]

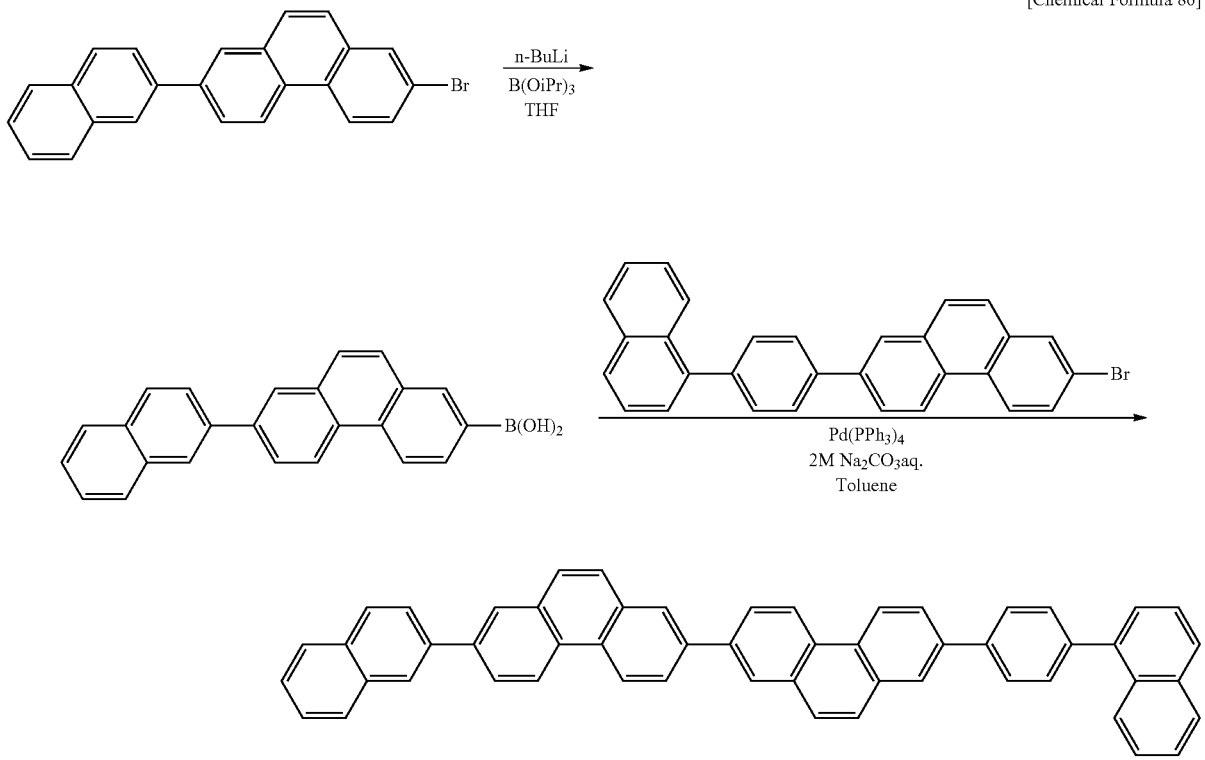

1-64

The compound 1-64 was synthesized in the same manner as the compound 1-63, except that 2-bromo-7-(4-(naphthalene-1-yl)phenyl)phenanthrene was used in place of 2-bromo-7-(4-(naphthalene-2-yl)phenyl)phenanthrene.

Mass-spectrum analysis consequently showed that m/e was equal to 682 while a calculated molecular weight was 682.27.

[Synthesis Example 1-10] Synthesis of Compound 1-65

The compound 1-65 was synthesized in the same manner as the compound 1-63, except that 2-bromo-7-(3-(naphthalene-2-yl)phenyl)phenanthrene was used in place of 2-bromo-7-(4-(naphthalene-2-yl)phenyl)phenanthrene.

Mass-spectrum analysis consequently showed that m/e was equal to 682 while a calculated molecular weight was 682.27.

[Chemical Formula 87]

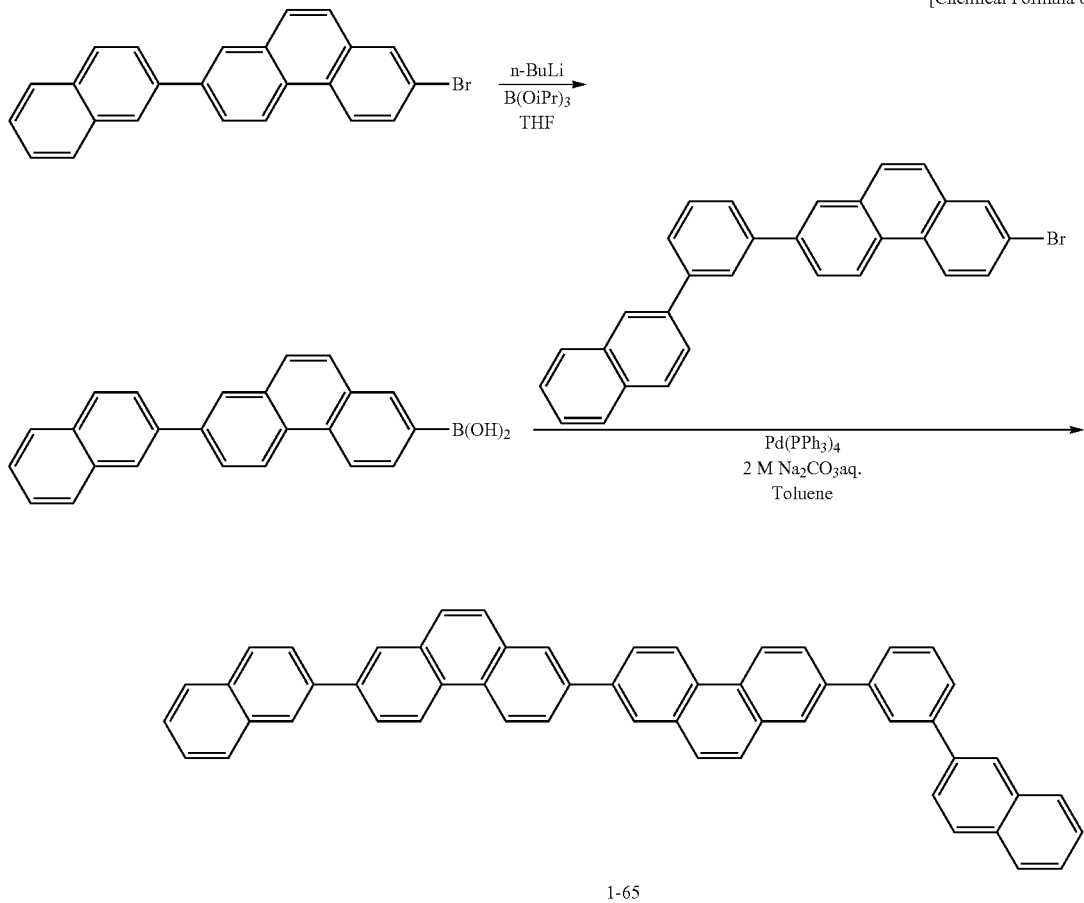

1-65

[Synthesis Example 1-11] Synthesis of Compound 1-99

[Chemical Formula 88]

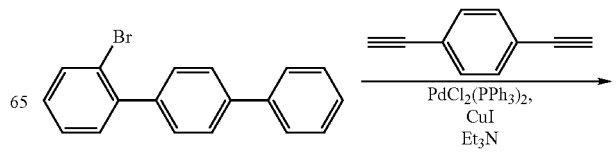

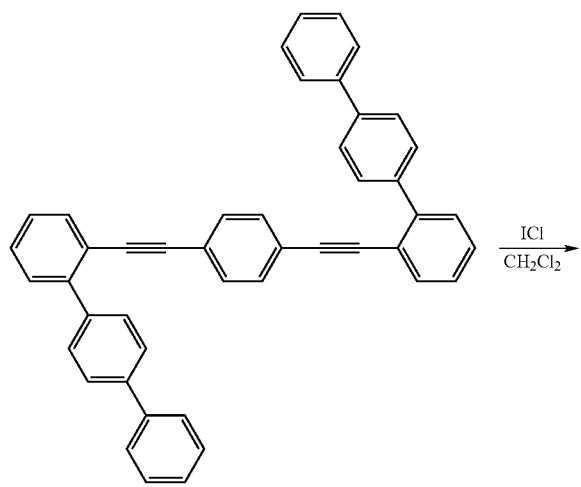

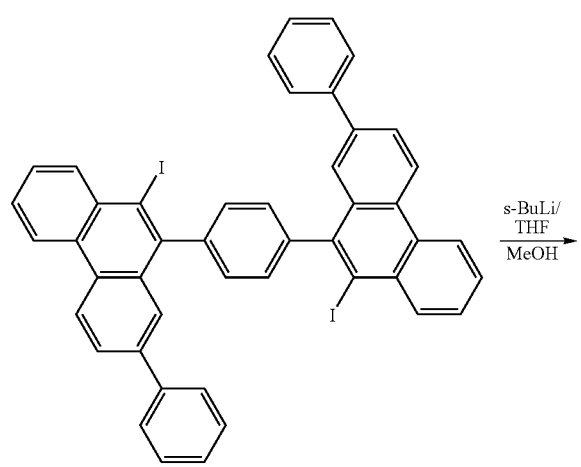

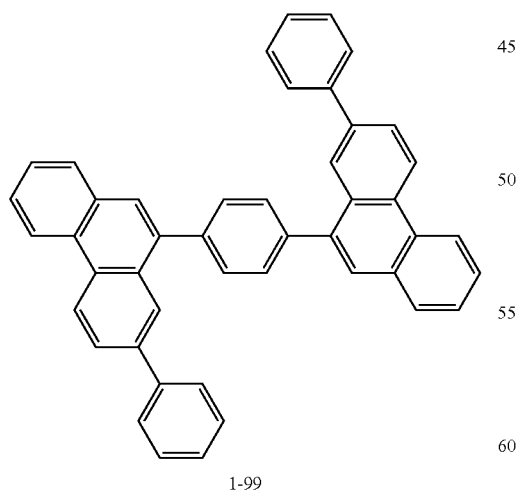

1-99

Under an argon gas atmosphere, a mixture of 10.0 g (32.3 mmol) of 2-bromo-p-terphenyl, 2.04 g (16.2 mmol) of 1,4-diethynylbenzene and 45 mL of triethylamine was added with 0.79 g (0.65 mmol) of $PdCl_2(PPh_3)_2$ and 0.25 g (1.29 mmol) of CuI. Then, the mixture was stirred at 60 degrees C. for 4 hours. After the reaction was over, insoluble matters were removed by filtration, and the solvent was distilled away under reduced pressure. The mixture was added with aqueous solution of hydrochloric acid, and extracted with toluene. Organic phase thereof was washed with aqueous solution of sodium hydrogencarbonate, and subsequently washed with saturated sodium chloride solution. After liquid separation, the organic phase was dried with anhydrous sodium sulfate and followed by filtration, and the solvent was then distilled away. The residue was refined by column chromatography, so that 11.4 g of 1,4-bis((p-terphenyl-2-yl)ethynyl)benzene was obtained at an yield of 61%.

Under an argon gas atmosphere, a mixture of 5.00 g (8.58 mmol) of 1,4-bis((p-terphenyl-2-yl)ethynyl)benzene and 85 mL of dichloromethane was cooled down to minus 78 degree C., and added with a mixture containing 3.34 g (20.6 mmol) of ICl and 30 mL of dichloromethane. The mixture was stirred at minus 78 degrees C. for 1 hour.

The reaction mixture was added with aqueous solution of sodium bisulfite, and extracted with dichloromethane. The organic phase was washed with saturated sodium chloride solution. The organic phase was dried with anhydrous sodium sulfate and followed by filtration, and the solvent was distilled away. Then, the residue was refined by flash column chromatography, so that 6.0 g of 1,4-bis(10-iodo-7-phenylphenanthrene-9-yl)benzene was obtained at an yield of 84%.

Under an argon gas atmosphere, a mixture of 3.0 g (3.59 mmol) of 1,4-bis(10-iodo-7-phenylphenanthrene-9-yl)benzene and 60 mL of dehydrated THF was cooled down to minus 70 degree C. Then, 10.8 ml (10.8 mmol) of hexane solution of 1.00M s-butyllithium was dropped into the mixture while the mixture was being stirred. The mixture was stirred at minus 70 degrees C. for 2 hours. The reaction mixture was added with MeOH, warmed up to room temperature and stirred for 1 hour. The reaction mixture was added with aqueous solution of hydrochloric acid, and extracted with toluene. The organic phase was washed with saturated sodium chloride solution. The organic phase was dried with anhydrous sodium sulfate. After filtration, the solvent was distilled away. Then, the residue was refined by flash column chromatography, so that 1.32 g of the compound 1-99 was obtained at an yield of 63%.

Mass-spectrum analysis consequently showed that m/e was equal to 582 while a calculated molecular weight was 582.23.

[Synthesis Example 1-12] Synthesis of Compound 1-100

[Chemical Formula 89]

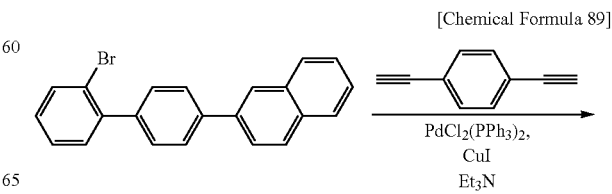

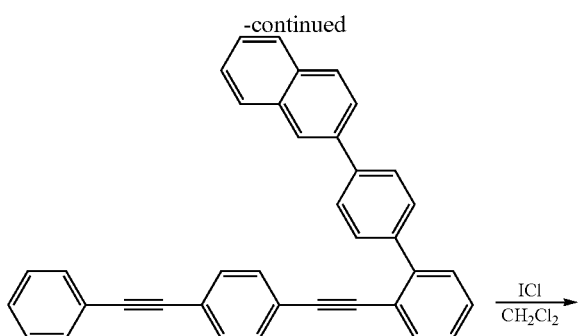
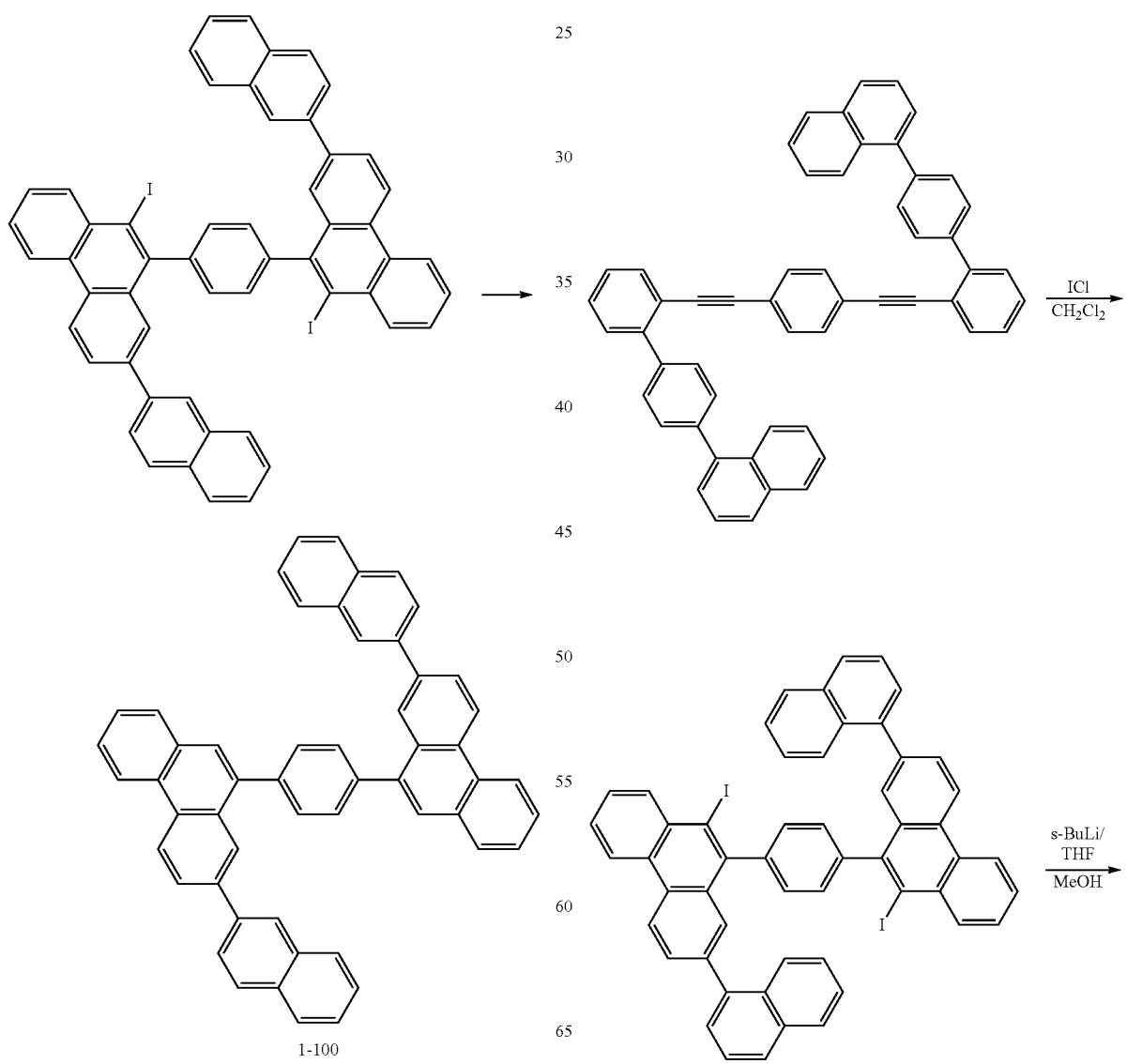
The compound 1-100 was synthesized in the same manner as the compound 1-99, except that 1-(4-bromophenyl)-4-(naphthalene-2-yl)benzene was used in place of 2-bromo-p-terphenyl.
Mass-spectrum analysis consequently showed that m/e was equal to 682 while a calculated molecular weight was 682.27.
[Synthesis Example 1-13] Synthesis of Compound 1-101
[Chemical Formula 90]
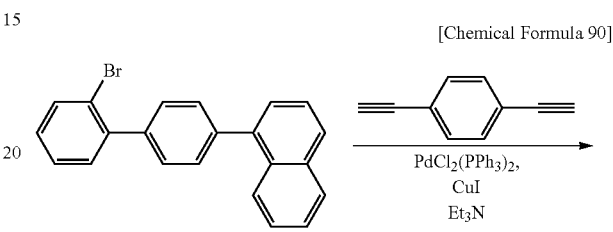

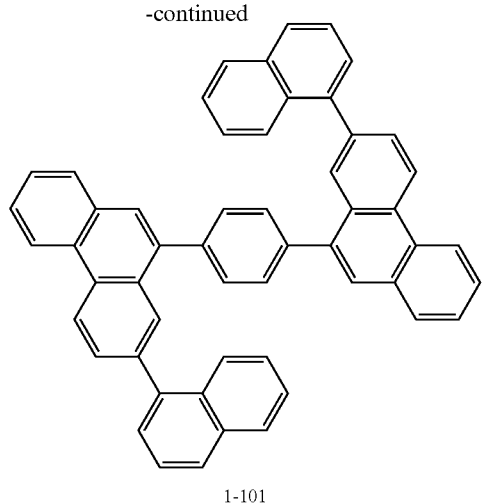
1-101
The compound 1-101 was synthesized in the same manner as the compound 1-99, except that 1-(4-bromophenyl)-4-(naphthalene-1-yl)benzene was used in place of 2-bromo-p-terphenyl.
Mass-spectrum analysis consequently showed that m/e was equal to 682 while a calculated molecular weight was 682.27.
[Synthesis Example 1-14] Synthesis of Compound 1-108
[Chemical Formula 91]
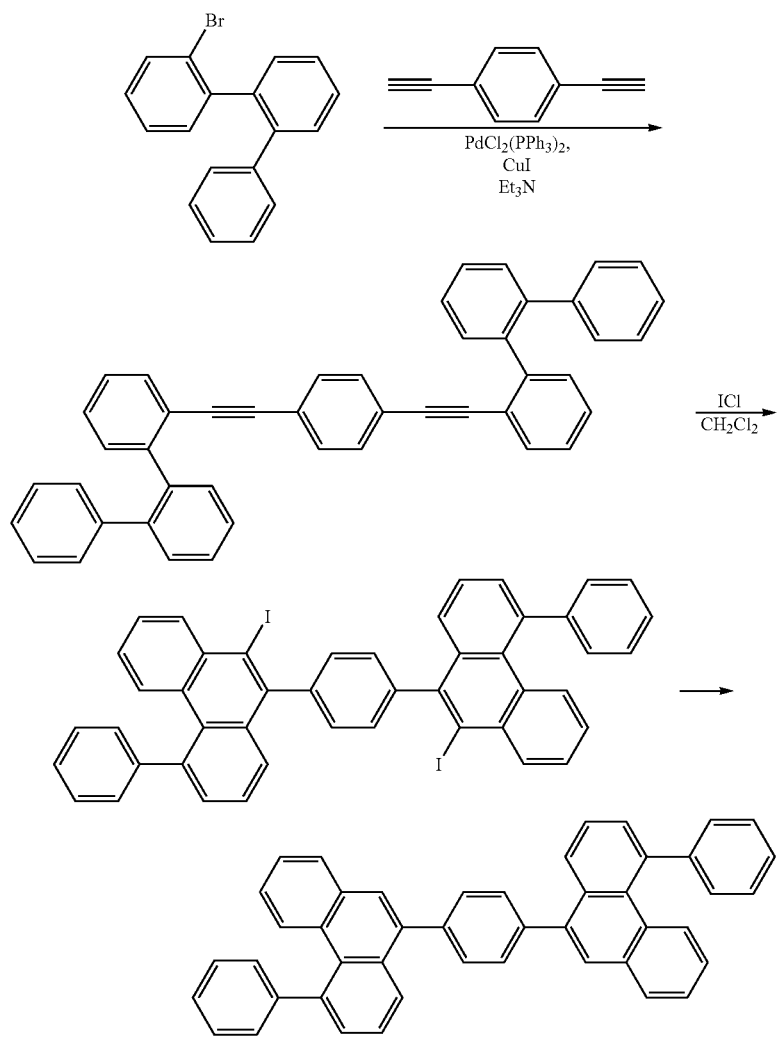
1-108

The compound 1-108 was synthesized in the same manner as the compound 1-99, except that 2-bromo-o-terphenyl was used in place of 2-bromo-p-terphenyl.

Mass-spectrum analysis consequently showed that m/e was equal to 582 while a calculated molecular weight was 582.23.

[Synthesis Example 1-15] Synthesis of Compound 1-119 sodium sulfate and followed by filtration, and the solvent was then distilled away. The residue was refined by column chromatography, so that 6.9 g of 1,4-bis(biphenyl-2-ylethynyl)benzene was obtained at an yield of 75%.

Under an argon gas atmosphere, a mixture of 6.90 g (16.0 mmol) of 1,4-bis(biphenyl-2-ylethynyl)benzene and 140 mL of dichloromethane was cooled down to minus 78 degree C., and added with a mixture containing 6.24 g (38.5 mmol) of ICl and 70 mL of dichloromethane. The mixture was stirred at minus 78 degrees C. for 1 hour.

[Chemical Formula 92]

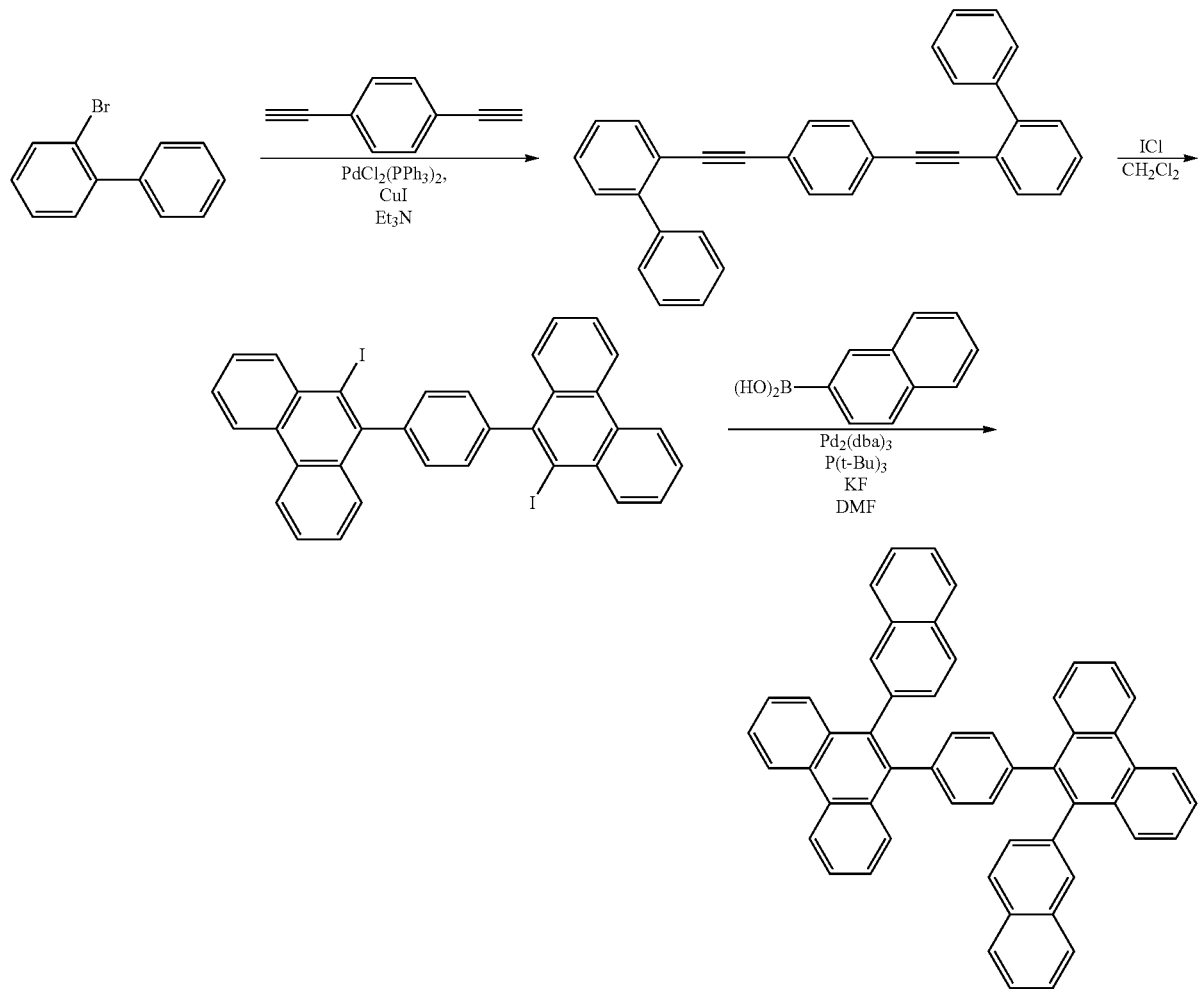

1-119

Under an argon gas atmosphere, a mixture of 10.0 g (42.90 mmol) of 2-bromobiphenyl, 2.71 g (21.5 mmol) of 1,4-diethynylbenzene and 60 mL of triethylamine was added with 1.05 g (0.86 mmol) of PdCl$_2$(PPh$_3$)$_2$ and 0.33 g (1.72 mmol) of CuI. Then, the mixture was stirred at 60 degrees C. for 4 hours. After the reaction was over, insoluble matters were removed by filtration, and the solvent was distilled away under reduced pressure. Then, the mixture was added with aqueous solution of hydrochloric acid, and extracted with toluene. Organic phase thereof was washed with aqueous solution of sodium hydrogencarbonate, and subsequently washed with saturated sodium chloride solution. After liquid separation, the organic phase was dried with anhydrous The reaction mixture was added with aqueous solution of sodium bisulfite, and extracted with dichloromethane. The organic phase was washed with saturated sodium chloride solution. The organic phase was dried with anhydrous sodium sulfate and followed by filtration, and the solvent was distilled away. Then, the residue was refined by flash column chromatography, so that 5.3 g of 1,4-bis(10-iodo-7-phenylphenanthrene-9-yl)benzene was obtained at an yield of 49%.

Under an argon gas atmosphere, a mixture of 5.0 g (7.33 mmol) of 1,4-bis(10-iodophenanthrene-9-yl)benzene, 3.02 g (17.6 mmol) of 2-naphthaleneboronic acid, 0.07 g (0.29 mmol) of palladium acetate, 0.36 g (105.5 mmol) of potassium fluoride and 100 mL of dehydrated DMF was added with 0.12 mL (0.30 mmol) of toluene solution of 50% tri-tertiarybutylphosphine, and stirred at 80 degrees C. for 2 hours, at 100 degrees C. for 2 hours and at 130 degrees C. for 4 hours. Subsequently, the reaction mixture was cooled down to room temperature, added with water and stirred for 1 hour. Then, the reaction mixture was added with methanole, and the solid was filtrated. The solid was washed with methanol, DME and toluene. The obtained solid was refined by silica-gel column chromatography and recrystallized by toluene-hexane, such that 0.50 g of the compound 1-119 was obtained at an yield of 10%.

Mass-spectrum analysis consequently showed that m/e was equal to 682 while a calculated molecular weight was 682.27.

[Synthesis Example 1-16] Synthesis of Compound 1-124

[Chemical Formula 93]

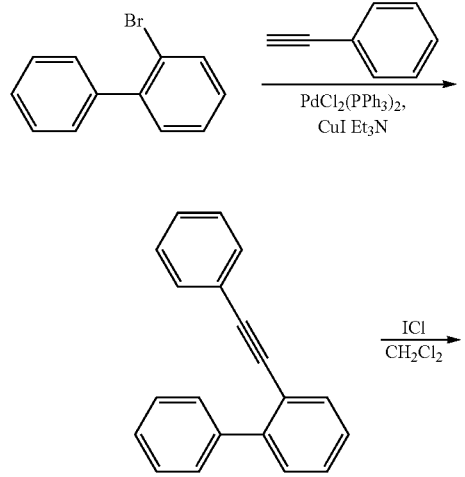

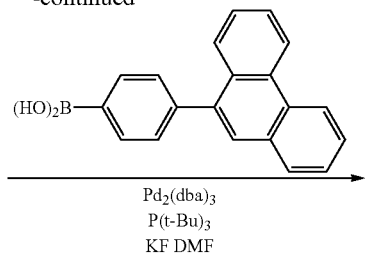

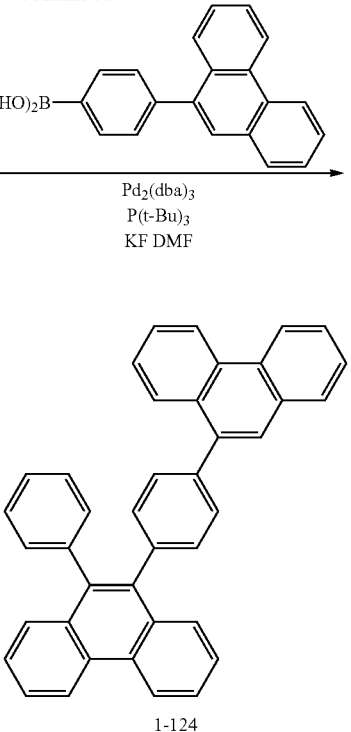

1-124

The compound 1-124 was synthesized in the same manner as the compound 1-119, except that ethynylbenzene was used in place of 1,4-diethynylbenzene and that 4-(phenanthrene-9-yl)boronic acid was used in place of 2-naphthaleneboronic acid.

Mass-spectrum analysis consequently showed that m/e was equal to 506 while a calculated molecular weight was 506.20.

[Synthesis Example 1-17] Synthesis of Compound 1-142

[Chemical Formula 94]

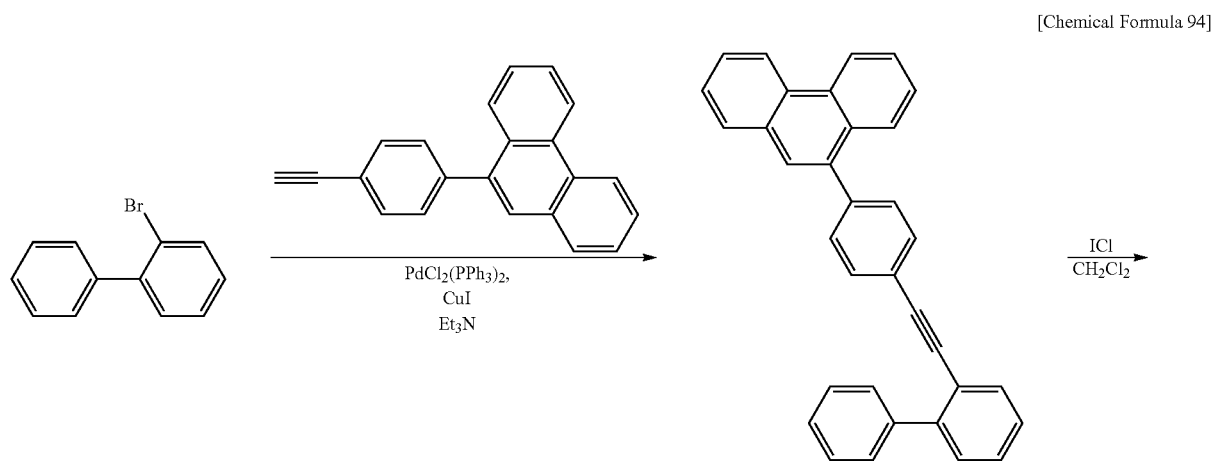

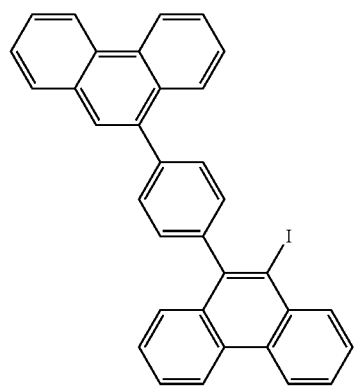
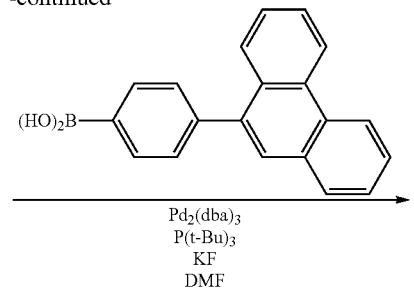

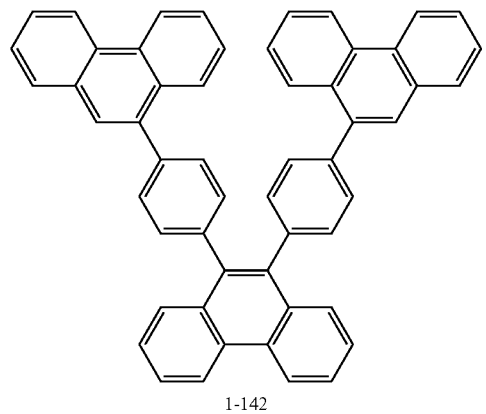

1-142

The compound 1-142 was synthesized in the same manner as the compound 1-119, except that 9-(4-ethynylphenyl) phenanthrene was used in place of 1,4-diethynylbenzene and that 4-(phenanthrene-9-yl)boronic acid was used in place of 2-naphthaleneboronic acid.

Mass-spectrum analysis consequently showed that m/e was equal to 682 while a calculated molecular weight was 682.27.

[Synthesis Example 1-18] Synthesis of Compound 1-145

[Chemical Formula 95]

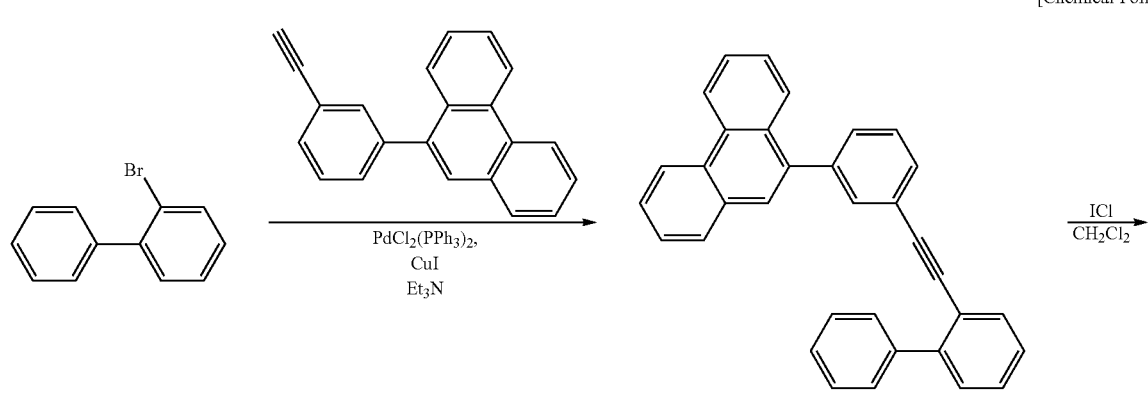

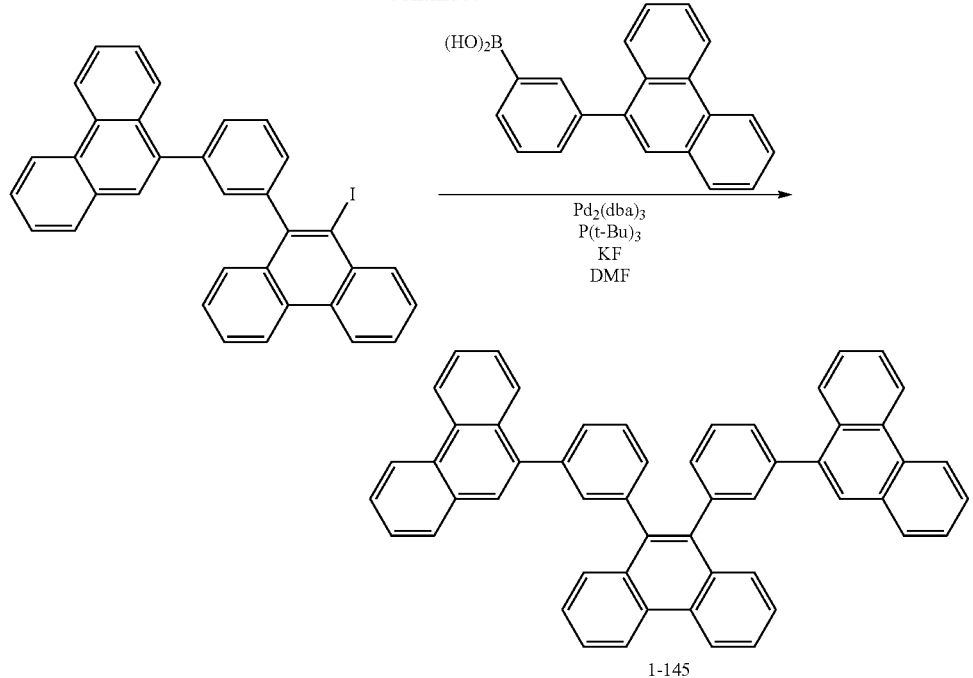

The compound 1-145 was synthesized in the same manner as the compound 1-119, except that 9-(3-ethynylphenyl)phenanthrene was used in place of 1,4-diethynylbenzene and that 3-(phenanthrene-9-yl)boronic acid was used in place of 2-naphthaleneboronic acid.

Mass-spectrum analysis consequently showed that m/e was equal to 682 while a calculated molecular weight was 682.27.

[Synthesis Example 1-19] Synthesis of Compound 1-159

[Chemical Formula 96]

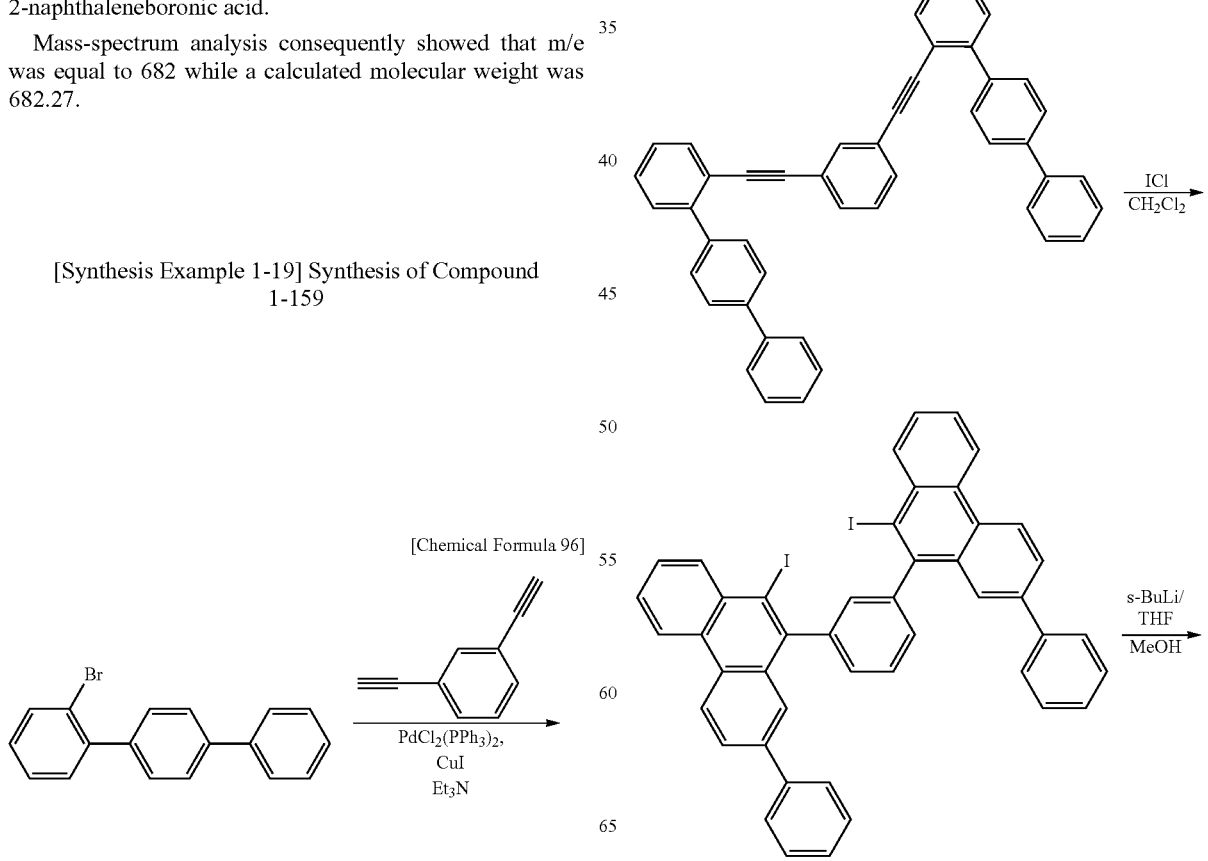

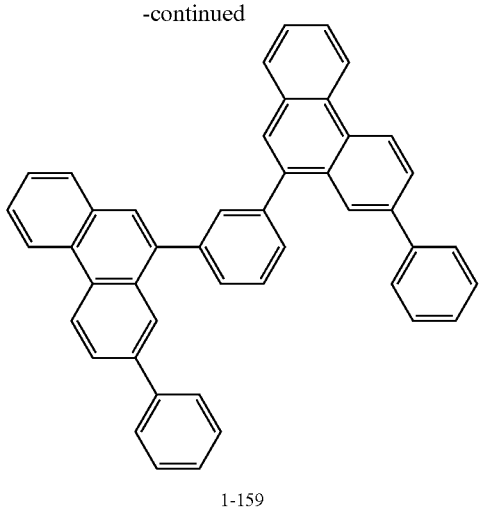

1-159

The compound 1-159 was synthesized in the same manner as the compound 1-99, except that 1,3-diethynylbenzene was used in place of 1,4-diethynylbenzene.

Mass-spectrum analysis consequently showed that m/e was equal to 582 while a calculated molecular weight was 582.23.

An equipment used in the measurement of mass spectrometry and measurement conditions thereof in the above synthesis examples will be described below.

| Equipment: | JSM-700 (manufactured by Japan Electron Optics Laboratories Ltd.) |
|---|---|
| Condition: | accelerating voltage 8 kV scanning range m/z = 50 to 3000 |
| Emitter type: | carbon |
| Emitter currency: | 0 mA→2 mA/minute→40 mA (maintained for 10 minutes) |

EXAMPLES

Next, the invention will be described in further detail with reference to examples. However, the invention is not limited to such examples.

Structures of compounds used in Examples and Comparatives will be shown below.

[Chemical Formula 97]

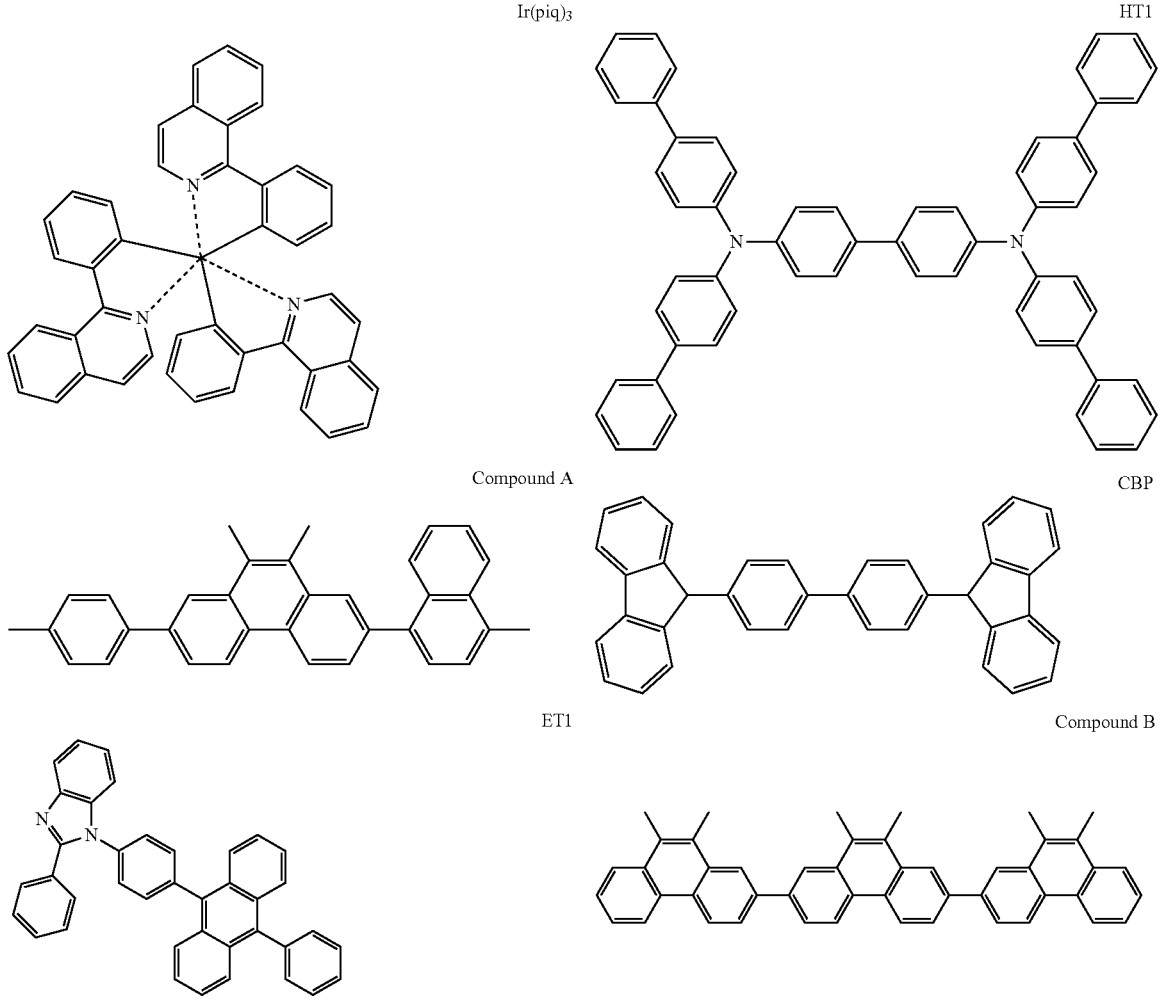

-continued
[Chemical Formula 98]
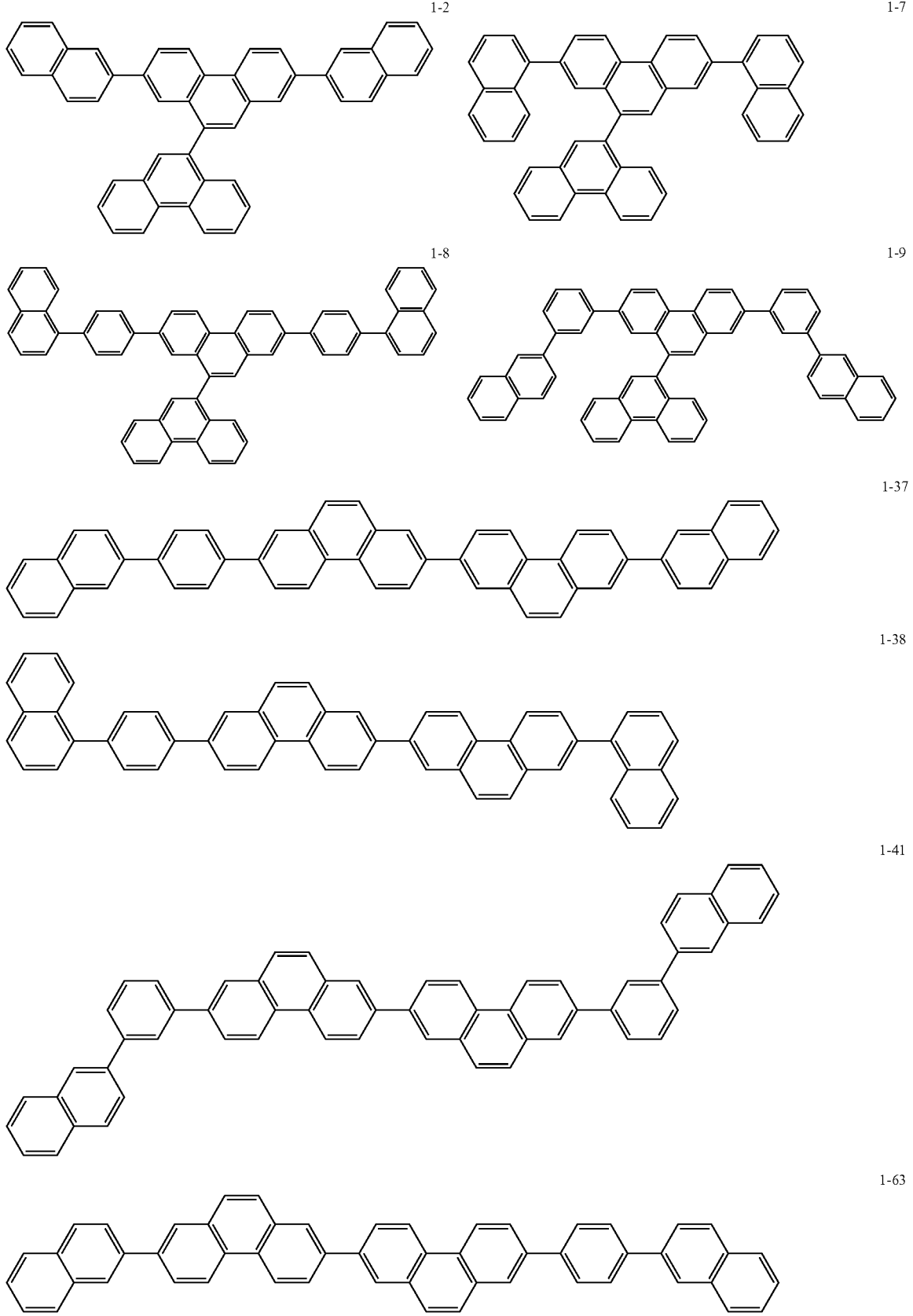

-continued
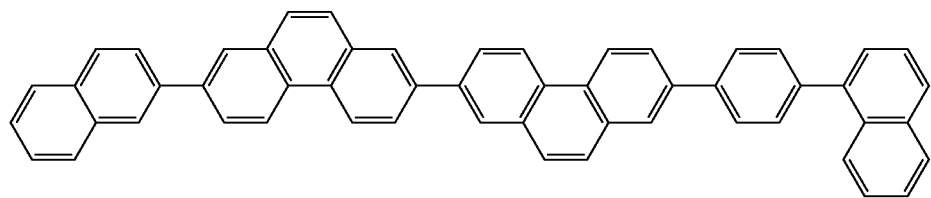

-continued 1-119
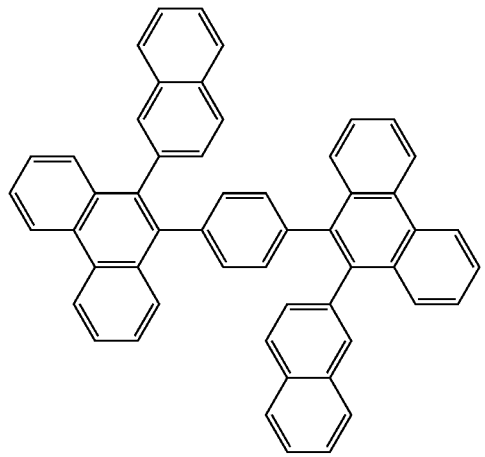

1-124
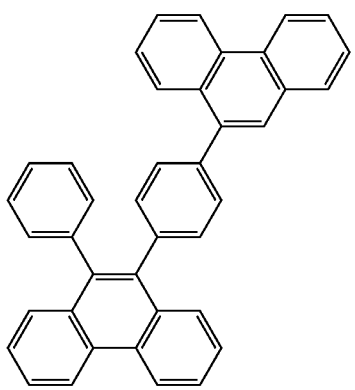

1-142
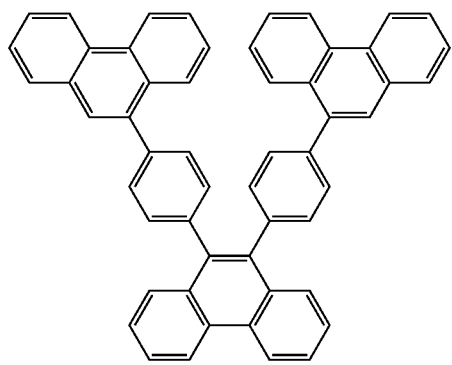

1-145
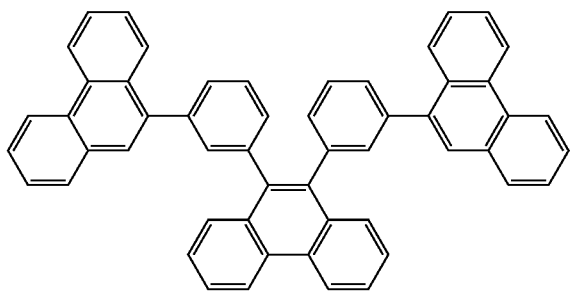

1-159
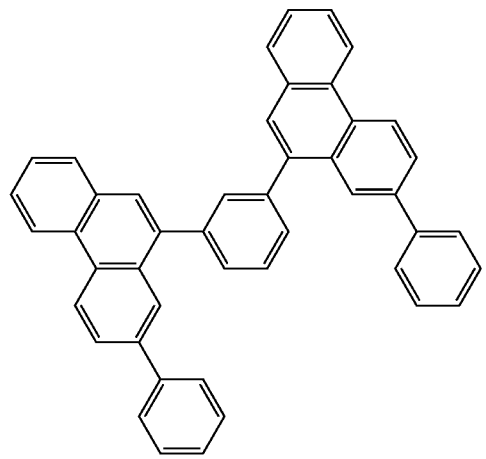

Example 1

Manufacturing of Organic EL Device

A glass substrate (size: 25 mm×75 mm×0.7 mm thick) having an ITO transparent electrode (manufactured by Asahi Glass Co., Ltd) was ultrasonic-cleaned in isopropyl alcohol for five minutes, and then UV/ozone-cleaned for 30 minutes. After the glass substrate having the transparent electrode line was cleaned, the glass substrate was mounted on a substrate holder of a vacuum deposition apparatus, so that 50-nm thick film of HT1 was initially formed on a surface of the glass substrate where the transparent electrode line was provided so as to cover the transparent electrode. The HT1 film serves as a hole injecting/transporting layer. Subsequently to the formation of the hole injecting/transporting layer, 40-nm thick film of the new host compound 1-2 and Ir(piq)$_3$ as a phosphorescent-emitting dopant were co-deposited by resistance heating so that Ir(piq)$_3$ was contained therein at a content of 10 mass %. The co-deposited film serves as an emitting layer (phosphorescent-emitting layer). After the film of the emitting layer was formed, 40-nm thick film of ET1 was formed. The film of ET1 serves as an electron transporting layer. Then, 0.5-nm thick film of LiF was formed as an electron-injecting electrode (cathode) at a film-forming speed of 1

Å/min. Metal (Al) was vapor-deposited on the LiF film to form a 150-nm thick metal cathode, thereby providing the organic EL device.

Examples 2 to 19 and Comparatives 1 to 3

The organic EL devices according respectively to Examples 2 to 20 and Comparatives 1 to 3 were formed in the same manner as Example 1 except that host compounds shown in Table 1 were respectively used in place of the new host compound 1-2.

[Evaluation on Emitting Performance of Organic EL Device]

The organic EL devices according to Examples 1 to 19 and Comparatives 1 to 3 each were driven by direct-current electricity to emit light, so that voltage, luminous efficiency and time elapsed until the initial luminance intensity of 3000 cd/m² was reduced to the half (i.e., time until half-life) at a current density of 10 mA/cm² were measured for each organic EL device. Then, pixel uniformity when each organic EL device was driven at 70 degrees C. was visually checked, among which devices having uniform pixels are rated as A while devices having non-uniform pixels are rated as B. The results of the evaluation are shown in Table 1.

TABLE 1

| Example | Host Compound | Voltage (V) | Luminous Efficiency (cd/A) | Time until Half-Life (hour) | Pixel Uniformity when Driven at 70 C. ° |
|---|---|---|---|---|---|
| Example 1 | 1-2 | 5.2 | 8.4 | 5800 | A |
| Example 2 | 1-7 | 5.2 | 8.0 | 6200 | A |
| Example 3 | 1-8 | 5.1 | 8.2 | 5100 | A |
| Example 4 | 1-9 | 5.2 | 7.6 | 5000 | A |
| Example 5 | 1-37 | 4.8 | 7.7 | 3950 | A |
| Example 6 | 1-38 | 4.8 | 8.4 | 3600 | A |
| Example 7 | 1-41 | 4.7 | 7.4 | 4100 | A |
| Example 8 | 1-63 | 4.9 | 8.2 | 3000 | A |
| Example 9 | 1-64 | 4.8 | 7.9 | 3300 | A |
| Example 10 | 1-65 | 4.8 | 8.4 | 3200 | A |
| Example 11 | 1-99 | 4.9 | 8.2 | 4100 | A |
| Example 12 | 1-100 | 5.0 | 7.6 | 4500 | A |
| Example 13 | 1-101 | 5.1 | 8.0 | 4200 | A |
| Example 14 | 1-108 | 5.1 | 8.4 | 4800 | A |
| Example 15 | 1-119 | 5.0 | 7.8 | 4600 | A |
| Example 16 | 1-124 | 4.9 | 7.7 | 4200 | A |
| Example 17 | 1-142 | 5.0 | 8.1 | 4800 | A |
| Example 18 | 1-145 | 5.1 | 7.4 | 5000 | A |
| Example 19 | 1-159 | 5.1 | 8.8 | 4000 | A |
| Comparative 1 | CBP | 5.4 | 6.3 | 1200 | B |
| Comparative 2 | Compound A | 5.5 | 7.2 | 800 | B |
| Comparative 3 | Compound B | 5.4 | 5.9 | 850 | B |

As appreciated from the above, in comparison with Comparatives 1 to 3, the organic EL devices according to Examples 1 to 19, in which the phenanthrene derivative according to the aspect of the invention was used as the host of the phosphorescent-emitting layer, were excellent in terms of the time until half-life, pixel uniformity when driven at as high a temperature as 70 degrees C. and luminous efficiency.

Accordingly, the organic EL device according to the aspect of the invention are excellent in luminous efficiency, heat resistance and lifetime and free from pixel defects.

The invention claimed is:

1. A phenanthrene compound, represented by a formula (1) below

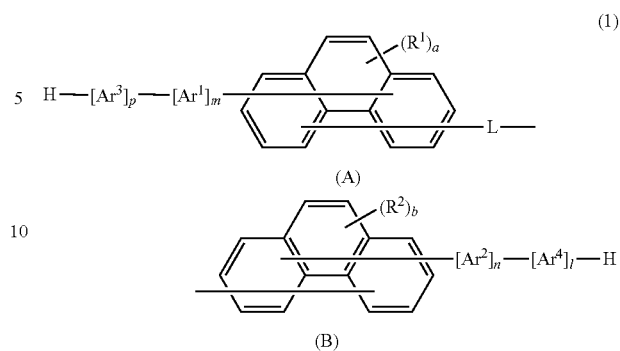

where $Ar^1$ to $Ar^4$ each represent an aromatic hydrocarbon ring group having 6 to 18 carbon atoms for forming the ring, the aromatic hydrocarbon ring group comprising none of anthracence skeleton, pyrene skeleton, aceanthrylene skeleton and naphtacene skeleton, wherein $Ar^1$ to $Ar^4$ are bonded in any positions of a phenanthrene skeleton;

$R^1$ and $R^2$ each represent an alkyl group having 1 to 30 carbon atoms, cycloalkyl group having 3 to 30 carbon atoms, alkoxy group having 1 to 20 carbon atoms, cyano group, silyl group having 3 to 30 carbon atoms, halogen atom or aryl group having 6 to 30 carbon atoms, wherein $R^1$ and $R^2$ are bonded in any positions of the phenanthrene skeleton;

L is bonded in the 2nd or 9th position of the phenanthrene skeleton and represents a single bond, a substituted or unsubstituted benzene skeleton, naphthalene skeleton, fluorene skeleton, fluoranthene skeleton, triphenylene skeleton, chrysene skeleton, phenyl-naphthalene skeleton, binaphthalene skeleton, benzophenanthrene skeleton, dibenzophenanthrene skeleton, benzotriphenylene skeleton, picene skeleton or benzo[b]fluoranthene skeleton, wherein, when L is a single bond, $Ar^1$ and $Ar^2$ represent an aromatic hydrocarbon ring group having 6 to 18 carbon atoms for forming the ring comprising none of phenanthrene skeleton, anthracene skeleton, pyrene skeleton, aceanthrylene skeleton, and naphthacene skeleton, $Ar^1$ and $Ar^3$ not simultaneously representing phenanthrene skeleton and $Ar^2$ and $Ar^4$ not simultaneously representing phenanthrene skeleton;

a represents the number of substituents $R^1$ directly bonded to a phenanthrene main chain;

b represents the number of the substituents $R^2$ directly bonded to a phenanthrene main chain;

a and b each represent an integer of 0 to 8;

m, n, l and p each represent 0 or 1 while satisfying m+n+l+p≥1 (m,n≥l,p); and a structure represented by a formula (1-X) below is excluded (1-X)

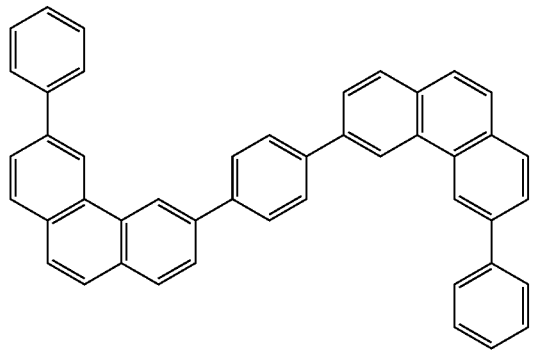

2. The phenanthrene compound according to claim 1, wherein $Ar^1$ to $Ar^4$ in the formula (1) each represent a group selected from a substituted or unsubstituted benzene skeleton, naphthalene skeleton, fluorene skeleton, phenanthrene skeleton, fluoranthene skeleton, triphenylene skeleton, chrysene skeleton, benzophenanthrene skeleton, dibenzophenanthrene skeleton, benzotriphenylene skeleton, picene skeleton and benzo[b]fluoranthene skeleton.

3. The phenanthrene compound according to claim 1, wherein a or b in the formula (1) is 0, 1 or 2.

4. The phenanthrene compound according to claim 1, wherein a or b in the formula (1) is 0.

5. The phenanthrene compound according to claim 1, wherein
when $Ar^1$ to $Ar^4$ and L in the formula (1) have substituent(s), the substituent(s) is a group selected from an alkyl group, cycloalkyl group, alkoxy group, cyano group, silyl group, aryl group and halogen atom.

6. The phenanthrene compound according to claim 1, wherein the formula (1) is represented by any one of formulae (1-a) to (1-f) below (1-a)

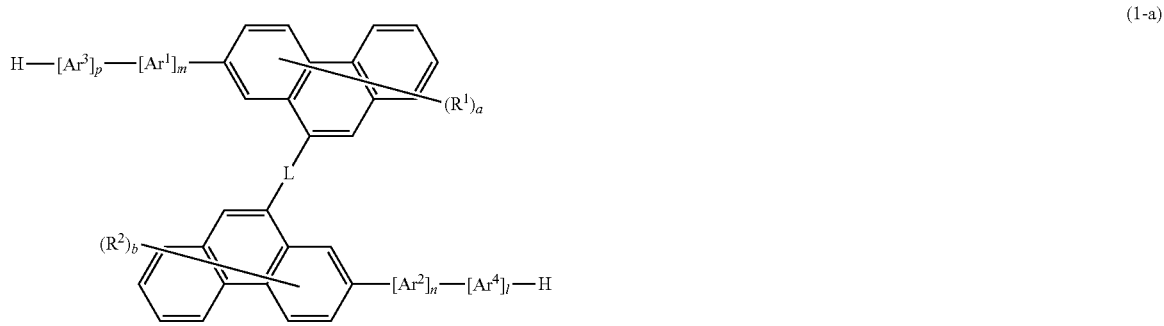

(1-b)

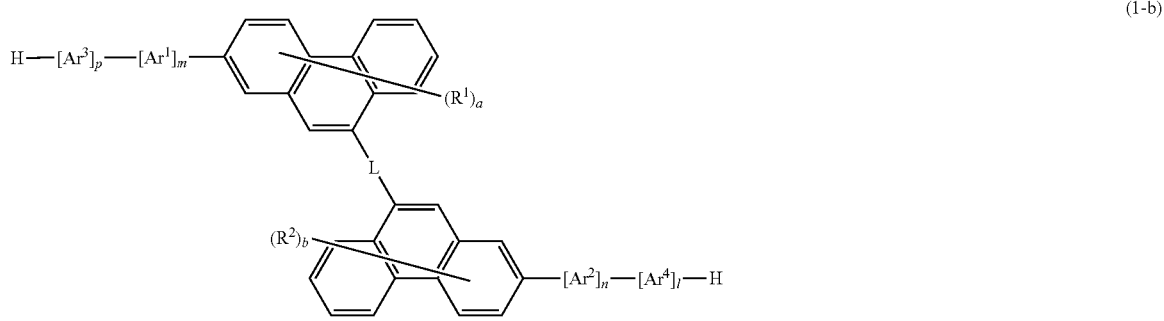

-continued (1-c)
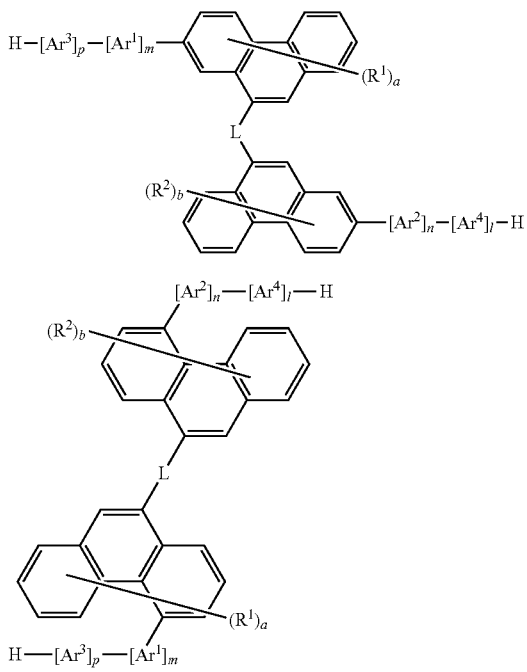

(1-d)
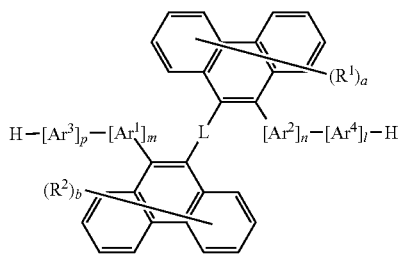

(1-e)
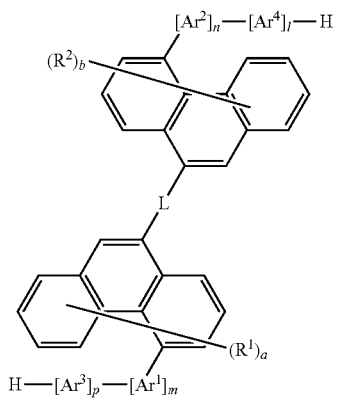

(1-f)
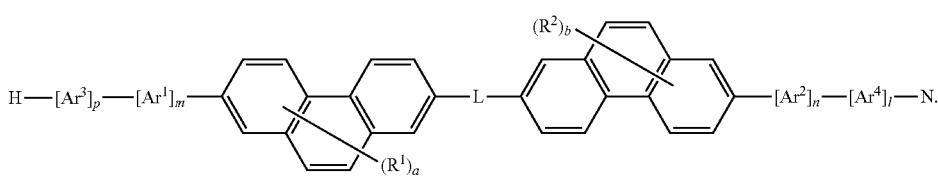

7. A material for organic EL devices, comprising the phenanthrene compound according to claim 1.

8. The material for organic EL devices according to claim 7, wherein the material for organic EL devices is combined with a phosphorescent-emitting material.

9. The material for organic EL devices according to claim 7, wherein the material for organic EL devices is a host material of an emitting layer.

10. An organic electroluminescent device, comprising:
an anode, an organic emitting layer and a cathode,
wherein the organic emitting layer is between the anode and the cathode and comprises the phenanthrene compound of claim 1 as a host material.

11. The organic electroluminescent device of claim 10, wherein the organic emitting layer further comprises a phosphorescent-emitting material.

12. The organic electroluminescent device of claim 10, further comprising a hole injecting/transporting layer between the anode and the cathode.

13. The organic electroluminescent device of claim 12, wherein the organic emitting layer further comprises Ir(piq)$_3$ as a phosphorescent-emitting dopant.

14. The phenanthrene compound according to claim 1, selected from the group consisting of:

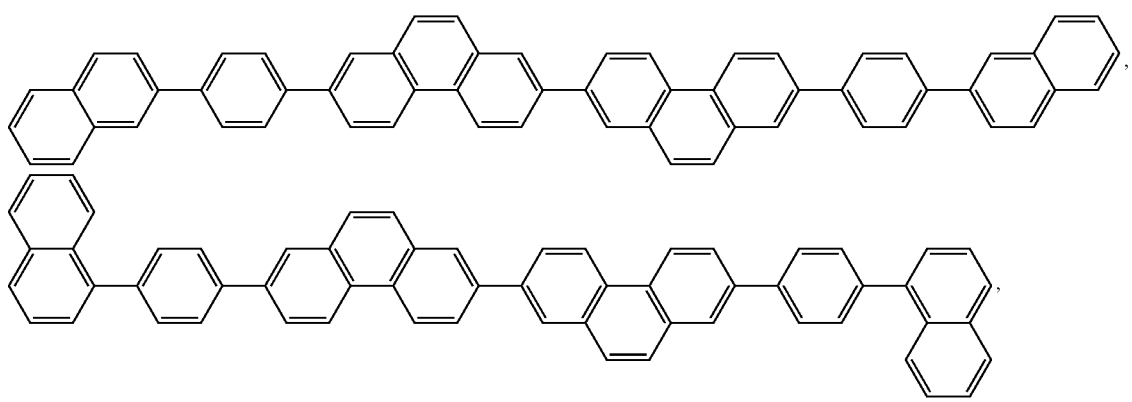

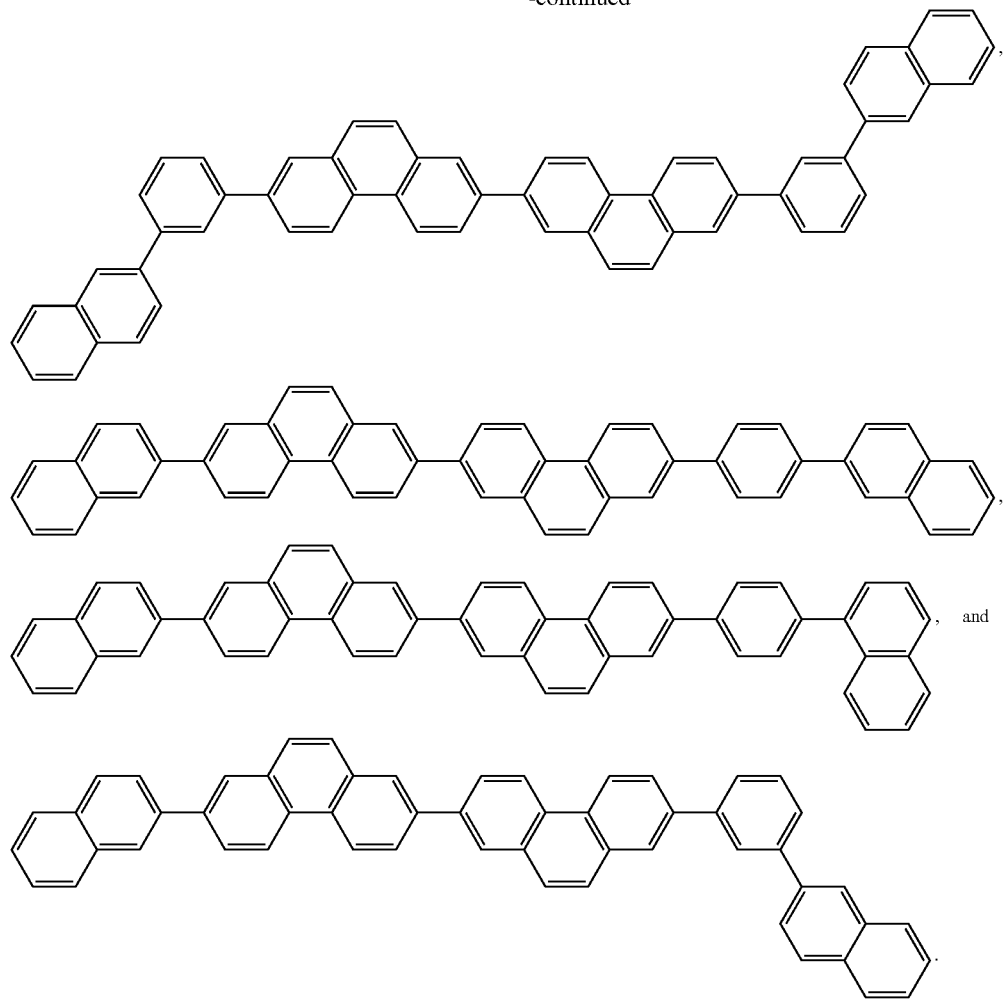

15. The phenanthrene compound according to claim 1, wherein L is a single bond or a substituted or unsubstituted benzene skeleton.

16. The phenanthrene compound according to claim 1, wherein L is a substituted or unsubstituted benzene skeleton bonded in a 9th position of the phenanthrene skeleton.

17. The phenanthrene compound according to claim 1, wherein L is a single bond or a substituted or unsubstituted benzene skeleton and, when L is bonded in 2nd position of the phenanthrene skeleton, at least one of $Ar^1$ and $Ar^2$ is a phenylene group.

* * * * *